US008871361B2

(12) United States Patent
Xia et al.

(10) Patent No.: US 8,871,361 B2
(45) Date of Patent: Oct. 28, 2014

(54) TETRADENTATE PLATINUM COMPLEXES

(75) Inventors: Chuanjun Xia, Lawrenceville, NJ (US); Walter Yeager, Yardley, PA (US); David Zenan Li, Princeton, NJ (US); James Fiordelisio, Yardley, PA (US); Bin Ma, Plainsboro, NJ (US); Zeinab Elshenawy, Holland, PA (US); Suman Layek, Lawrenceville, NJ (US); Ed Barron, Hamilton, NJ (US); Gregg Kottas, Ewing, NJ (US); Jason Brooks, Philadelphia, PA (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 13/414,479

(22) Filed: Mar. 7, 2012

(65) Prior Publication Data

US 2012/0223634 A1 Sep. 6, 2012

Related U.S. Application Data

(63) Continuation of application No. PCT/US2012/026396, filed on Feb. 23, 2012.

(60) Provisional application No. 61/445,864, filed on Feb. 23, 2011, provisional application No. 61/547,461, filed on Oct. 14, 2011.

(51) Int. Cl.
| | | |
|---|---|---|
| *H01L 51/54* | (2006.01) | |
| *C09K 11/06* | (2006.01) | |
| *C07F 15/00* | (2006.01) | |
| *H05B 33/14* | (2006.01) | |
| *H01L 51/00* | (2006.01) | |

(52) U.S. Cl.
CPC ........ *H01L 51/0087* (2013.01); *C07F 15/0086* (2013.01); *H01L 51/0074* (2013.01); *C09K 2211/1044* (2013.01); *H01L 51/0072* (2013.01); *H01L 51/0094* (2013.01); *C09K 11/06* (2013.01); *H05B 33/14* (2013.01); *C09K 2211/185* (2013.01); *Y10S 428/917* (2013.01)
USPC .... 428/690; 428/917; 313/504; 257/E51.044; 548/103; 548/108; 546/4; 546/10

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,442,797 B2 | 10/2008 | Itoh et al. | |
| 7,445,855 B2 | 11/2008 | Mackenzie et al. | |
| 7,501,190 B2 | 3/2009 | Ise | |
| 7,534,505 B2 | 5/2009 | Lin et al. | |
| 7,655,323 B2 | 2/2010 | Walters et al. | |
| 7,771,845 B2 | 8/2010 | Sano et al. | |
| 7,781,074 B2 | 8/2010 | Sano et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Derwent Acc. No. 2010-M67154, abstract for JP 4551480 B1 (Sep. 2010).*

(Continued)

*Primary Examiner* — Marie R. Yamnitzky

(74) *Attorney, Agent, or Firm* — Duane Morris LLP

(57) ABSTRACT

Novel phosphorescent tetradentate platinum (II) compounds comprising a twisted aryl group are provided. Also provided are novel phosphorescent tetradentate platinum (II) compounds comprising an imidazo[1,2-f]phenanthridine moiety. The compounds may be used in organic light emitting devices to provide improved device efficiency, line shape and lifetime.

12 Claims, 4 Drawing Sheets

(56) References Cited

U.S. PATENT DOCUMENTS

| | | |
|---|---|---|
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0020219 A1 | 1/2006 | Zinser, Jr. et al. |
| 2006/0073359 A1 | 4/2006 | Ise et al. |
| 2006/0202194 A1 | 9/2006 | Jeong et al. |
| 2006/0202197 A1 | 9/2006 | Nakayama et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0059552 A1 | 3/2007 | Takeda et al. |
| 2007/0103060 A1 | 5/2007 | Itoh et al. |
| 2007/0190359 A1 | 8/2007 | Knowles et al. |
| 2007/0278938 A1 | 12/2007 | Yabunouchi et al. |
| 2008/0001530 A1 | 1/2008 | Ise et al. |
| 2008/0015355 A1 | 1/2008 | Schafer et al. |
| 2008/0018221 A1 | 1/2008 | Egen et al. |
| 2008/0036373 A1 | 2/2008 | Itoh et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0128008 A1 | 5/2009 | Ise et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0049496 A1* | 3/2011 | Fukuzaki ............ 257/40 |
| 2011/0073848 A1 | 3/2011 | Takada et al. |
| 2012/0153816 A1* | 6/2012 | Takizawa et al. ......... 313/504 |

FOREIGN PATENT DOCUMENTS

| | | |
|---|---|---|
| EP | 2031037 | 3/2009 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2008103535 | 5/2008 |
| JP | 2009016718 | 1/2009 |
| JP | 2009/267244 | 11/2009 |
| JP | 2009267171 | 11/2009 |
| JP | 4551480 B1 * | 9/2010 |
| JP | 2011129744 | 6/2011 |
| WO | WO 01/39234 | 5/2001 |
| WO | WO 02/02714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2009107497 | 9/2009 |
| WO | WO 2010118026 | 10/2010 |

OTHER PUBLICATIONS

Machine translation of JP 2009-267244 A (Nov. 2009).*
Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 1, 4-6 (1999).
Vezzu et al., Inorg. Chem. 2010, 49, 5107-5119.
International application No. PCT/US2012/026396 filed Feb. 23, 2012, (published as WO 2012/116231 A2 on Aug. 30, 2012).
U.S. Appl. No. 61/445,864, filed Feb. 23, 2011.
U.S. Appl. No. 61/547,461, filed Oct. 14, 2011.
U.S. Appl. No. 61/529,634, filed Aug. 31, 2011.
The Partial International Search Report in PCT/US2012/026396 application.
Database CA [Online] Chemical Abstracts Service. Columbus, Ohio. US; 2009, Takeda, Rei et al: "Organicelectroluminescent device" XP002674739, abstract for JP 2009-267244 (Nov. 2009).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Tung, Yung-Liang et al., "Organic Light-Emitting Diodes Based on Charge-Neutral $Ru^{II}$ PHosphorescent Emitters," Adv. Mater., 17(8):1059-1064 (2005).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Wong, Wai-Yeung, "Multifunctional Iridium Complexes Based on Carbazole Modules as Highly Efficient Electrophosphors," Angew. Chem. Int. Ed., 45:7800-7803 (2006).
Tang, C.W. and VanSlyke, S.A., "Organic Electroluminescent Diodes," Appl. Phys. Lett., 51(12):913-915 (1987).

(56) References Cited

OTHER PUBLICATIONS

Adachi, Chihaya et al., "Organic Electroluminescent Device Having a Hole Conductor as an Emitting Layer," *Appl. Phys. Lett.*, 55(15):1489-1491 (1989).
Ma, Yuguang et al., "Triplet Luminescent Dinuclear-Gold(*I*) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of $CHF_3$,"*Appl. Phys. Lett.*, 78(5):673-675 (2001).
Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al., A Novel Class of Phosphorescent Gold(III) Alkynyl-Based Organic Light-Emitting Devices with Tunable Colour, *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).
Sakamoto,Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al. "1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).

* cited by examiner

Formula I

Formula I'

TETRADENTATE PLATINUM COMPLEXES

CROSS-REFERENCES TO RELATED APPLICATIONS

This application is a continuation of international application No. PCT/US2012/026396 filed Feb. 23, 2012, which designates the United States, incorporated by reference herein, and which claims the benefit of priority from U.S. Patent Application Ser. No. 61/445,864, filed Feb. 23, 2011, and U.S. Patent Application Ser. No. 61/547,461, filed Oct. 14, 2011, which are incorporated herein by reference for all purposes and in their entireties.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention is related to phosphorescent tetradentate platinum materials comprising a twisted aryl substituent. Additionally, the invention relates to tetradentate platinum (II) compounds comprising an imidazo[1,2-f]phenanthridine moiety. These materials may be used in OLEDs to provide devices having improved performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

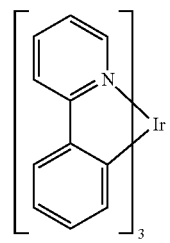

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Phosphorescent tetradentate platinum compounds comprising a twisted aryl substituent are provided. The compounds have the formula:

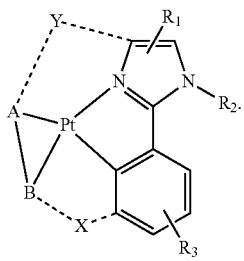

Formula I

A and B are independently selected from the group consisting of a 5-membered or 6-membered carbocyclic or heterocyclic ring. A-B connects to Pt through one covalent bond and one coordination bond. X and Y are independently selected from the group consisting of BR, NR, PR, O, S, Se, C=O, S=O, $SO_2$, CRR', SiRR', and GeRR'. At least one of X and Y forms a bond between A-B and the 2-phenylimidazole. R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ and $R_3$ may represent mono, di, or tri substitutions. $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$, $R_2$, and $R_3$ are optionally joined to form a fused ring. At least one of $R_1$ and $R_2$ is:

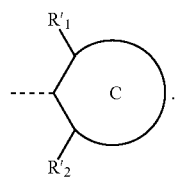

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is 5 or 6-membered carbocyclic or heterocyclic ring that is optionally further substituted. Preferably, C is benzene.

In one aspect, the compound has the formula:

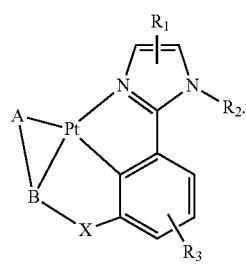

Formula II

In another aspect, the compound has the formula:

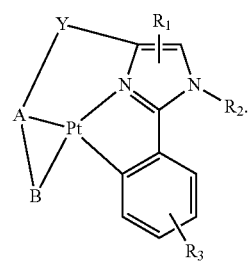

Formula III

In yet another aspect, the compound has the formula:

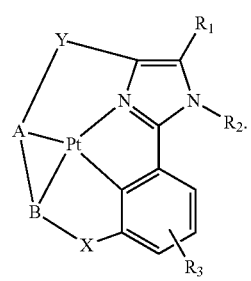

Formula IV

In one aspect, at least one of $R'_1$ and $R'_2$ is an alkyl and the other of $R'_1$ and $R'_2$ is hydrogen or detuerium. In another aspect, at least one of $R'_1$ and $R'_2$ is an alkyl having two or more carbon atoms and the other of $R'_1$ and $R'_2$ is hydrogen or deuterium. In yet another aspect, at least one of $R'_1$ and $R'_2$ is an alkyl having three or more carbon atoms and the other of $R'_1$ and $R'_2$ is hydrogen or deuterium.

In one aspect, each of $R'_1$ and $R'_2$ is an alkyl. In another aspect, each of $R'_1$ and $R'_2$ is an alkyl having two or more carbon atoms. In yet another aspect, each of $R'_1$ and $R'_2$ is an alkyl having three or more carbon atoms.

In one aspect, at least one of $R'_1$ and $R'_2$ is an aryl and the other of $R'_1$ and $R'_2$ is hydrogen or deuterium. In another aspect, one of R'₁ and R'₂ is an alkyl and the other of R'₁ and R'₂ is an aryl. In yet another aspect, each of R'₁ and R'₂ is an aryl.

In one aspect, the compound has a formula selected from the group consisting of:

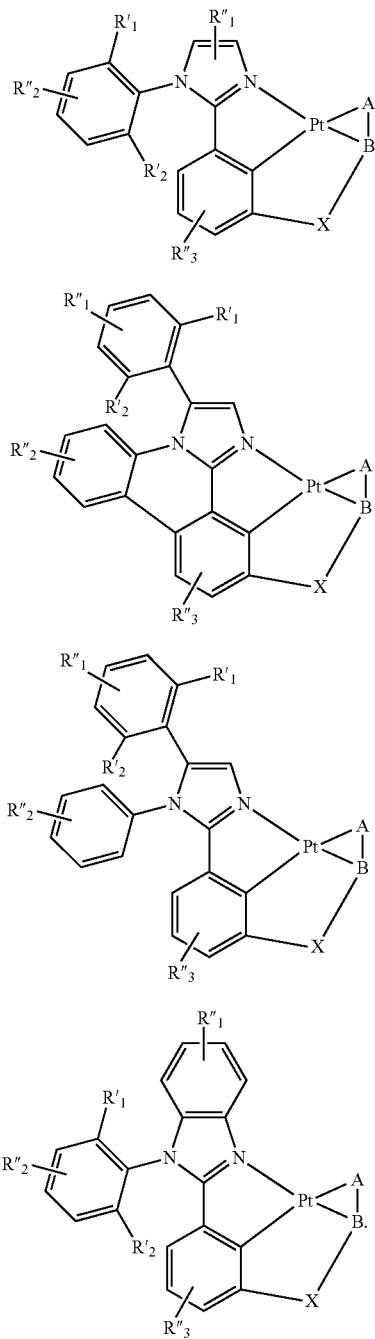

Formula V

Formula VI

Formula VII

Formula VIII

R"₁, R"₂, and R"₃ may represent mono, di, tri, or tetra substitutions. R"₁, R"₂, and R"₃ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of R"₁, R"₂, and R"₃ are optionally joined to form a fused ring.

In another aspect, the compound has a formula selected from the group consisting of:

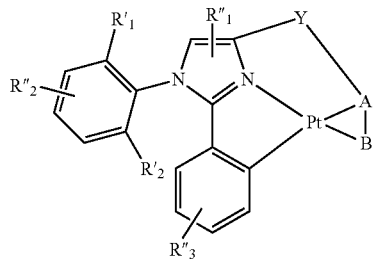

Formula IX

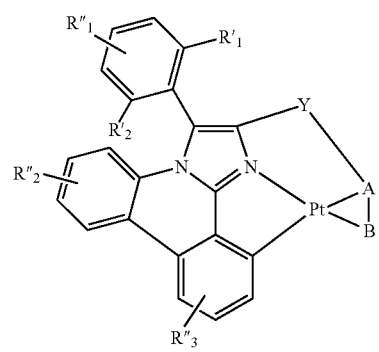

Formula X

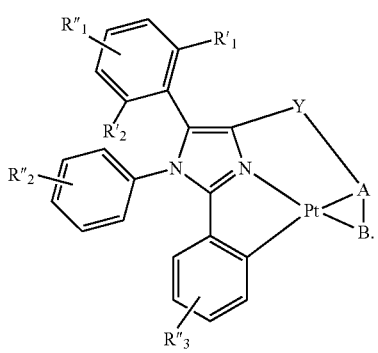

Formula XI

R"₁, R"₂, and R"₃ may represent mono, di, tri, or tetra substitutions. R"₁, R"₂, and R"₃ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of R"₁, R"₂, and R"₃ are optionally joined to form a fused ring.

In another aspect, A-B is selected from the group consisting of:

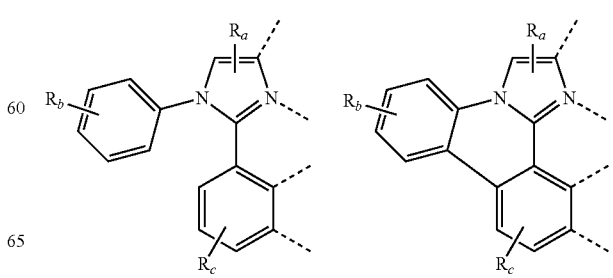

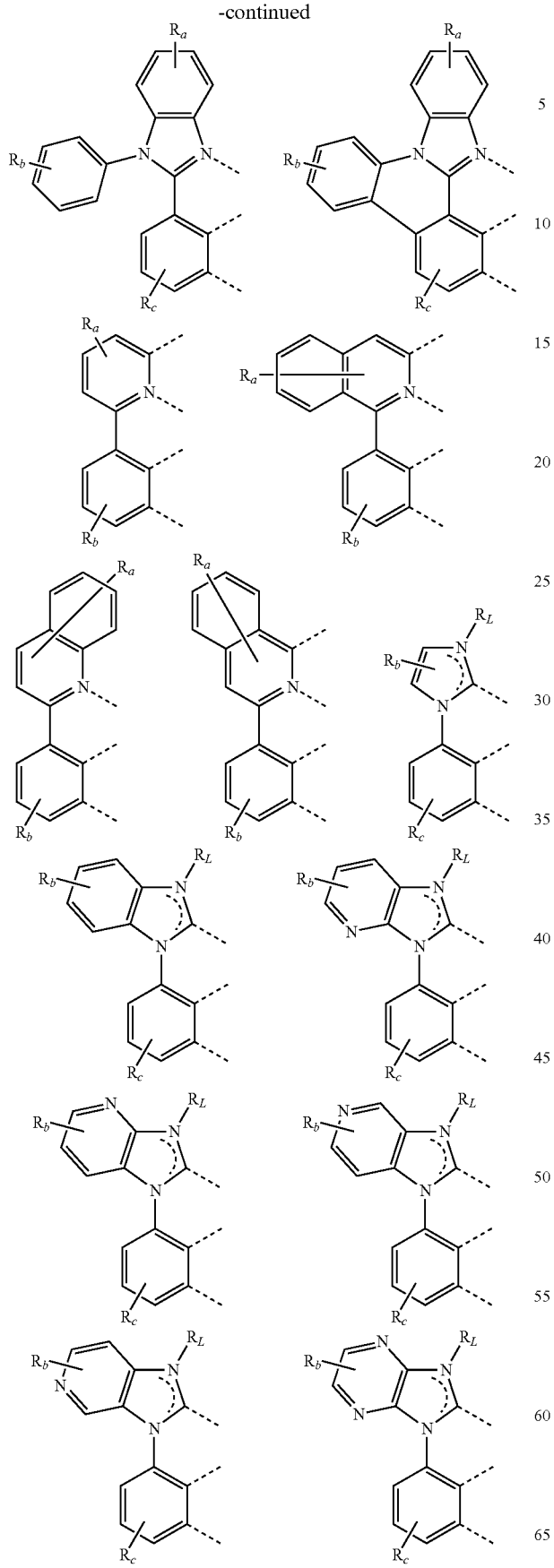

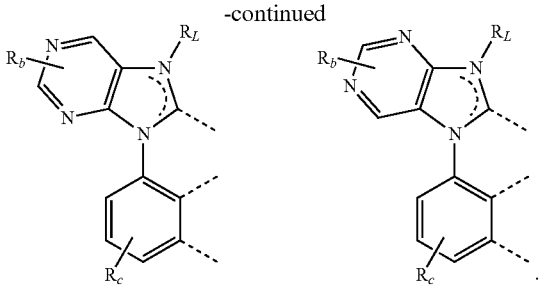

$R_a$, $R_b$, $R_c$ and $R_L$ may represent mono, di, tri or tetra substitutions. $R_a$, $R_b$, $R_c$ and $R_L$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, $R_c$ and $R_L$ are optionally joined to form a fused ring. $R_L$ is optionally a linker to connect A-B and 2-phenylimidazole.

Specific, non-limiting examples of the platinum complexes are provided. In one aspect, the compound is selected from the group consisting of Compound 1G-Compound 42G. Specific structures of platinum compounds include, but are not limited to, Compound 1-Compound 166.

Additionally, a first device comprising an organic light emitting device is provided. The organic light emitting device further comprises an anode, a cathode, and an organic layer disposed between the anode and the cathode. The organic layer comprises a compound having the formula:

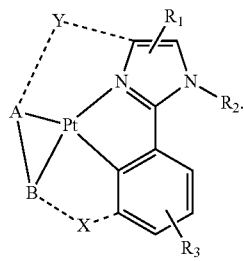

Formula I

A and B are independently selected from the group consisting of a 5-membered or 6-membered carbocyclic or heterocyclic ring. A-B connects to Pt through one covalent bond and one coordination bond. X and Y are independently selected from the group consisting of BR, NR, PR, O, S, Se, C=O, S=O, SO$_2$, CRR', SiRR', and GeRR'. At least one of X and Y forms a bond between A-B and the 2-phenylimidazole. R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ and $R_3$ may represent mono, di, or tri substitutions. $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$, $R_2$, and $R_3$ are optionally joined to form a fused ring. At least one of $R_1$ and $R_2$ is:

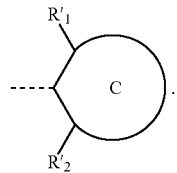

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is 5 or 6-membered carbocyclic or heterocyclic ring that is optionally further substituted. Preferably, C is benzene.

The various specific aspects discussed above for compounds having Formula I are also applicable to a compound having Formula I when used in the first device. In particular, the various specific aspects of $R'_1$, $R'_2$, A, B, C, X, Y, $R''_1$, $R''_2$, $R''_3$, Formula II, Formula III, Formula IV, Formula V, Formula VI, Formula VII, Formula VIII, Formula IX, Formula X, Formula XI, A-B, $R_a$, $R_b$, $R_c$ and $R_L$ of the compound having Formula I, as discussed above, are also applicable to the compound having Formula I that is used in the first device.

Specific, non-limiting examples of devices comprising the platinum complexes are provided. In one aspect, the compound is selected from the group consisting of Compound 1G-Compound 42G. Specific structures of platinum compounds that may be used in such devices include, but are not limited to, Compound 1-Compound 166.

In one aspect, the organic layer is an emissive layer and the compound is an emissive dopant. In another aspect, the organic layer further comprises a host.

In one aspect, the host is a compound that comprises at least one of the chemical groups selected from the group consisting of:

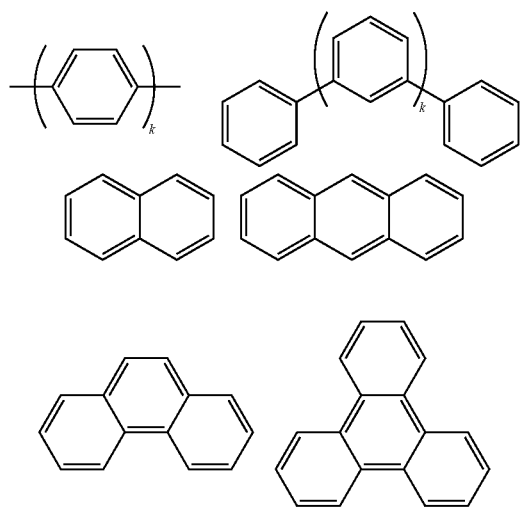

Each of $R'''_1$, $R'''_2$, $R'''_3$, $R'''_4$, $R'''_5$, $R'''_6$ and $R'''_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. k is an integer from 0 to 20. Each of $X^1$, $X^2$, $X^3$, $X^4$, $X^5$, $X^6$, $X^7$ and $X^8$ are independently selected from the group consisting of CH and N.

In another aspect, the host is a compound comprising a triphenylene containing benzo-fused thiophene or benzo-fused furan. Any substituent in the compound is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C≡CHC_nH_{2n+1}$, $Ar_1$, $Ar_1-Ar_2$, $C_nH_{2n}-Ar_1$, or no substitution. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. Preferably, the host has the formula:

Compound A

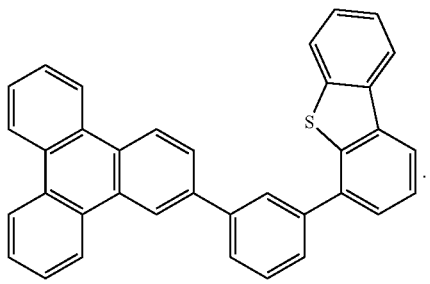

In yet another aspect, the host is a metal complex. In a further aspect, the metal complex is selected from the group consisting of:

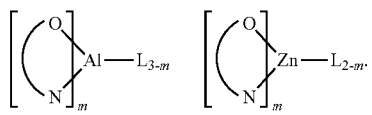

(O—N) is a bidentate ligand having metal coordinated to atoms O and N. L is an ancillary ligand. m is an integer value from 1 to the maximum number of ligands that may be attached to the metal. Preferably, the host is a metal 8-hydroxyquinolate.

In one aspect, the first device is a consumer product. In another aspect, the first device is an organic light emitting device.

Tetradentate platinum (II) compounds comprising an imidazo[1,2-f]phenanthridine moiety are provided. The compounds have the formula:

Formula I'

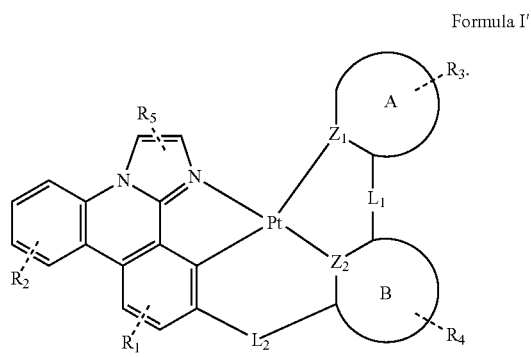

Ring A and ring B are each independently a 5- or 6-membered carbocyclic or heterocyclic ring. $L_1$ and $L_2$ are independently selected from the group consisting of a single bond, BR, NR, PR, O, S, Se, C=O, S=O, $SO_2$, CRR', SiRR', and GeRR'. $Z_1$ and $Z_2$ are independently a nitrogen atom or a carbon atom. $R_1$, $R_2$, $R_3$, $R_4$, and $R_5$ may represent mono, di, tri, or tetra substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, het- eroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substitutents of R, R', $R_1$, $R_2$, $R_3$, $R_4$, and $R_5$ are optionally joined to form a fused ring.

In one aspect, $L_1$ is selected from the group consisting of BR, NR, PR, O, S, Se, C=O, S=O, $SO_2$, CRR', SiRR', and GeRR'.

In one aspect, $R_5$ is aryl or substituted aryl. In another aspect, $R_5$ is a 2,6-disubstituted aryl.

Preferably, $R_5$ is

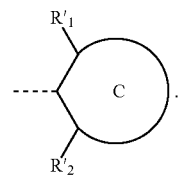

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is 5-membered or 6-membered carbocyclic or heterocyclic ring that is optionally further substituted.

In one aspect, at least one fused ring is formed by joining two adjacent substituents of R, R', $R_1$, $R_2$, $R_3$, $R_4$, and $R_5$. In another aspect, R or R' is joined to $R_3$ or $R_4$ to form a fused ring.

In one aspect, the ligand

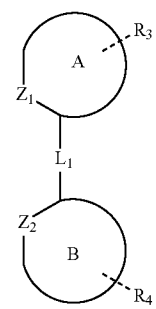

has a triplet energy higher than or equal to the triplet energy of

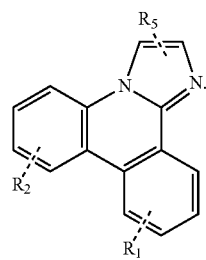

In one aspect, the compound has the formula:

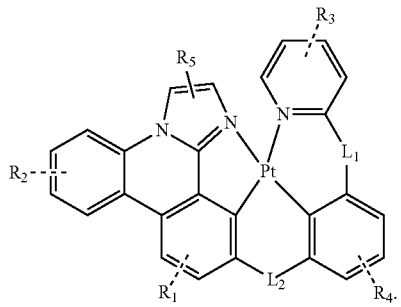

Formula II'

In another aspect, the compound has the formula:

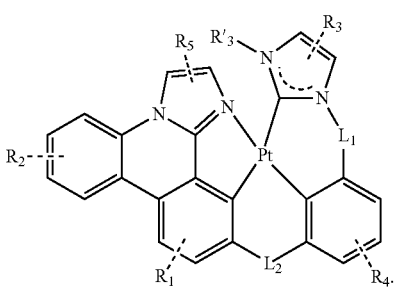

Formula III'

$R'_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another aspect, the compound has the formula:

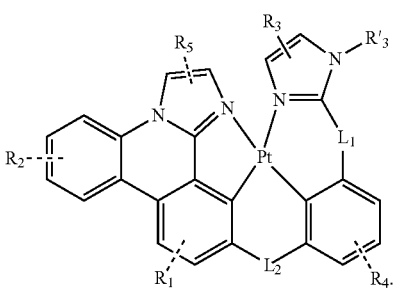

Formula IV'

$R'_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

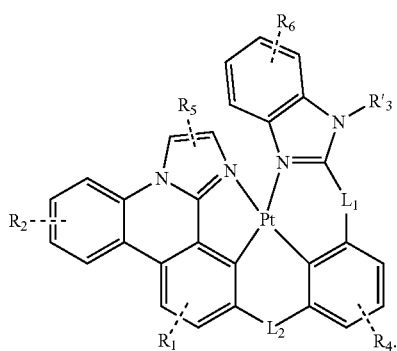

Formula V'

$R_6$ may represent mono, di, tri, or tetra substitutions. $R'_3$ and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

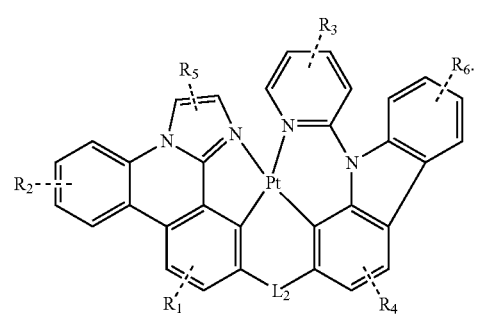

Formula VI'

$R_6$ may represent mono, di, tri, or tetra substitutions. $R'_3$ and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another aspect, the compound has the formula:

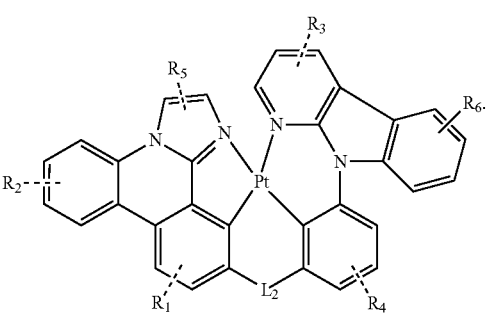

Formula VII'

$R_6$ may represent mono, di, tri, or tetra substitutions. $R'_3$ and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

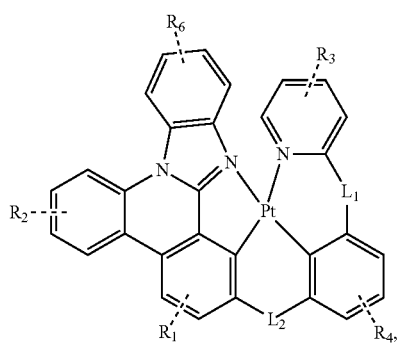

Formula VIII'

$R_6$ may represent mono, di, tri, or tetra substitutions. $R_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

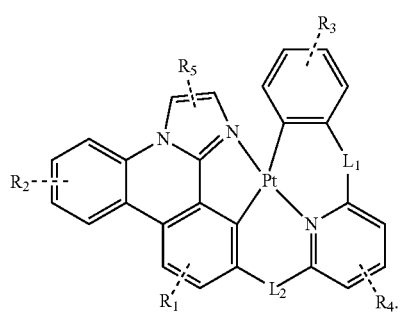

Formula IX'

In yet another aspect, the compound has the formula:

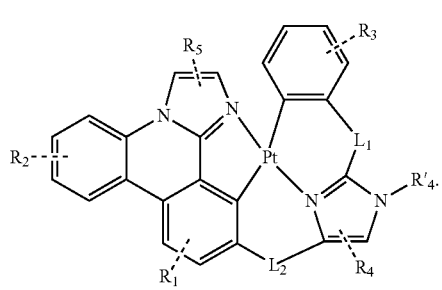

Formula X'

$R'_4$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

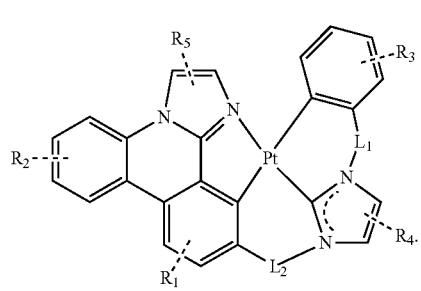

Formula XI'

Specific, non-limiting examples of the tetradentate platinum (II) compounds are provided. In one aspect, the compound is selected from the group consisting of:

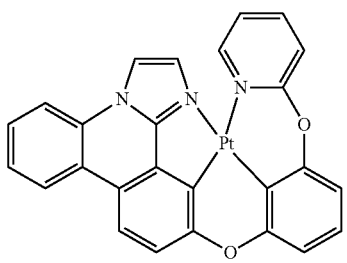

Compound 1'

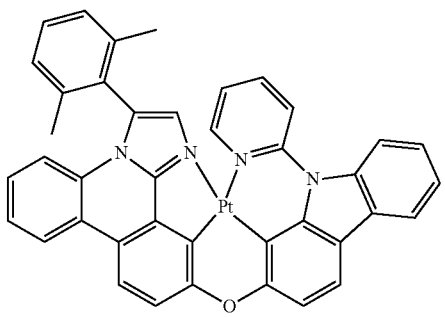

Compound 2'

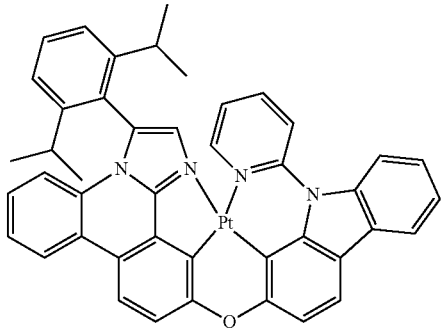

Compound 3'

-continued
Compound 4'
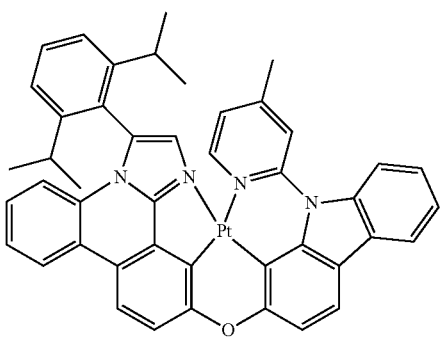
Compound 5'
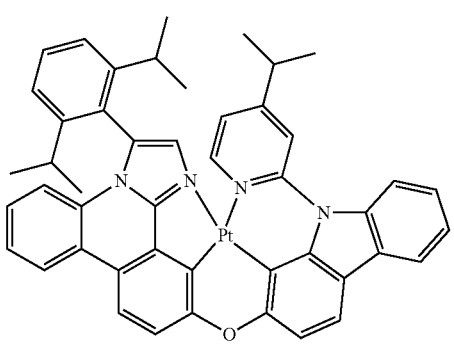
Compound 6'
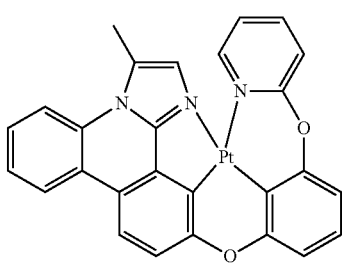
Compound 7'
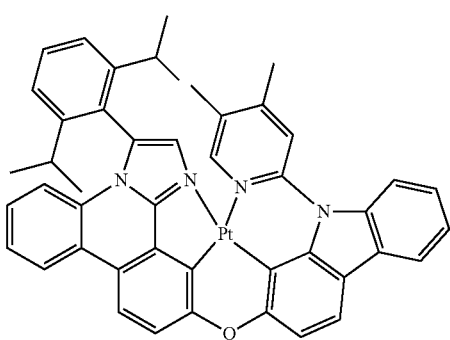
-continued
Compound 8'
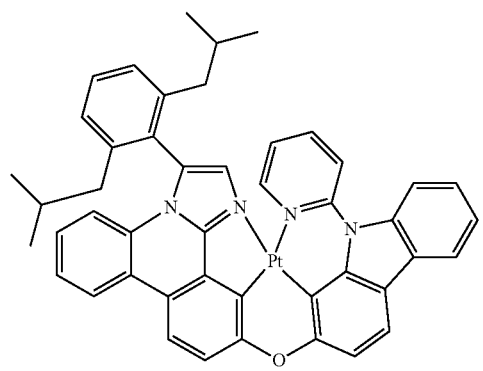
Compound 9'
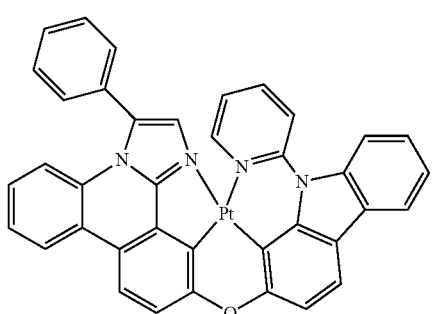
Compound 10'
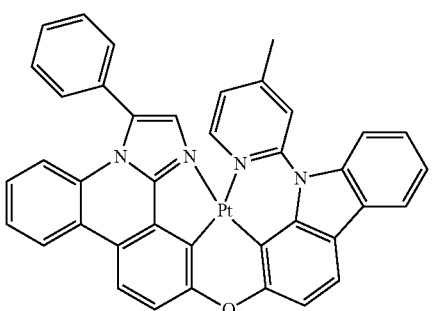
Compound 11'
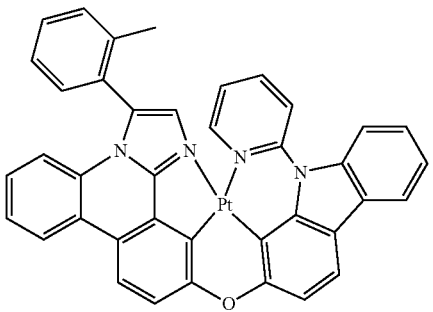

Compound 12'
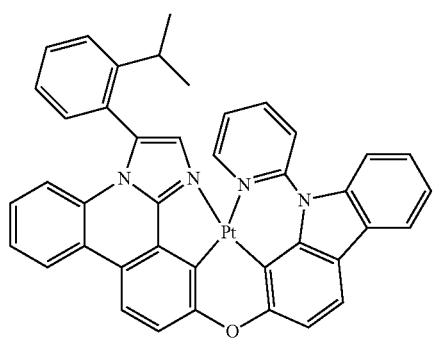
Compound 13'
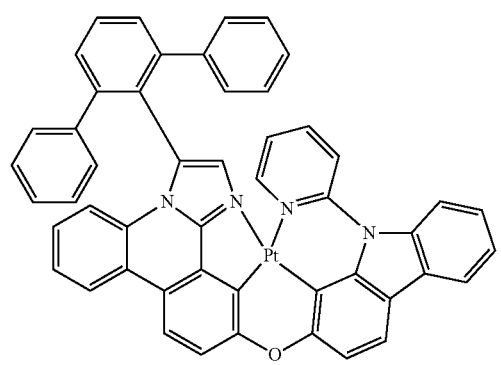
Compound 14'
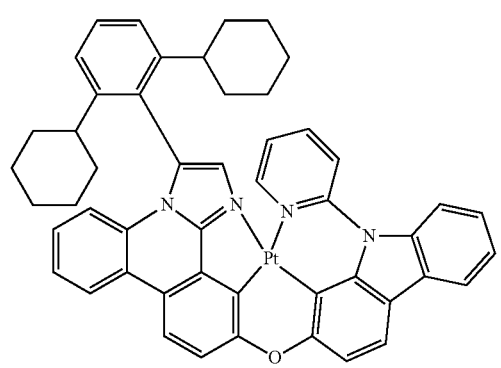
Compound 15'
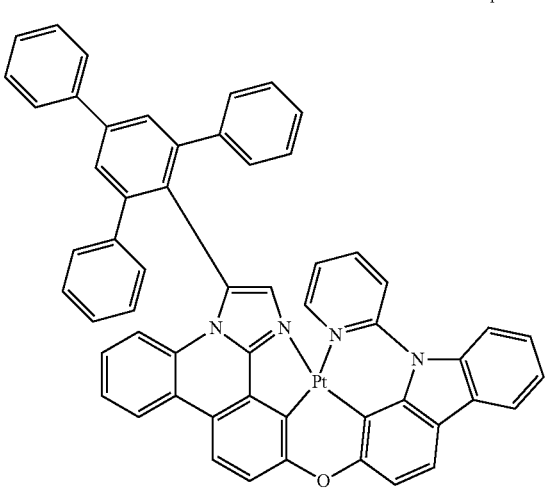
Compound 16'
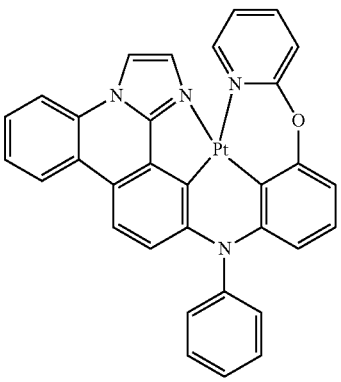
Compound 17'
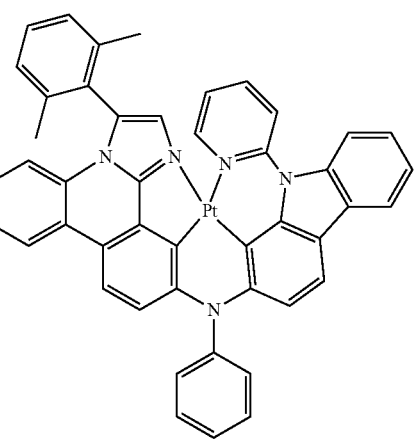
Compound 18'
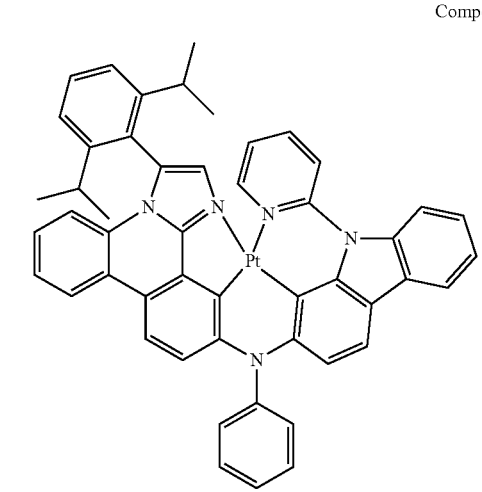

-continued
Compound 19'
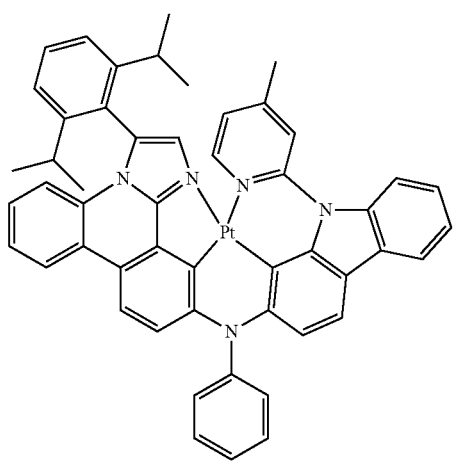
Compound 20'
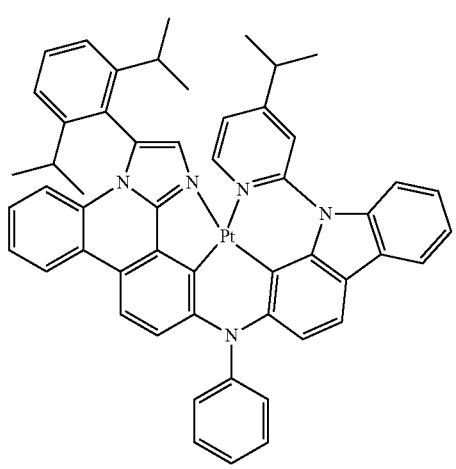
Compound 21'
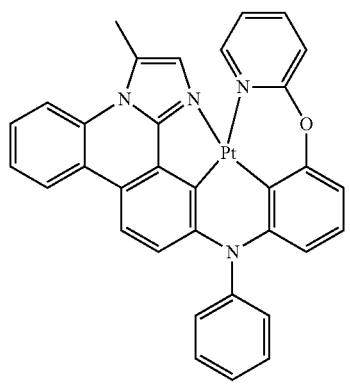
-continued
Compound 22'
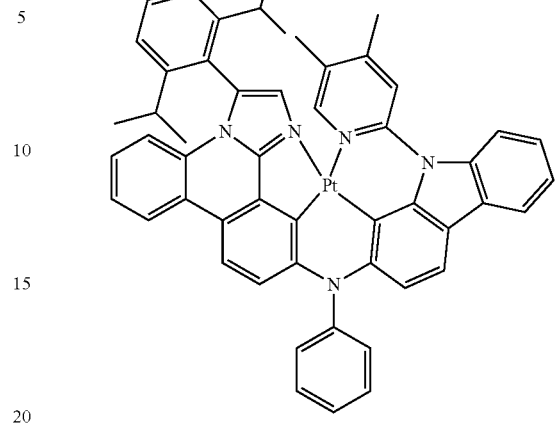
Compound 23'
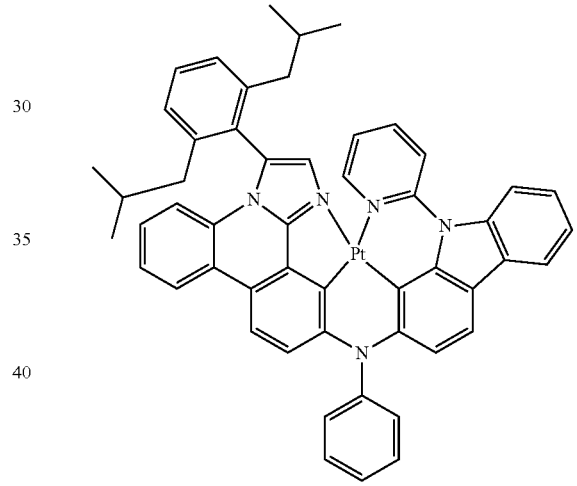
Compound 24'
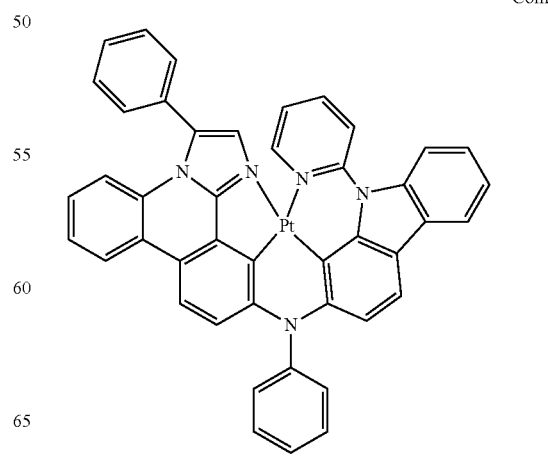

Compound 25'
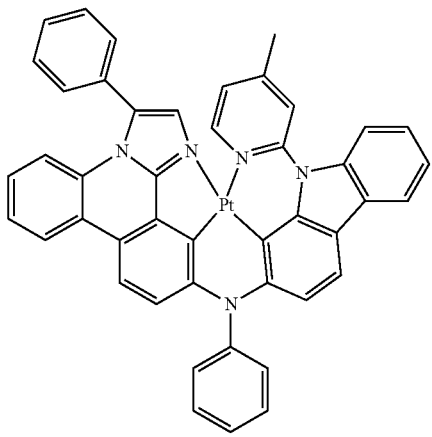
Compound 26'
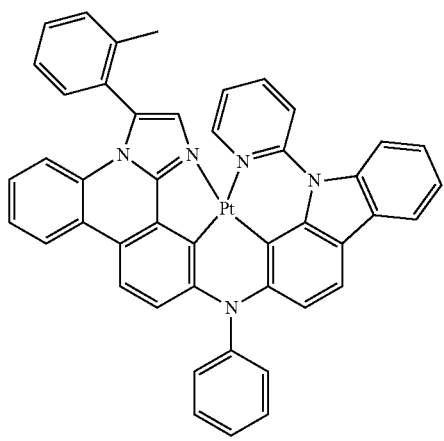
Compound 27'
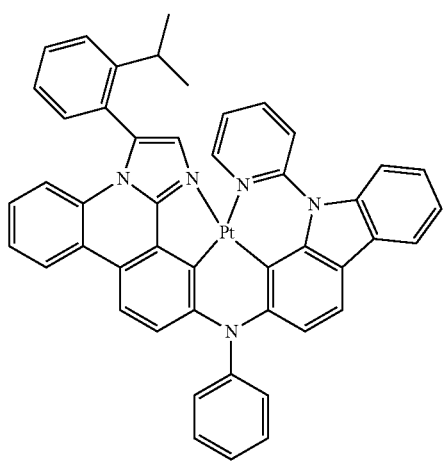
Compound 28'
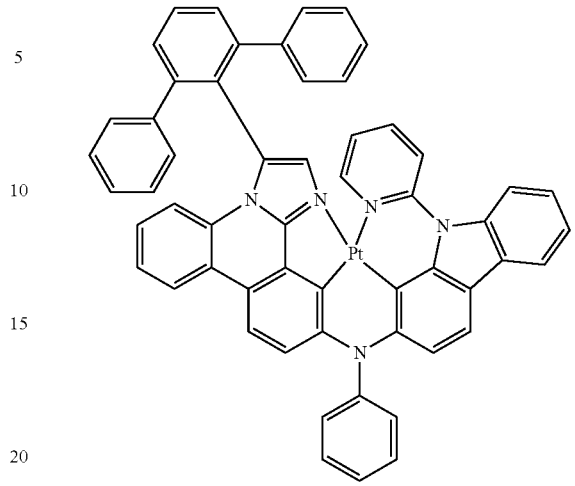
Compound 29'
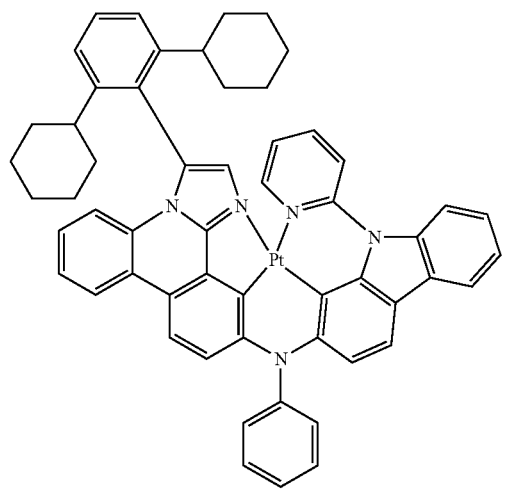
Compound 30'
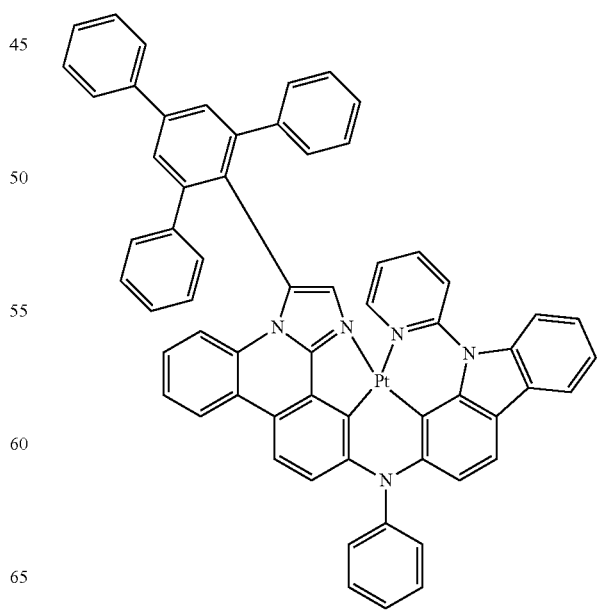

-continued
Compound 31'
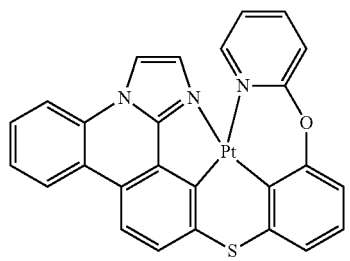
Compound 32'
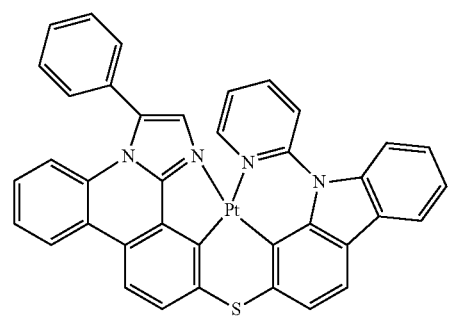
Compound 33'
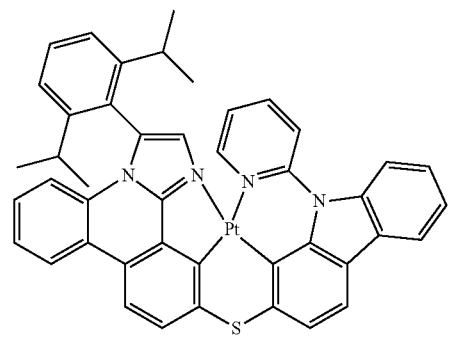
Compound 34'
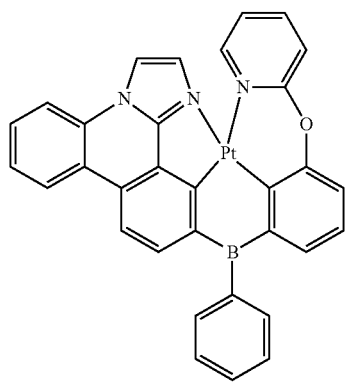
-continued
Compound 35'
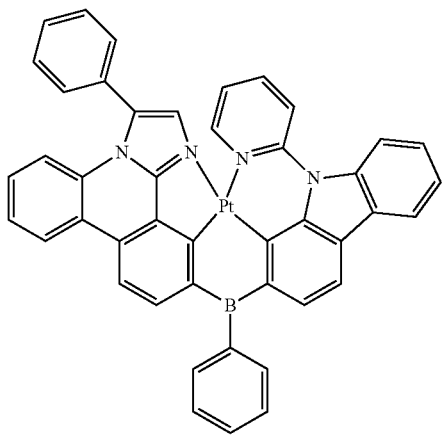
Compound 36'
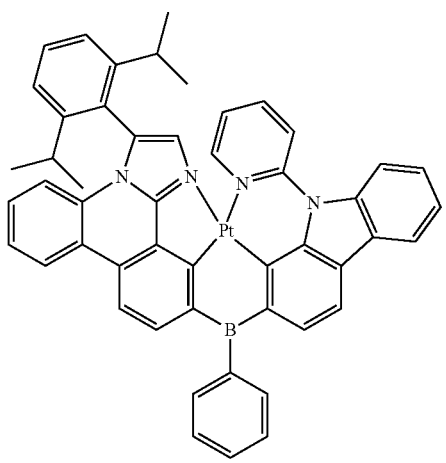
Compound 37'
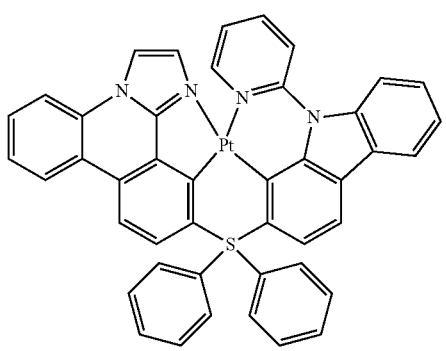

Compound 38'
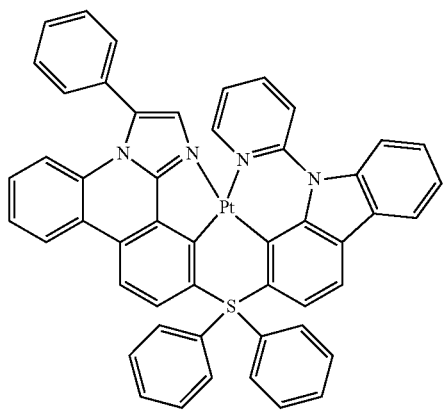
Compound 39'
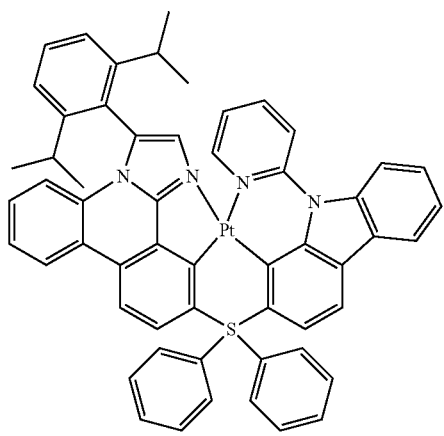
Compound 40'
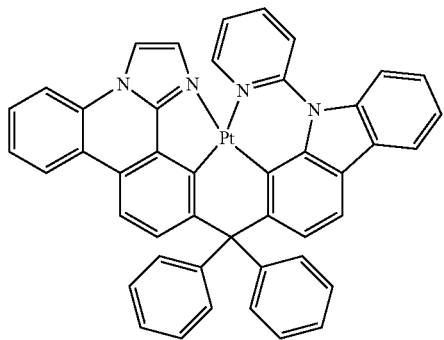
Compound 41'
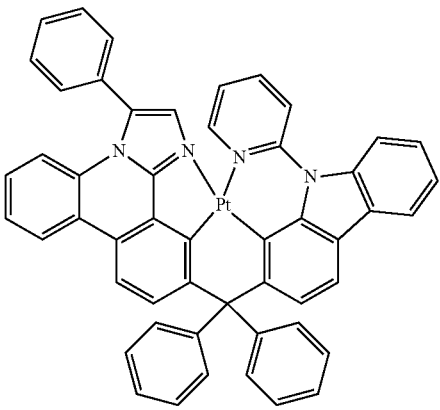
Compound 42'
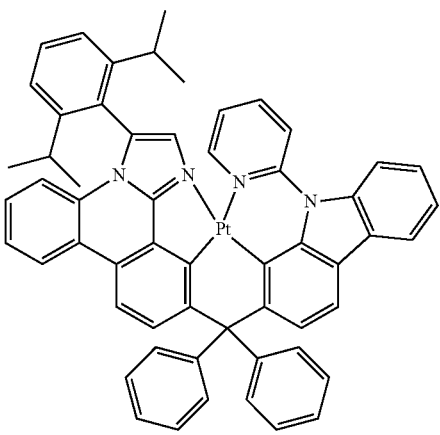
Compound 43'
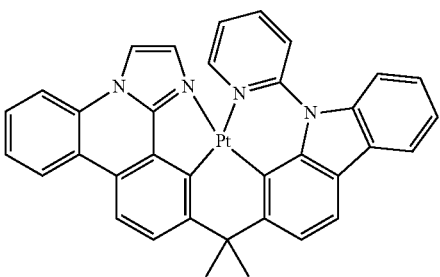
Compound 44'
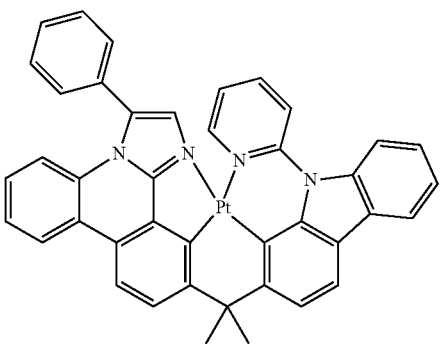

Compound 45'
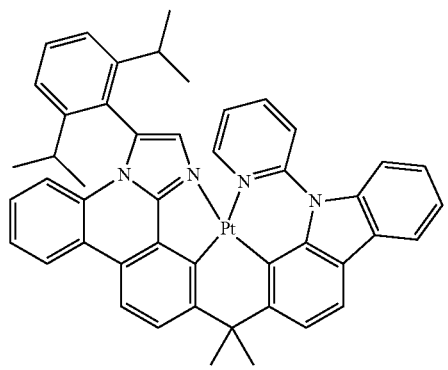
Compound 46'
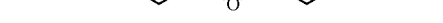
Compound 47'
Compound 48'
Compound 49'
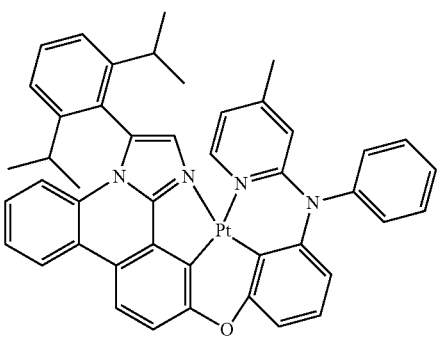
Compound 50'
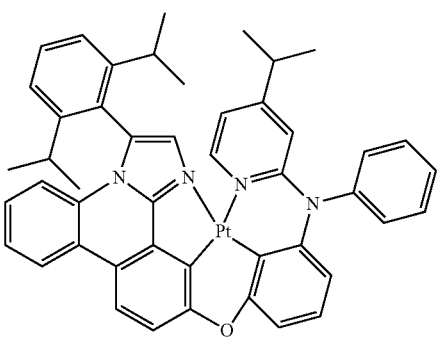
Compound 51'
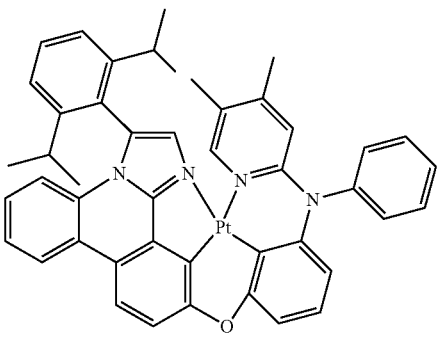
Compound 52'
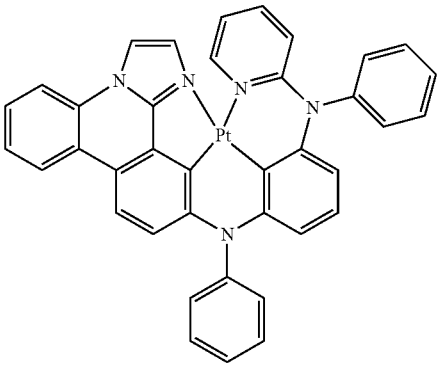

Compound 53'
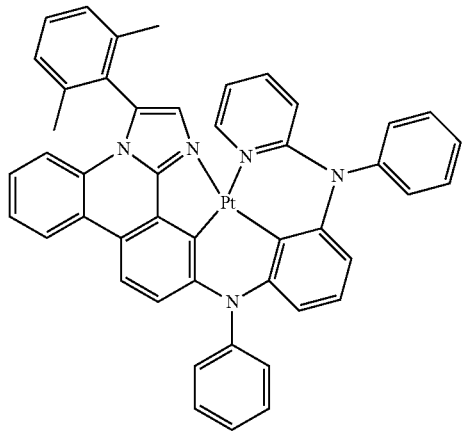
Compound 54'
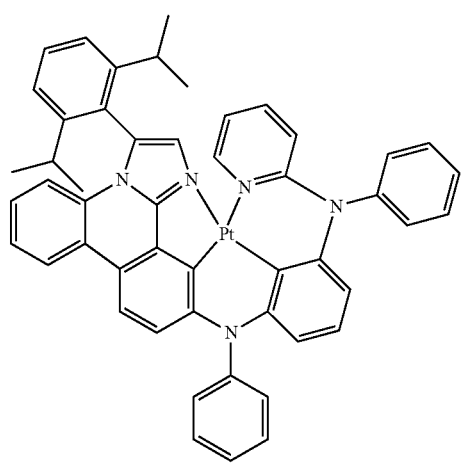
Compound 55'
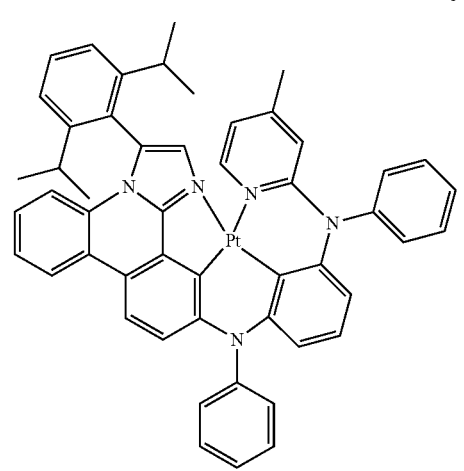
Compound 56'
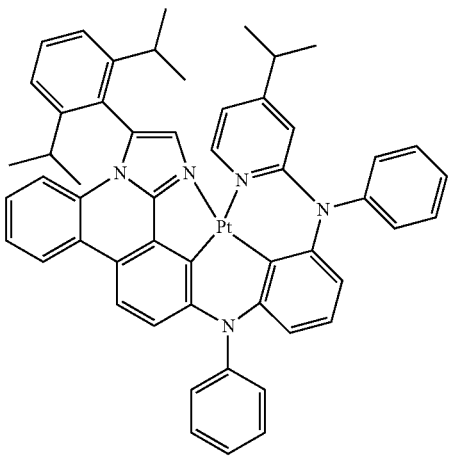
Compound 57'
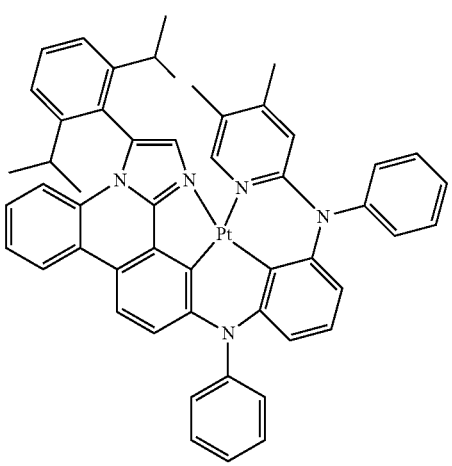
Compound 58'
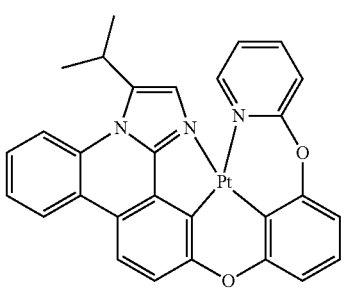
Compound 59'
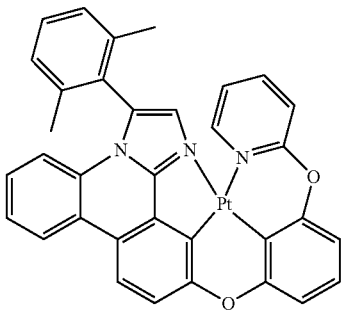

-continued
Compound 60'
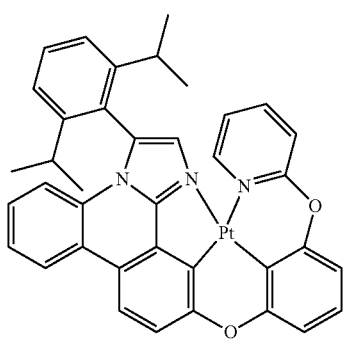
Compound 61'
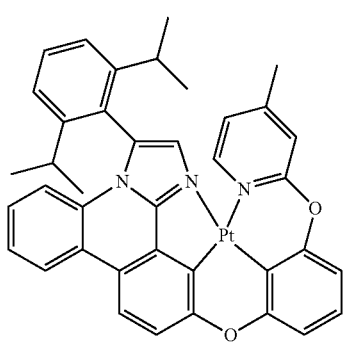
Compound 62'
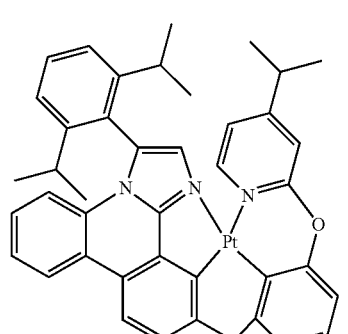
Compound 63'
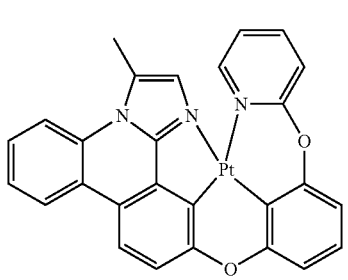
Compound 64'
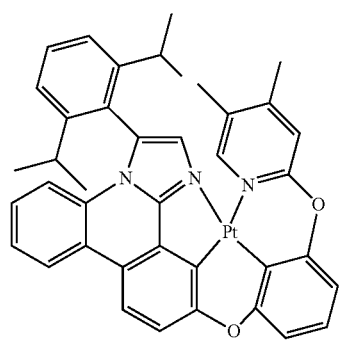
-continued
Compound 65'
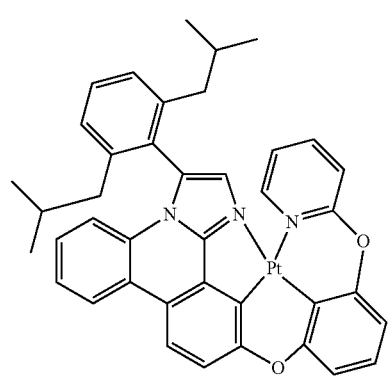
Compound 66'
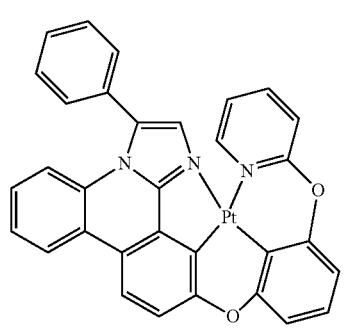
Compound 67'
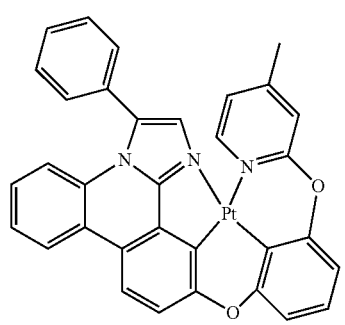
Compound 68'
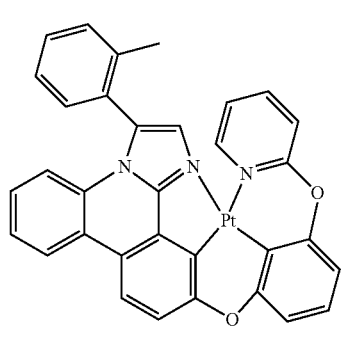

Compound 69'
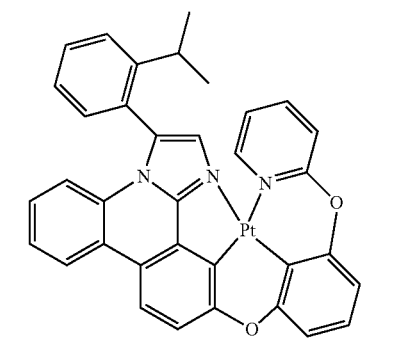
Compound 70'
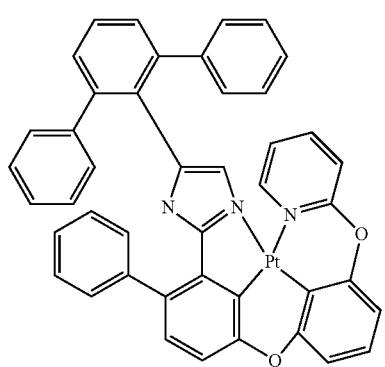
Compound 71'
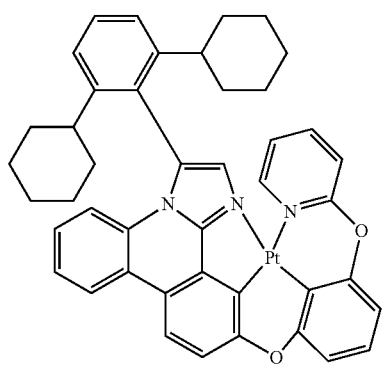
Compound 72'
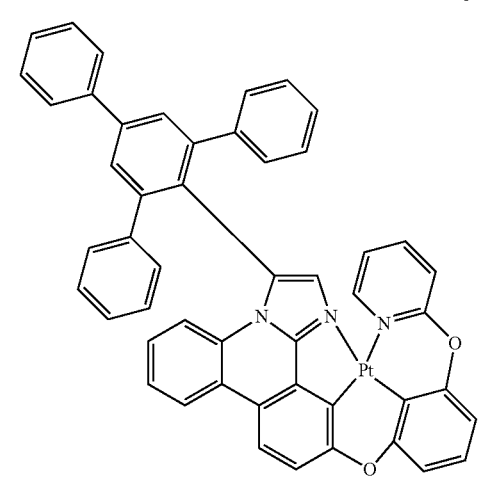
Compound 73'
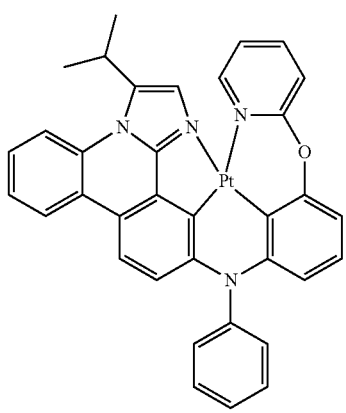
Compound 74'
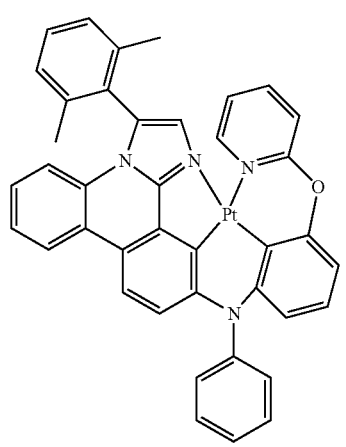
Compound 75'
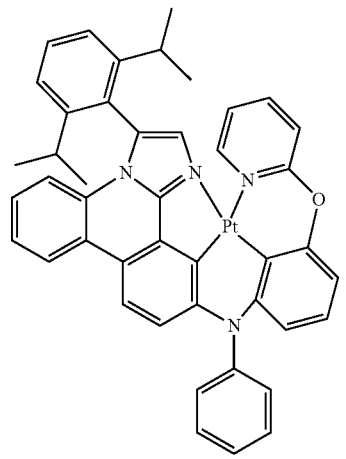

Compound 76'
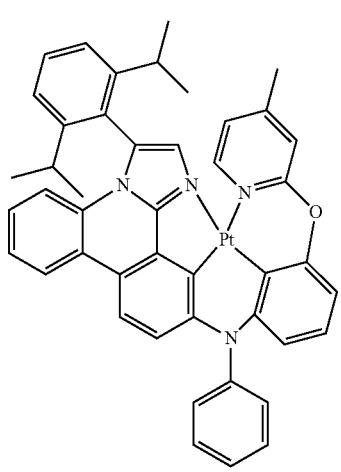
Compound 77'
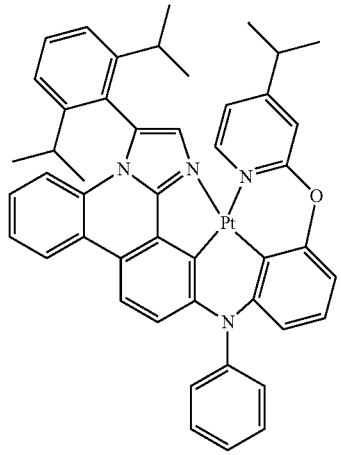
Compound 78'
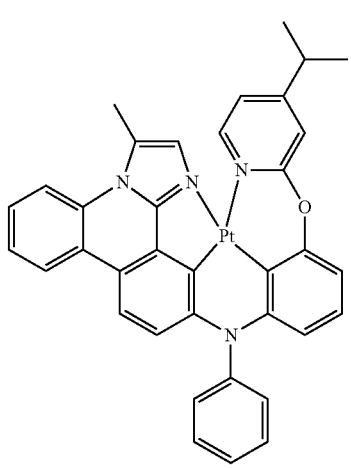
Compound 79'
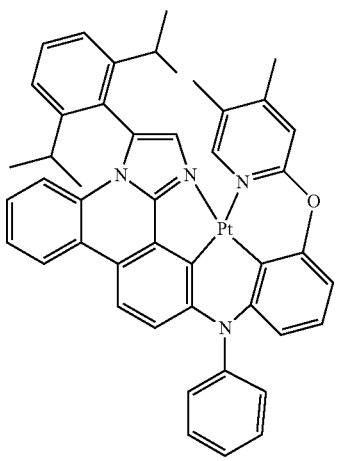
Compound 80'
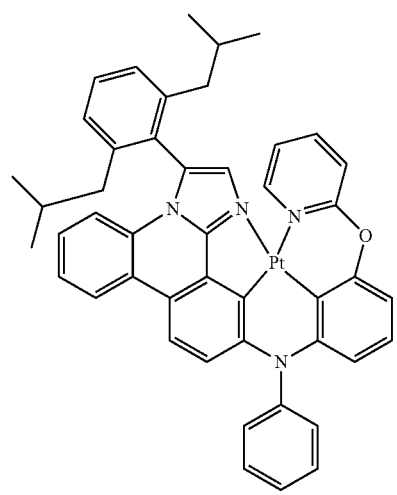
Compound 81'
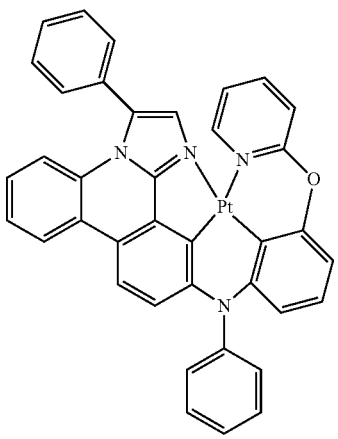

Compound 82'
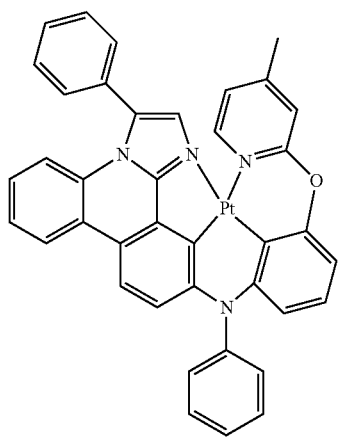
Compound 83'
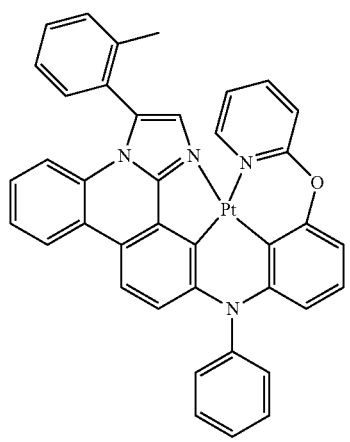
Compound 84'
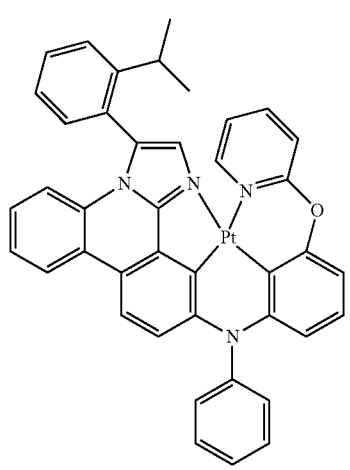
Compound 85'
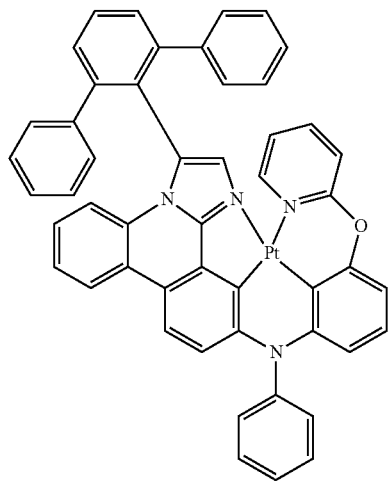
Compound 86'
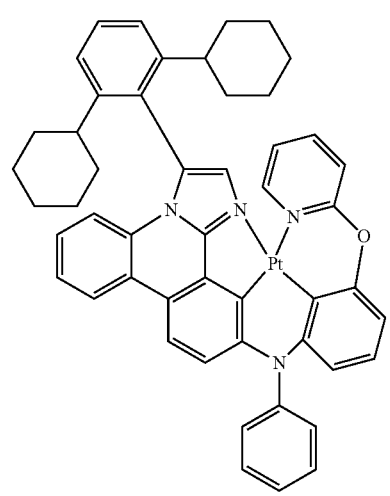
Compound 87'
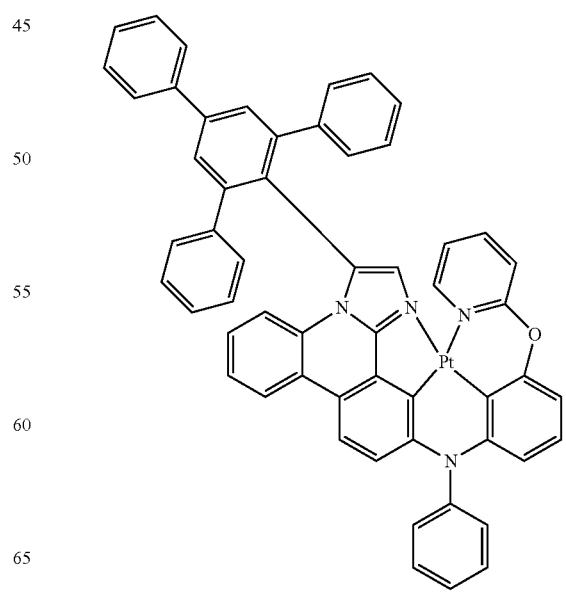

Compound 88'
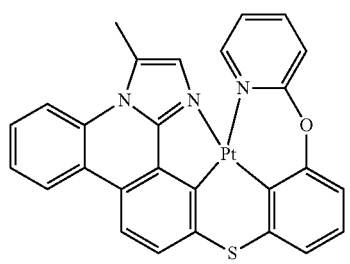
Compound 89'
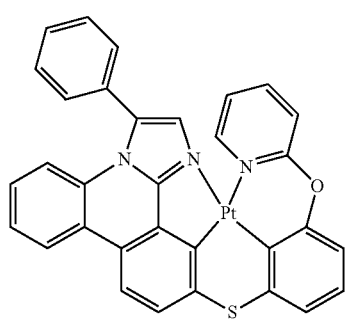
Compound 90'
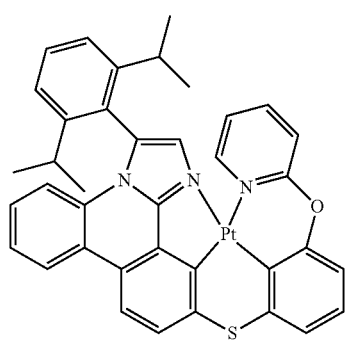
Compound 91'
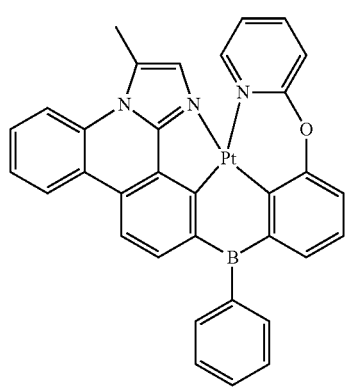
Compound 92'
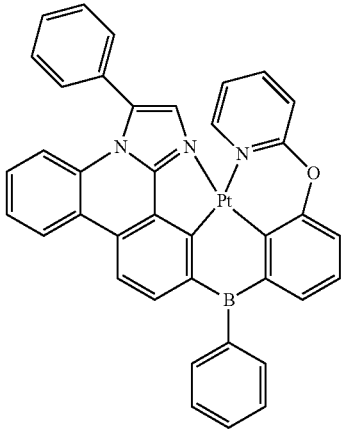
Compound 93'
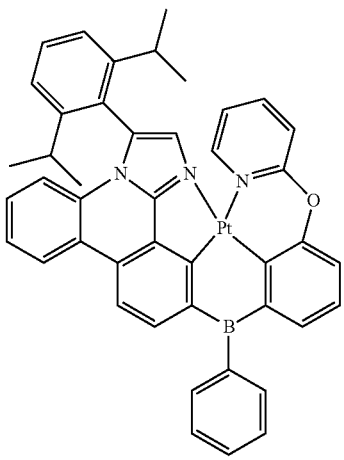
Compound 94'
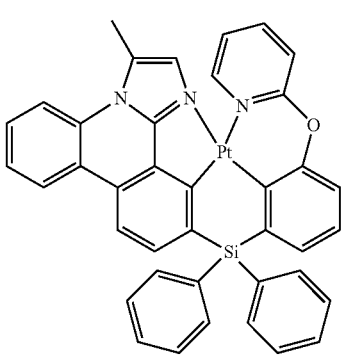
Compound 95'
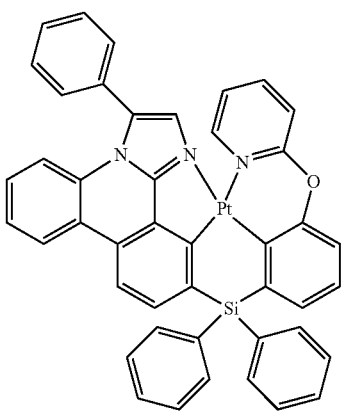

Compound 96'
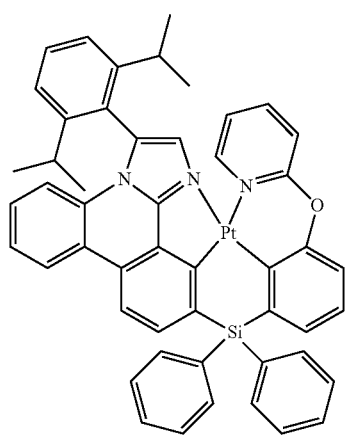
Compound 97'
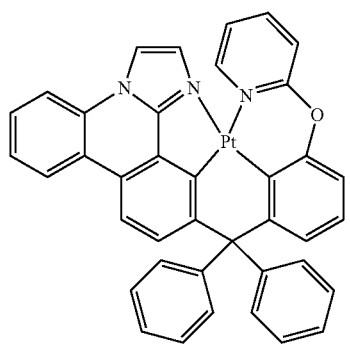
Compound 98'
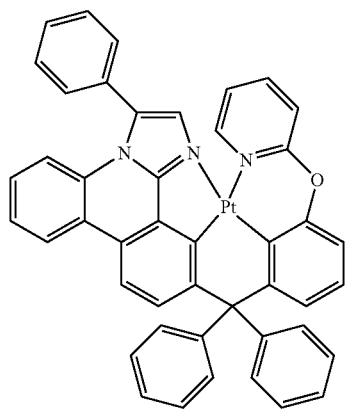
Compound 99'
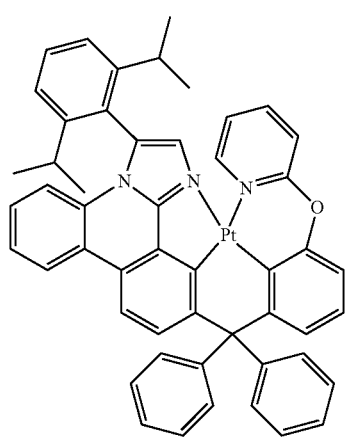
Compound 100'
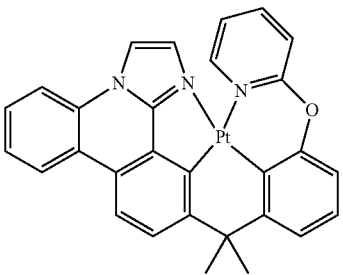
Compound 101'
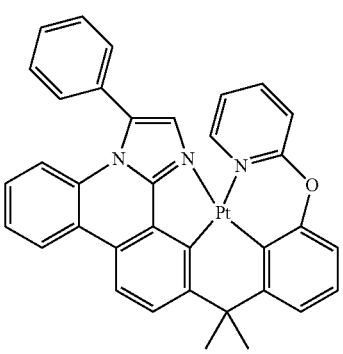
Compound 102'
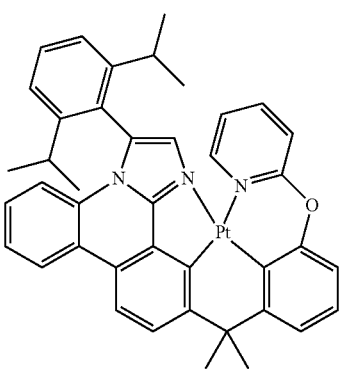
Compound 103'
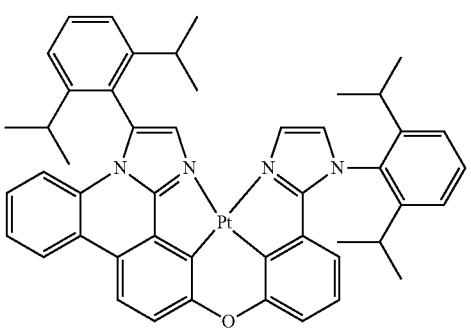

Compound 104'
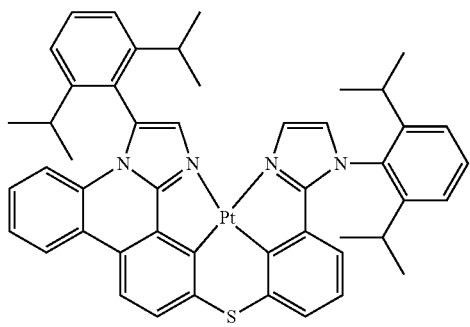
Compound 105"
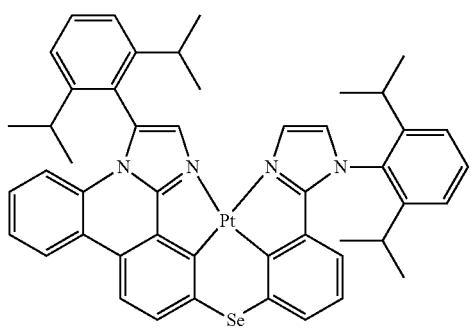
Compound 106'
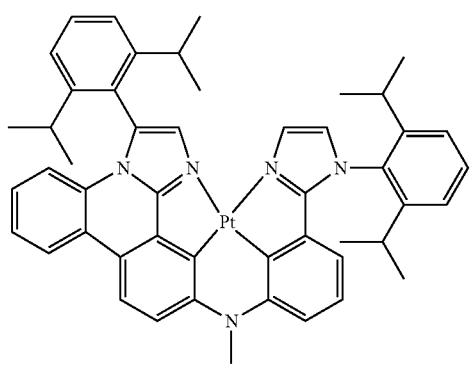
Compound 107'
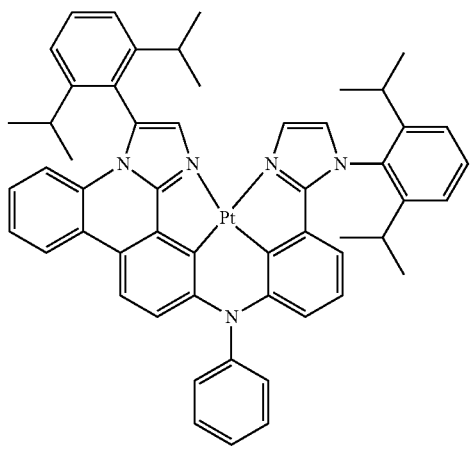
Compound 108'
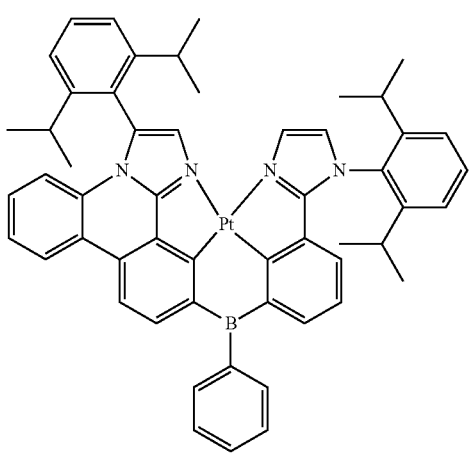
Compound 109'
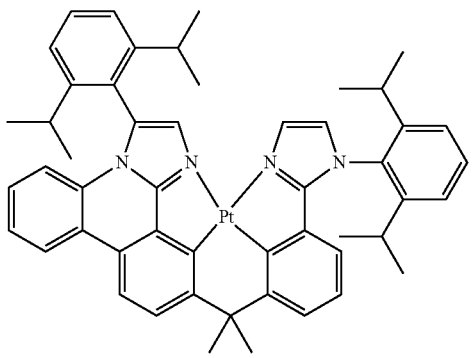
Compound 110'
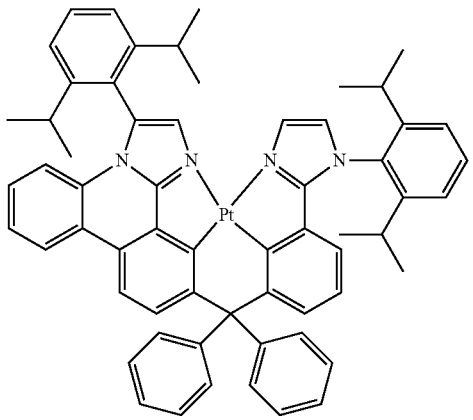

Compound 111'
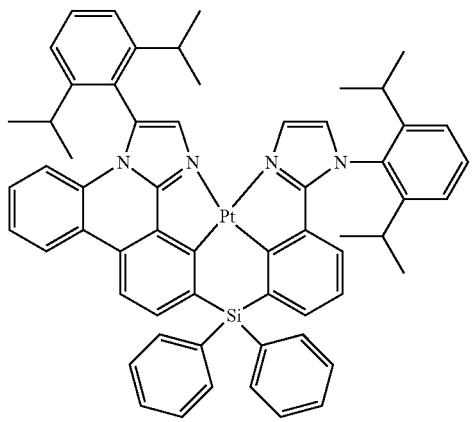
Compound 112'
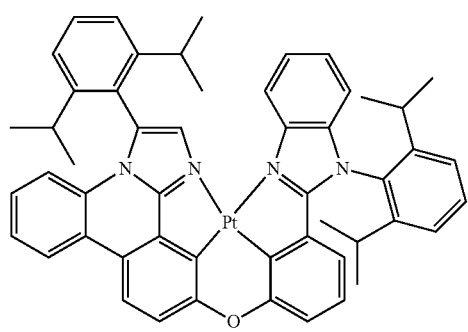
Compound 113'
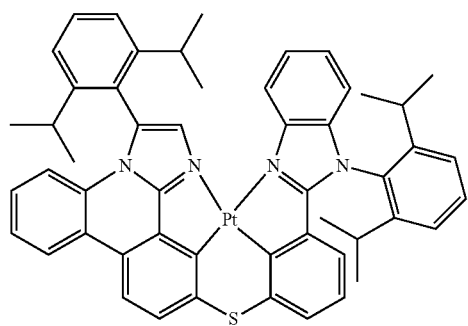
Compound 114'
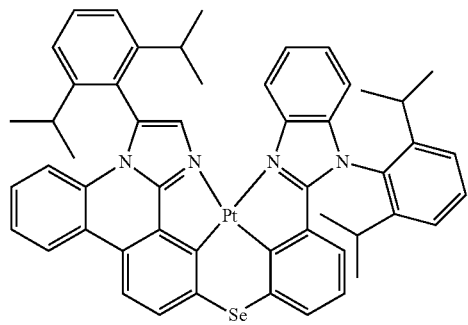
Compound 115'
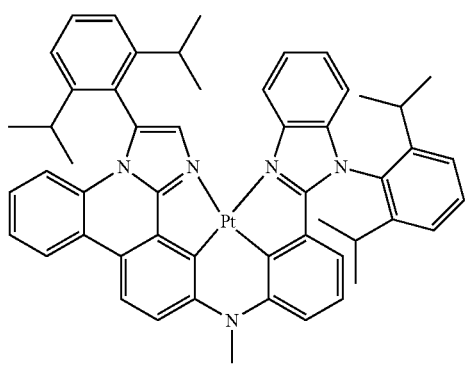
Compound 116'
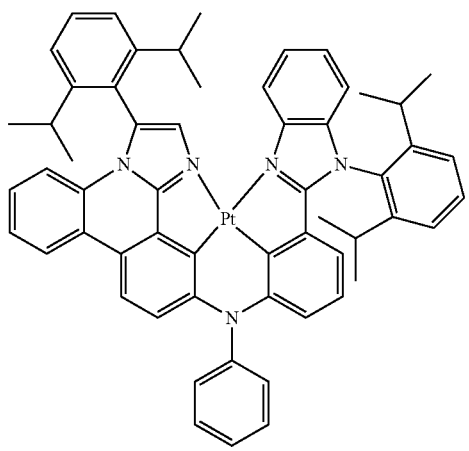
Compound 117'
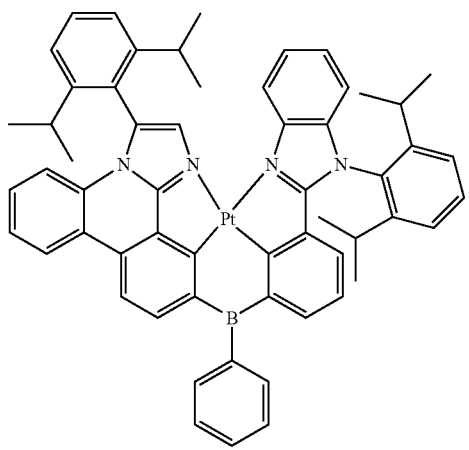

Compound 118'
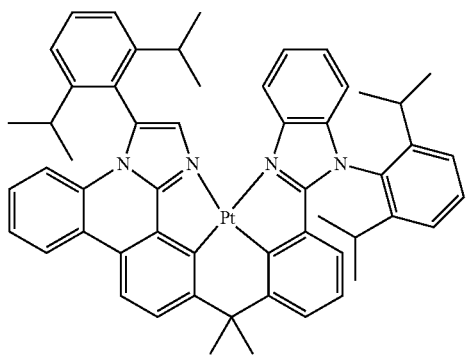
Compound 119'
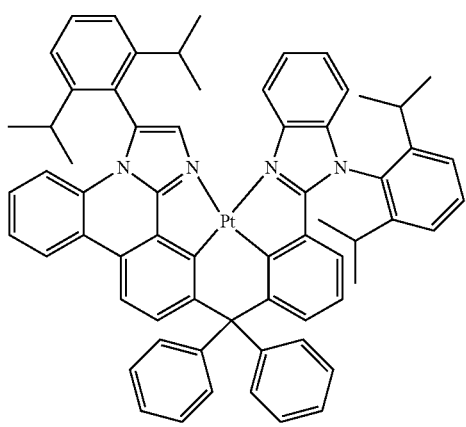
Compound 120'
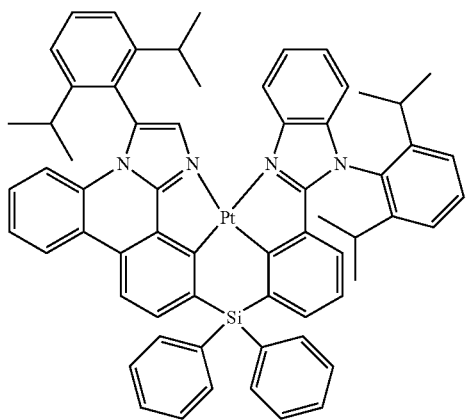
Compound 121'
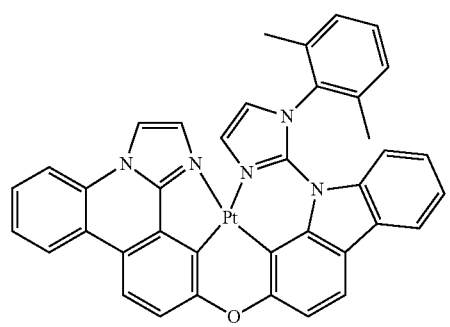
Compound 122'
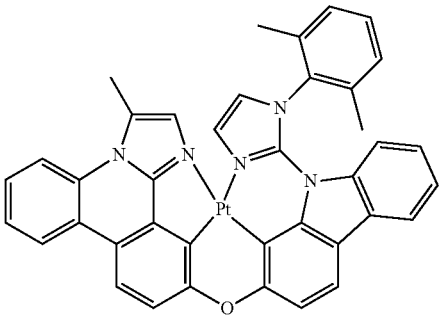
Compound 123'
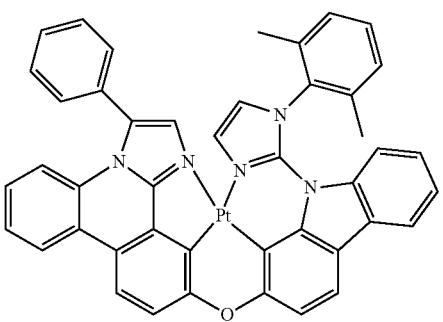
Compound 124'
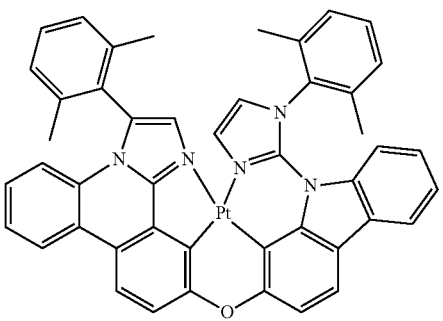
Compound 125'
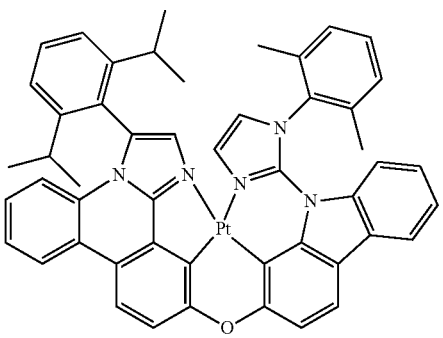

Compound 126'
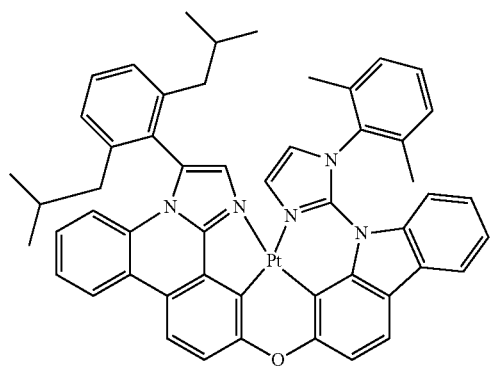
Compound 127'
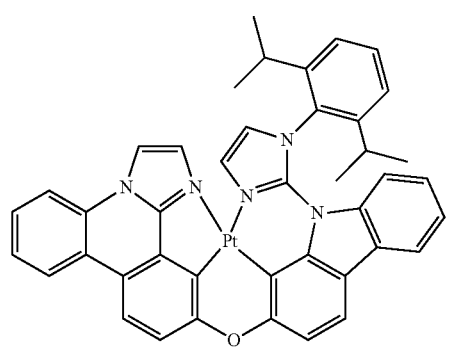
Compound 128'
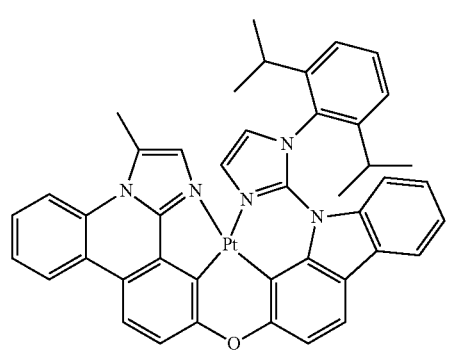
Compound 129'
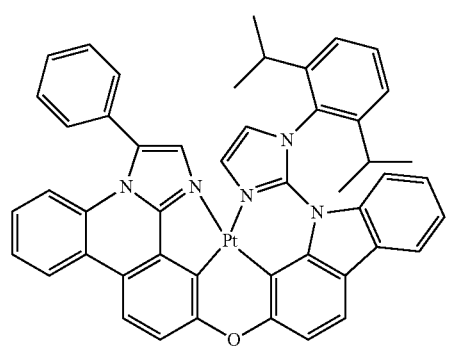
Compound 130'
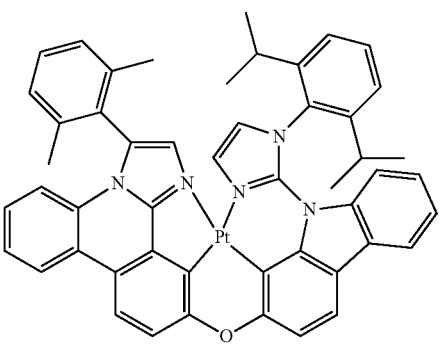
Compound 131'
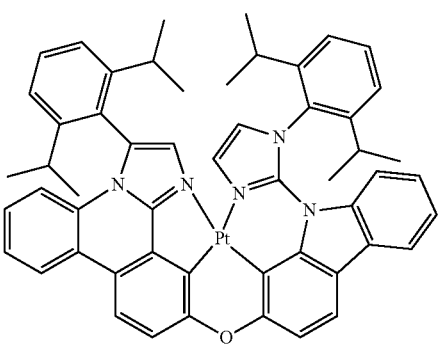
Compound 132'
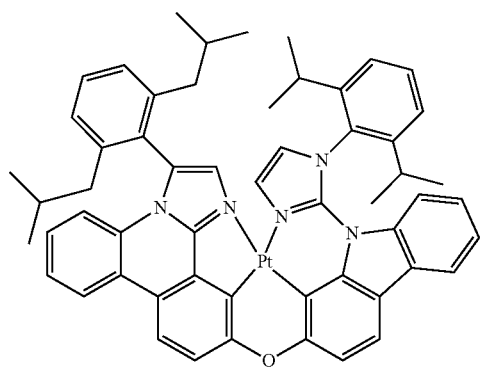
Compound 133'
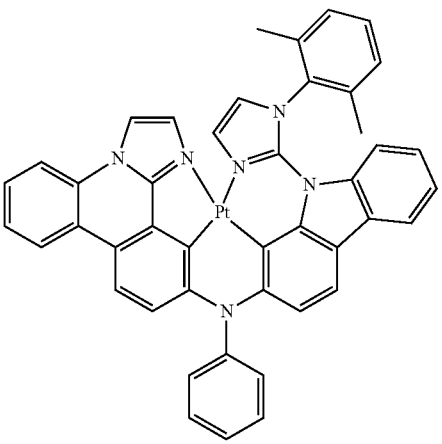

-continued
Compound 134'
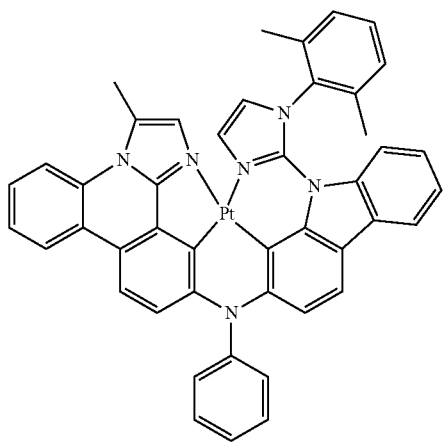
Compound 135'
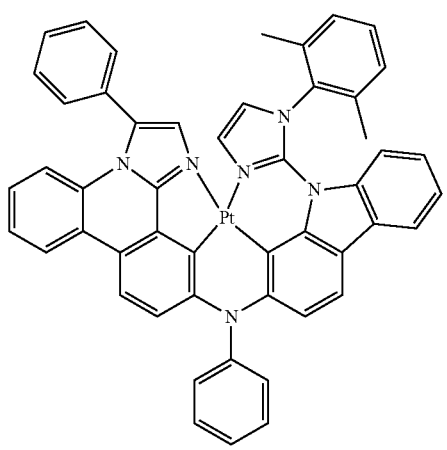
Compound 136'
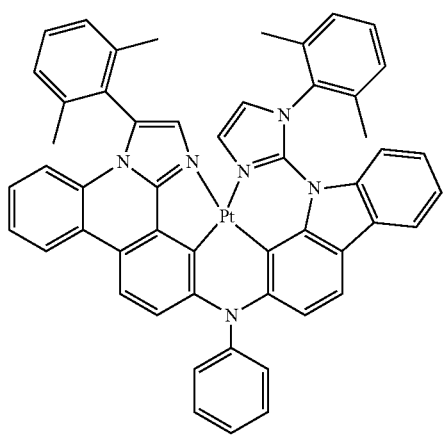
-continued
Compound 137'
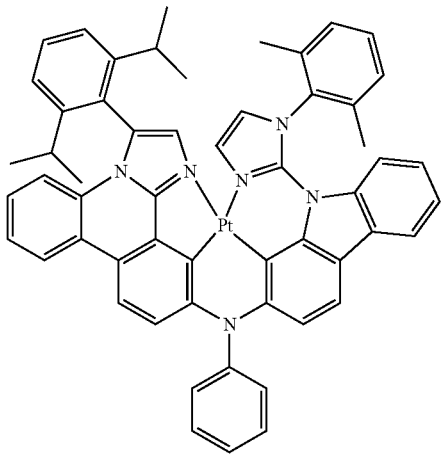
Compound 138'
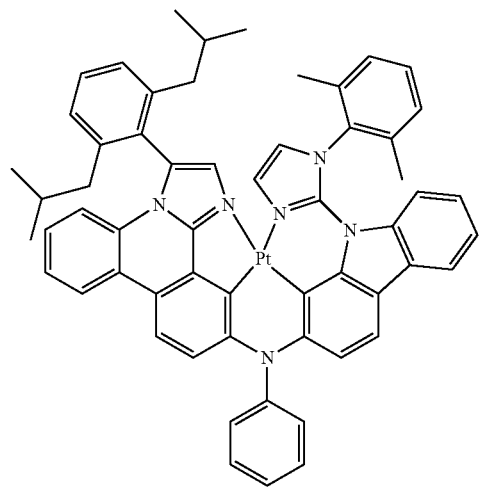
Compound 139'
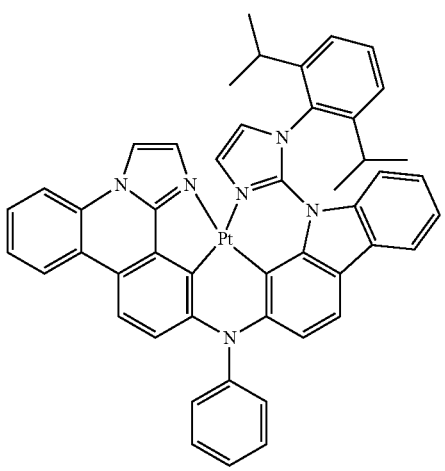

Compound 140'
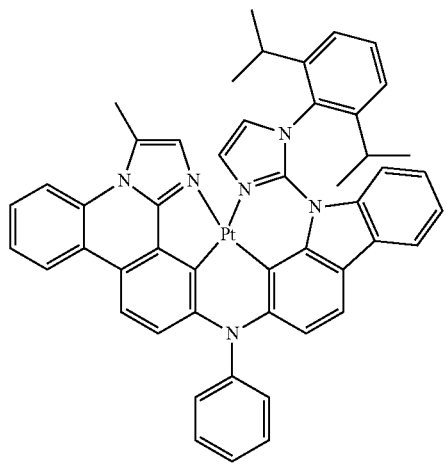
Compound 141'
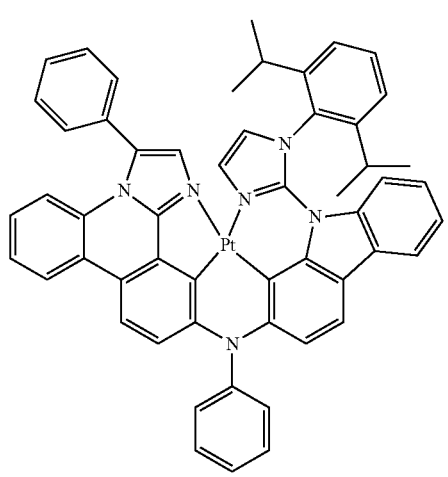
Compound 142'
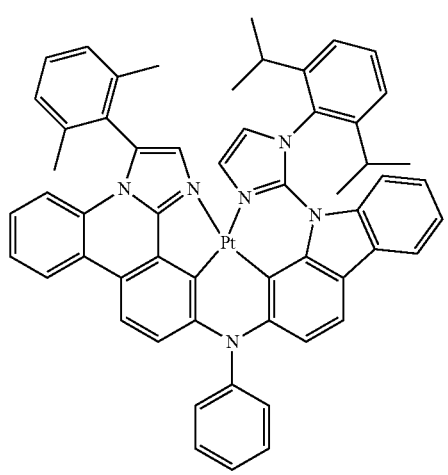
Compound 143'
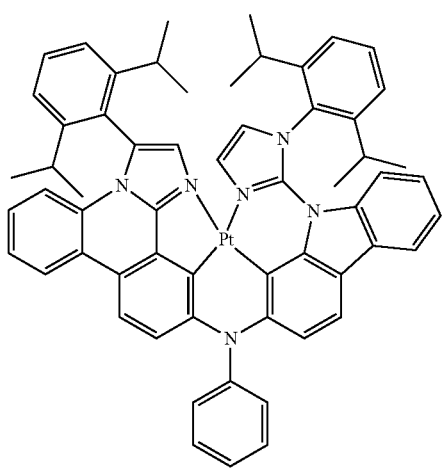
Compound 144'
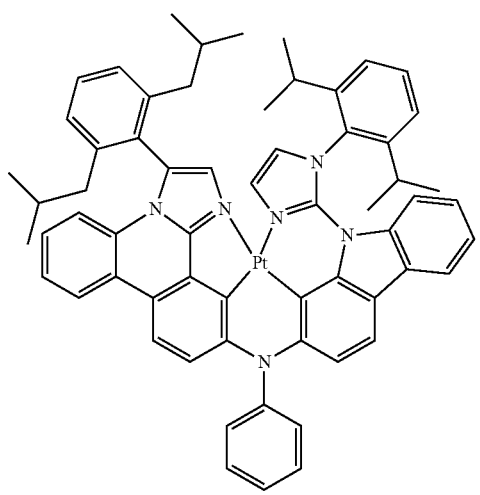
Compound 145'
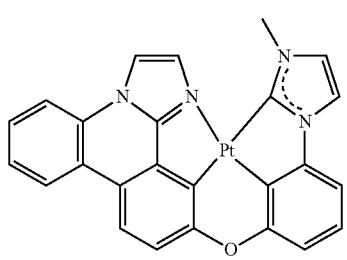
Compound 146'
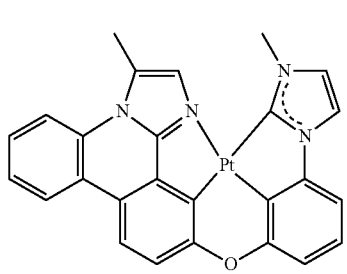

Compound 147'
Compound 148'
Compound 149'
Compound 150'
Compound 151'
Compound 152'
Compound 153'
Compound 154'
Compound 155'
Compound 156'
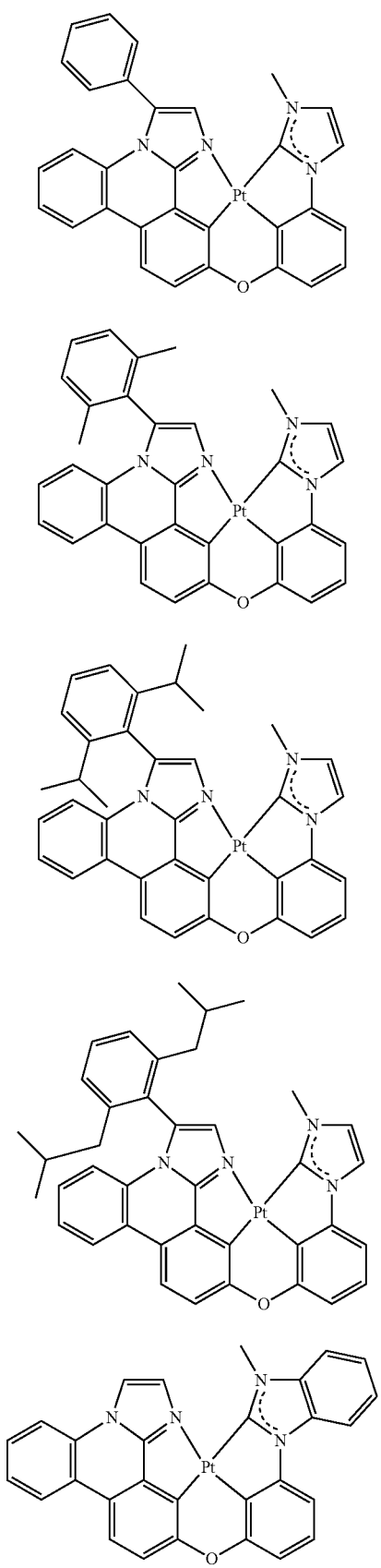
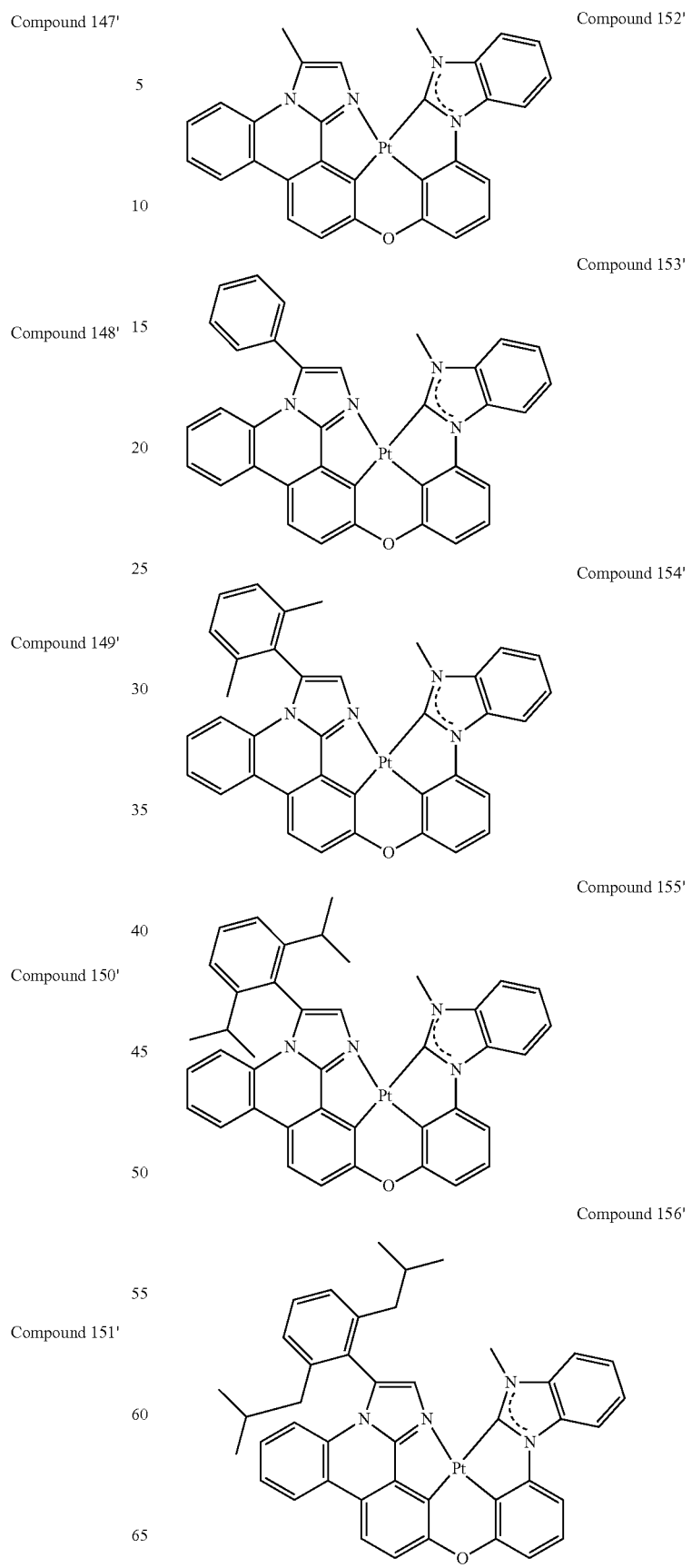

Compound 157'
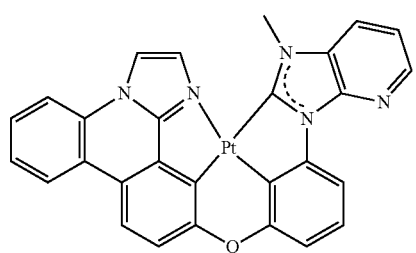
Compound 158'
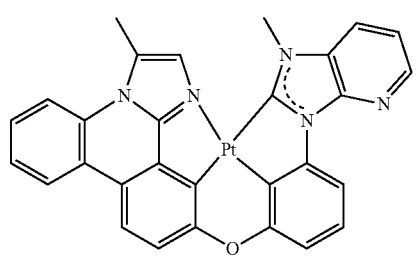
Compound 159'
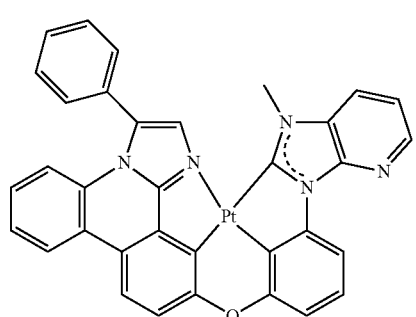
Compound 160'
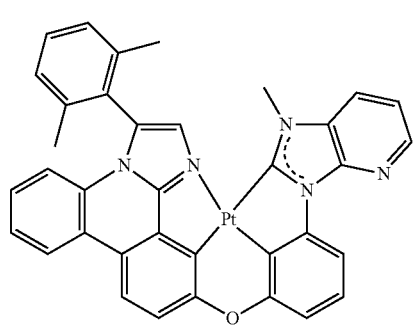
Compound 161'
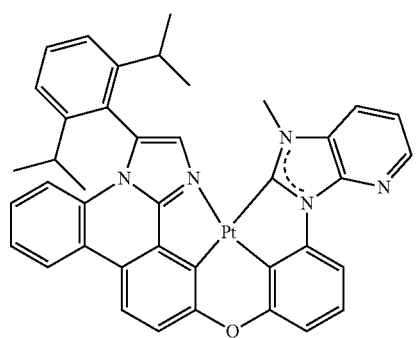
Compound 162'
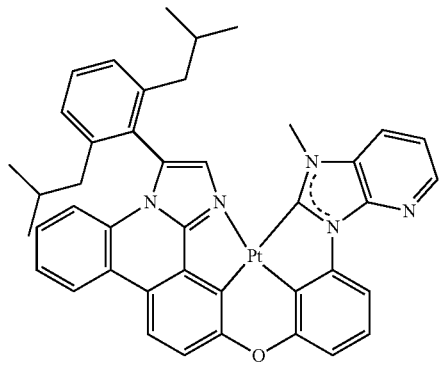
Compound 163'
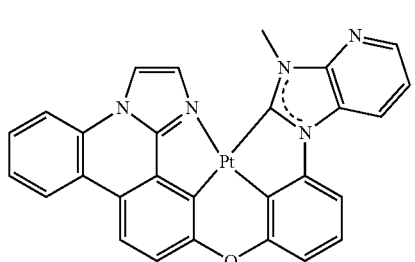
Compound 164'
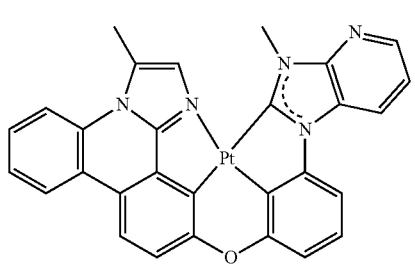
Compound 165'
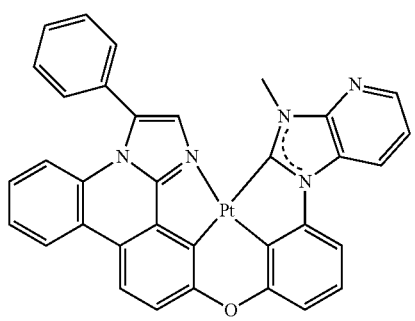
Compound 166'
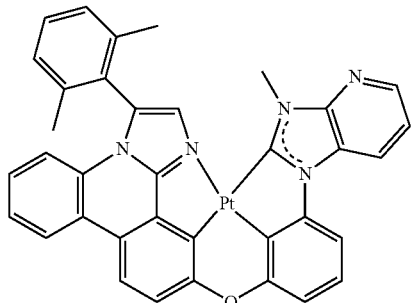

-continued
Compound 167'
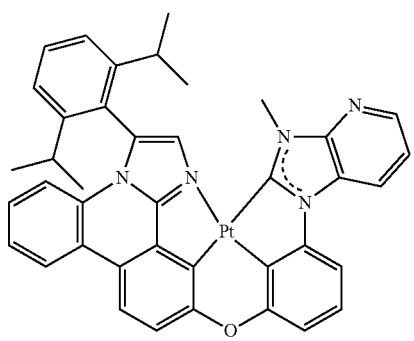
Compound 168'
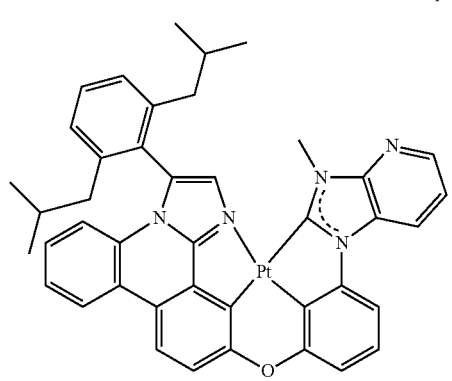
Compound 169'
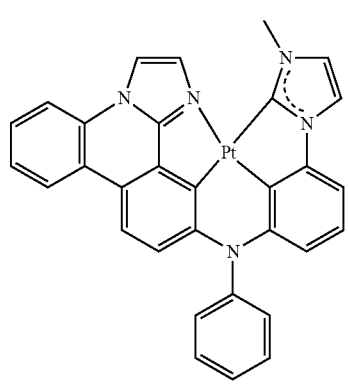
Compound 170'
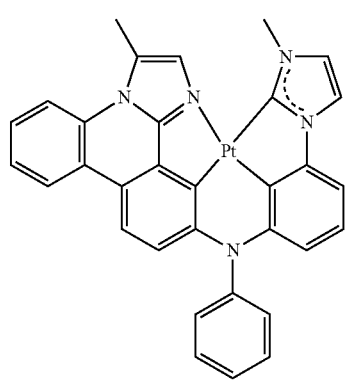
-continued
Compound 171'
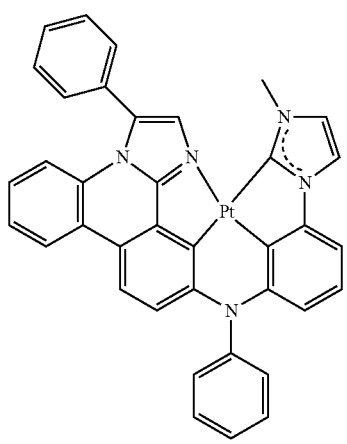
Compound 172'
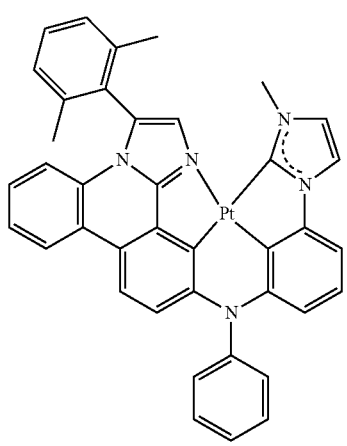
Compound 173'
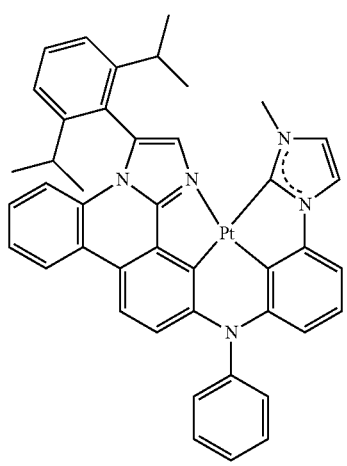

Compound 174'
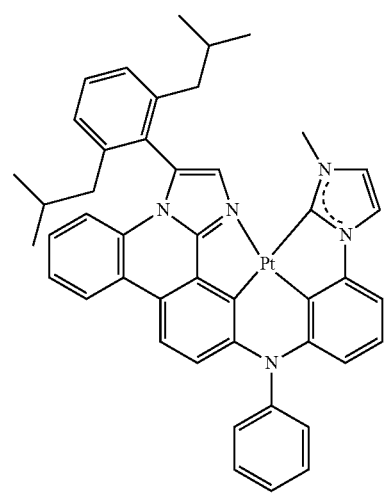
Compound 175'
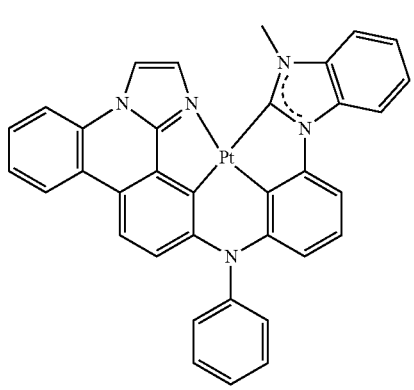
Compound 176'
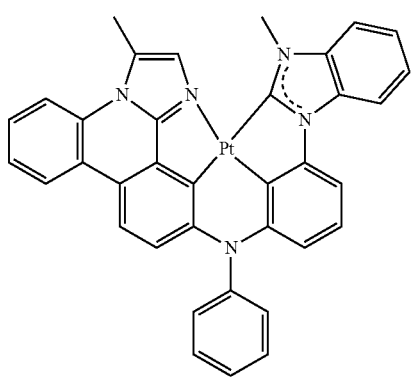
Compound 177'
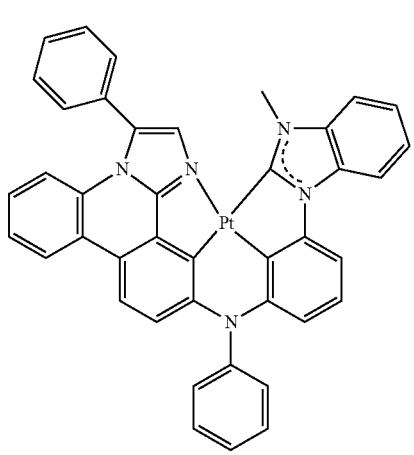
Compound 178'
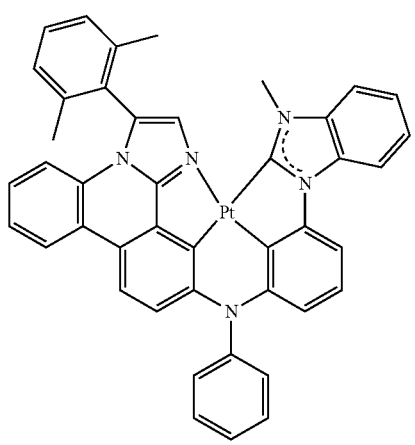
Compound 179'
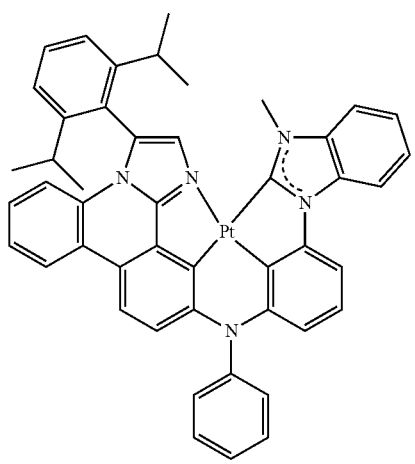
Compound 180'
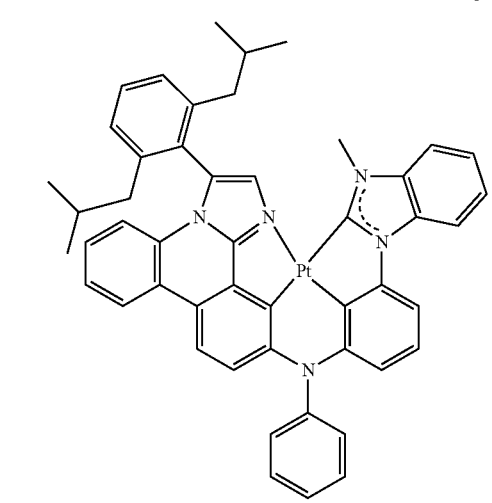

Compound 181'
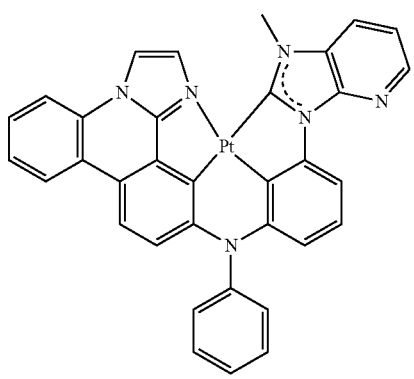
Compound 182'
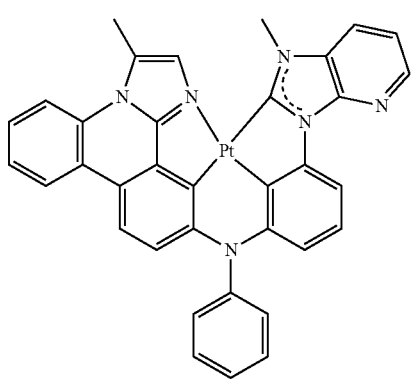
Compound 183'
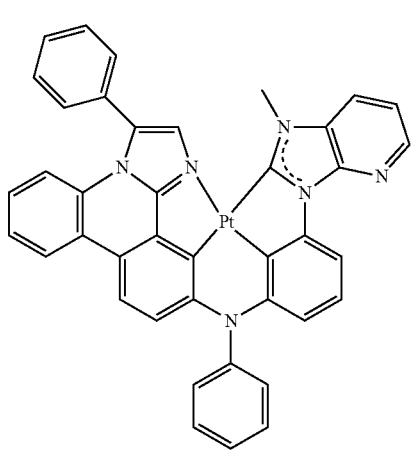
Compound 184'
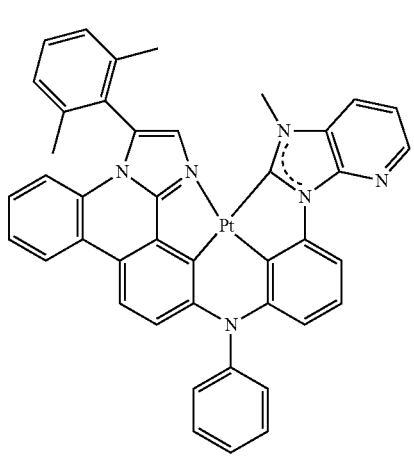
Compound 185'
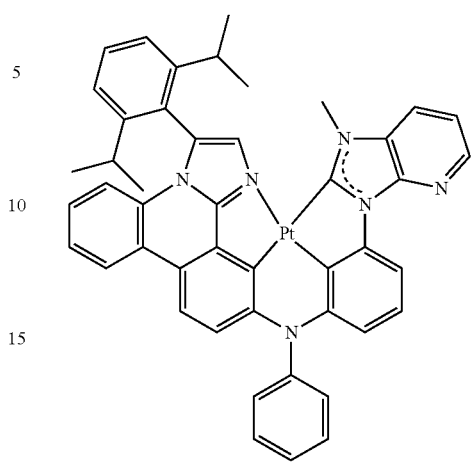
Compound 186'
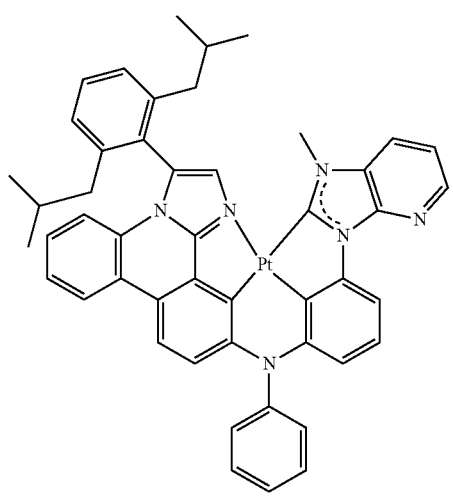
Compound 187'
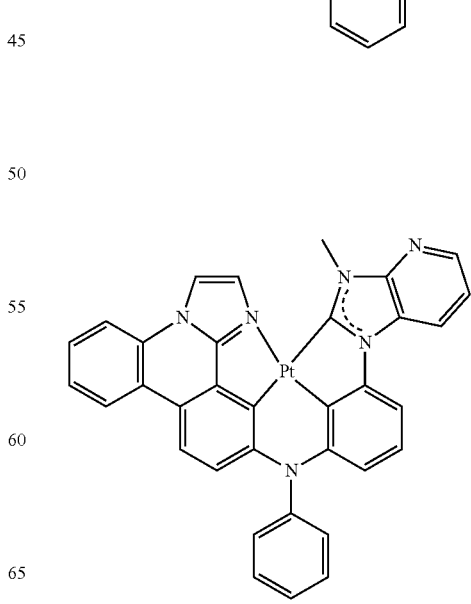

Compound 188'
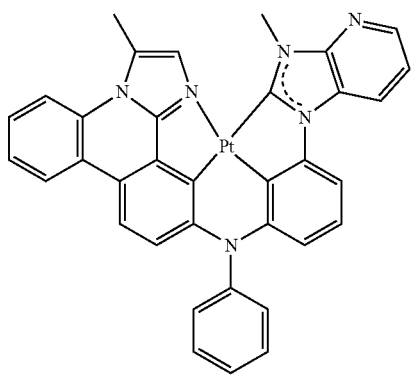
Compound 189'
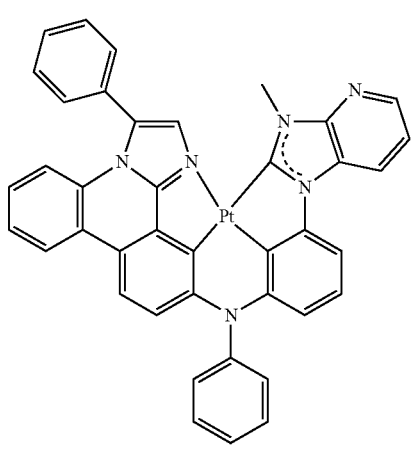
Compound 190'
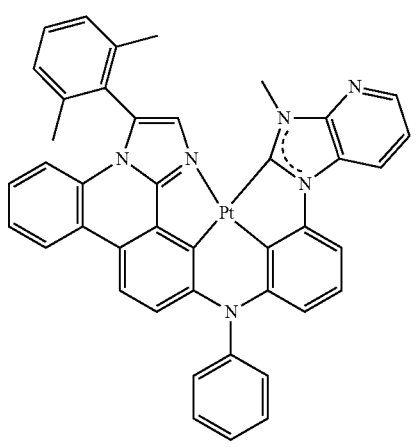
Compound 191'
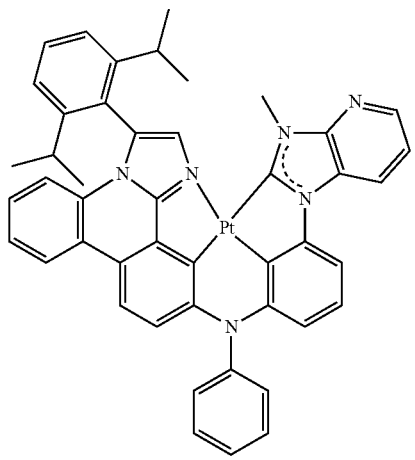
Compound 192'
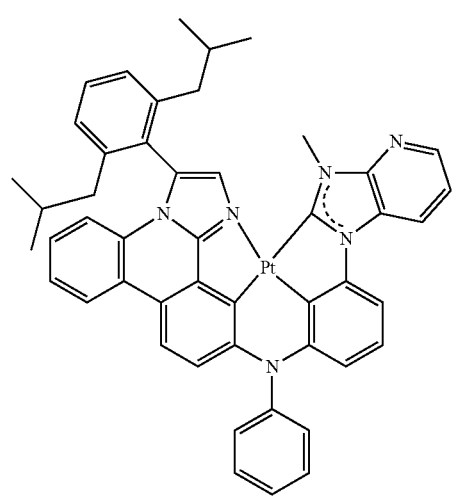
Compound 193'
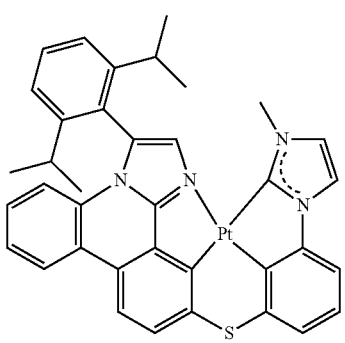
Compound 194'
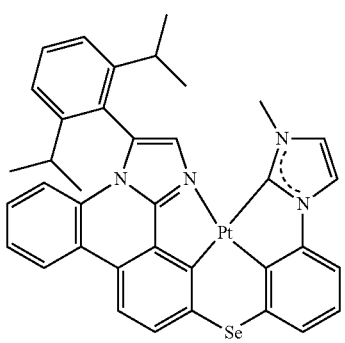

Compound 195'
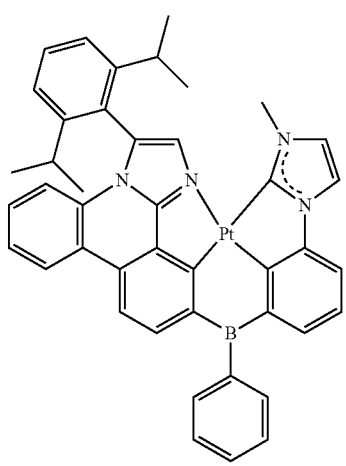
Compound 196'
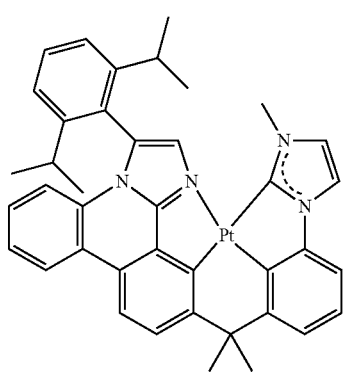
Compound 197'
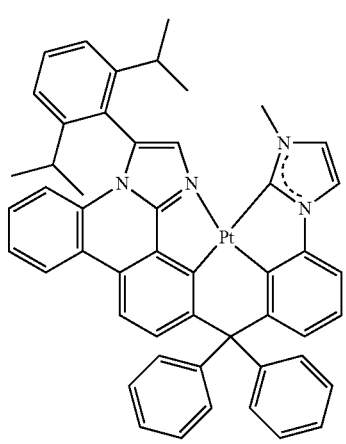
Compound 198'
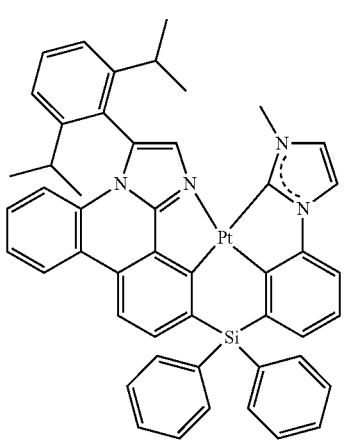
Compound 199'
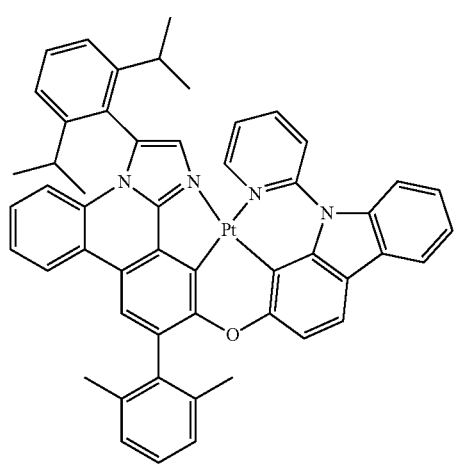
Compound 200'
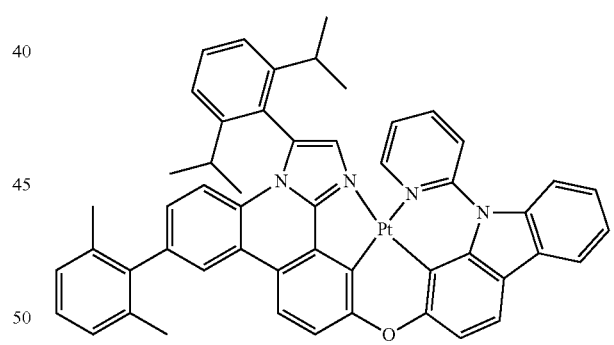
Compound 201'
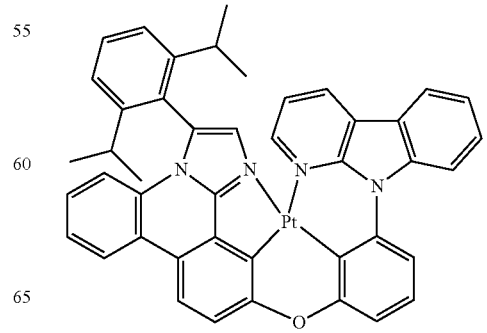

Compound 202'
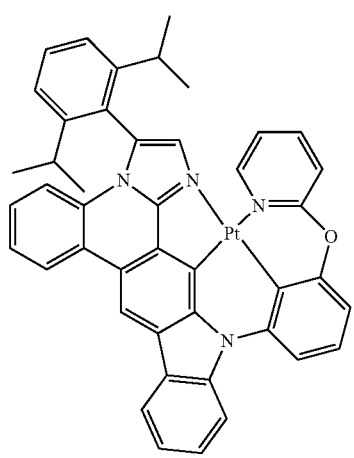
Compound 203'
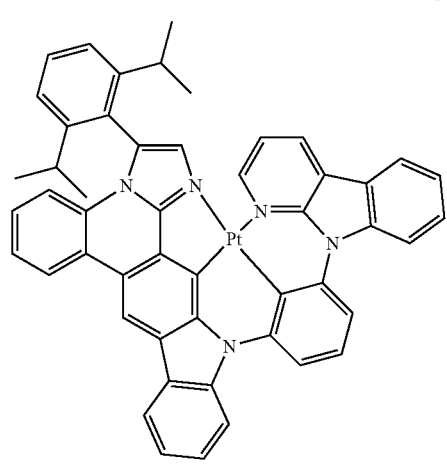
Compound 204'
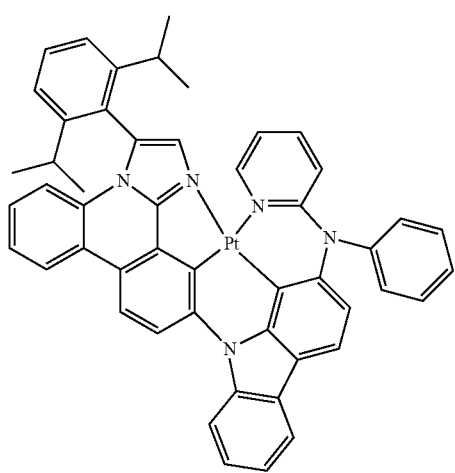
Compound 205'
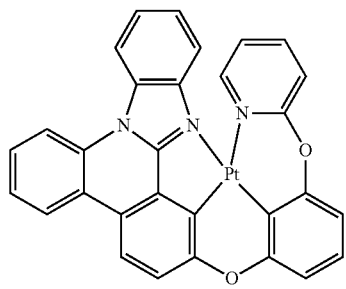
Compound 206'
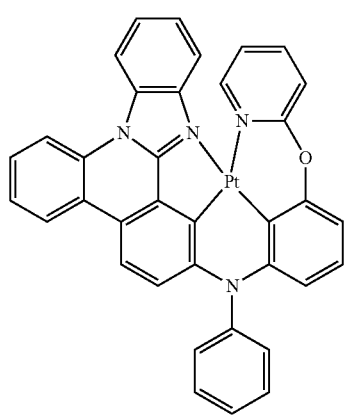
Compound 207'
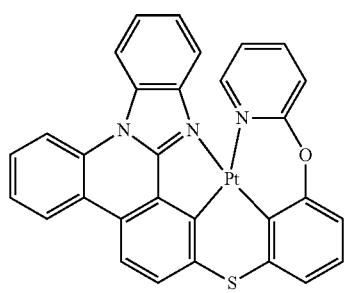
Compound 208'
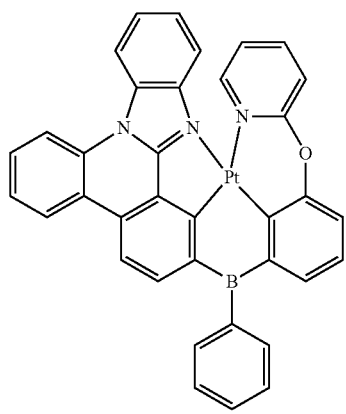

Compound 209'
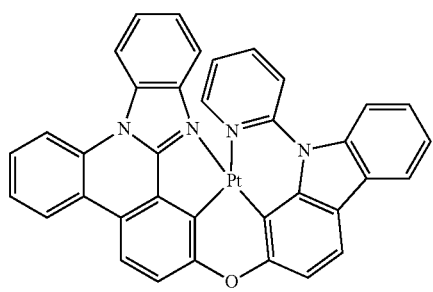
Compound 210'
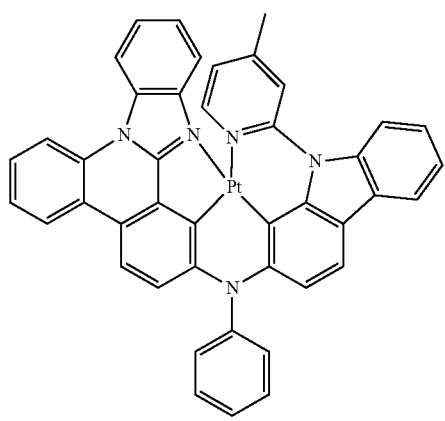
Compound 211'
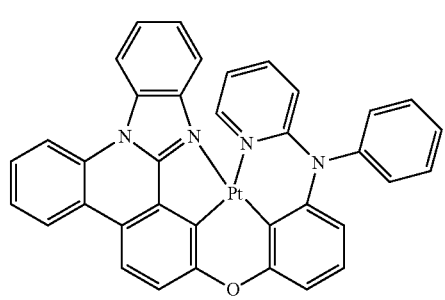
Compound 212'
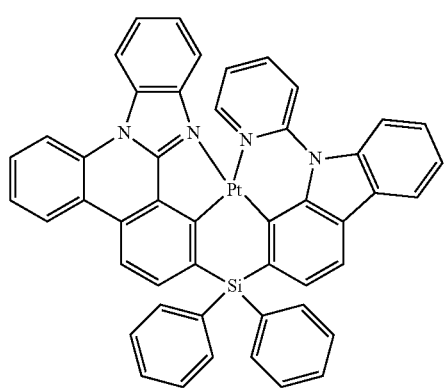
Compound 213'
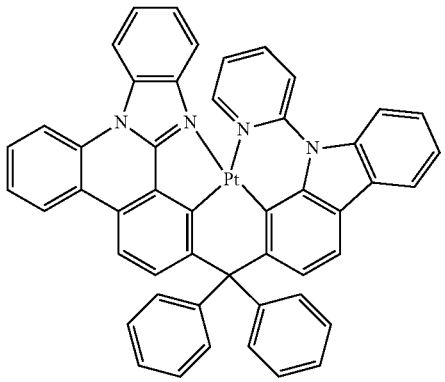
Compound 214'
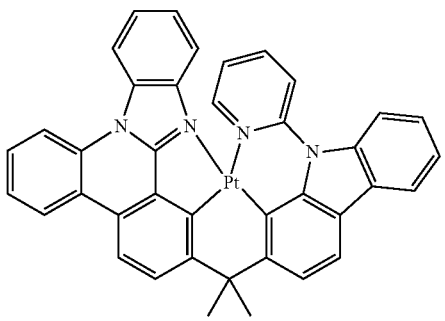
Compound 215'
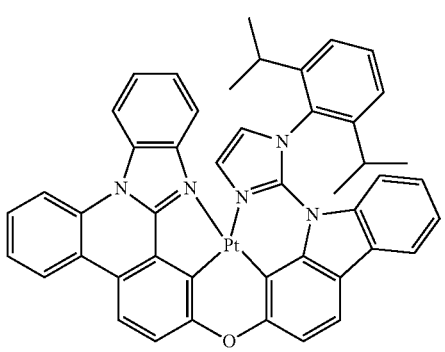
Ciompound 216'
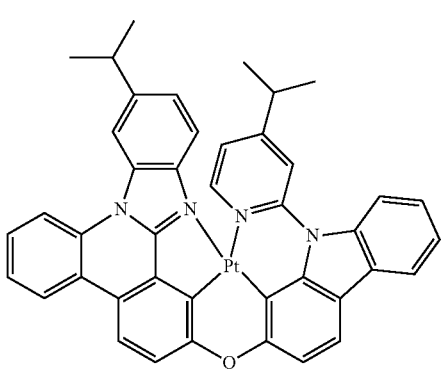

Compound 217'
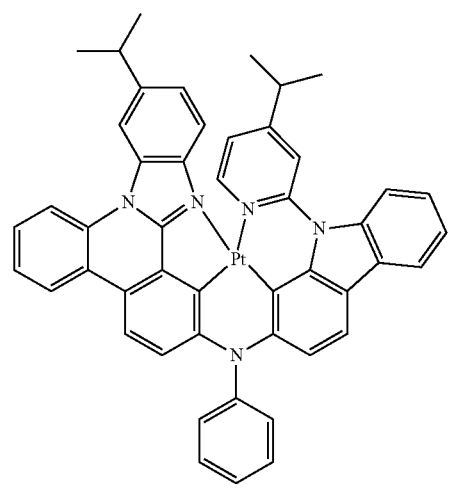
Compound 218'
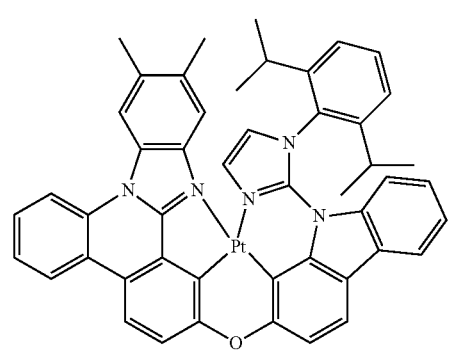
Compound 219'
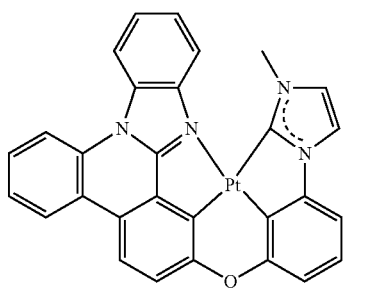
Compound 220'
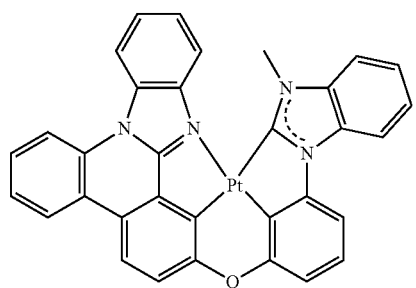
Compound 221'
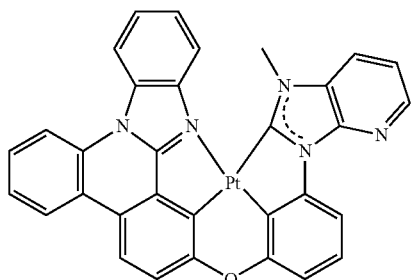
Compound 222'
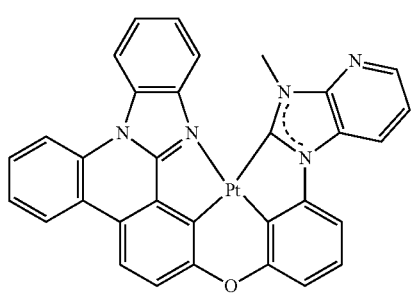
Compound 223'
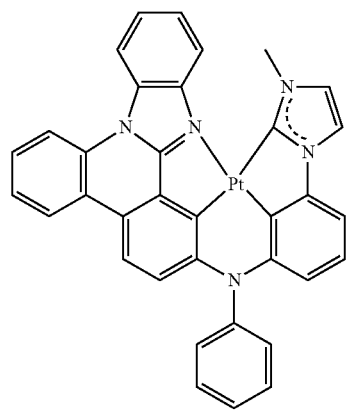
Compound 224'
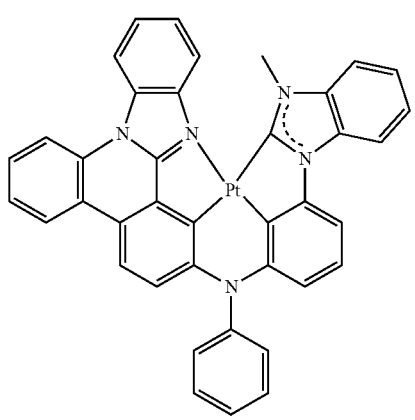

Compound 225'
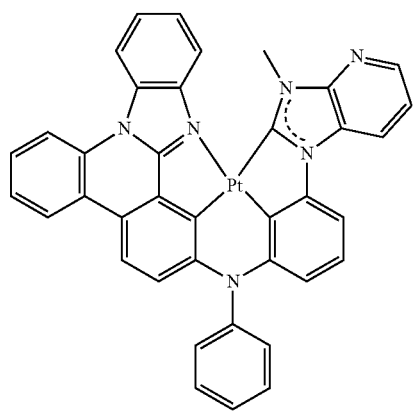
Compound 226'
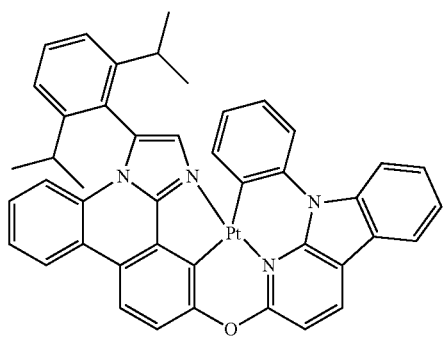
Compound 227'
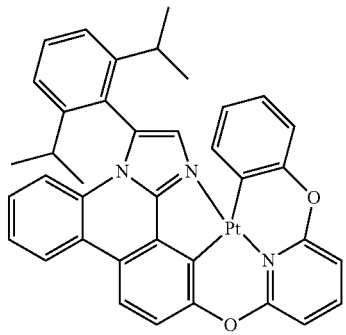
Compound 228'
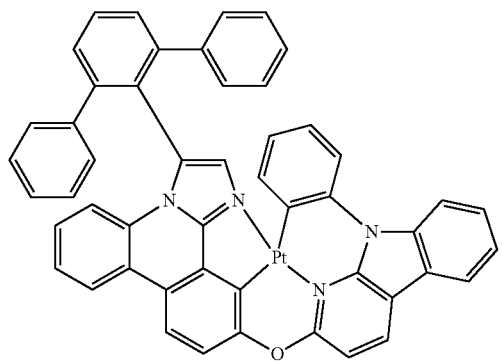
Compound 229'
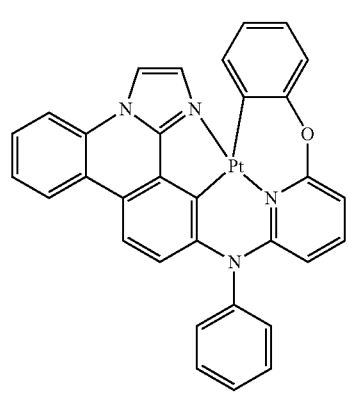
Compound 230'
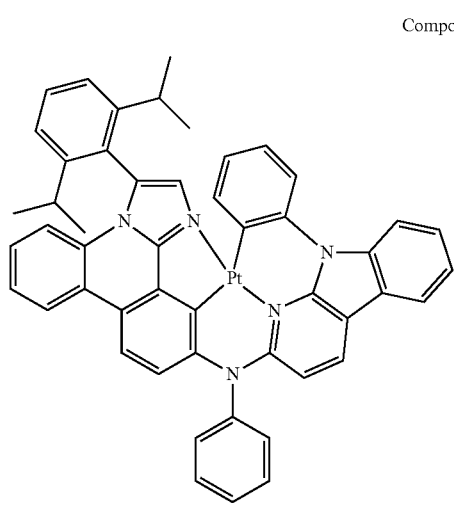
Compound 231'
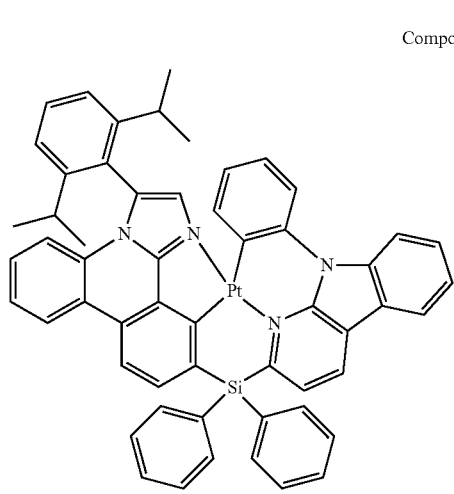

Compound 232'
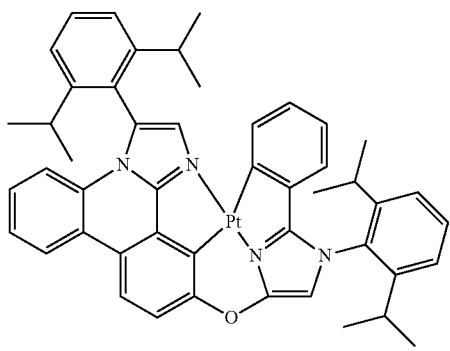
Compound 233'
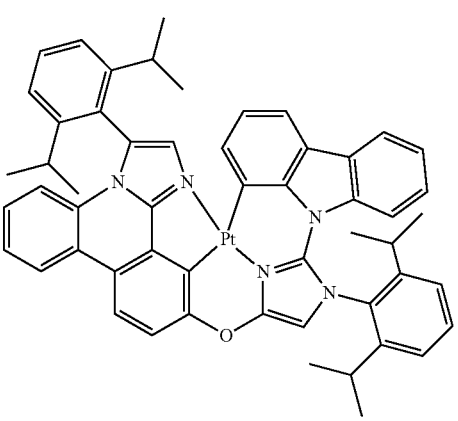
Compound 234'
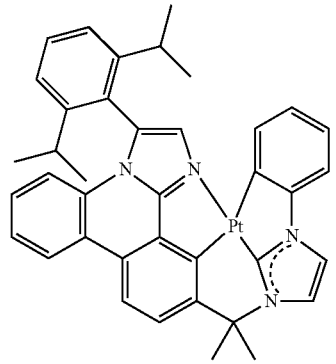
Compound 235'
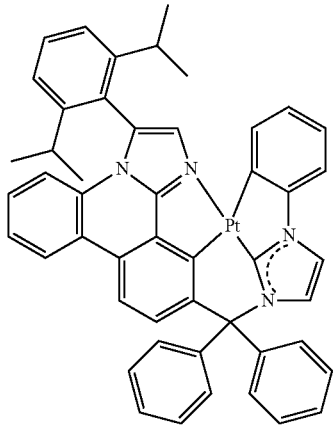
Compound 236'
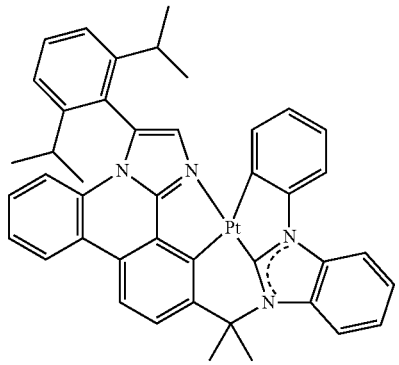
Compound 237'
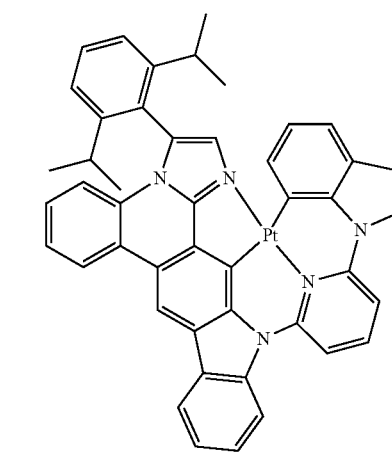
Compound 238'
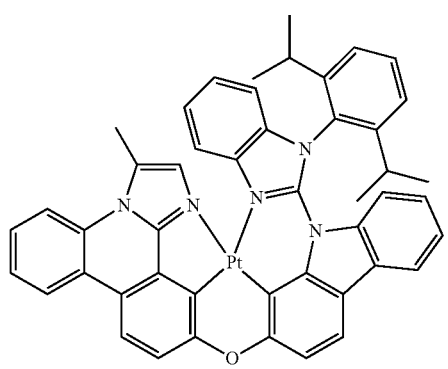
Compound 239'
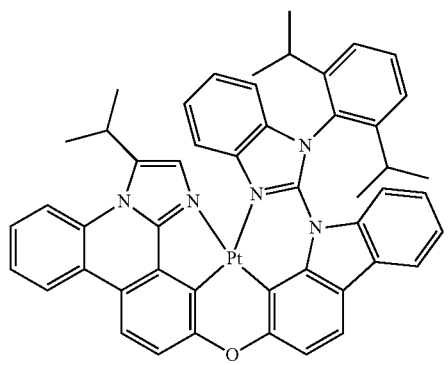

Compound 240'

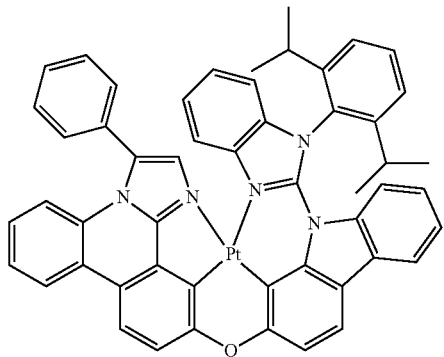

Compound 241'

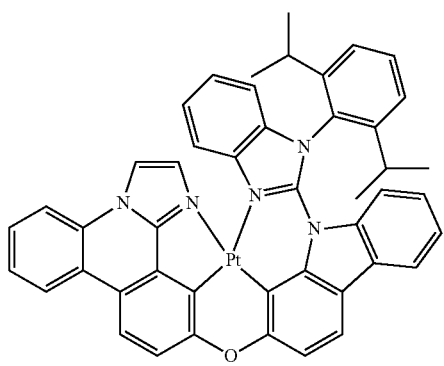

Additionally, a first device is provided. The first device comprises an organic light emitting device. The first organic light emitting device further comprises an anode, a cathode, and an organic layer, disposed between the anode and the cathode. The organic layer comprises a compound having the formula:

Formula I'

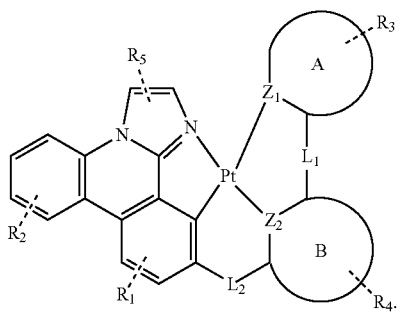

Ring A and ring B are each independently a 5- or 6-membered carbocyclic or heterocyclic ring. $L_1$ and $L_2$ are independently selected from the group consisting of a single bond, BR, NR, PR, O, S, Se, C=O, S=O, $SO_2$, CRR', SiRR', and GeRR'. $Z_1$ and $Z_2$ are independently a nitrogen atom or a carbon atom. $R_1$, $R_2$, $R_3$, $R_4$, and $R_5$ may represent mono, di, tri, or tetra substitutions. R, R', $R'_1$, $R'_2$, $R'_3$, $R'_4$, $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substitutents of R, R', $R_1$, $R_2$, $R_3$, $R_4$, and $R_5$ are optionally joined to form a fused ring.

The various aspects discussed above for compounds having Formula I' are also applicable to a compound having Formula I' that is used in the first device. In particular, specific aspects of ring A, ring B, $L_1$, $L_2$, R, R', $R'_1$, $R'_2$, $R'_3$, $R_1$, $R_2$, $R_3$, $R_4$, $R_5$, $R_6$, Formulas I'-XI', and Compounds 1'-237' of the compound having Formula I' are also applicable to a compound having Formula I' that is used in the first device.

In one aspect, $L_1$ is selected from the group consisting of BR, NR, PR, O, S, Se, C=O, S=O, $SO_2$, CRR', SiRR', and GeRR'.

In one aspect, the organic layer is an emissive layer and the compound is an emissive dopant. In another aspect, the organic layer further comprises a host.

In one aspect, the host comprises an organic molecule containing at least one group selected from the group consisting of carbazole, dibenzothiphene, dibenzofuran, azacarbazole, aza-dibenzothiophene, and aza-dibenzofuran.

In yet another aspect, the host has the formula:

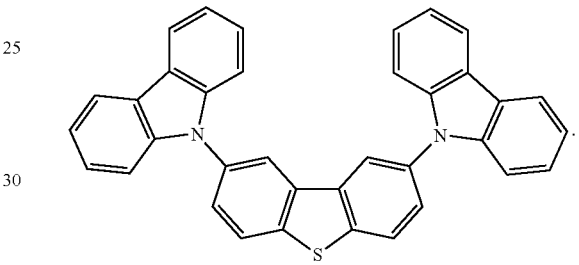

In a further aspect, the host is a metal complex.

In one aspect, the organic layer is an emissive layer and the compound is a non-emissive dopant.

In one aspect, the first device is a consumer product. In another aspect, the first device is an organic light-emitting device. In yet another aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
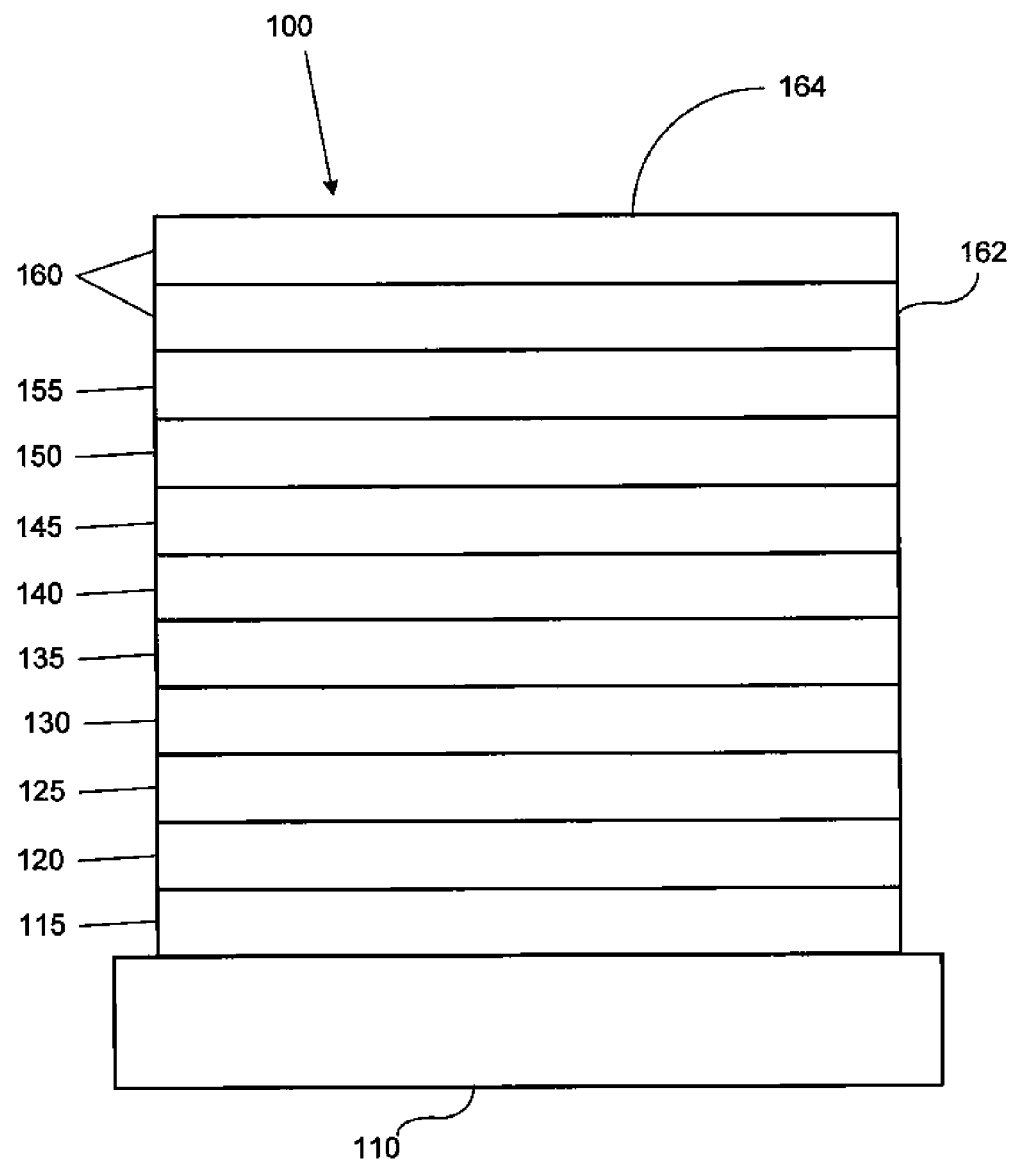
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
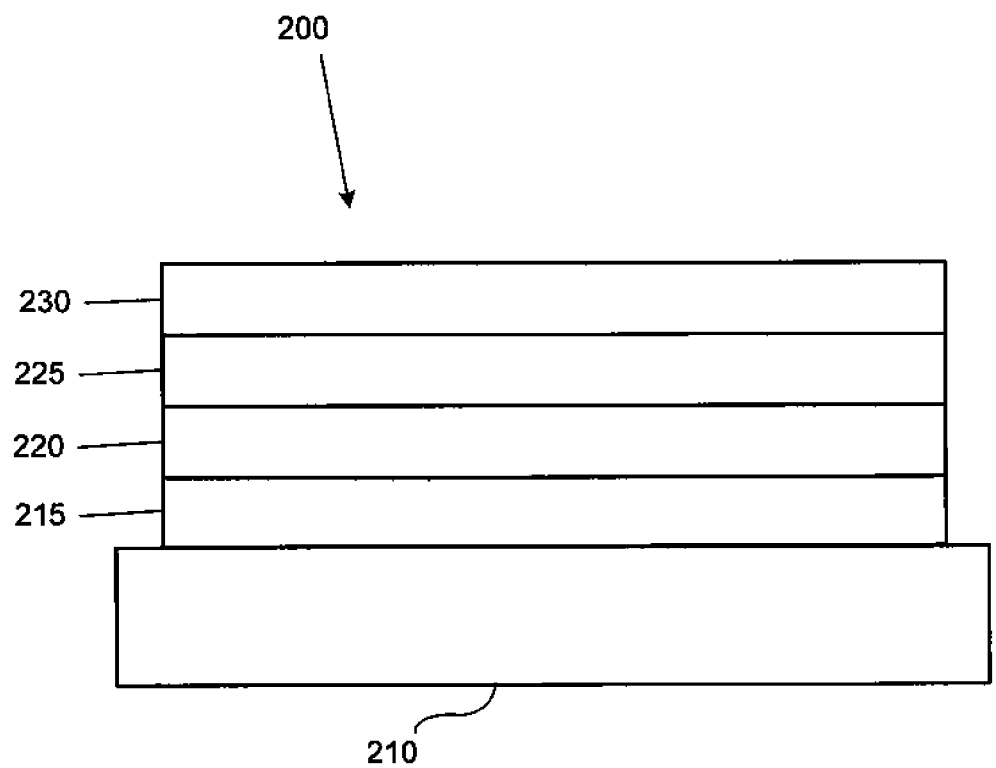
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

The first PHOLED was demonstrated with a platinum complex, namely 2,3,7,8,12,13,17,18-octaethyl-21H,23H-porphine platinum(II) (PtOEP). See, Nature, 1998, 395, 151. However, platinum complexes have not found practical use in state-of-the-art PHOLEDs. Generally, platinumn (II) complexes have relatively long excited state lifetime and lower quantum yield compared to iridium complexes. In addition, platinum (II) complexes adopt a square planar geometry, which often causes excimer formation. This results in a broadened emission spectrum at higher doping concentration in OLEDs. Therefore, certain aspects of device performance and properties, such as device efficiency, line shape, and/or lifetime, remain problematic.

Bidentate and tridentate Pt(II) complexes have been well studied. However, these complexes have limited practical application in OLEDs, in part, because of their poor thermal stability and device stability. Additionally, tetradentate Pt(II) complexes have been reported in the literature. See, e.g., U.S. Pat. No. 7,501,190; U.S. Pat. No. 7,771,845; U.S. Pat. No. 7,781,074; US2007103060; US20060202197; and US20080036373. However, some of the devices comprising these compounds show excimer formation at high doping concentrations. See, e.g., Inorg. Chem. 2010, 49, 5107. Therefore, previously reported platinum complexes may have serious limitations. The compounds provided herein are Pt(II) complexes having a short excited state lifetime, high quantum efficiency, minimal excimer formation, and long device lifetime.

Figure 3:
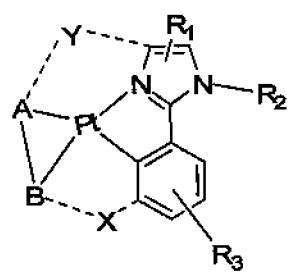
FIG. 3 shows a tetradentate platinum complex with a twisted aryl group.
Figure 4:
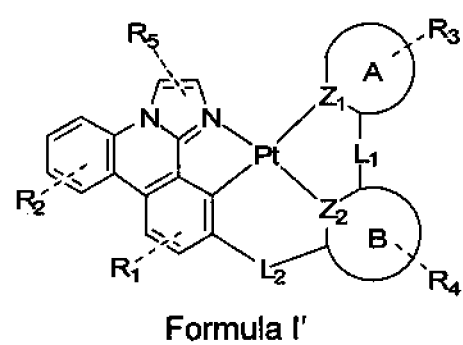
FIG. 4 shows a tetradentate platinum (II) compound comprising an imidazo[1,2-f]phenanthridine moiety.

Tetradentate platinum compounds with a twisted aryl group are provided herein (as illustrated in FIG. 3). These compounds may be advantageously used in OLEDs to provide devices demonstrating high efficiency, narrow line-shape, and/or long lifetime. Without being bound by theory, it is believed that the twisted aryl group on these compounds may provide certain beneficial properties and the tetradentate ligands may provide additional beneficial properties. In particular, it is thought that the twisted aryl group may prevent excimer formation and increase efficiency. Additionally, it is thought that the twisted aryl group can improve sublimation. On the other hand, it is believed that the tetradentate ligand may provide stability. Taken together, the combination of the twisted aryl group and the tetradentate ligand in the same compound may provide for improved device efficiency, line shape and lifetime.

Phosphorescent tetradentate platinum compounds comprising a twisted aryl substituent are provided. The compounds have the formula:

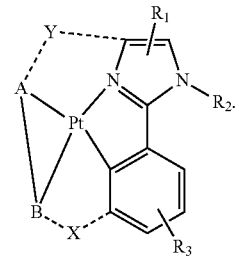

Formula I

A and B are independently selected from the group consisting of a 5-membered or 6-membered carbocyclic or heterocyclic ring. A-B connects to Pt through one covalent bond and one coordination bond. X and Y are independently selected from the group consisting of BR, NR, PR, O, S, Se, C=O, S=O, $SO_2$, CRR', SiRR', and GeRR'. At least one of X and Y forms a bond between A-B and the 2-phenylimidazole. R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ and $R_3$ may represent mono, di, or tri substitutions. $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$, $R_2$, and $R_3$ are optionally joined to form a ring. At least one of $R_1$ and $R_2$ is:

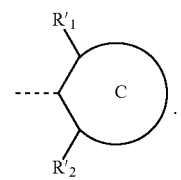

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is a 5-membered or 6-membered carbocyclic or heterocyclic ring that is optionally further substituted. Preferably, C is benzene.

The C ring is twisted out of plane, i.e., a twisted aryl, because at least one of the substitutions $R'_1$ and $R'_2$ is not hydrogen or deuterium. The twisted aryl group may reduce packing in the solid state as well as protect the imidazole ring from oxidation. As a result of the twisted aryl, i.e., C ring, the compounds may have reduced excimer formation, increased efficiency and/or improved sublimation.

The dashed lines used in Formula I for X and Y indicate that the bond may or may not be formed. As stated above, at least one of X and Y forms a bond between the ligand A-B and the 2-phenylimidazole. For example, only X may form a bond between the ligand A-B and the 2-phenylimidazole. Alternatively, only Y may form a bond between the ligand A-B and the 2-phenylimidazole. Additionally, in some embodiments, both X and Y may each form a bond between the ligand A-B and the 2-phenylimidazole.

In one aspect, the compound has the formula:

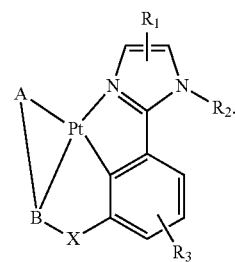

Formula II

In another aspect, the compound has the formula:

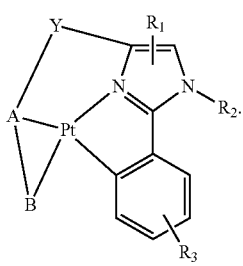

Formula III

In yet another aspect, the compound has the formula:

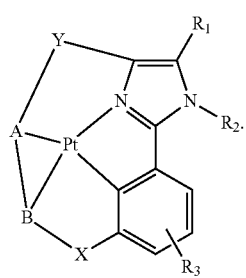

Formula IV

In one aspect, at least one of $R'_1$ and $R'_2$ is an alkyl and the other of $R'_1$ and $R'_2$ is hydrogen or deuterium. In another aspect, at least one of $R'_1$ and $R'_2$ is an alkyl having two or more carbon atoms and the other of $R'_1$ and $R'_2$ is hydrogen or deuterium. In yet another aspect, at least one of $R'_1$ and $R'_2$ is an alkyl having three or more carbon atoms and the other of $R'_1$ and $R'_2$ is hydrogen or deuterium.

In one aspect, each of $R'_1$ and $R'_2$ is an alkyl. In another aspect, each of $R'_1$ and $R'_2$ is an alkyl having two or more carbon atoms. In yet another aspect, each of $R'_1$ and $R'_2$ is an alkyl having three or more carbon atoms.

In one aspect, at least one of $R'_1$ and $R'_2$ is an aryl and the other of $R'_1$ and $R'_2$ is hydrogen or deuterium. In another aspect, one of $R'_1$ and $R'_2$ is an alkyl and the other of $R'_1$ and $R'_2$ is an aryl. In yet another aspect, each of $R'_1$ and $R'_2$ is an aryl.

In one aspect, the compound has the formula:

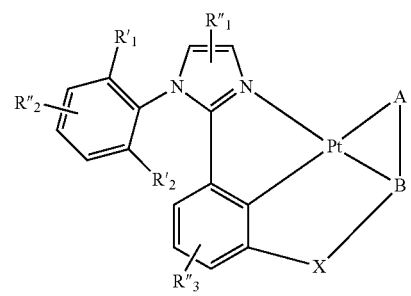

Formula V

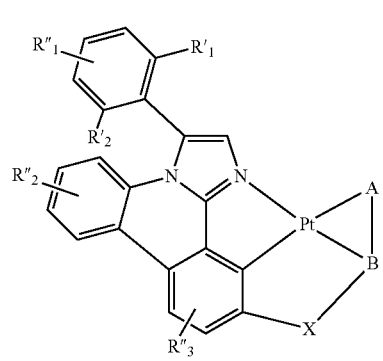

Formula VI

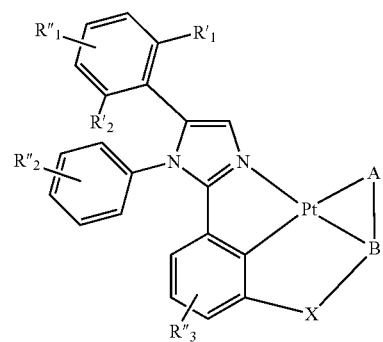

Formula VII

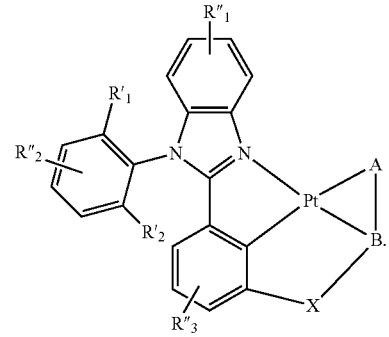

Formula VIII $R''_1$, $R''_2$, and $R''_3$ may represent mono, di, tri, or tetra substitutions. $R''_1$, $R''_2$, and $R''_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R''_1$, $R''_2$, and $R''_3$ are optionally fused to form a ring.

In another aspect, the compound has a formula selected form the group consisting of:

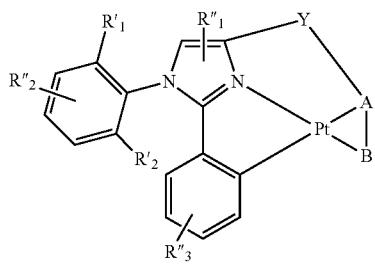

Formula IX

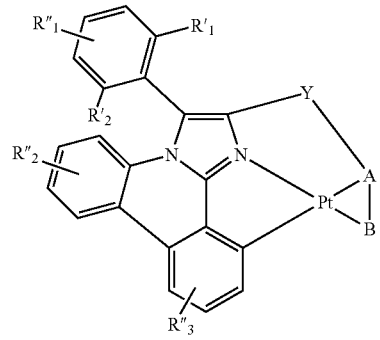

Formula X

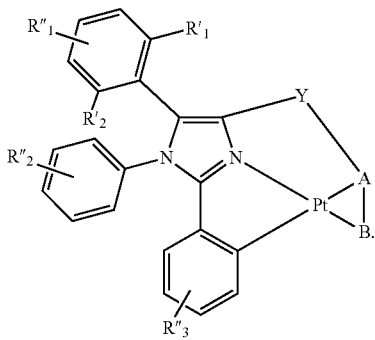

Formula XI $R''_1$, $R''_2$, and $R''_3$ may represent mono, di, tri, or tetra substitutions. $R''_1$, $R''_2$, and $R''_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R''_1$, $R''_2$, and $R''_3$ are optionally fused to form a ring.

As used herein, the term A-B means a bidentate ligand that is connected to Pt. A-B comprises a moiety A and a moiety B, of which A and B are independently selected from the group consisting of a 5-membered or 6-membered carbocyclic or heterocyclic ring, as described above. The moiety A and the moiety B are bound to one another to form the A-B ligand. A-B is connected to Pt through one covalent bond and one coordination bond.

As drawn herein, the structures of A-B include three or four dashed lines, each of which represents a different point of attachment. The dashed line from the N heteroatom in the imidazole ring represents a point of connection to Pt. The dashed line from the C in the imidazole ring represent a point of connection to Y, e.g., the topmost dashed line in the exemplary A-B structures with 4 dashed lines. The top dashed line on the lower carbocyclic ring represents a point of connection to the Pt. The bottom dashed line on the lower carbocyclic ring, represents a point of connection to X.

In another aspect, A-B is selected from the group consisting of:

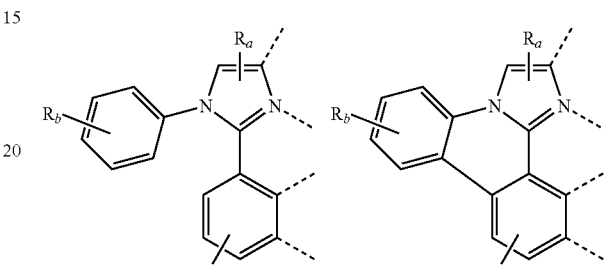

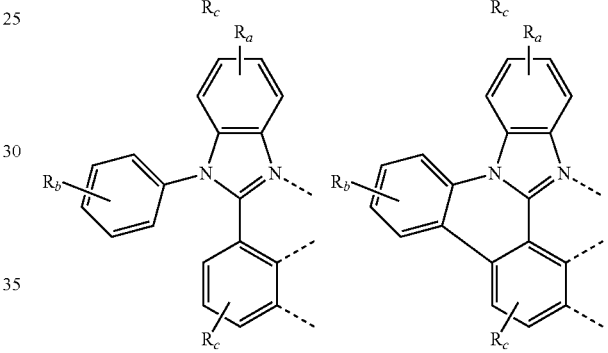

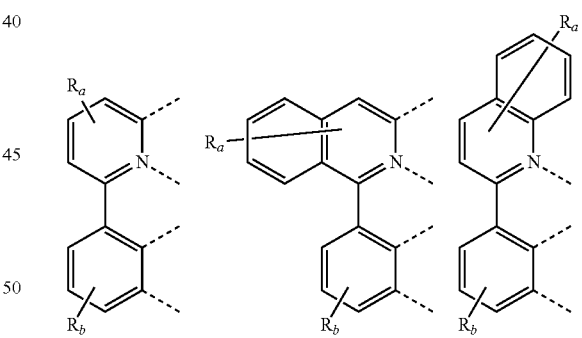

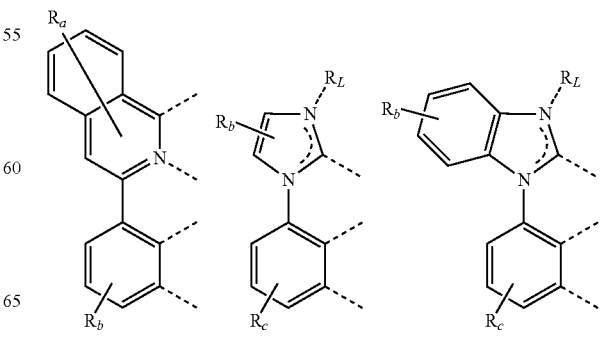

-continued

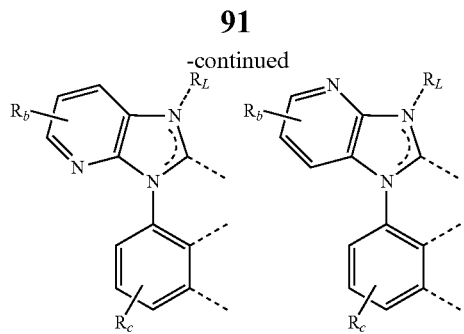

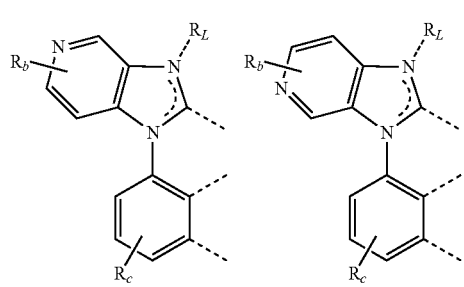

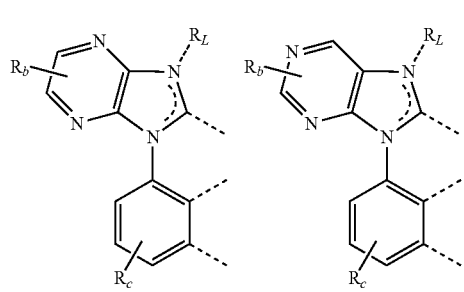

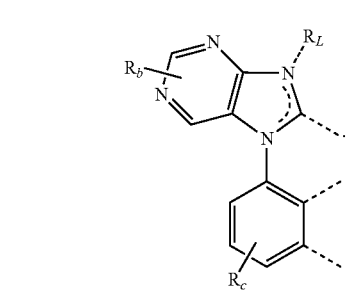

$R_a$, $R_b$, $R_c$ and $R_L$ may represent mono, di, tri or tetra substitutions. $R_a$, $R_b$, $R_c$ and $R_L$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, $R_c$ and $R_L$ are optionally joined to form a fused ring. $R_L$ is optionally a linker to connect A-B and 2-phenylimidazole.

Examples of generic structures of the platinum complexes are provided. In one aspect, the compound is selected form the group consisting of:

Compound 1G
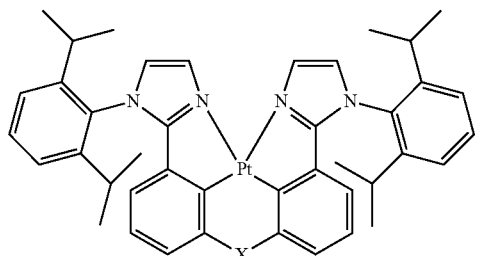

Compound 2G
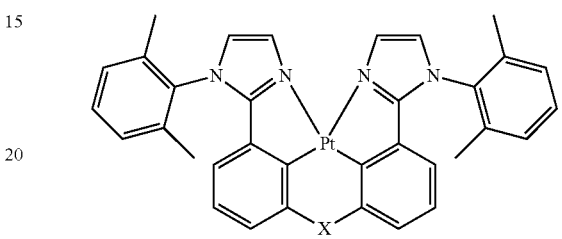

Compound 3G
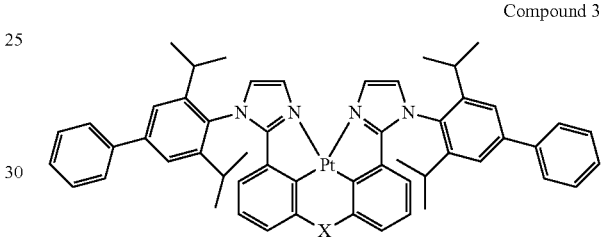

Compound 4G
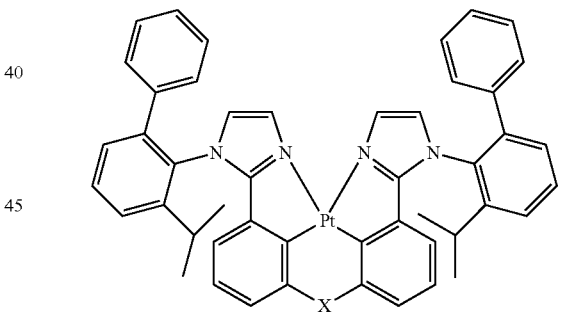

Compound 5G
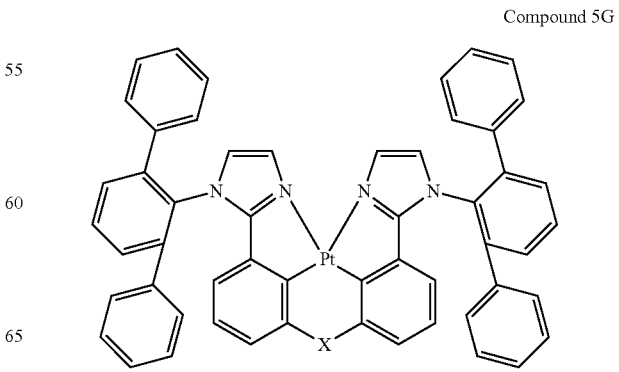

-continued
Compound 6G
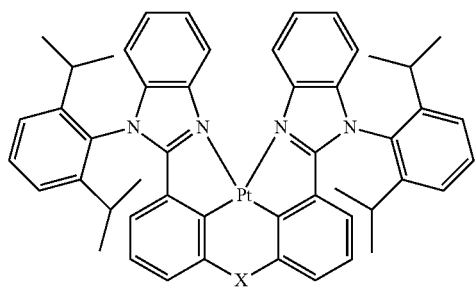
Compound 7G
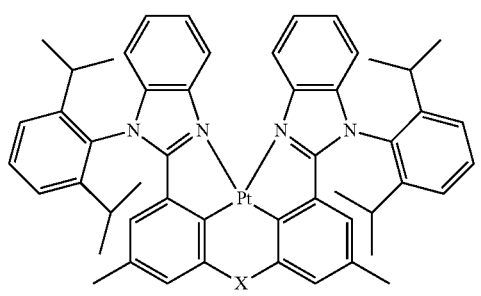
Compound 8G
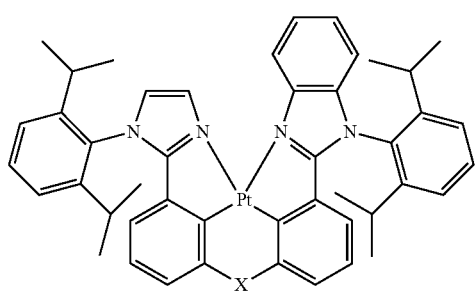
Compound 9G
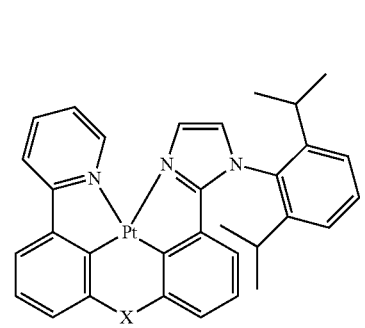
Compound 10G
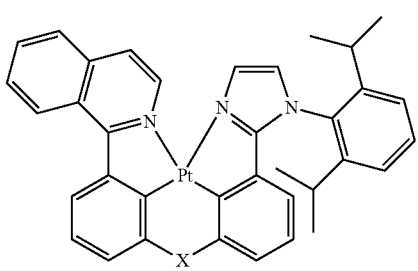
-continued
Compound 11G
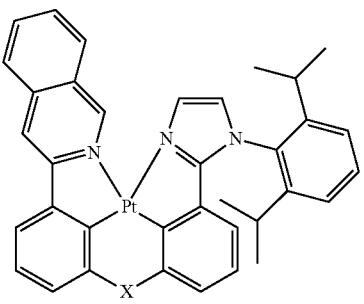
Compound 12G
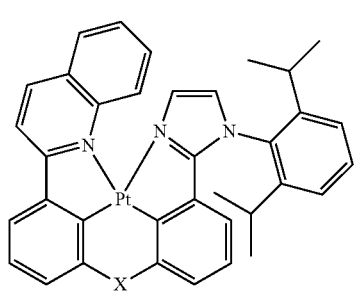
Compound 13G
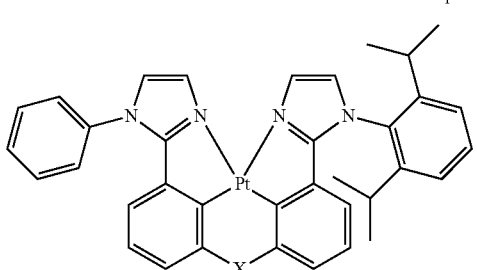
Compound 14G
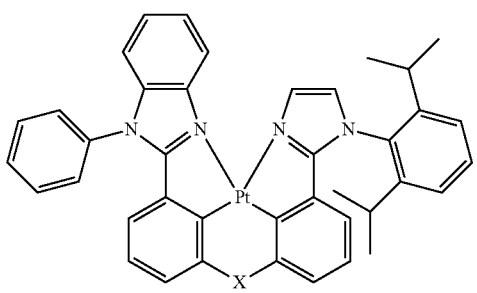
Compound 15G
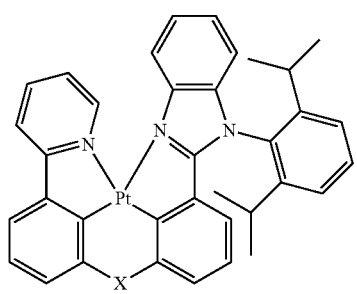

Compound 16G
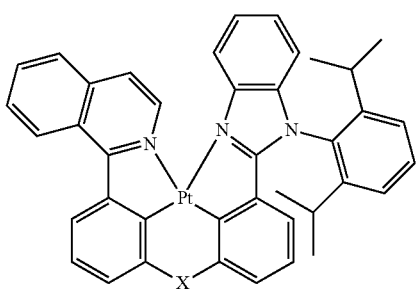
Compound 17G
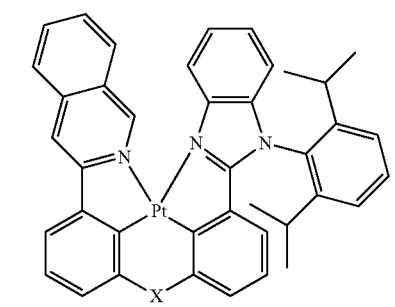
Compound 18G
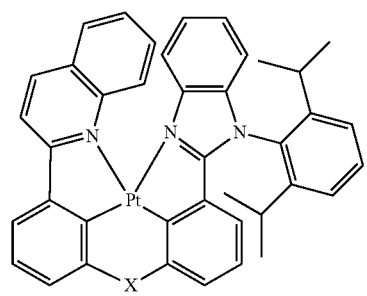
Compound 19G
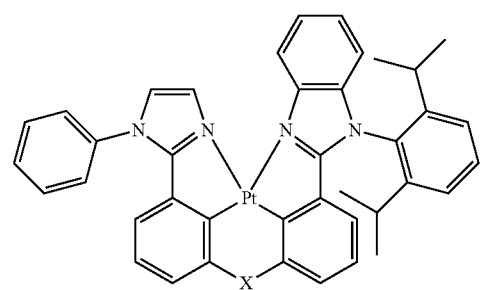
Compound 20G
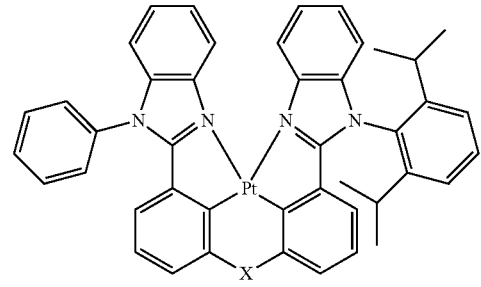
Compound 21G
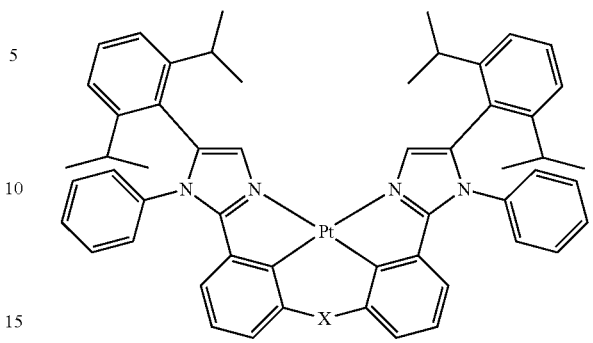
Compound 22G
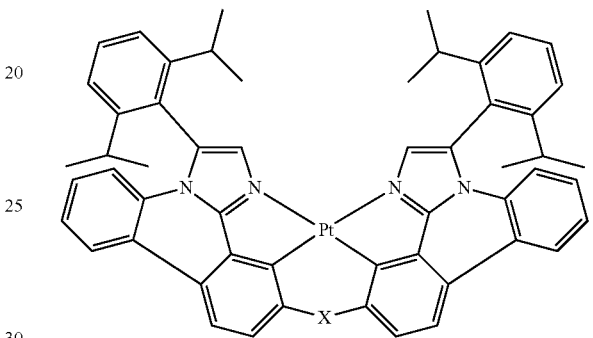
Compound 23G
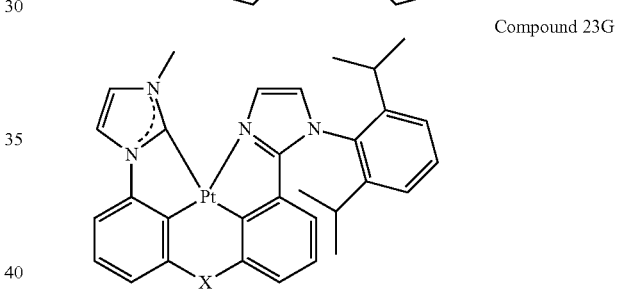
Compound 24G
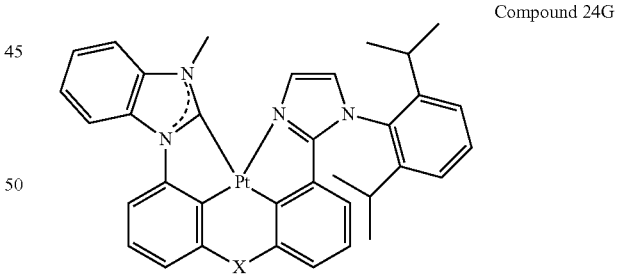
Compound 25G
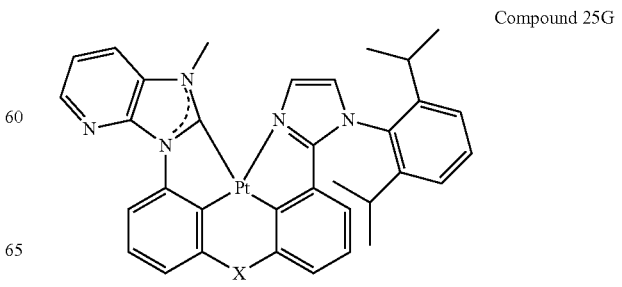

Compound 26G
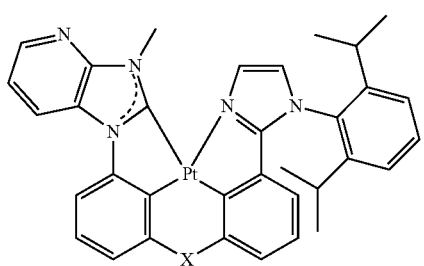
Compound 27G
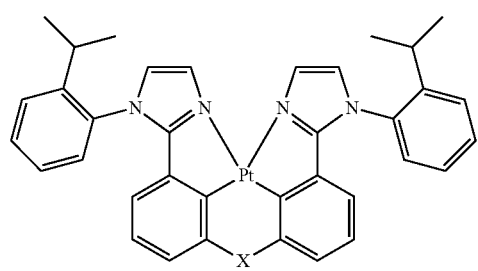
Compound 28G
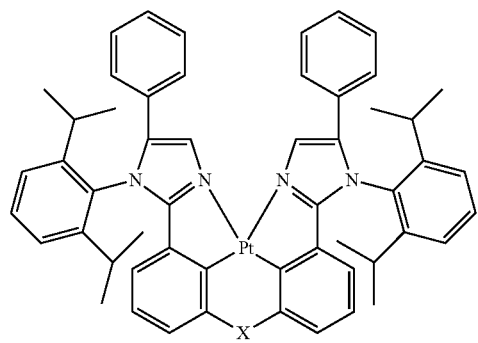
Compound 29G
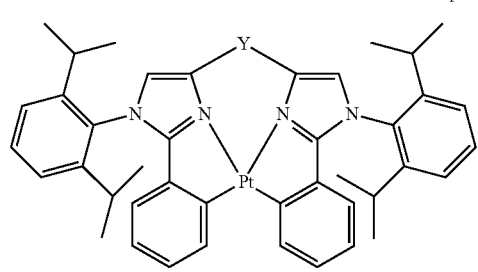
Compound 30G
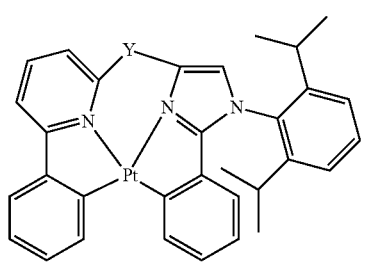
Compound 31G
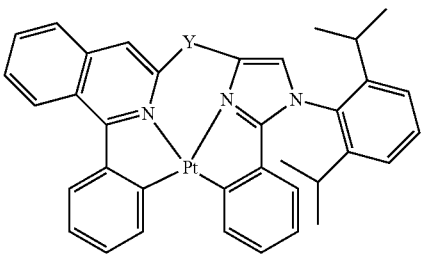
Compound 32G
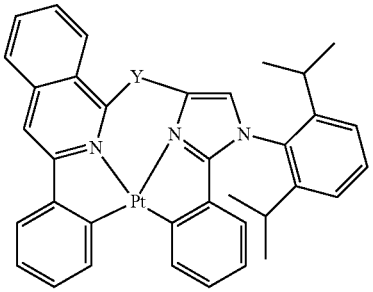
Compound 33G
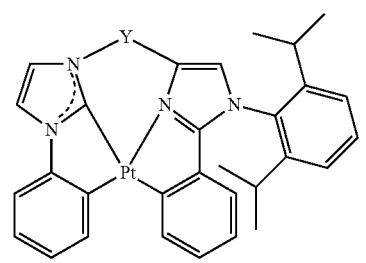
Compound 34G
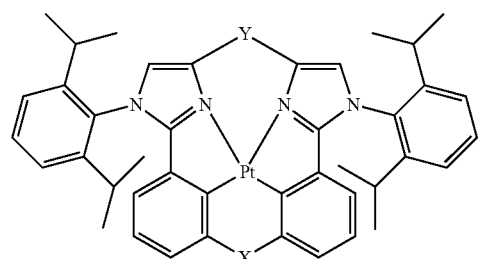
Compound 35G
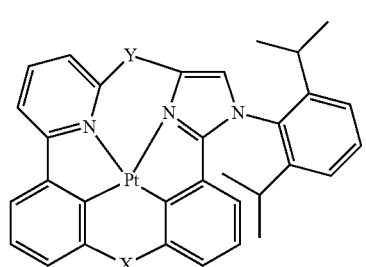
Compound 36G
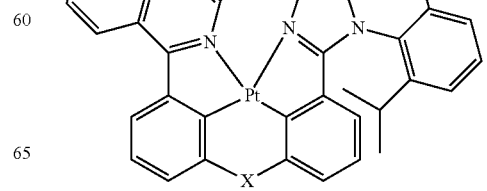

Compound 37G
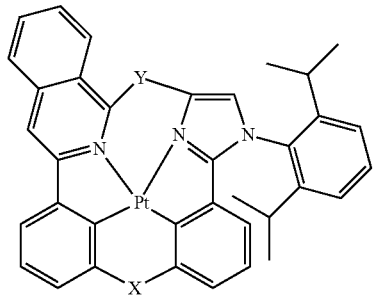
Compound 38G
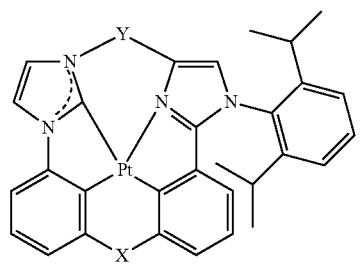
Compound 39G
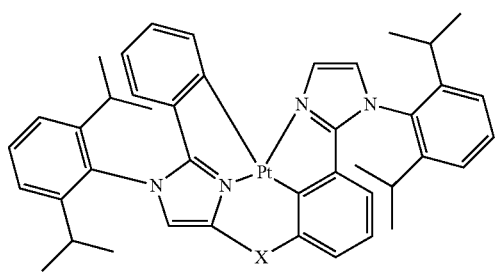
Compound 40G
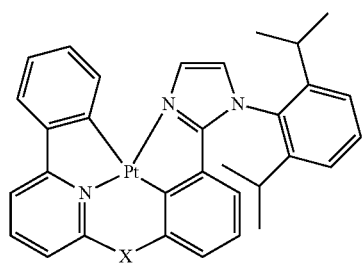
Compound 41G
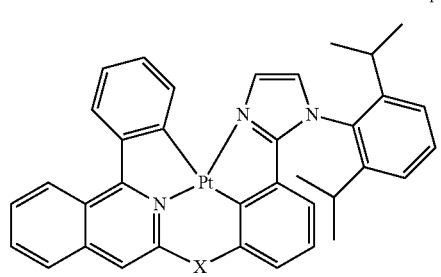
Compound 42G
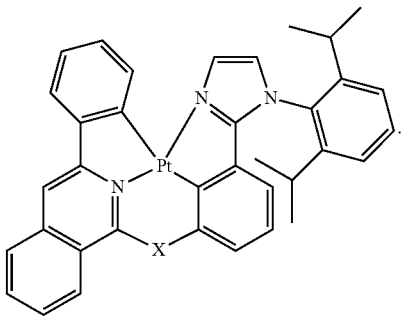
Specific examples of the platinum complexes include, but are not limited to, the following compounds:
Compound 1
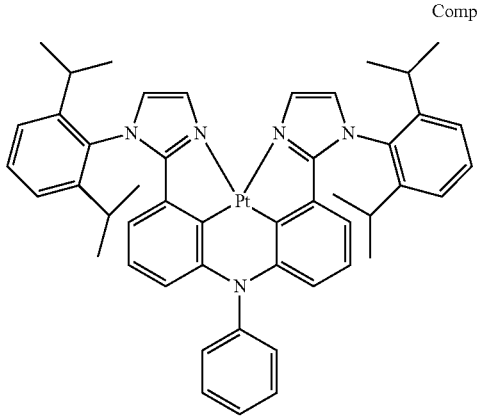
Compound 2
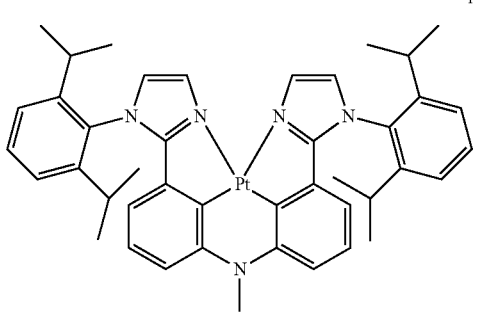
Compound 3
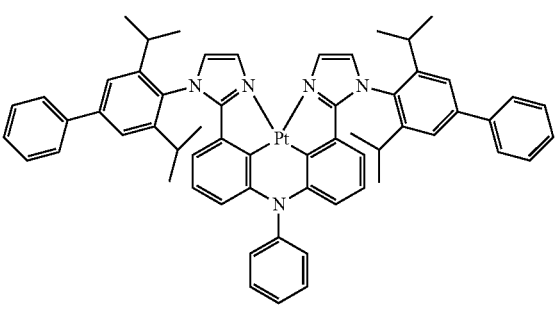

Compound 4
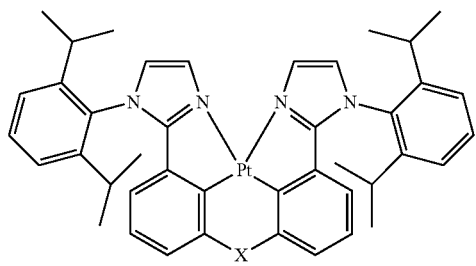
Compound 5
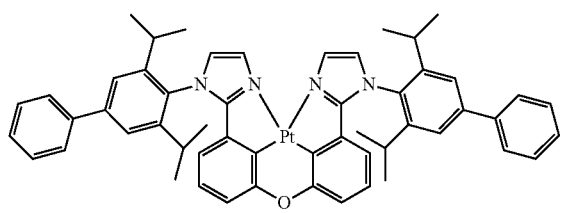
Compound 6
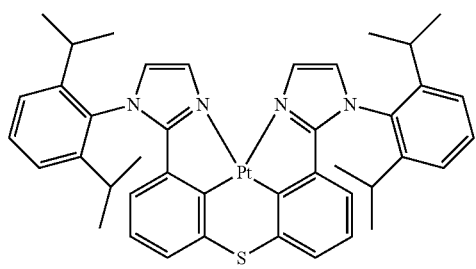
Compound 7
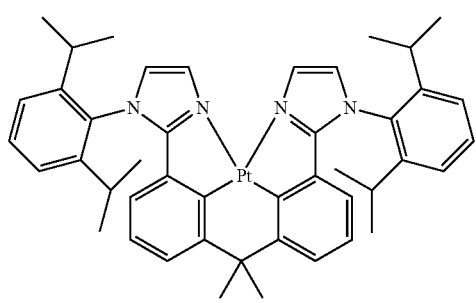
Compound 8
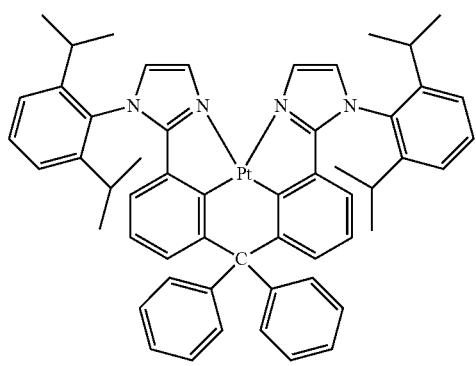
Compound 9
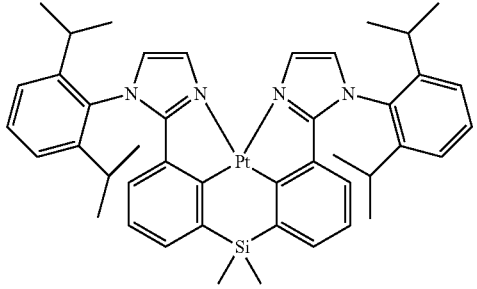
Compound 10
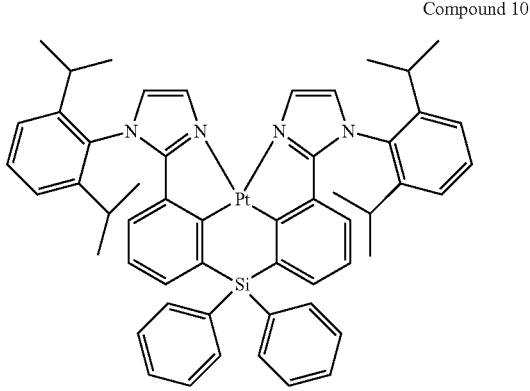
Compound 11
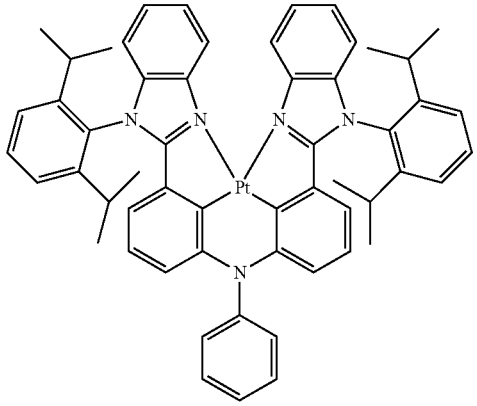
Compound 12
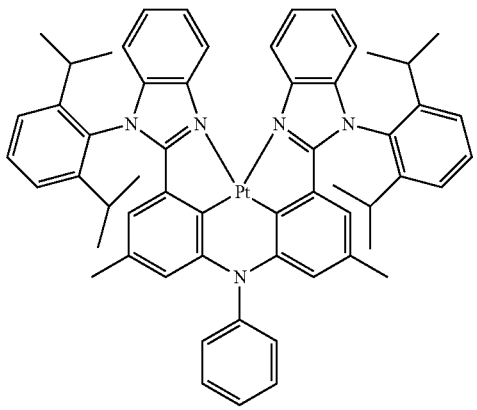

-continued
Compound 13
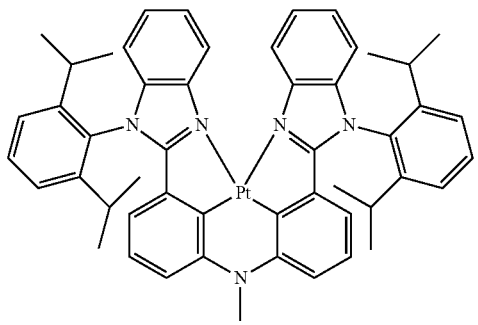
Compound 14
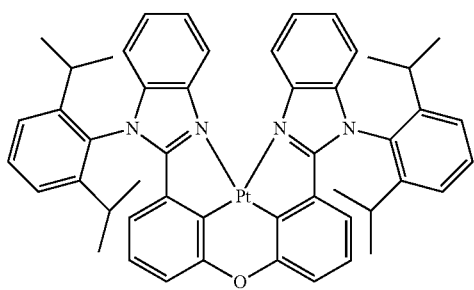
Compound 15
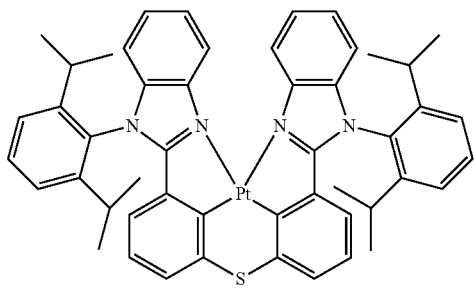
Compound 16
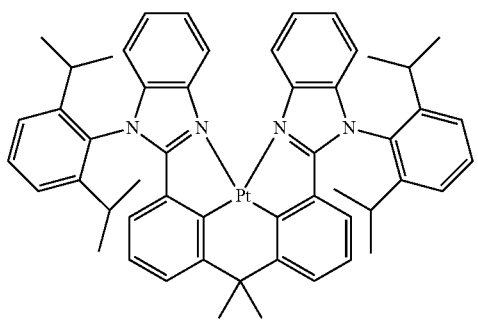
-continued
Compound 17
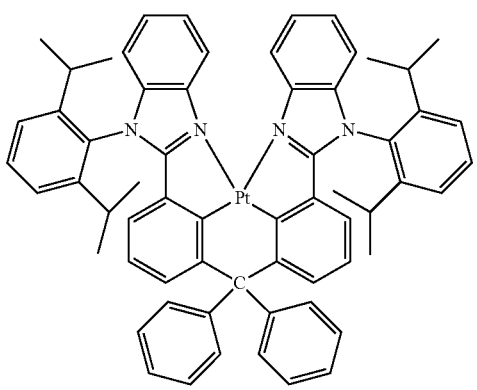
Compound 18
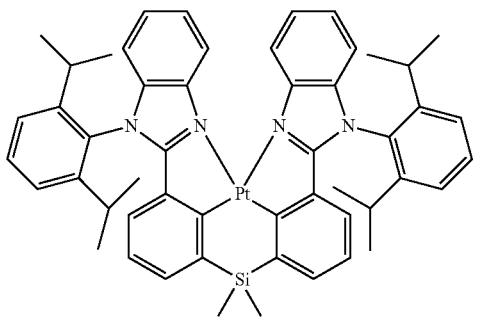
Compound 19
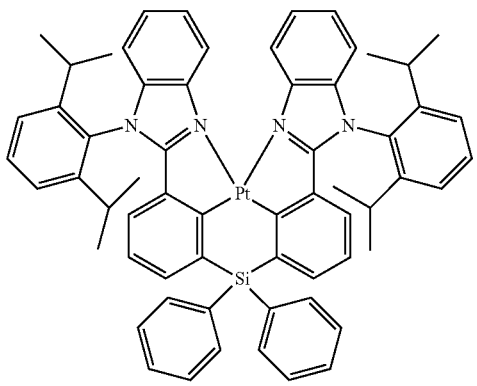
Compound 20
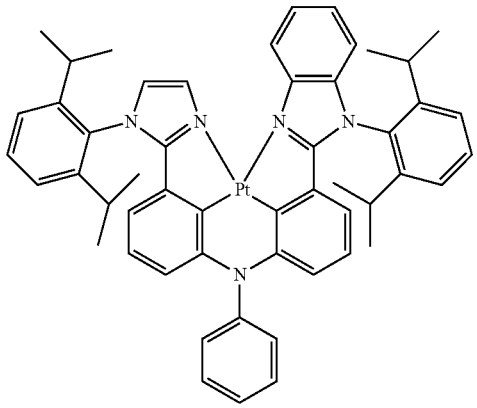

Compound 21
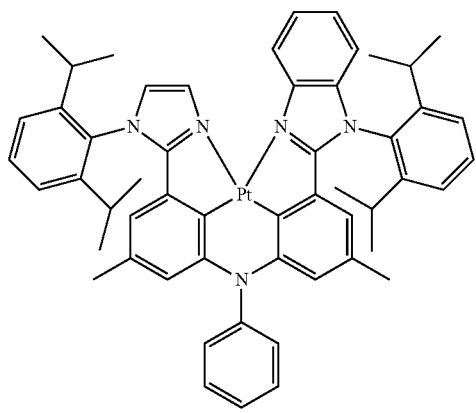
Compound 22
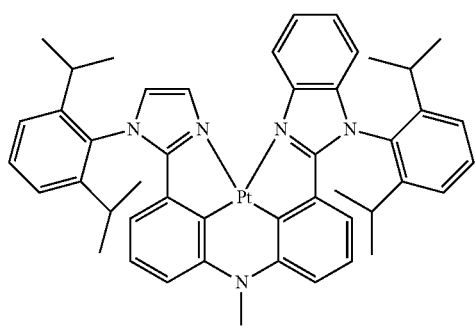
Compound 23
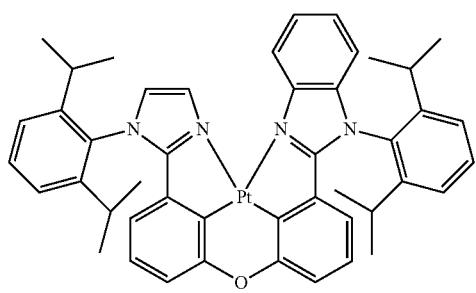
Compound 24
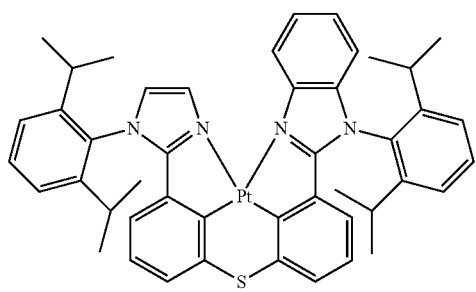
Compound 25
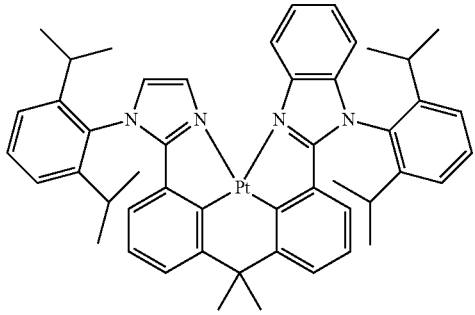
Compound 26
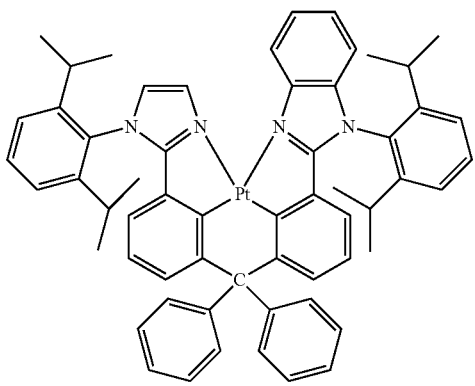
Compound 27
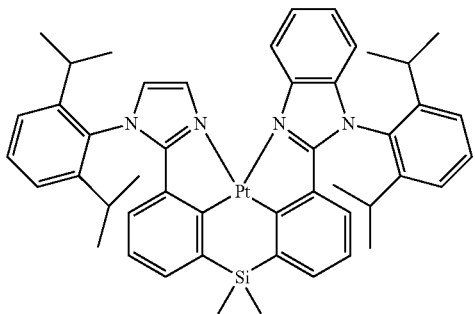
Compound 28
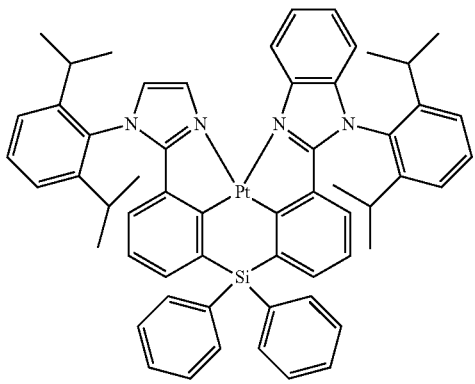

-continued
Compound 29
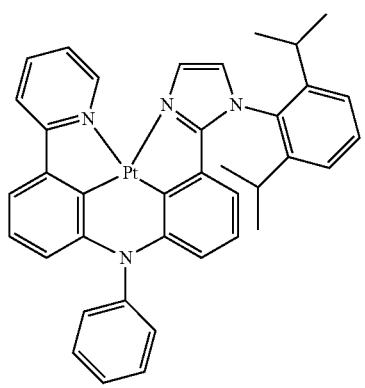
Compound 30
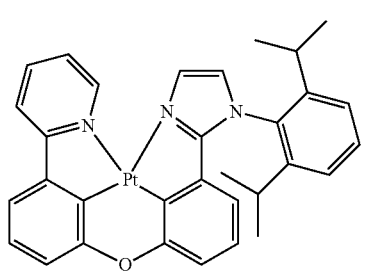
Compound 31
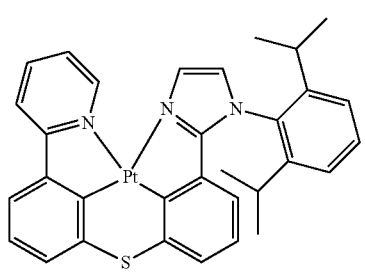
Compound 32
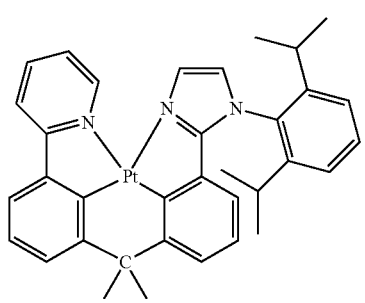
Compound 33
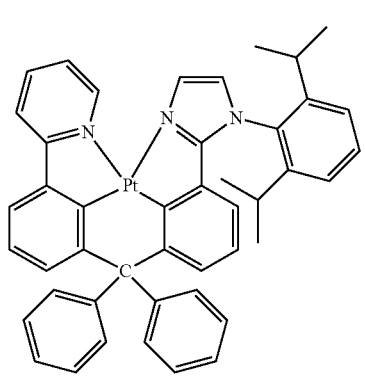
Compound 34
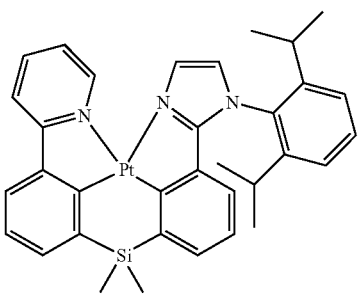
Compound 35
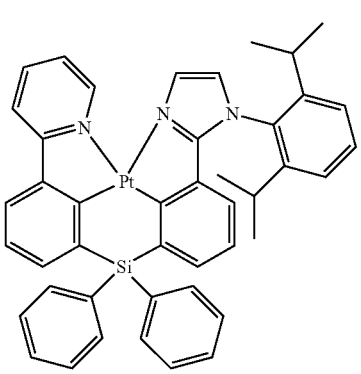
Compound 36
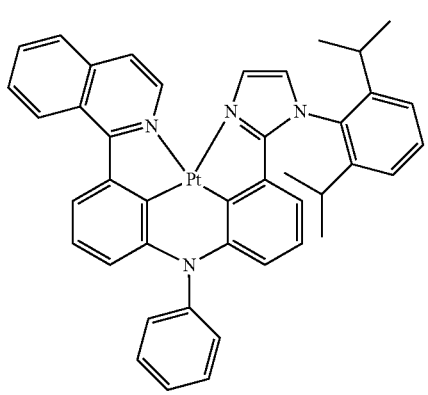
Compound 37
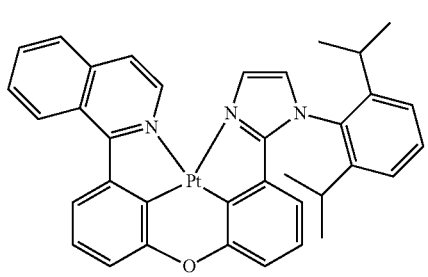
Compound 38
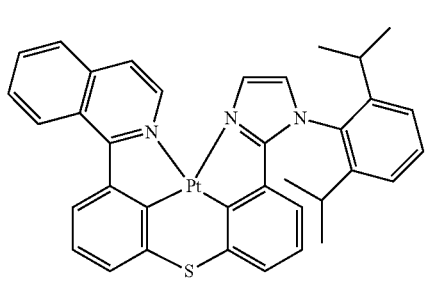

Compound 39
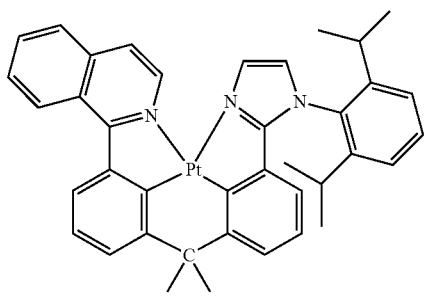
Compound 40
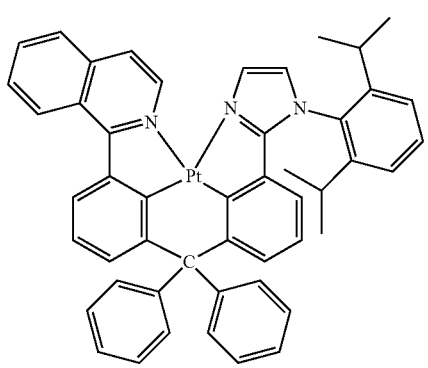
Compound 41
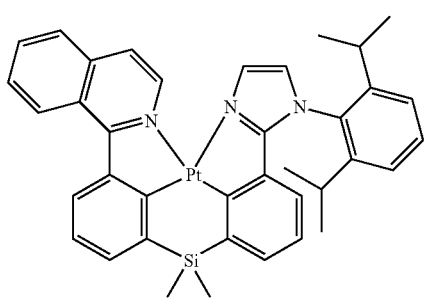
Compound 42
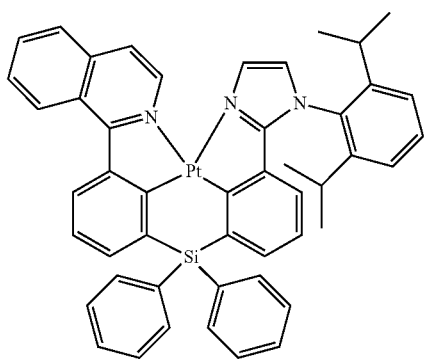
Compound 43
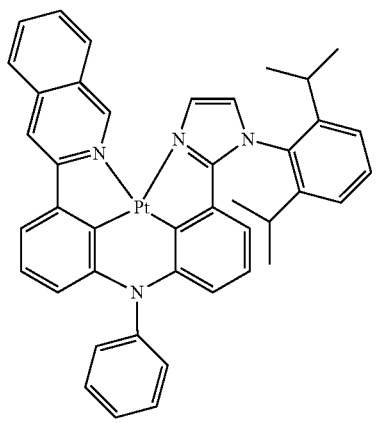
Compound 44
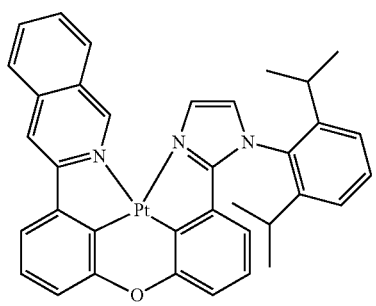
Compound 45
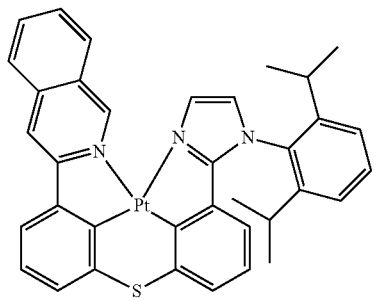
Compound 46
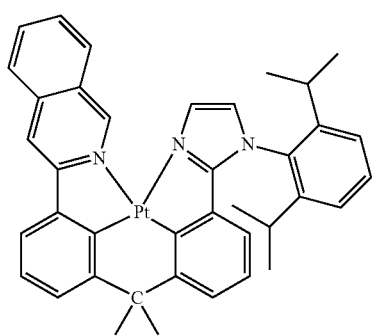

Compound 47
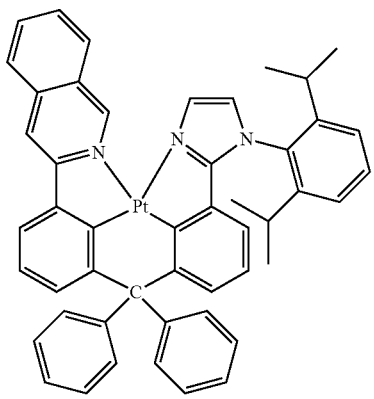
Compound 48
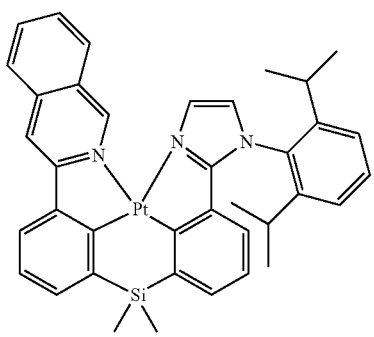
Compound 49
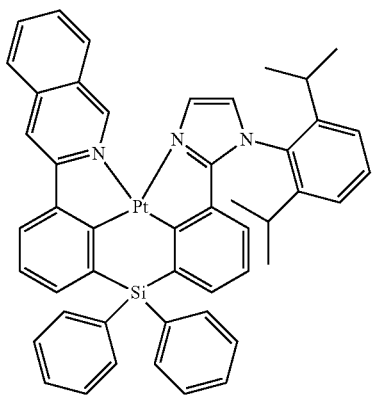
Compound 50
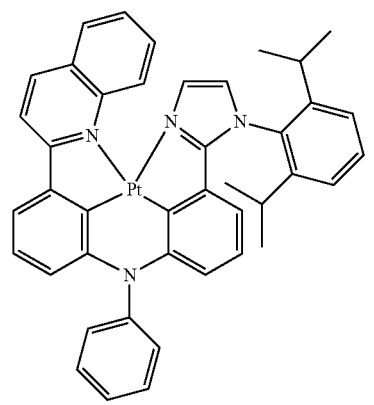
Compound 51
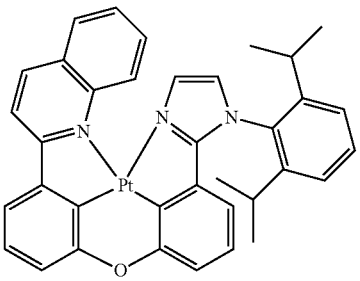
Compound 52
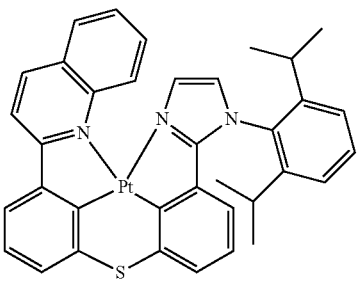
Compound 53
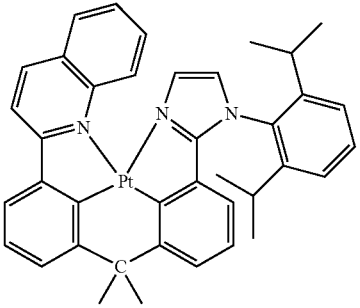
Compound 54
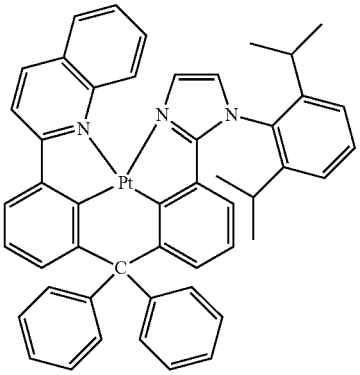

Compound 55
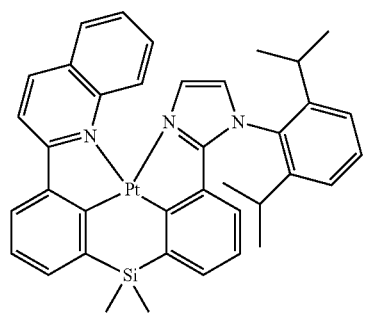
Compound 56
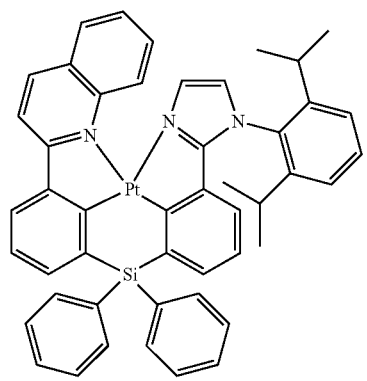
Compound 57
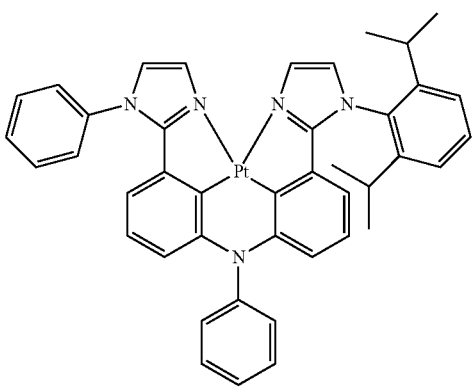
Compound 58
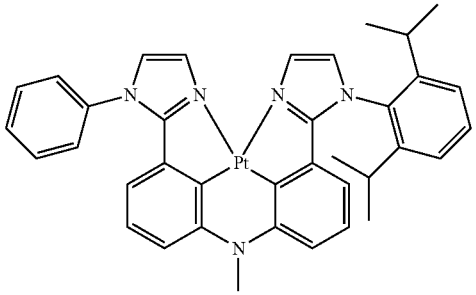
Compound 59
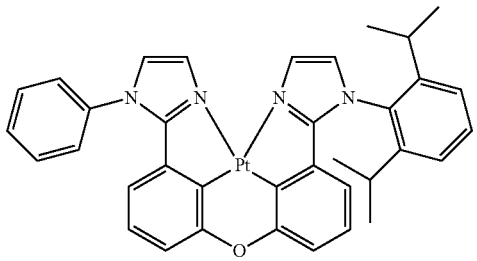
Compound 60
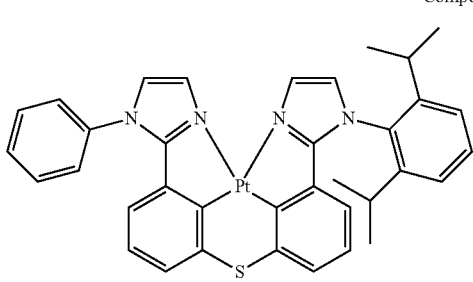
Compound 61
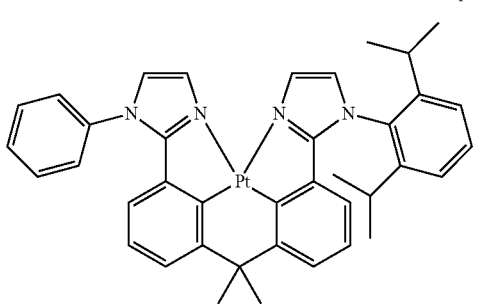
Compound 62
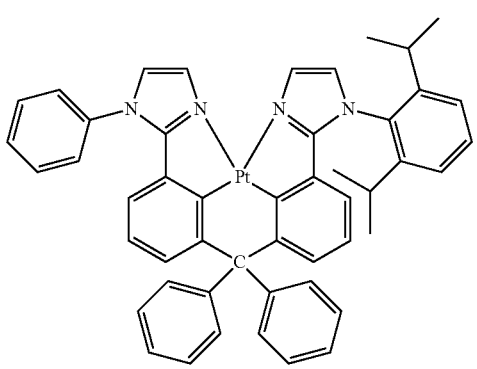
Compound 63
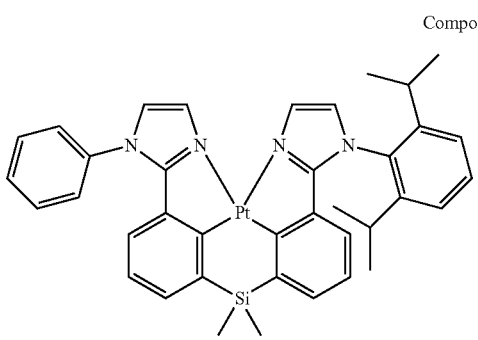

Compound 64
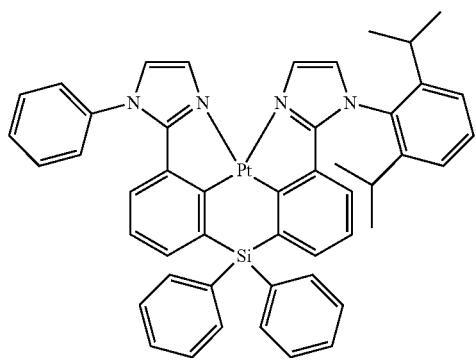
Compound 65
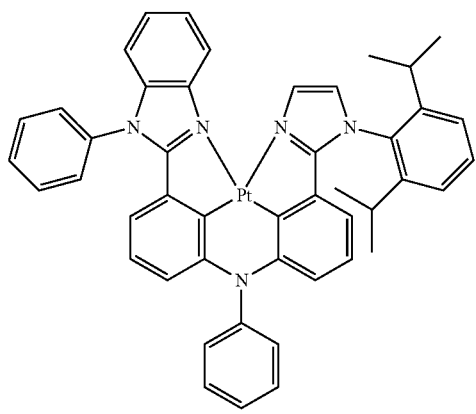
Compound 66
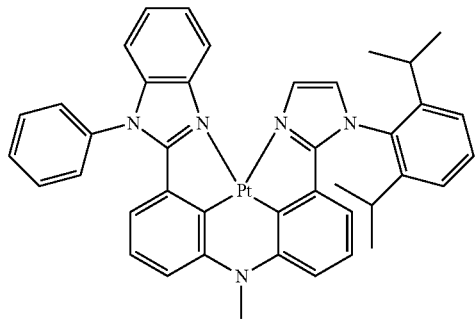
Compound 67
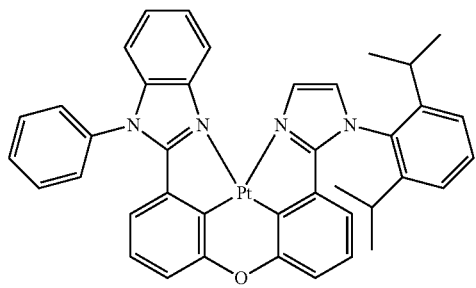
Compound 68
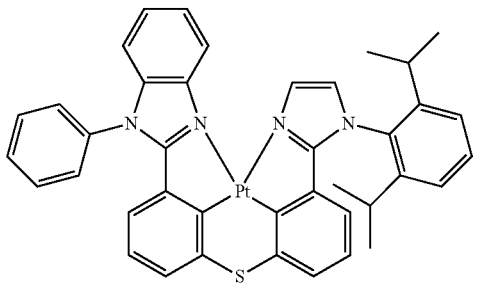
Compound 69
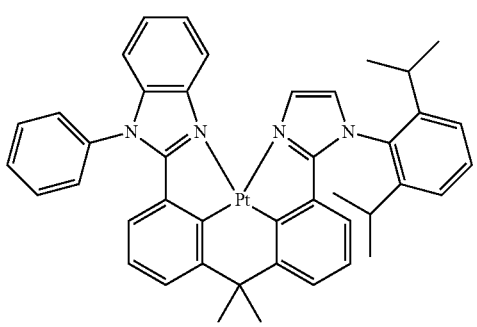
Compound 70
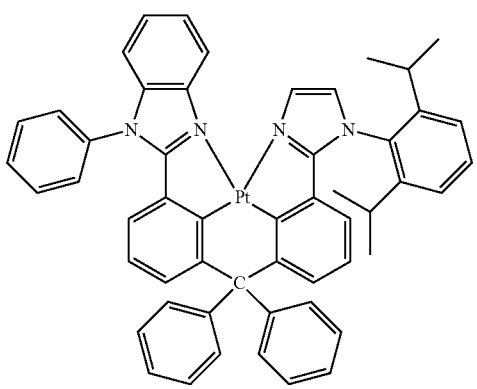
Compound 71
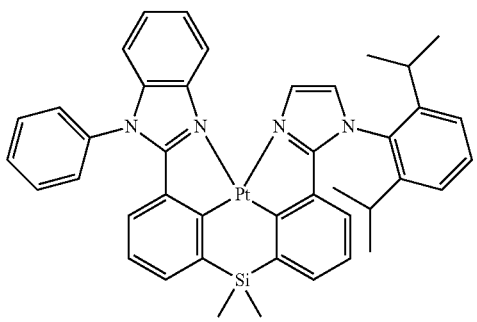

Compound 72
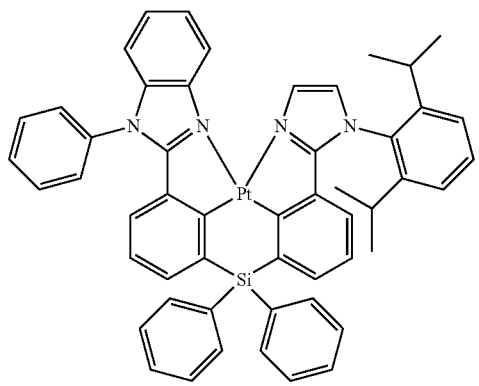
Compound 73
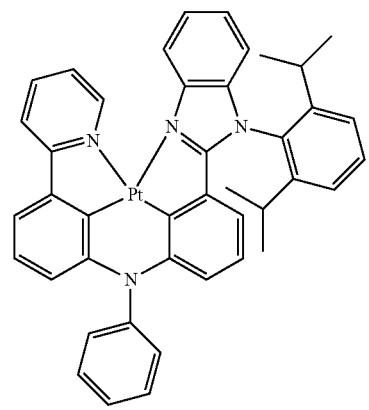
Compound 74
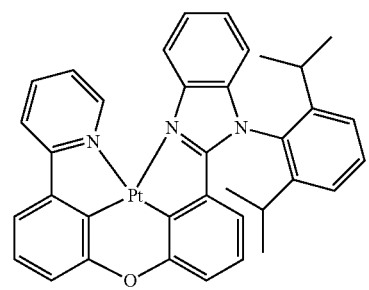
Compound 75
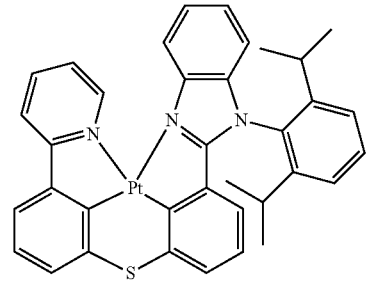
Compound 76
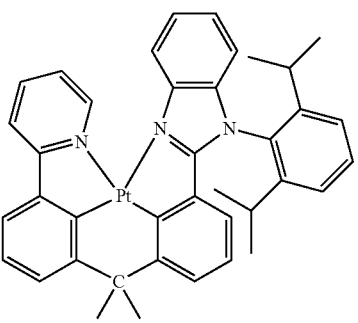
Compound 77
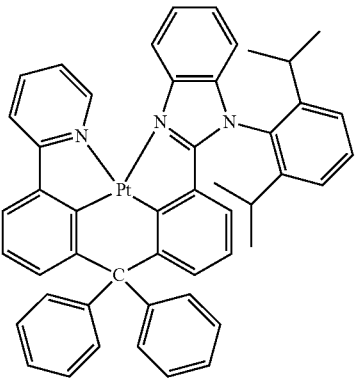
Compound 78
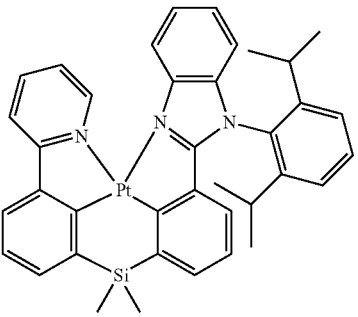
Compound 79
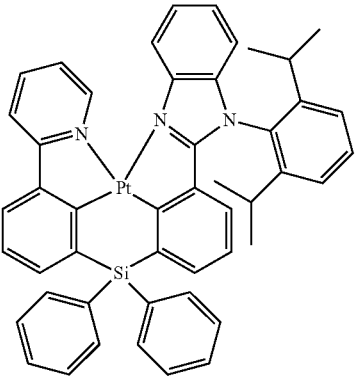

Compound 80
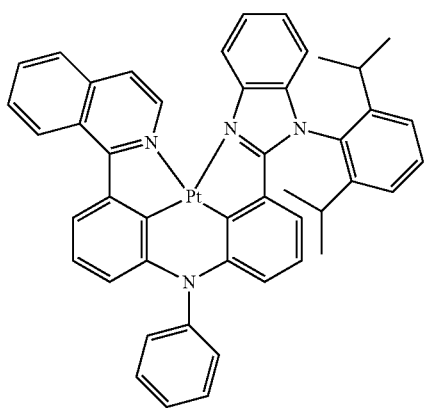
Compound 81
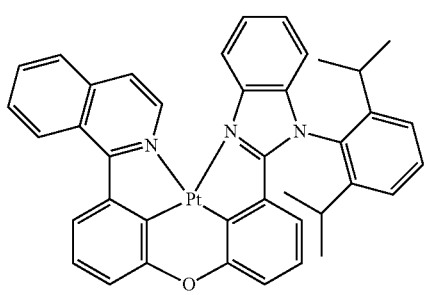
Compound 82
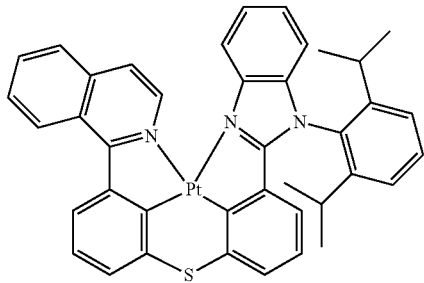
Compound 83
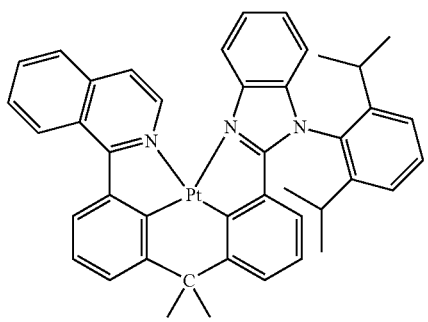
Compound 84
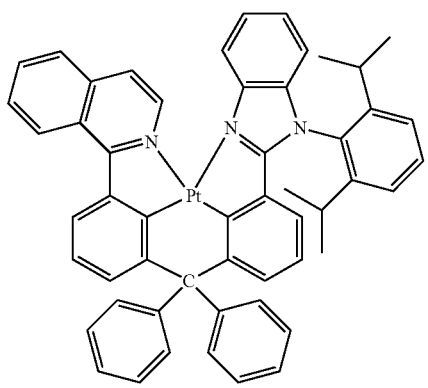
Compound 85
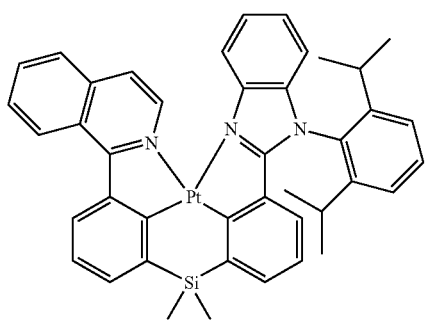
Compound 86
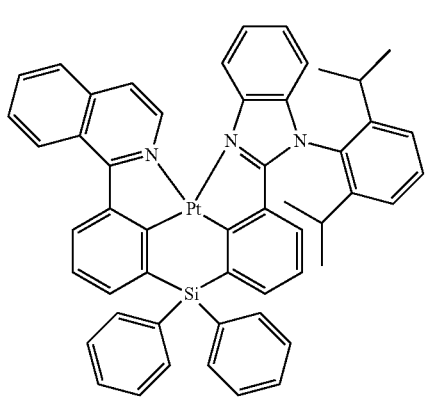
Compound 87
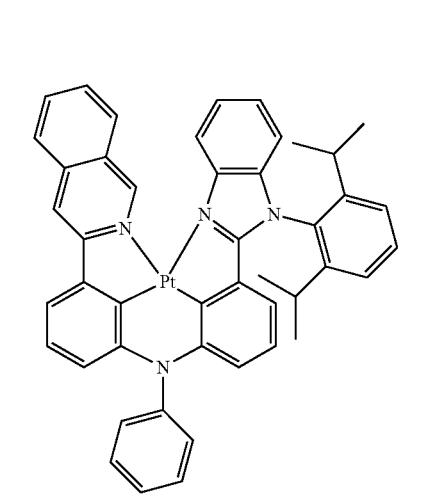

Compound 88
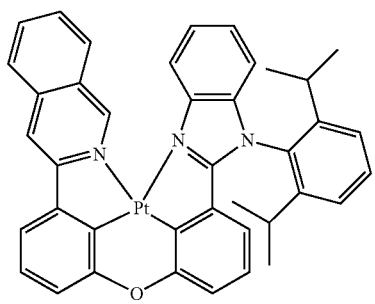
Compound 89
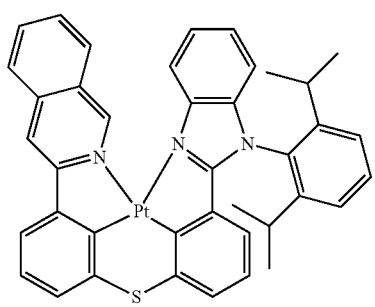
Compound 90
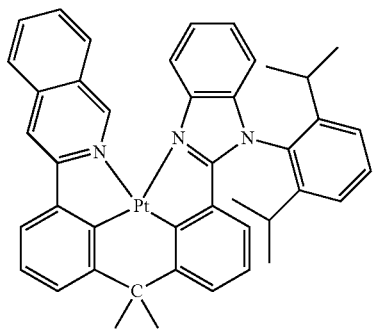
Compound 91
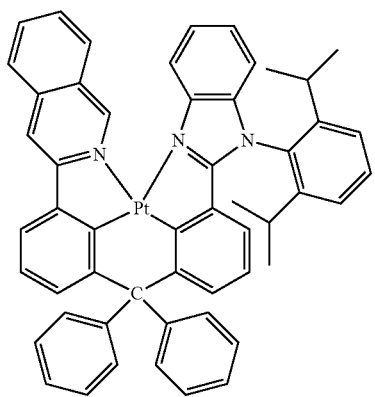
Compound 92
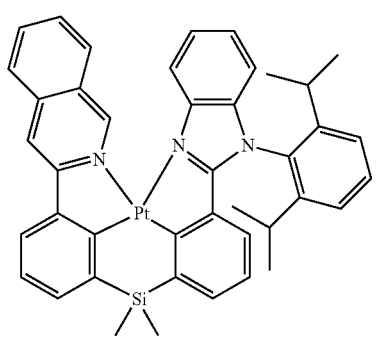
Compound 93
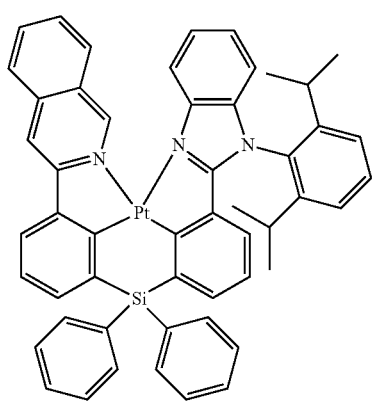
Compound 94
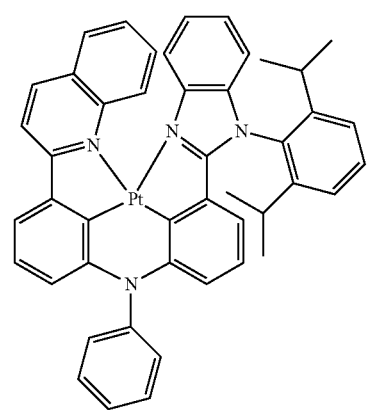
Compound 95
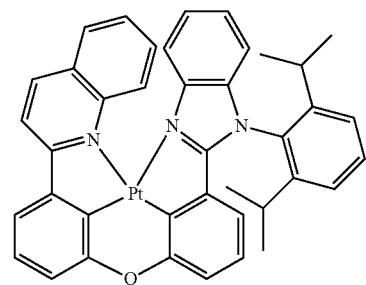

-continued
Compound 96
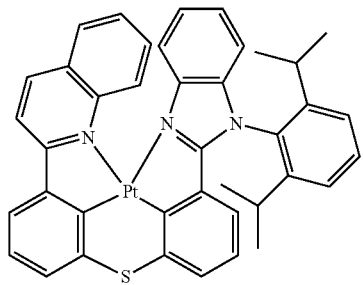
Compound 97
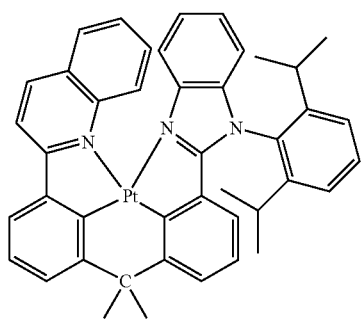
Compound 98
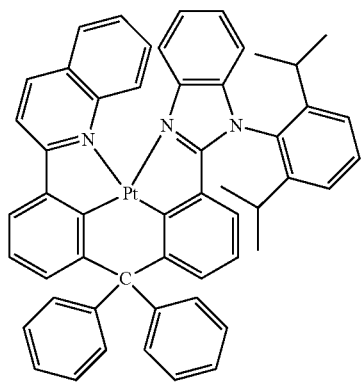
Compound 99
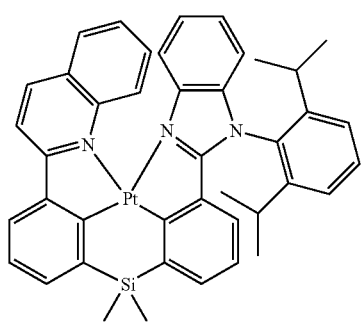
-continued
Compound 100
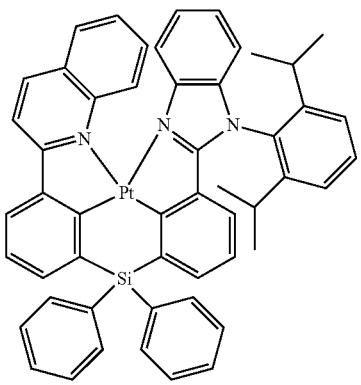
Compound 101
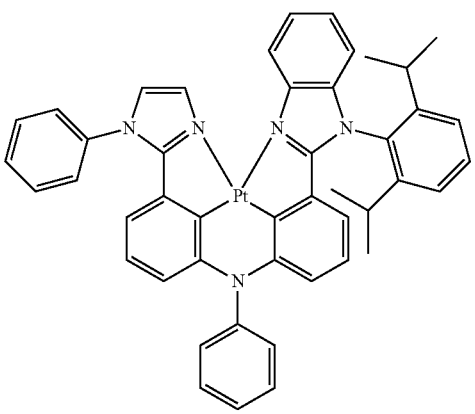
Compound 102
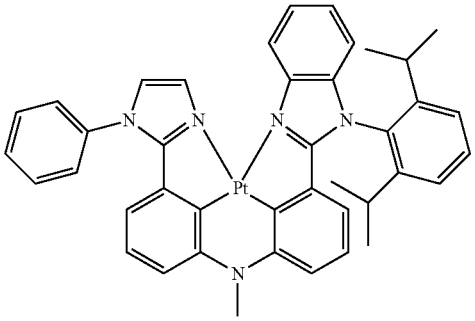
Compound 103
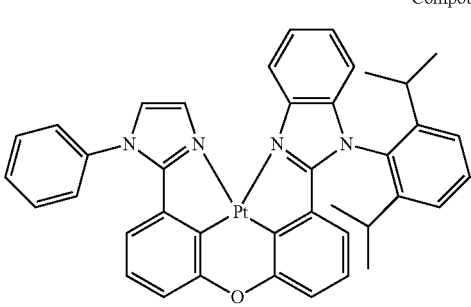

Compound 104
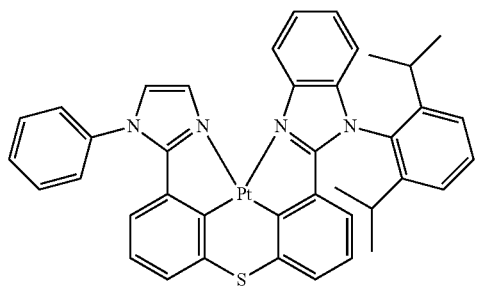
Compound 105
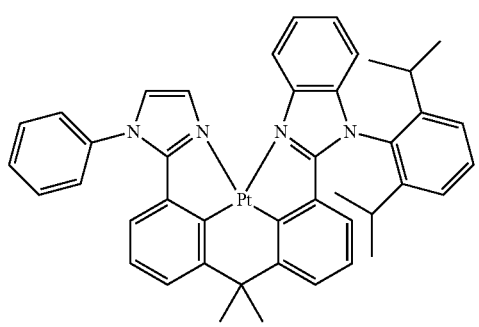
Compound 106
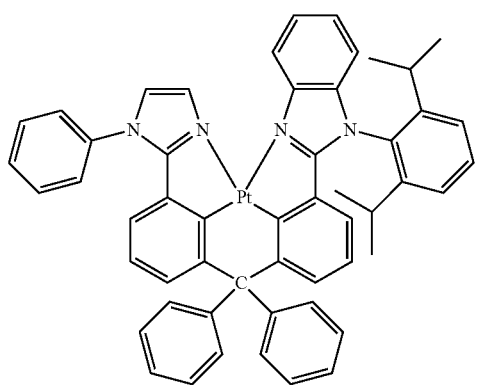
Compound 107
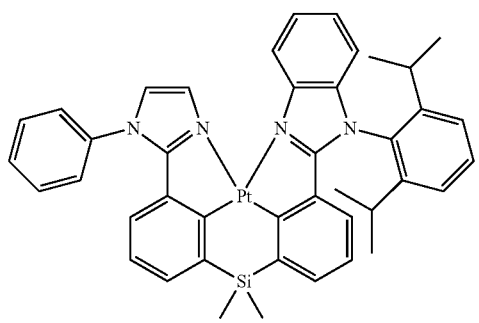
Compound 108
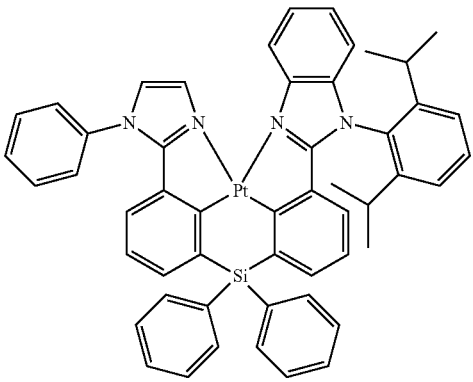
Compound 109
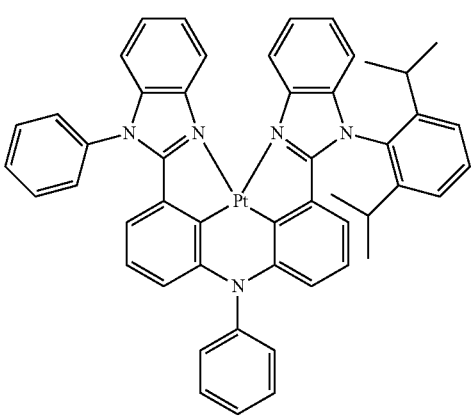
Compound 110
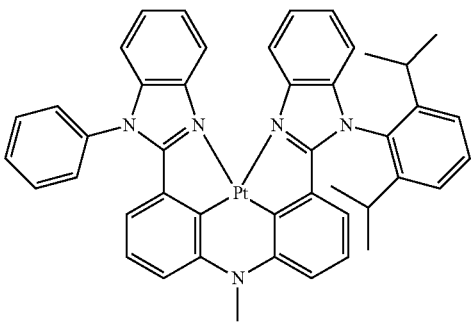
Compound 111
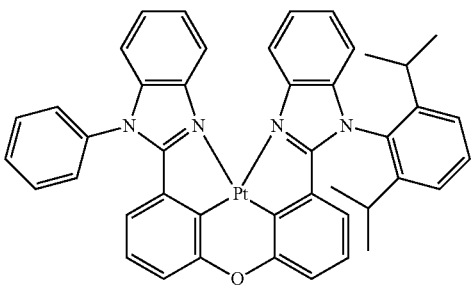

Compound 112
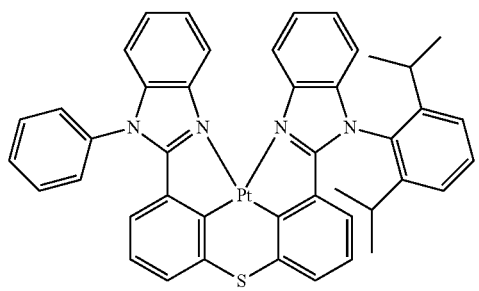
Compound 113
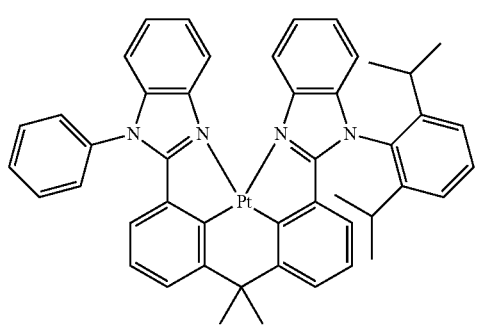
Compound 114
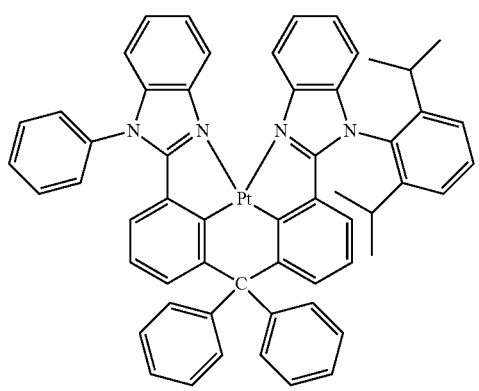
Compound 115
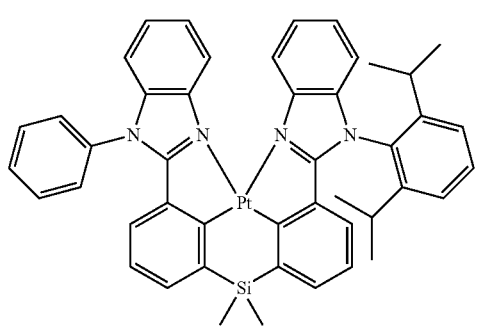
Compound 116
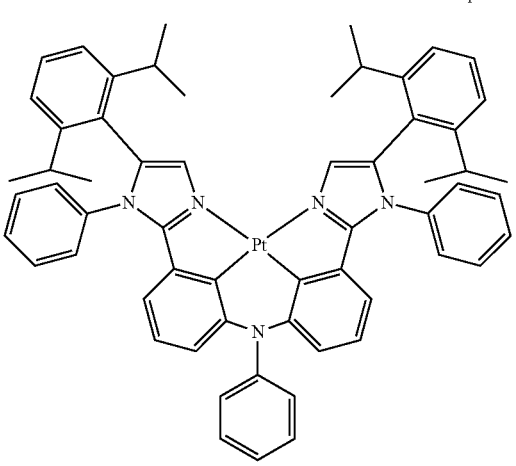
Compound 117
Compound 118
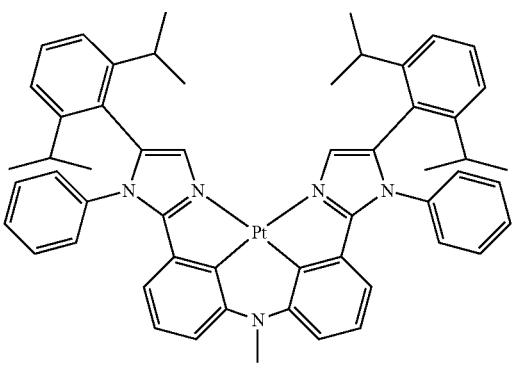
Compound 119
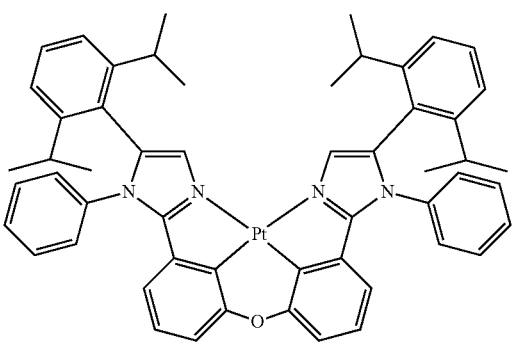

-continued
Compound 120
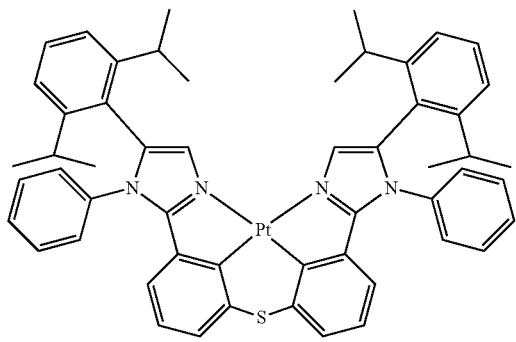
Compound 121
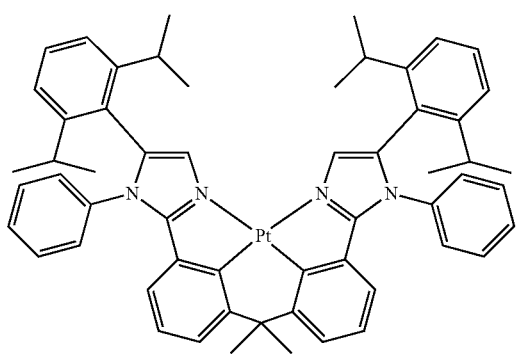
Compound 122
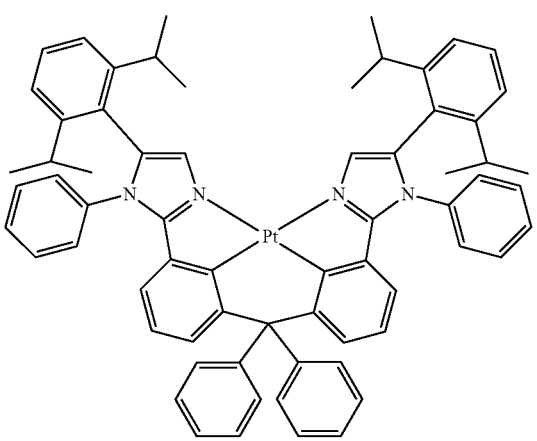
Compound 123
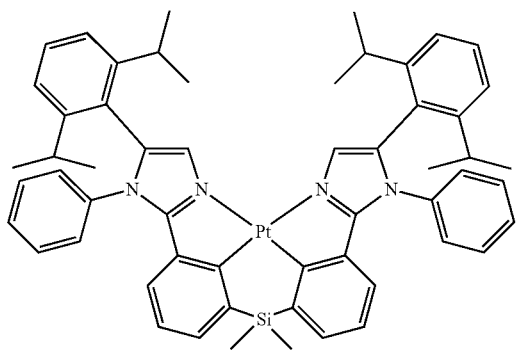
-continued
Compound 124
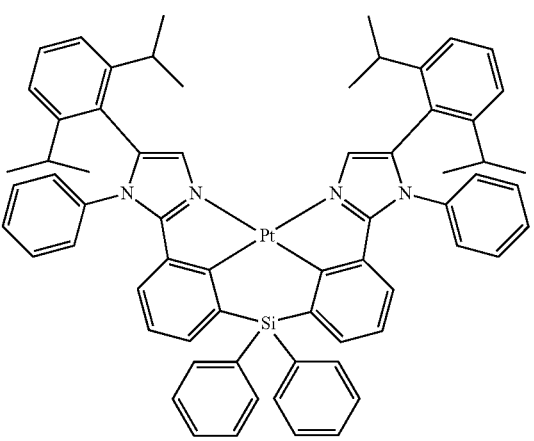
Compound 125
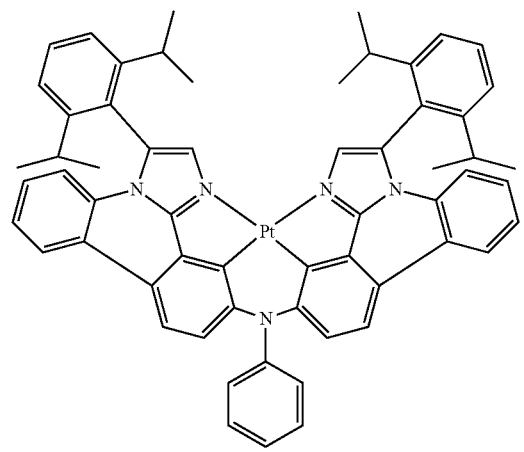
Compound 126
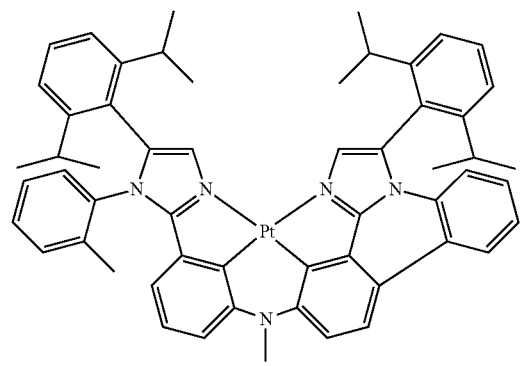

-continued
Compound 127
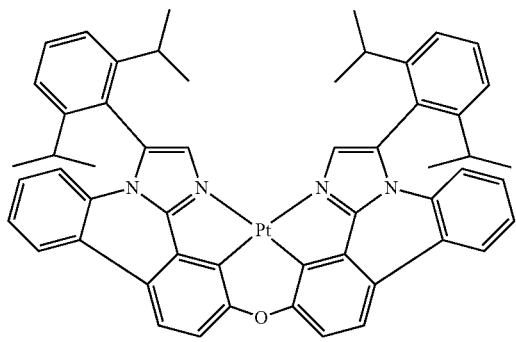
Compound 128
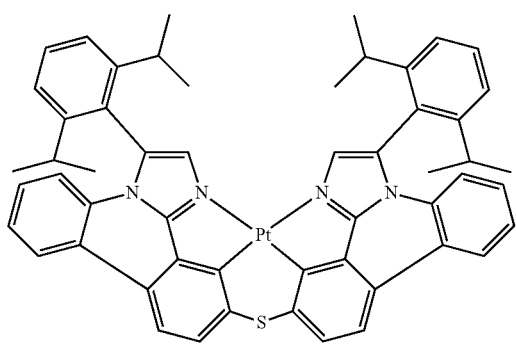
Compound 129
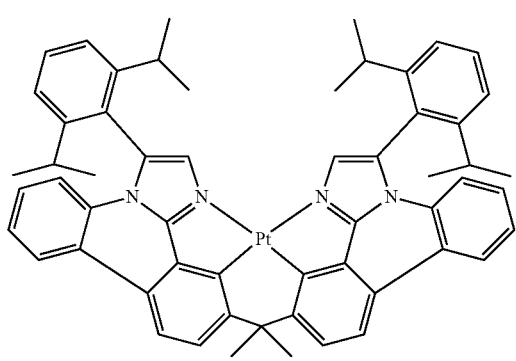
Compound 130
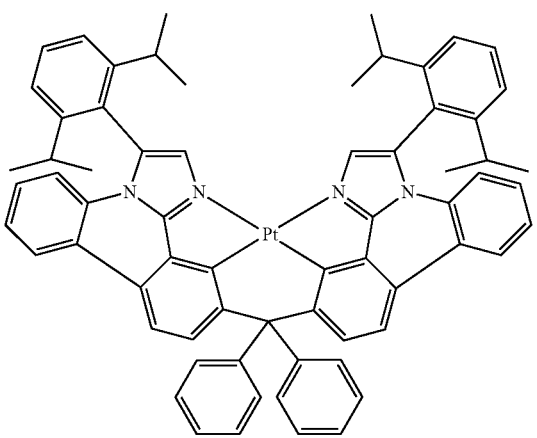
-continued
Compound 131
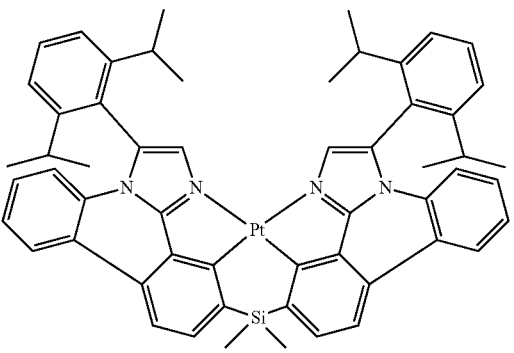
Compound 132
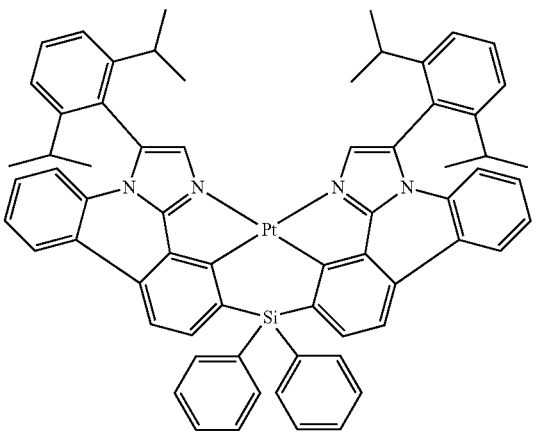
Compound 133
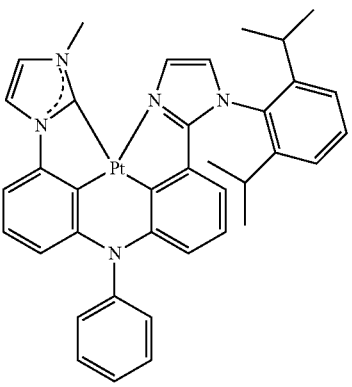
Compound 134
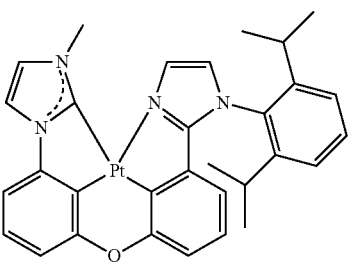

Compound 135
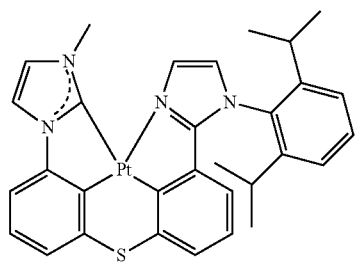
Compound 139
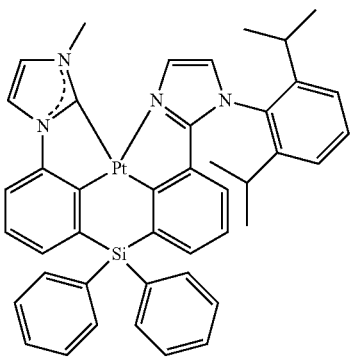
Compound 136
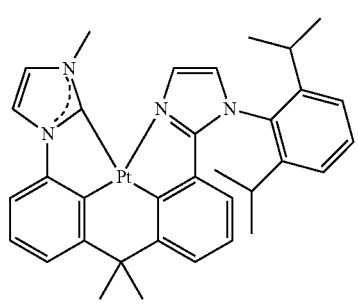
Compound 140
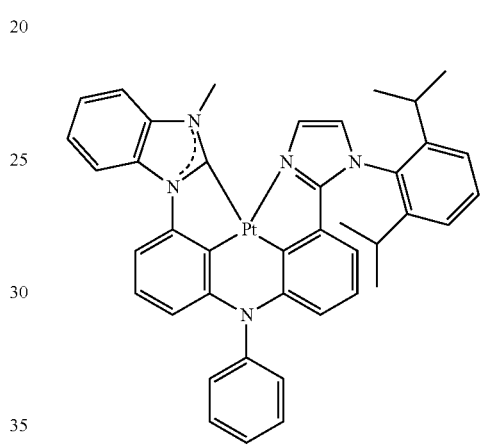
Compound 137
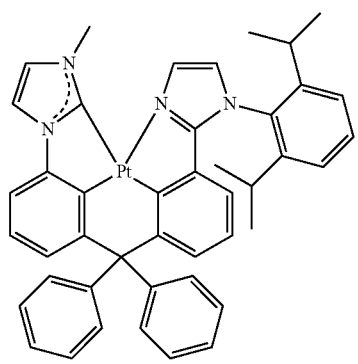
Compound 141
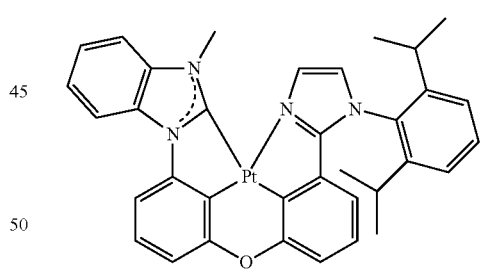
Compound 138
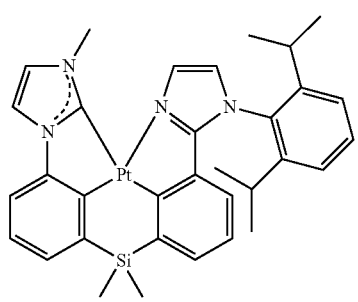
Compound 142
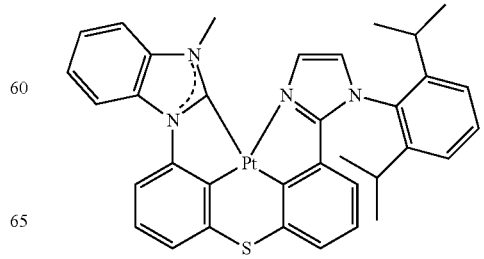

Compound 143
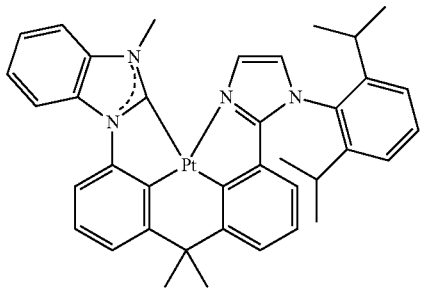
Compound 144
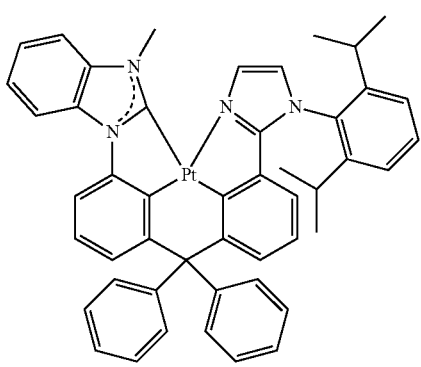
Compound 145
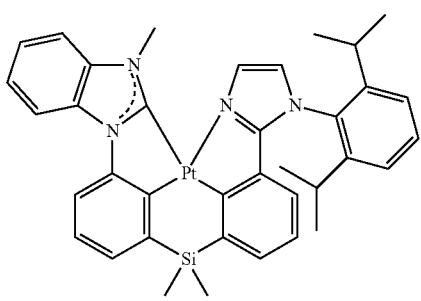
Compound 146
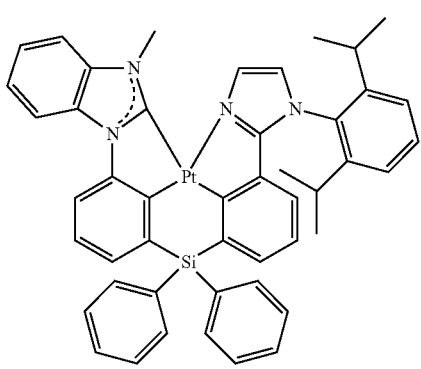
Compound 147
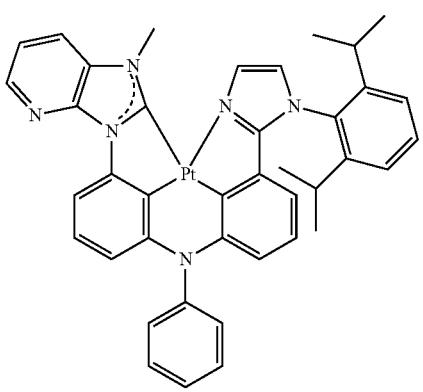
Compound 148
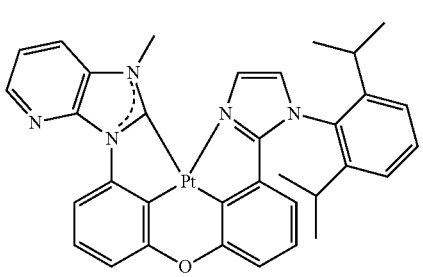
Compound 149
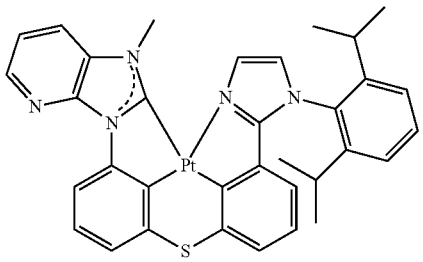
Compound 150
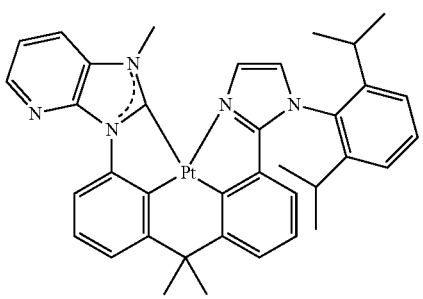

Compound 151
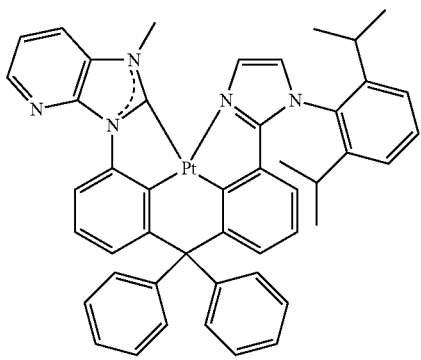
Compound 152
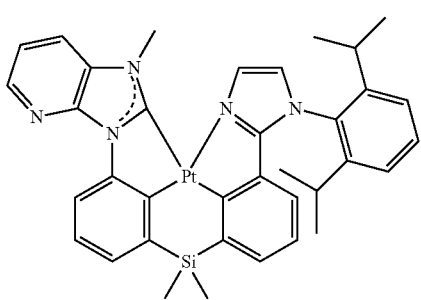
Compound 153
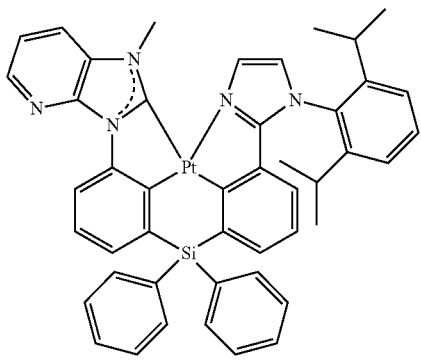
Compound 154
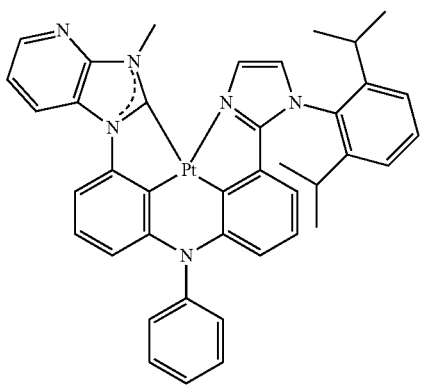
Compound 155
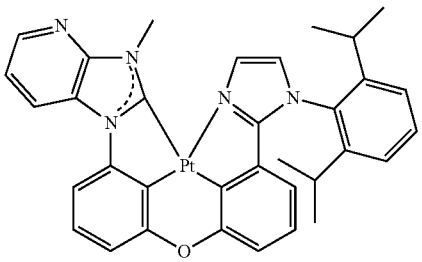
Compound 156
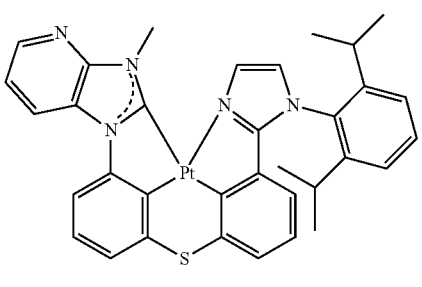
Compound 157

Compound 158
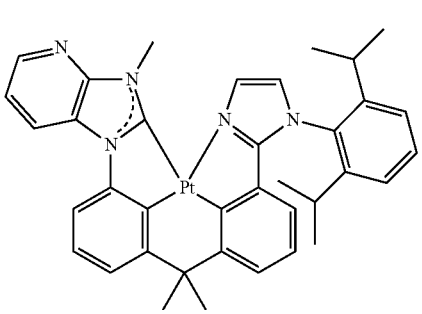
Compound 159
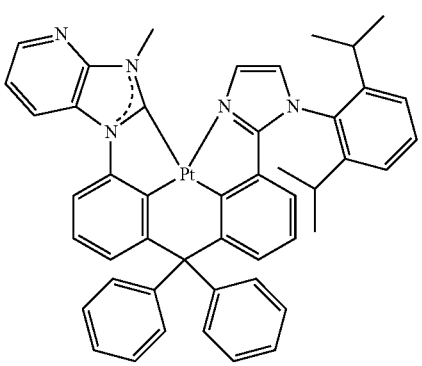

Compound 160

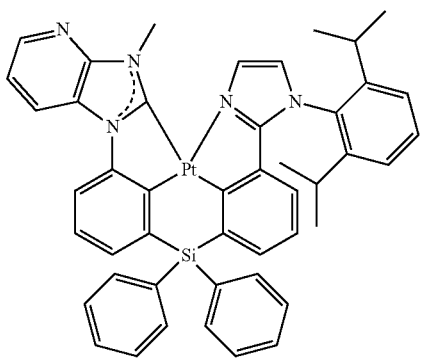

Compound 161

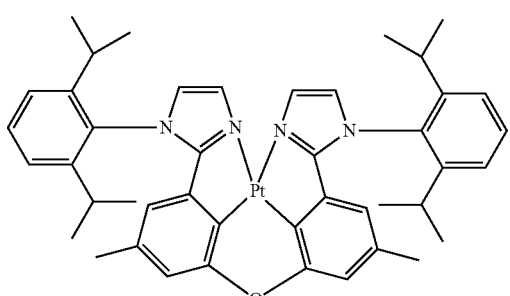

Compound 162

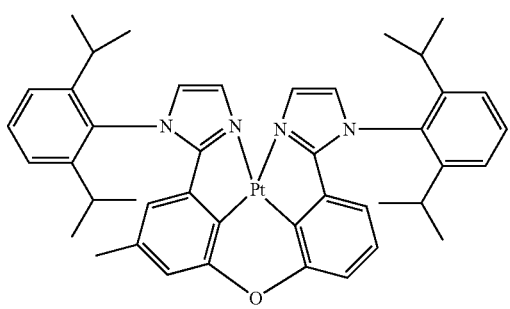

Compound 163

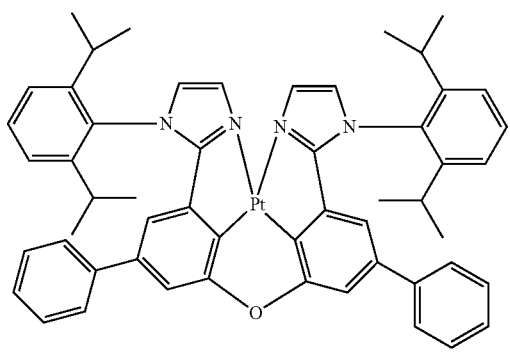

Compound 164

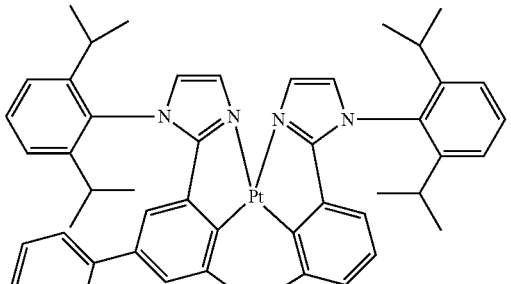

Compound 165

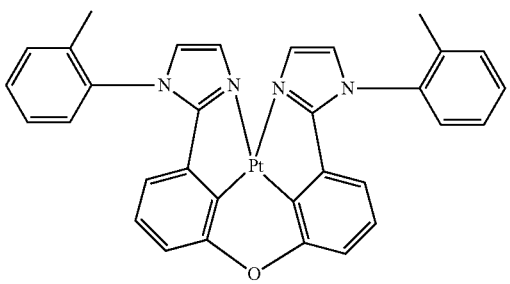

Compound 166

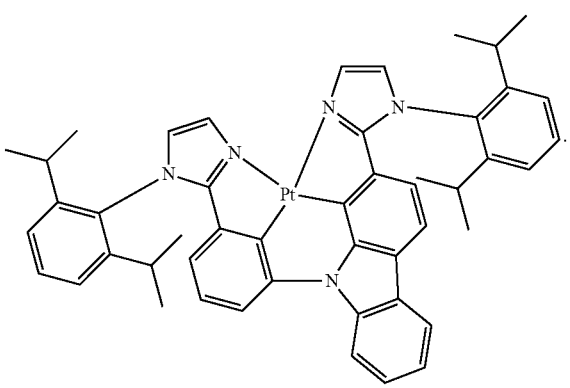

Additionally, a first device comprising an organic light emitting device is provided. The organic light emitting device further comprises an anode, a cathode, and an organic layer disposed between the anode and the cathode. The organic layer comprises a compound having the formula:

Formula I

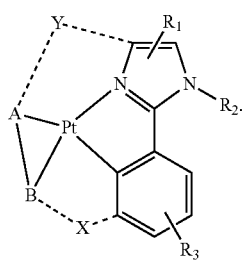

A and B are independently selected from the group consisting of a 5-membered or 6-membered carbocyclic or heterocyclic ring. A-B connects to Pt through one covalent bond and one coordination bond. X and Y are independently selected from the group consisting of BR, NR, PR, O, S, Se, C=O, S=O, SO$_2$, CRR', SiRR', and GeRR'. At least one of X and Y forms a bond between A-B and the 2-phenylimidazole. R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R_1$ and $R_3$ may represent mono, di, or tri substitutions. $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$, $R_2$, and $R_3$ are optionally joined to form a fused ring. At least one of $R_1$ and $R_2$ is:

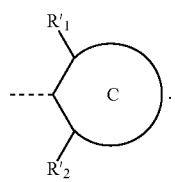

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is a 5-membered or 6-membered carbocyclic or heterocyclic ring that is optionally further substituted. Preferably, C is benzene.

In one aspect, the compound has the formula:

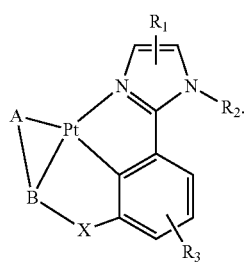

Formula II

In another aspect, the compound has the formula:

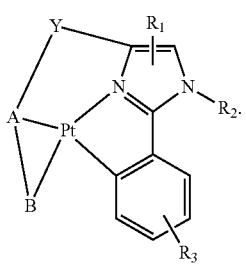

Formula III

In yet another aspect, the compound has the formula:

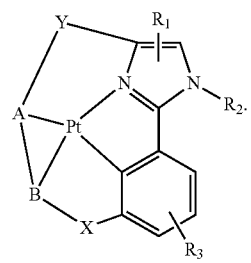

Formula IV

In one aspect, at least one of $R'_1$ and $R'_2$ is an alkyl and the other of $R'_1$ and $R'_2$ is hydrogen or deuterium. In another aspect, at least one of $R'_1$ and $R'_2$ is an alkyl having two or more carbon atoms and the other of $R'_1$ and $R'_2$ is hydrogen or deuterium. In yet another aspect, at least one of $R'_1$ and $R'_2$ is an alkyl having three or more carbon atoms and the other of $R'_1$ and $R'_2$ is hydrogen or deuterium.

In one aspect, each of $R'_1$ and $R'_2$ is an alkyl. In another aspect, each of $R'_1$ and $R'_2$ is an alkyl having two or more carbon atoms. In yet another aspect, each of $R'_1$ and $R'_2$ is an alkyl having three or more carbon atoms.

In one aspect, at least one of $R'_1$ and $R'_2$ is an aryl and the other of $R'_1$ and $R'_2$ is hydrogen or deuterium. In another aspect, each of $R'_1$ and $R'_2$ is an aryl. In yet another aspect, one of $R'_1$ and $R'_2$ is an alkyl and the other of $R'_1$ and $R'_2$ is an aryl.

In one aspect, the compound has the formula:

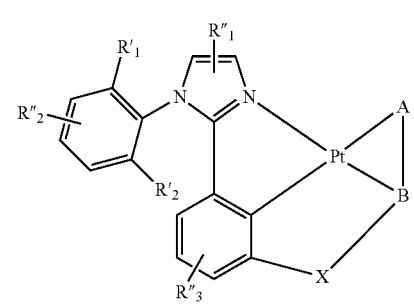

Formula V

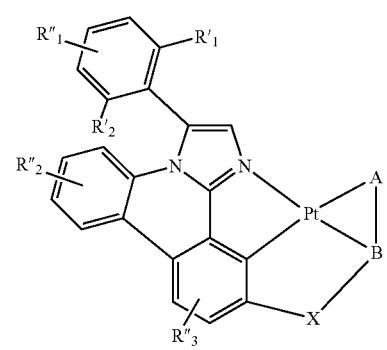

Formula VI

Formula VII

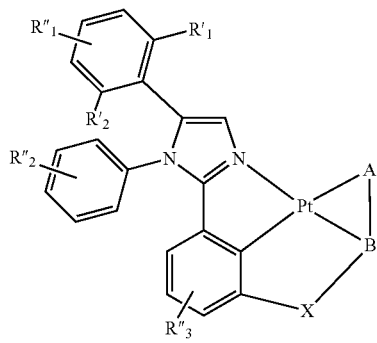

Formula VIII

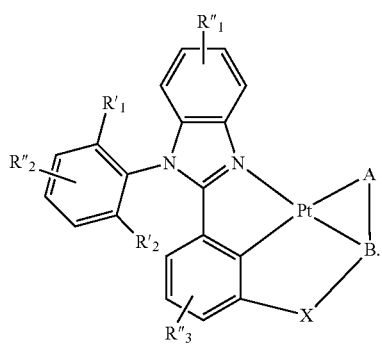

R"₁, R"₂, and R"₃ may represent mono, di, tri, or tetra substitutions. R"₁, R"₂, and R"₃ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of R"₁, R"₂, and R"₃ are optionally joined to form a fused ring.

In another aspect, the compound has a formula selected from the group consisting of:

Formula IX

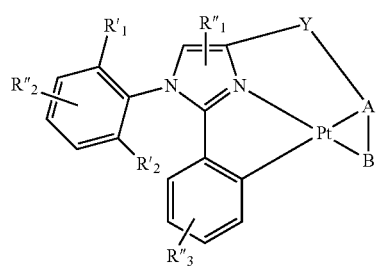

Formula X

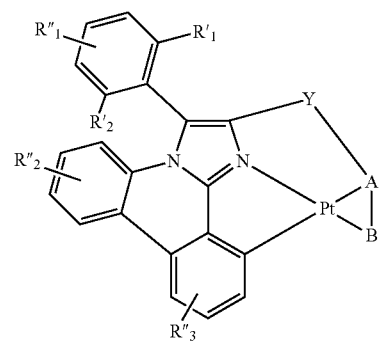

Formula XI

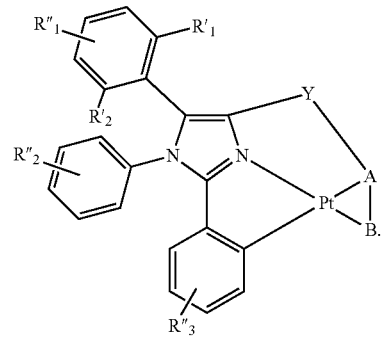

R"₁, R"₂, and R"₃ may represent mono, di, tri, or tetra substitutions. R"₁, R"₂, and R"₃ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of R"₁, R"₂, and R"₃ are optionally joined to form a fused ring.

In another aspect, A-B is selected from the group consisting of:

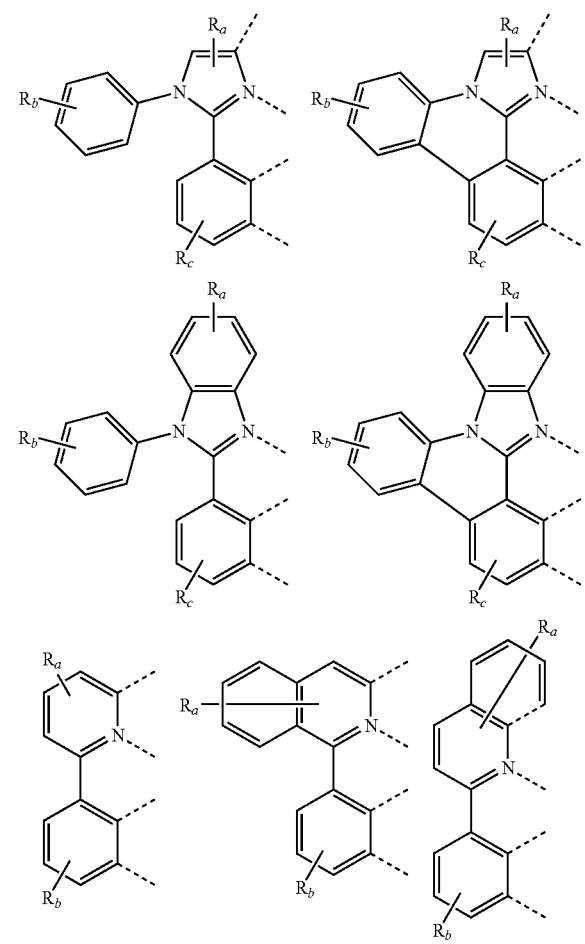

-continued

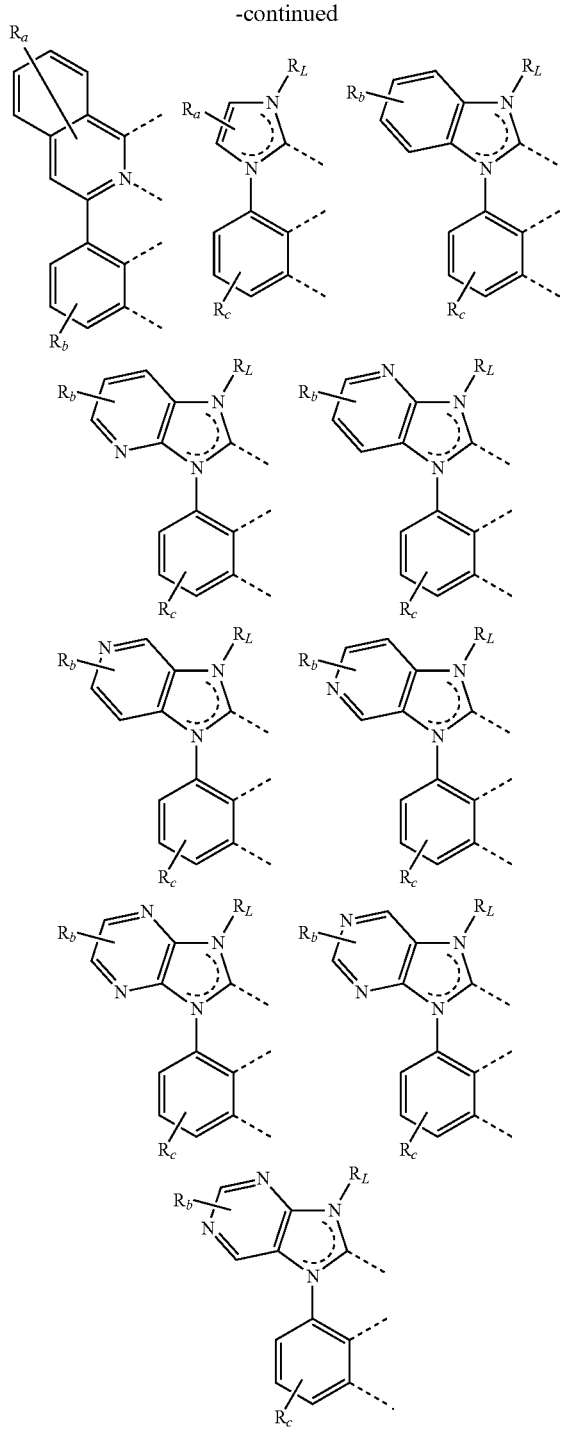

$R_a$, $R_b$, $R_c$ and $R_L$, may represent mono, di, tri or tetra substitutions. $R_a$, $R_b$, $R_c$ and $R_L$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, $R_c$ and $R_L$ are optionally joined to form a fused ring. $R_L$ is optionally a linker to connect A-B and 2-phenylimidazole.

Specific, non-limiting examples of devices comprising the platinum complexes are provided. In one aspect, the com- pound is selected from the group consisting of Compound 1G-Compound 42G. Specific examples of the platinum com- pounds that may be used in such devices include, but are not limited to, Compound 1-Compound 166.

In one aspect, the organic layer is an emissive layer and the compound is an emissive dopant. In another aspect, the organic layer further comprises a host.

In one aspect, the host is a compound that comprises at least one of the chemical groups selected from the group consisting of:

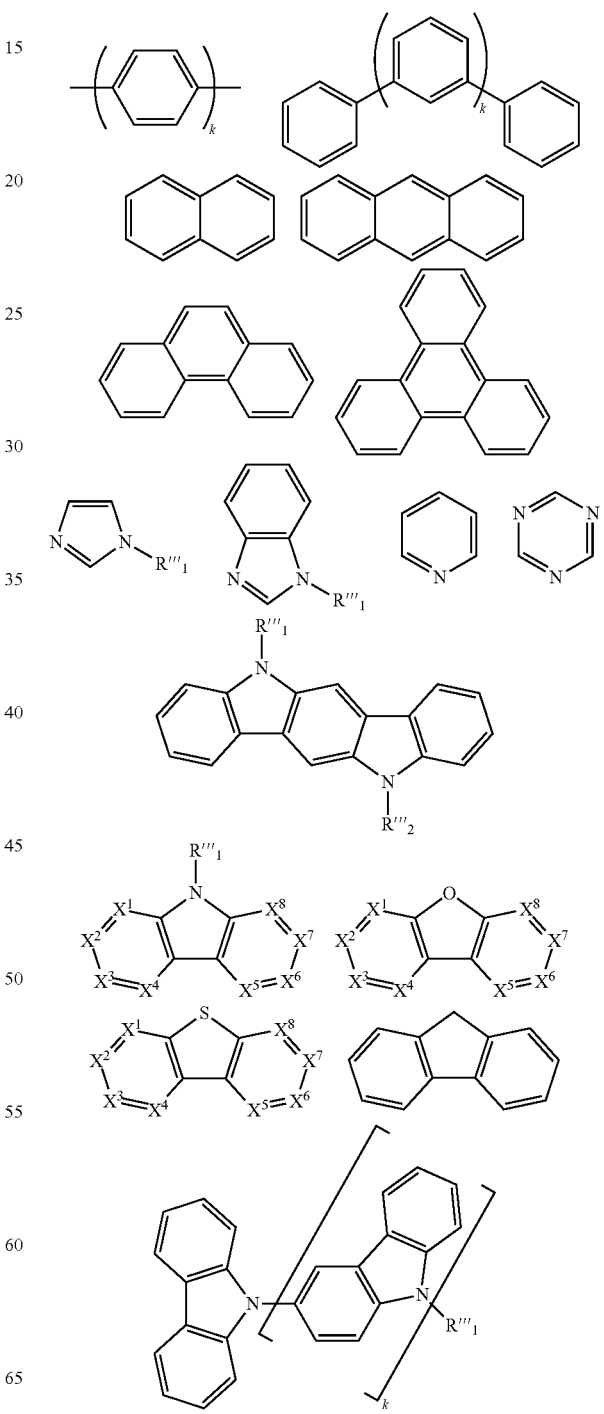

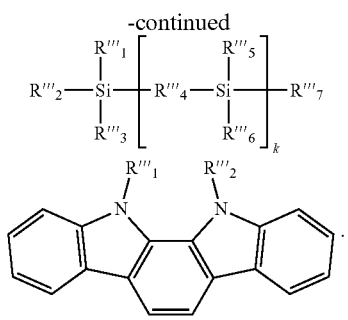

Each of $R'''_1$, $R'''_2$, $R'''_3$, $R'''_4$, $R'''_5$, $R'''_6$ and $R'''_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. k is an integer from 0 to 20. Each of $X^1$, $X^2$, $X^3$, $X^4$, $X^5$, $X^6$, $X^7$ and $X^8$ are independently selected from the group consisting of CH and N.

In another aspect, the host is a compound comprising a triphenylene containing benzo-fused thiophene or benzo-fused furan. Any substituent in the compound is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. n is 1, 2, 3, 4, 5, 6, 7, 8, 9, or 10. $Ar_1$ and $Ar_2$ are independently selected from the group consisting of benzene, biphenyl, naphthalene, triphenylene, carbazole, and heteroaromatic analogs thereof. Preferably, the host has the formula:

Compound A

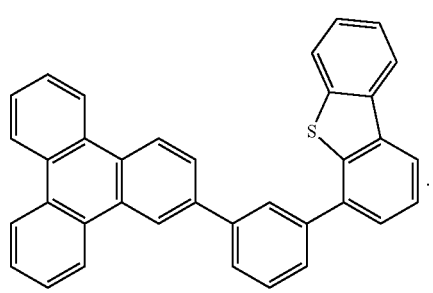

In yet another aspect, the host is a metal complex. In a further aspect, the metal complex is selected from the group consisting of:

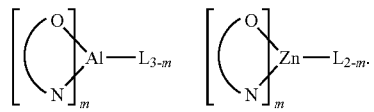

(O—N) is a bidentate ligand having metal coordinated to atoms O and N. L is an ancillary ligand. m is an integer value from 1 to the maximum number of ligands that may be attached to the metal. Preferably, the host is a metal 8-hydroxyquinolate.

In one aspect, the first device is a consumer product. In another aspect, the first device is an organic light emitting device.

A novel class of tetradentate platinum (II) compounds are provided (illustrated in FIG. 3). The compounds comprise an imidazo[1,2-f]phenanthridine moiety. The tetradentate platinum and the imidazo[1,2-f]phenanthridine moiety may provide improved efficiency and improved blue emission, respectively, making these compounds particularly suitable for use in an OLED.

Although the first demonstrated PHOLED contained a platinum complex, 2,3,7,8,12,13,17,18-octaethyl-21H,23H-porphine platinum (II) (PtOEP), platinum complexes have not found any practical use in state-of-the-art PHOLEDs. (Nature, 1998, 395, 151). Compared to iridium complexes, platinum (II) complexes generally have a relatively long excited state lifetime and a lower quantum yield. In addition, platinum (II) complexes adopt a square planar geometry, which often causes excimer formation. Therefore, these complexes may have broadened emission spectrum at a higher doping concentration in an OLED.

Bidentate and tridentate Pt (II) complexes have been reported, but, generally, these compounds have limited application in OLEDs. These complexes often have poor thermal stability and device stability, thereby limiting their application in OLEDs.

Tetradentate Pt (II) complexes have also been disclosed in literature, but, similar to the bidentate and tridentate Pt (II) complexes, these tetradentate Pt(II) complexes may have limited use in OLEDs.

As discussed above, the tetradentate platinum (II) complexes provided herein have several beneficial characteristics. First, the tetradentate platinum offers potential advantages compared to iridium. Tuning a tris(cyclometallated) iridium compound, such as Ir(ppy)$_3$, can be difficult because of the multiple ligands. Electronic tuning is generally achieved by substitution of the ligands bound to the metal, but the addition of substituents increases the sublimation temperature. Tris (cyclometallated) iridium compounds may have higher molecular weights and, thus, the number and type of substituents is limited by the sublimation temperature, e.g., <350° C. However, it may be more feasible to further tune a platinum tetradentate compound. Platinum tetradentate compounds have fewer ligands and, thus, a lower molecular weight. Therefore, a larger number of substituents and more varied substituents of higher molecular weight may be added to the cyclometallating ligands. Second, tetradentate platinum complexes may also have greater thermal stability than iridium complexes. A single ligand is bound to the metal four times in a tetradentate platinum complex, whereas a bidentate ligand in an iridium complex has only two binding sites to the metal. Third, platinum compounds have demonstrated increased photooxidative stability compared to analogous iridium compounds. Finally, the imidazo[1,2-f]phenanthridine moiety has a high triplet energy that may provide an improved blue color.

Taken together, these characteristics of the inventive compounds may provide beneficial properties that make these compounds particularly suitable for use in OLEDs. For example, the compounds may provide improved blue emission and improved efficiency.

Tetradentate platinum (II) compounds comprising an imidazo[1,2-f]phenanthridine moiety are provided. The compounds have the formula:

Formula I'

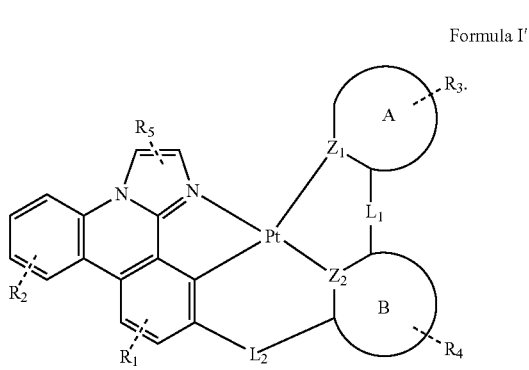

Ring A and ring B are each independently a 5- or 6-membered carbocyclic or heterocyclic ring. $L_1$ and $L_2$ are independently selected from the group consisting of a single bond, BR, NR, PR, O, S, Se, C=O, S=O, $SO_2$, CRR', SiRR', and GeRR'. Without being bound by theory, it is believed that linking the imidazo[1,2-f]phenanthridine ligand to the A-B ligand through the phenyl ring of imidazo[1,2-f]phenanthridine and the B ring of A-B, i.e., connected via $L_2$, may improve the stability and photoluminescent quantum yield of the compound.

$Z_1$ and $Z_2$ are independently a nitrogen atom or a carbon atom. $R_1$, $R_2$, $R_3$, $R_4$, and $R_5$ may represent mono, di, tri, or tetra substitutions. R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substitutents of R, R', $R_1$, $R_2$, $R_3$, $R_4$, and $R_5$ are optionally joined to form a fused ring.

Each substituent may have one or more points at which it is attached to the structure illustrated in Formula I'. Where there are multiple points of attachment, a fused ring or a more complex structure may be formed. Multiple points of attachment may be within the same R group, or may extend across different R groups. For example, within the same R group, $R_1$ may represent a phenyl ring fused to the appropriate phenyl of Formula I':

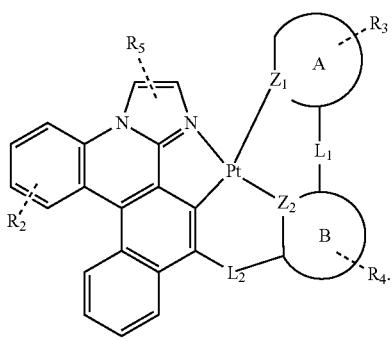

Across different R groups, for example, $R_1$ and $R_2$ may represent an alkyl chain attached to two different phenyl rings of Formula 'I:

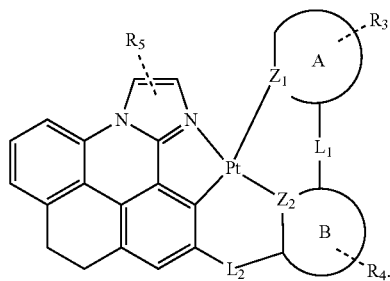

More generally, it is intended that the structure of Formula I' may be further substituted in any manner.

In one aspect, $L_1$ is selected from the group consisting of BR, NR, PR, O, S, Se, C=O, S=O, $SO_2$, CRR', SiRR', and GeRR'. Without being bound by theory, it is thought that a single bond between ring A and ring B in the A-B ligand may result in an undesired red-shifted emission, i.e., lower energy emission. For example, a compound having phenyl pyridine as the A-B ligand may have a red-shifted emission color than a compound where $L_1$ is selected from BR, NR, PR, O, S, Se, C=O, S=O, $SO_2$, CRR', SiRR', and GeRR', e.g., Compound 1 where $L_1$ is O, or Compound 2 where $L_1$ is N.

In one aspect, $R_5$ is aryl or substituted aryl. In another aspect, $R_5$ is a 2,6-disubstituted aryl.

Preferably, $R_5$ is

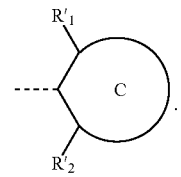

$R'_1$ and $R'_2$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. At least one of $R'_1$ and $R'_2$ is not hydrogen or deuterium. C is 5-membered or 6-membered carbocyclic or heterocyclic ring that is optionally further substituted.

In one aspect, at least one fused ring is formed by joining two adjacent substituents of R, R', $R_1$, $R_2$, $R_3$, $R_4$, and $R_5$. In another aspect, R or R' is joined to $R_3$ or $R_4$ to form a fused ring. When the adjacent substituents are joined to form a ring, the A-B ligand is more rigid because the substituents are not free to rotate. Without being bound by theory, it is believed that the increased rigidity of the A-B ligand, resulting from joining adjacent substituents to form fused rings, may provide a narrow spectrum.

In one aspect, the ligand

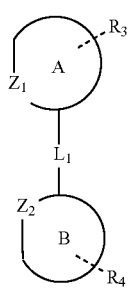

has a triplet energy higher than or equal to the triplet energy of

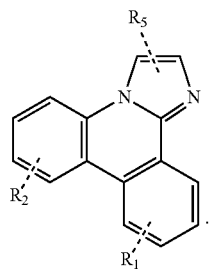

In one aspect, the compound has the formula:

Formula II'

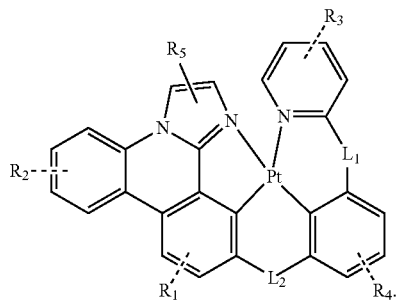

In another aspect, the compound has the formula:

Formula III'

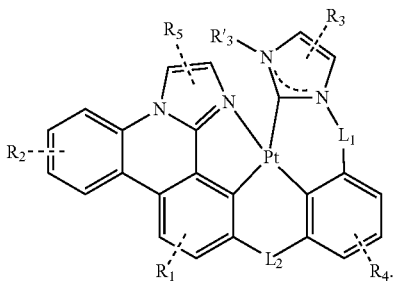

R'$_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another aspect, the compound has the formula:

Formula IV'

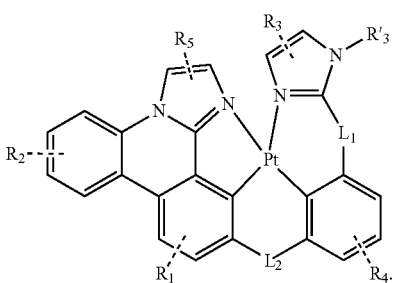

R'$_3$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

Formula V'

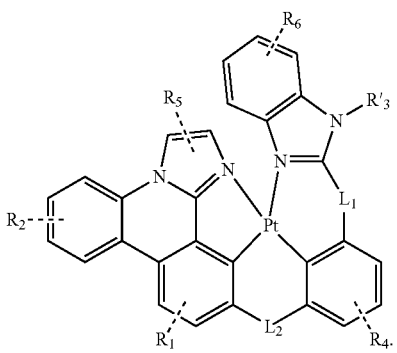

R$_6$ may represent mono, di, tri, or tetra substitutions. R'$_3$ and R$_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

Formula VI'

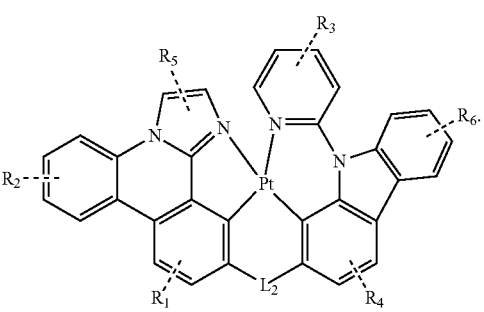

R$_6$ may represent mono, di, tri, or tetra substitutions. R$_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In yet another aspect, the compound has the formula:

Formula VII'

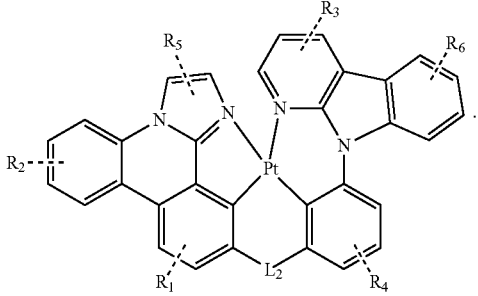

$R_6$ may represent mono, di, tri, or tetra substitutions. $R_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

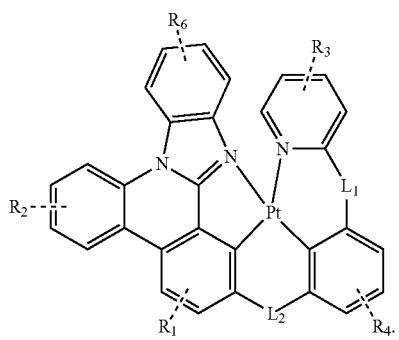

Formula VIII'

$R_6$ may represent mono, di, tri, or tetra substitutions. $R_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In another aspect, the compound has the formula:

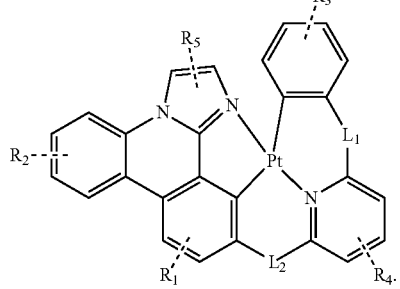

Formula IX'

In yet another aspect, the compound has the formula:

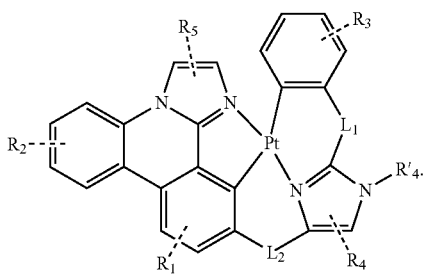

Formula X'

$R'_4$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In a further aspect, the compound has the formula:

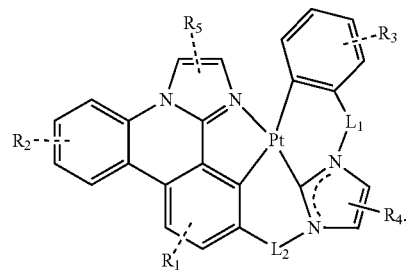

Formula XI'

Specific, non-limiting examples of the tetradentate platinum (II) compounds are provided. In one aspect, the compound is selected from the group consisting of Compounds 1'-241'.

Additionally, a first device is provided. The first device comprises an organic light emitting device. The first organic light emitting device further comprises an anode, a cathode, and an organic layer, disposed between the anode and the cathode. The organic layer comprises a compound having the formula:

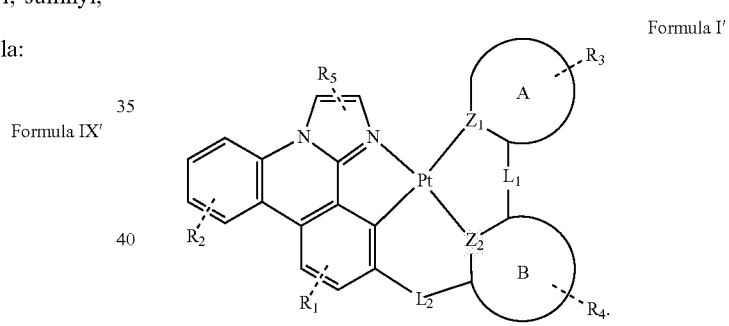

Formula I'

Ring A and ring B are each independently a 5- or 6-membered carbocyclic or heterocyclic ring. $L_1$ and $L_2$ are independently selected from the group consisting of a single bond, BR, NR, PR, O, S, Se, C=O, S=O, $SO_2$, CRR', SiRR', and GeRR'. $Z_1$ and $Z_2$ are independently a nitrogen atom or a carbon atom. $R_1$, $R_2$, $R_3$, $R_4$, and $R_5$ may represent mono, di, tri, or tetra substitutions. R, R', $R'_1$, $R'_2$, $R'_3$, $R'_4$, $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substitutents of R, R', $R_1$, $R_2$, $R_3$, $R_4$, and $R_5$ are optionally joined to form a fused ring.

The various aspects discussed above for compounds having Formula I' are also applicable to a compound having Formula I' that is used in the first device. In particular, specific aspects of ring A, ring B, $L_1$, $L_2$, R, R', $R'_1$, $R'_2$, $R'_3$, $R'_4$, $R_1$, $R_2$, $R_3$, $R_4$, $R_5$, $R_6$, Formulas I'-XI', and Compounds 1'-241' of the compound having Formula I' are also applicable to a compound having Formula I that is used in the first device.

In one aspect, $L_1$ is selected from the group consisting of BR, NR, PR, O, S, Se, C=O, S=O, $SO_2$, CRR', SiRR', and GeRR'.

In one aspect, the organic layer is an emissive layer and the compound is an emissive dopant. In another aspect, the organic layer further comprises a host.

In one aspect, the host comprises an organic molecule containing at least one group selected from the group consisting of carbazole, dibenzothiphene, dibenzofuran, azacarbazole, aza-dibenzothiophene, and aza-dibenzofuran.

In yet another aspect, the host has the formula:

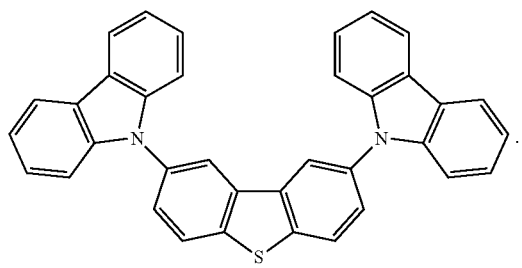 [SMILES: c1ccc2c(c1)c1ccccc1n2-c1ccc2sc3ccc(-n4c5ccccc5c5ccccc54)cc3c2c1]

In a further aspect, the host is a metal complex.

In one aspect, the organic layer is an emissive layer and the compound is a non-emissive dopant.

In one aspect, the first device is a consumer product. In another aspect, the first device is an organic light-emitting device. In yet another aspect, the first device comprises a lighting panel.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in some embodiments of the present invention is not particularly limited, and any compound may be used as long as the compound is typically used as a hole injecting/transporting material. Examples of the material may include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL may include, but are not limited to, the following general structures:

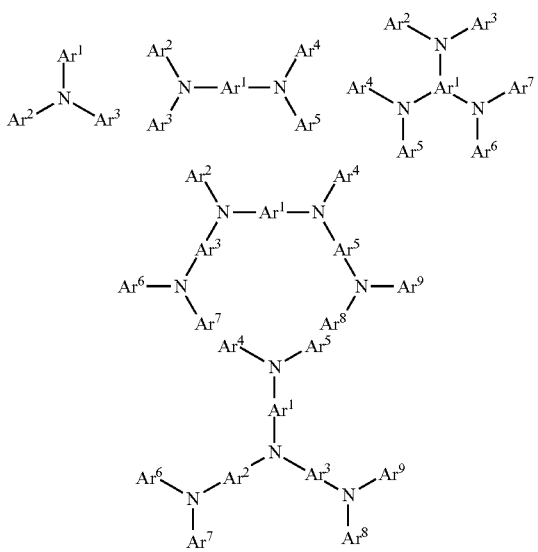

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

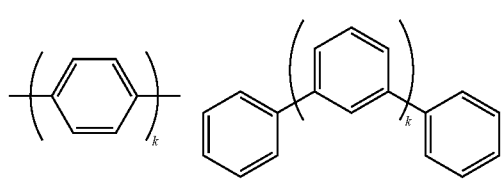

-continued

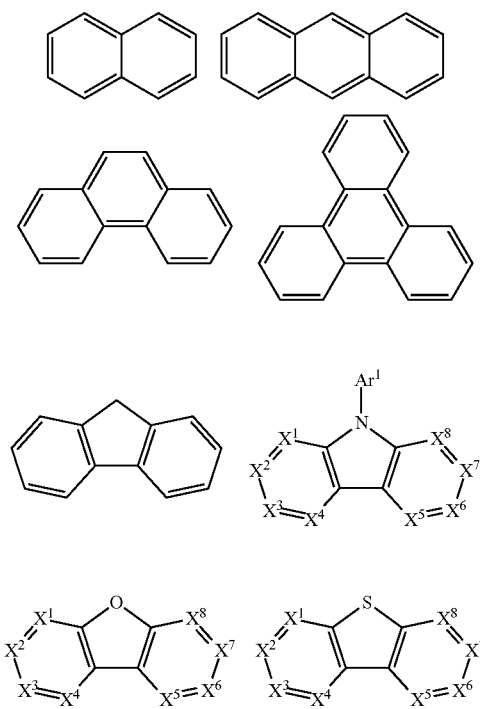

k is an integer from 1 to 20; $X^1$ to $X^8$ is CH or N; $Ar^1$ has the same group defined above.

Examples of metal complexes that may used in HIL or HTL include, but are not limited to, the following general formula:

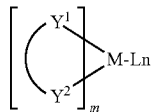

M is a metal having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device in some embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host materials are preferred to have the following general formula:

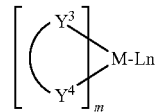

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

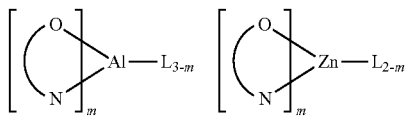

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host materials include materials selected from the group consisting of: aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

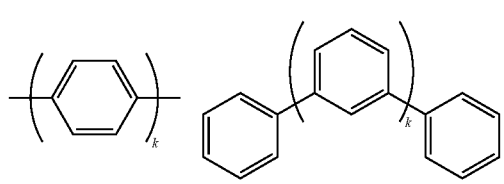

-continued

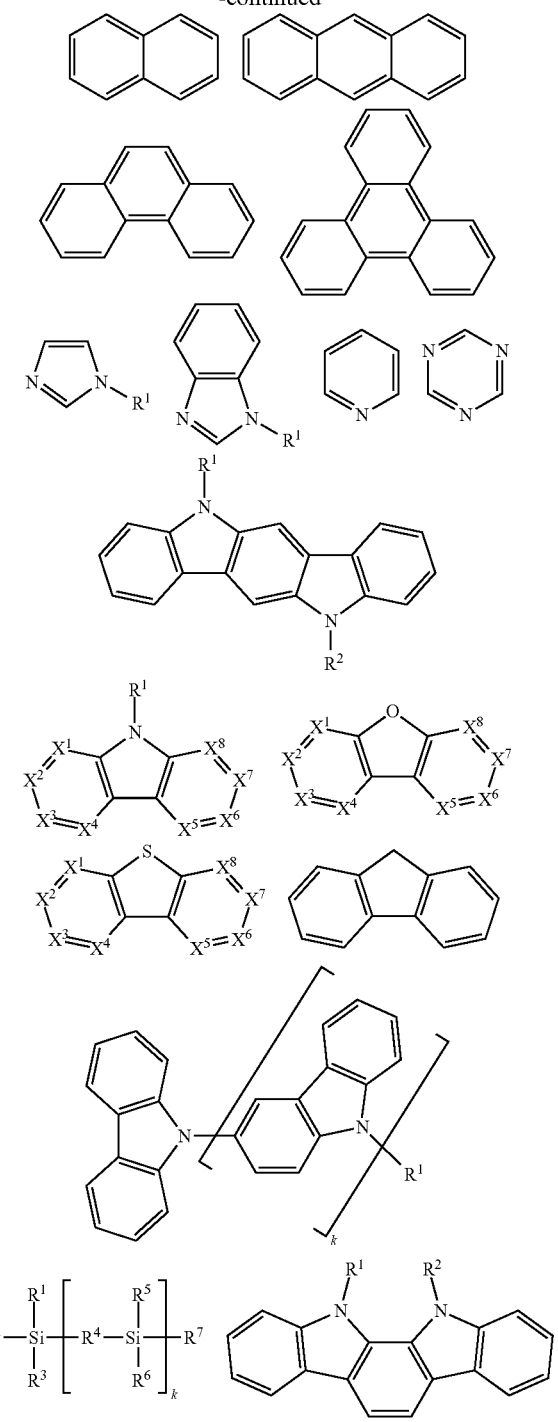

R[1] to R[7] is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When it is aryl or heteroaryl, it has the similar definition as Ar's mentioned above.

k is an integer from 0 to 20.

X[1] to X[8] is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule used as host described above.

In another aspect, the compound used in the HBL contains at least one of the following groups in the molecule:

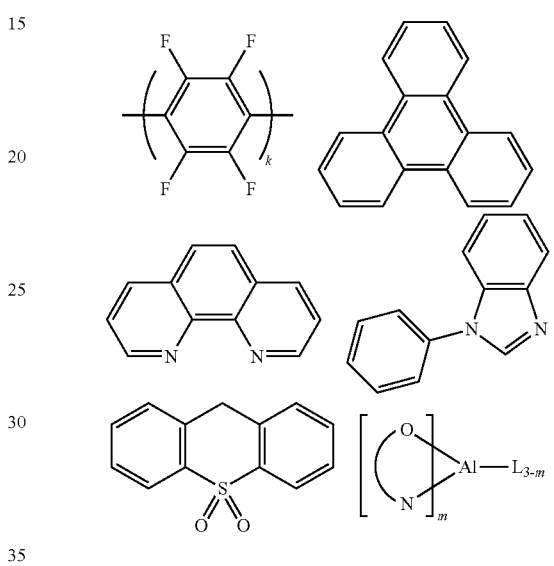

k is an integer from 0 to 20; L is an ancillary ligand, m is an integer from 1 to 3.

ETL:

The electron transport layer (ETL) may include a material capable of transporting electrons. The electron transport layer may be intrinsic (undoped) or doped. Doping may be used to enhance conductivity. Examples of the ETL material are not particularly limited, and any metal complexes or organic compounds may be used as long as they are typically used to transport electrons.

In one aspect, the compound used in the ETL contains at least one of the following groups in the molecule:

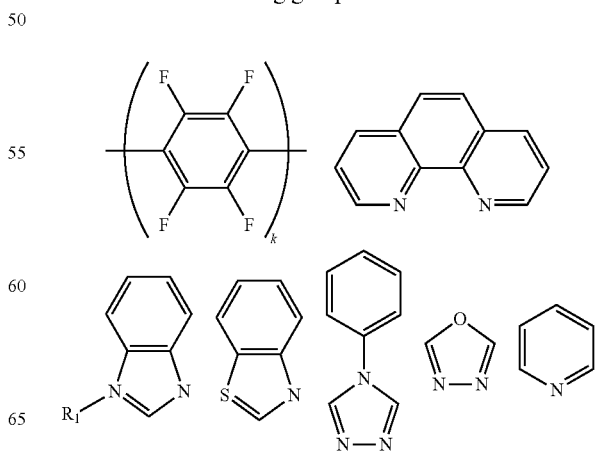

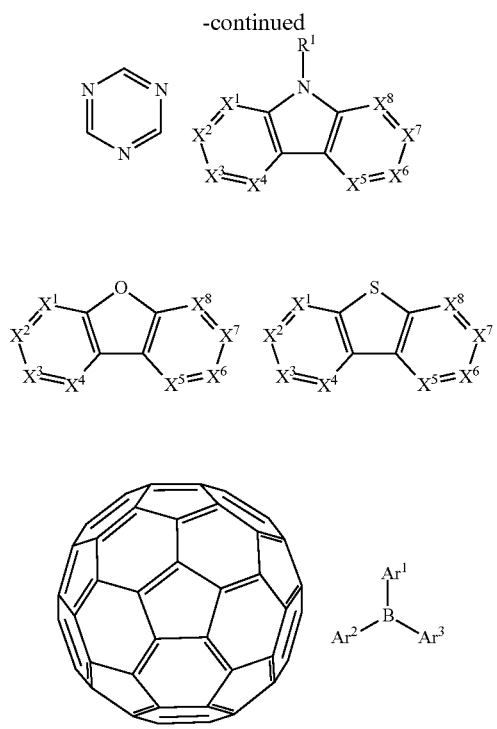

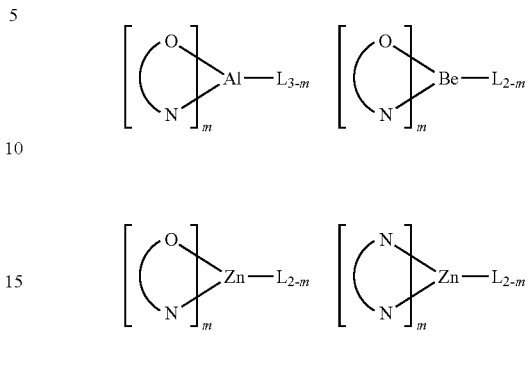

R¹ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When it is aryl or heteroaryl, it has the similar definition as Ar's mentioned above.

Ar¹ to Ar³ has the similar definition as Ar's mentioned above.

k is an integer from 0 to 20.

$X^1$ to $X^8$ is selected from CH or N.

In another aspect, the metal complexes used in the ETL may contain, but are not limit to, the following general formula:

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| | Hole injection materials | |
| Phthalocyanine and porphryin compounds | | Appl. Phys. Lett. 69, 2160 (1996) |

TABLE 1-continued
| MATERIAL | EXAMPLES OF MATERIAL | PUBLICATIONS |
|---|---|---|
| Starburst triarylamines | 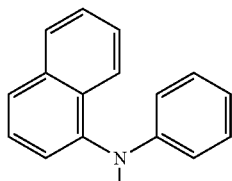 | J. Lumin. 72-74, 985 (1997) |
| CF$_x$ Fluorohydrocarbon polymer |  | Appl. Phys. Lett. 78, 673 (2001) |
| Conducting polymers (e.g., PEDOT:PSS, polyaniline, polypthiophene) | 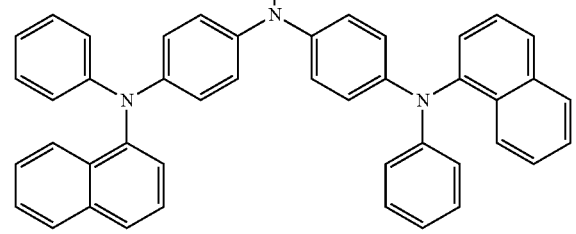 | Synth. Met. 87, 171 (1997) WO2007002683 |
| Phosphonic acid and silane SAMs | 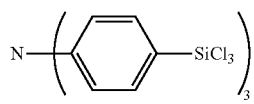 | US20030162053 |
| Triarylamine or polythiophene polymers with conductivity dopants | 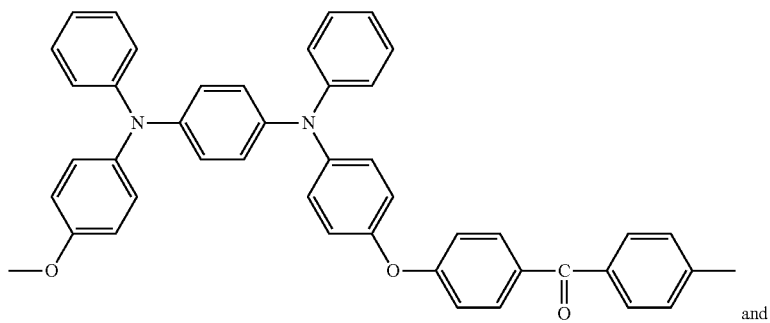 and | EA01725079A1 |

| MATERIAL | EXAMPLES OF MATERIAL | PUBLICATIONS |
|---|---|---|
| | 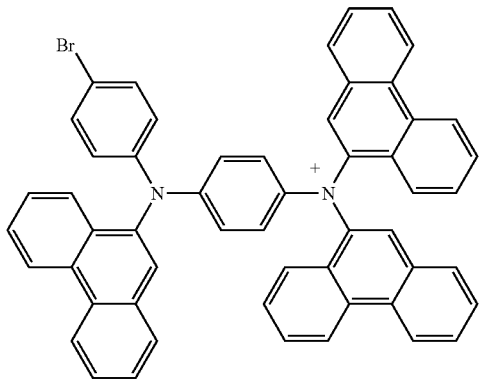 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| | 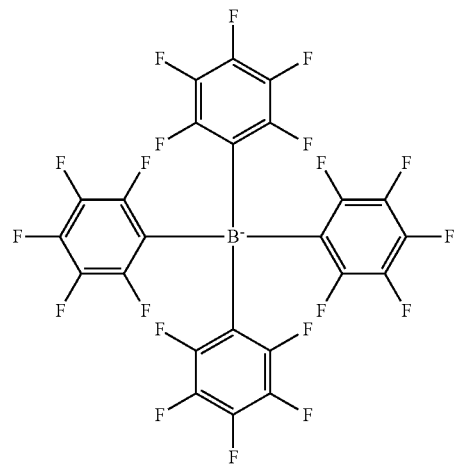 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 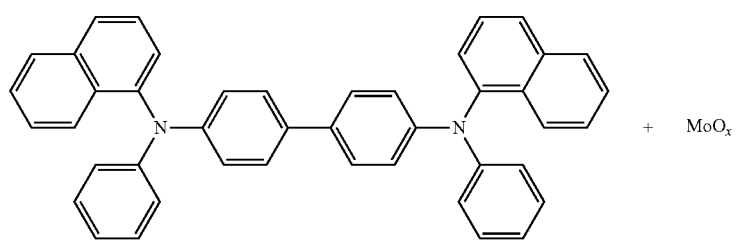 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| Semiconducting organic complexes | 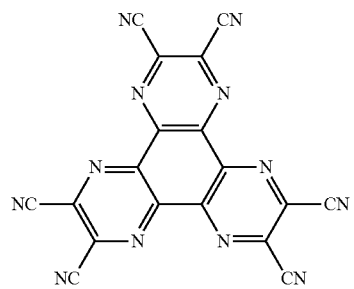 [SMILES: N#Cc1nc2c3nc(C#N)c(C#N)nc3c3nc(C#N)c(C#N)nc3c2nc1C#N] | US20020158242 |

TABLE 1-continued
| MATERIAL | EXAMPLES OF MATERIAL | PUBLICATIONS |
|---|---|---|
| Metal organometallic complexes | 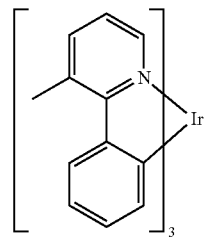 | US20060240279 |
| Cross-linkable compounds | 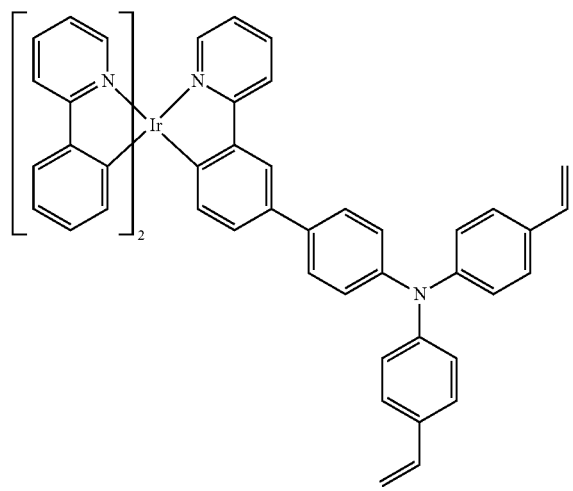 | US20080220265 |
| Hole transporting materials | | |
| Triarylamines (e.g., TPD, α-NPD) | 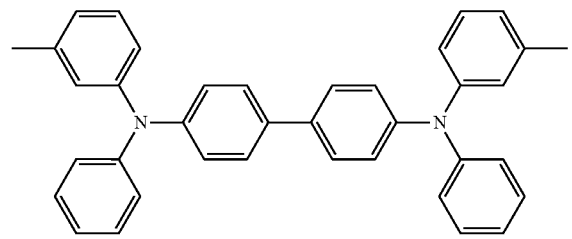 | Appl. Phys. Lett. 51, 913 (1987) |
| | 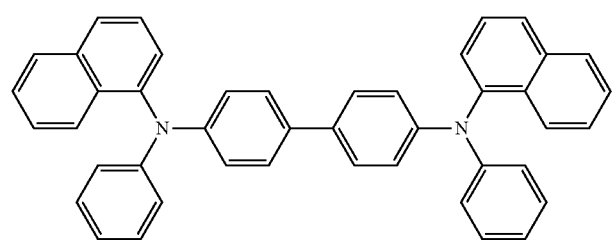 [SMILES: c1ccc(N(c2ccc(-c3ccc(N(c4ccccc4)c4cccc5ccccc45)cc3)cc2)c2cccc3ccccc23)cc1] | US5061569 |

TABLE 1-continued

| MATERIAL | EXAMPLES OF MATERIAL | PUBLICATIONS |
|---|---|---|
| | | EP650955 |
| | | J. Mater. Chem. 3, 319 (1993) |
| | | Appl. Phys. Lett. 90, 183503 (2007) |

TABLE 1-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)-benzothiophene/ (di)-benzofuran | | US20070278938, US20080106190 |

TABLE 1-continued

| MATERIAL | EXAMPLES OF MATERIAL | PUBLICATIONS |
|---|---|---|
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
|---|---|---|
| Arylcarbazoles | | Appl. Phys. Lett. 78, 1622 (2001) |

TABLE 1-continued

| MATERIAL | EXAMPLES OF MATERIAL | PUBLICATIONS |
|---|---|---|
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued
| MATERIAL | EXAMPLES OF MATERIAL | PUBLICATIONS |
|---|---|---|
| Zinc complexes | 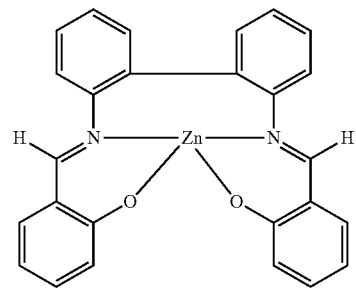 | WO2009062578 |
Green hosts
| | | |
|---|---|---|
| Arylcarbazoles | 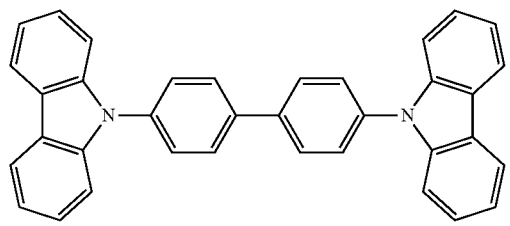 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 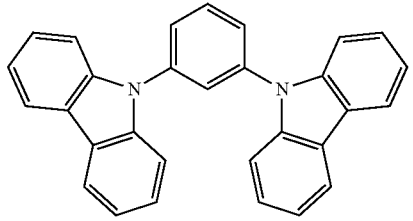 [SMILES: c1cc(-n2c3ccccc3c3ccccc32)cc(-n2c3ccccc3c3ccccc32)c1] | US20030175553 |
| | 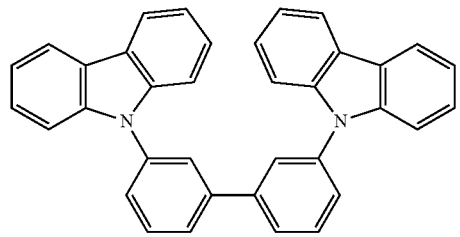 [SMILES: c1cc(-c2cccc(-n3c4ccccc4c4ccccc43)c2)cc(-n2c3ccccc3c3ccccc32)c1] | WO2001039234 |
| Aryltriphenylene compounds | 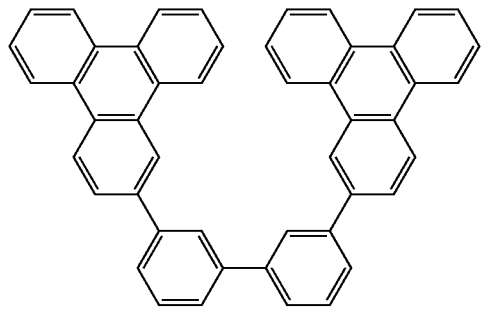 [SMILES: c1cc(-c2cccc(-c3ccc4c5ccccc5c5ccccc5c4c3)c2)cc(-c2ccc3c4ccccc4c4ccccc4c3c2)c1] | US20060280965 |

| MATE-RIAL | EXAMPLES OF MATERIAL | PUBLI-CATIONS |
|---|---|---|
| | 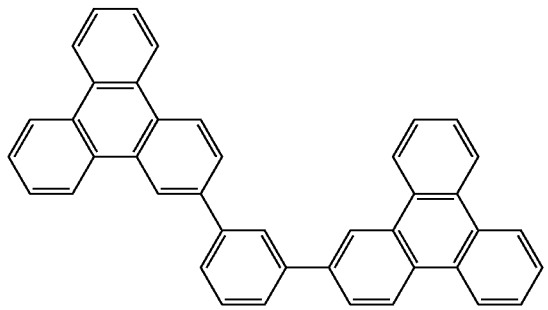 [SMILES: c1cc(-c2ccc3c4ccccc4c4ccccc4c3c2)cc(-c2ccc3c4ccccc4c4ccccc4c3c2)c1] | US20060280965 |
| | 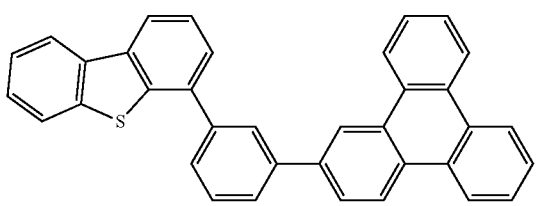 [SMILES: c1cc(-c2ccc3c4ccccc4c4ccccc4c3c2)cc(-c2cccc3c2sc2ccccc23)c1] | WO2009021126 |
| Donor acceptor type molecules | 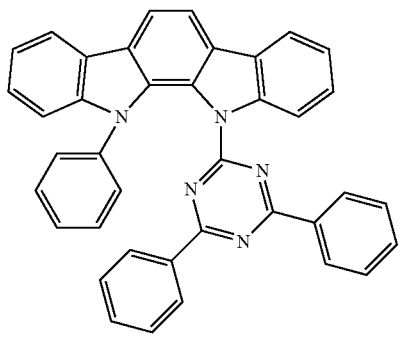 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carba-zole/ DBT/ DBF | 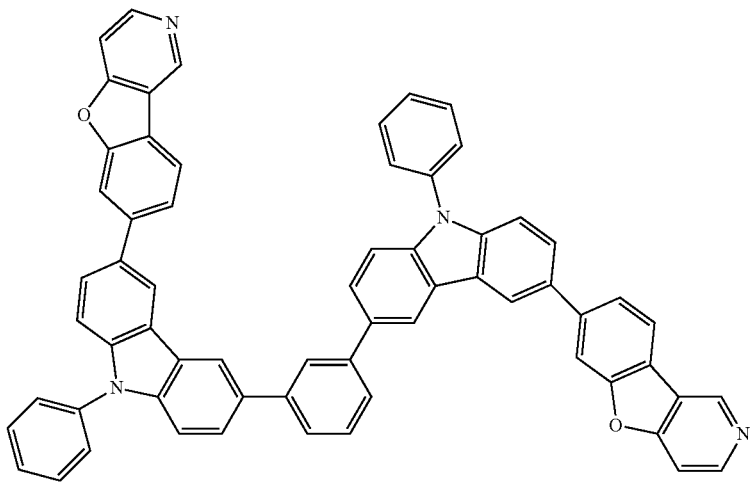 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 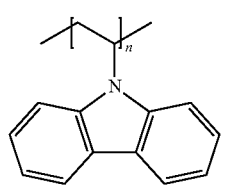 | Appl. Phys. Lett. 77, 2280 (2000) |

TABLE 1-continued
| MATERIAL | EXAMPLES OF MATERIAL | PUBLICATIONS |
|---|---|---|
| Spiro-fluorene compounds | 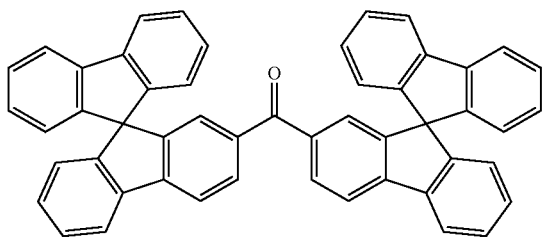 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzo-oxazole compounds | 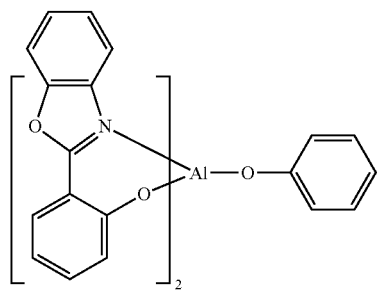 | WO2005089025 |
| | 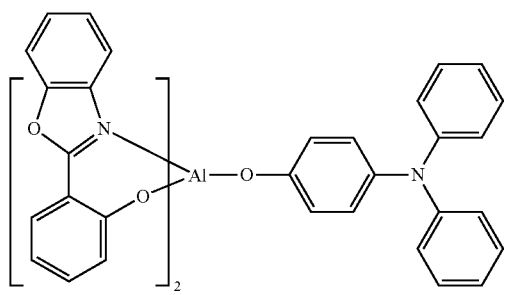 | WO2006132173 |
| | 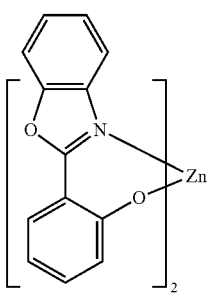 | JP200511610 |
| Spiro-fluorene-carbazole compounds | 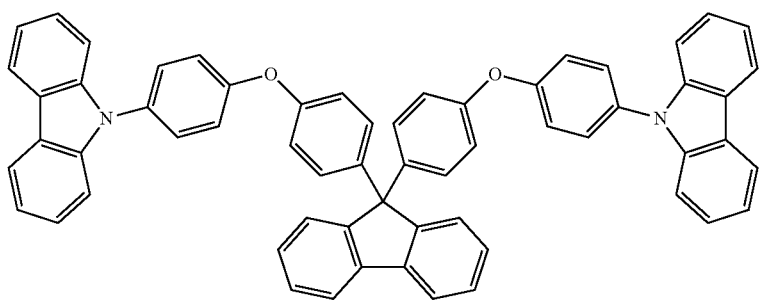 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 1-continued
| MATERIAL | EXAMPLES OF MATERIAL | PUBLICATIONS |
|---|---|---|
| | 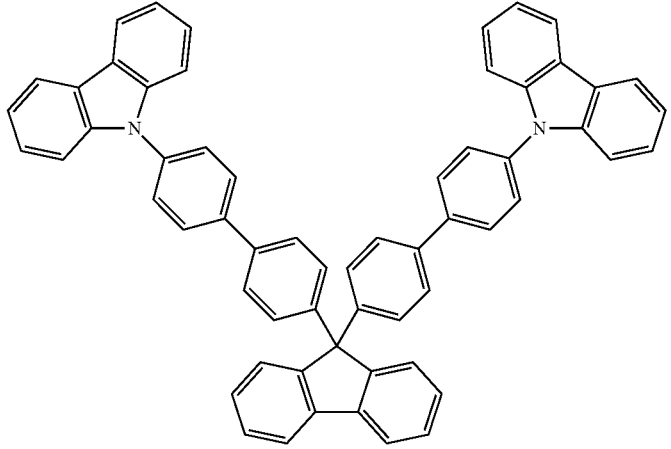 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 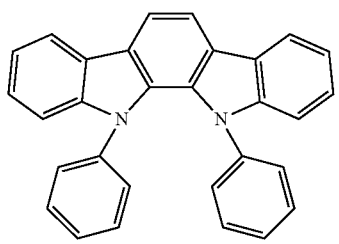 [SMILES: c1ccc(-n2c3ccccc3c3ccc4c5ccccc5n(-c5ccccc5)c4c32)cc1] | WO2007063796 |
| | 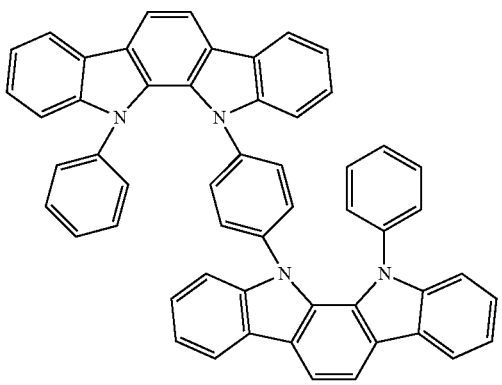 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 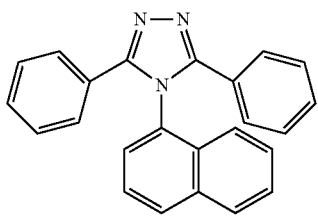 [SMILES: c1ccc(-c2nnc(-c3ccccc3)n2-c2cccc3ccccc23)cc1] | J. Appl. Phys. 90, 5048 (2001) |
| | 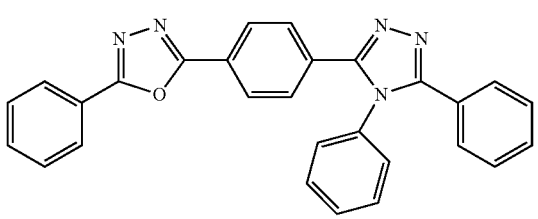 [SMILES: c1ccc(-c2nnc(-c3ccc(-c4nnc(-c5ccccc5)n4-c4ccccc4)cc3)o2)cc1] | WO2004107822 |

TABLE 1-continued

| MATERIAL | EXAMPLES OF MATERIAL | PUBLICATIONS |
|---|---|---|
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |

TABLE 1-continued
| MATERIAL | EXAMPLES OF MATERIAL | PUBLICATIONS |
|---|---|---|
| Dibenzothiophene/ Dibenzofuran-carbazole compounds | 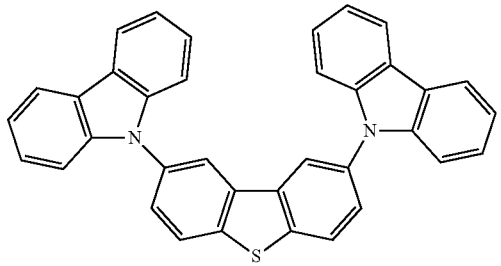 [SMILES: c1ccc2c(c1)c1ccccc1n2-c1ccc2sc3ccc(-n4c5ccccc5c5ccccc54)cc3c2c1] | WO2006114966, US20090167162 |
| | 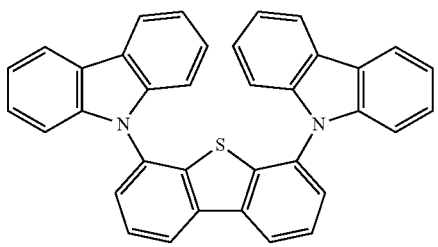 [SMILES: c1cc(-n2c3ccccc3c3ccccc32)c2sc3c(-n4c5ccccc5c5ccccc54)cccc3c2c1] | US20090167162 |
| | 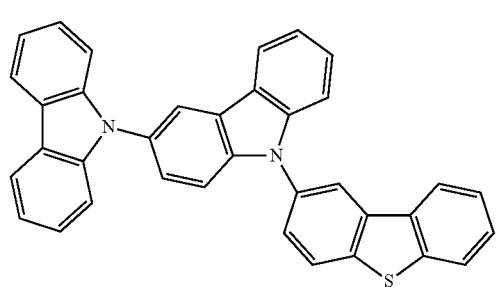 [SMILES: c1ccc2c(c1)sc1ccc(-n3c4ccccc4c4cc(-n5c6ccccc6c6ccccc65)ccc43)cc12] | WO2009086028 |
| | 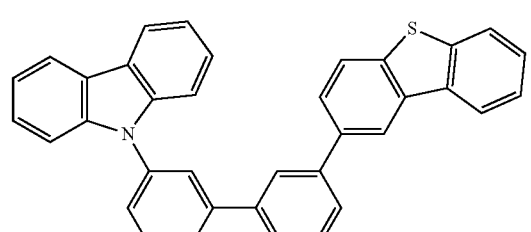 | US20090030202, US20090017330 |
| Silicon aryl compounds | 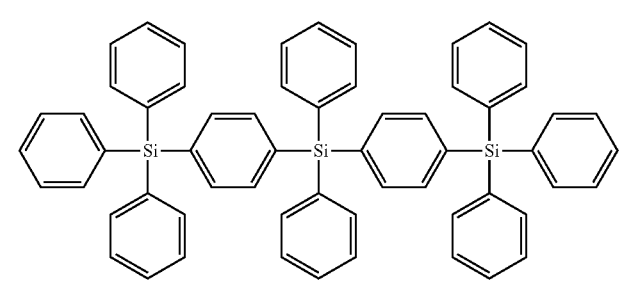 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 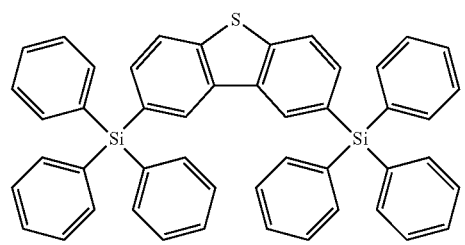 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| High triplet metal organometallic complex | | US7154114 |

Phosphorescent dopants
Red dopants

| | | |
|---|---|---|
| Heavy metal porphyrins (e.g., PtOEP) | | Nature 395, 151 (1998) |
| Iridium (III) organometallic complexes | | Appl. Phys. Lett. 78, 1622 (2001) |

TABLE 1-continued
| MATERIAL | EXAMPLES OF MATERIAL | PUBLICATIONS |
|---|---|---|
| | 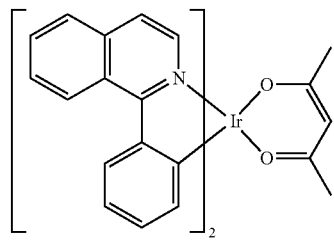 | US2006835469 |
| | 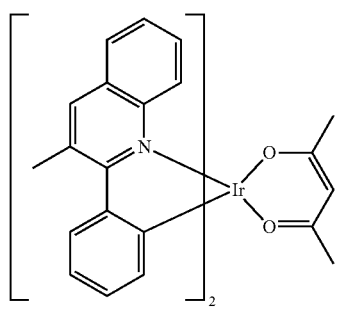 | US2006835469 |
| | 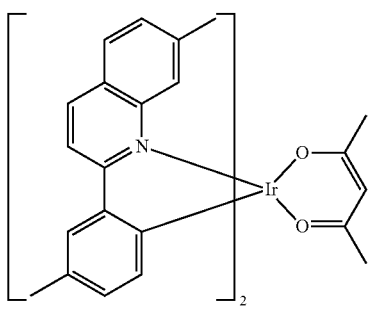 | US20060202194 |
| | 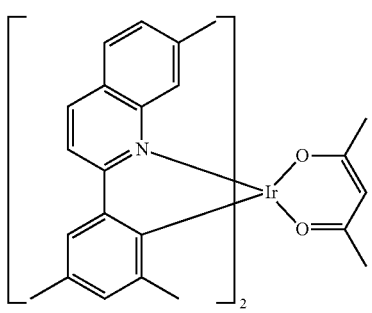 | US20060202194 |
| | 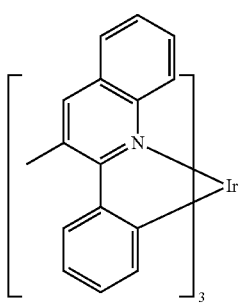 | US20070087321 |

| MATERIAL | EXAMPLES OF MATERIAL | PUBLICATIONS |
|---|---|---|
| | 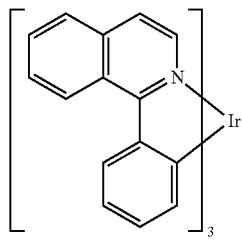 | US20070087321 |
| | 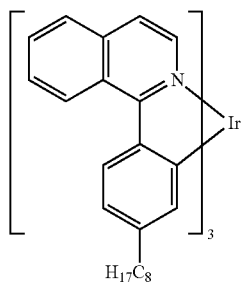 | Adv. Mater. 19, 739 (2007) |
| | 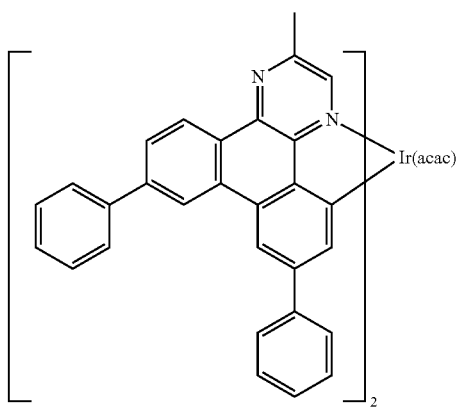 | WO2009100991 |
| | 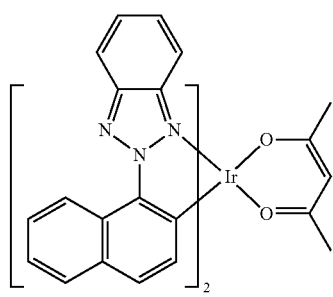 | WO2008101842 |
| Platinum (II) organometallic complexes | 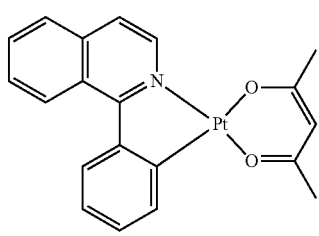 | WO2003040257 |

TABLE 1-continued
| MATERIAL | EXAMPLES OF MATERIAL | PUBLICATIONS |
|---|---|---|
| Osminum (III) complexes | 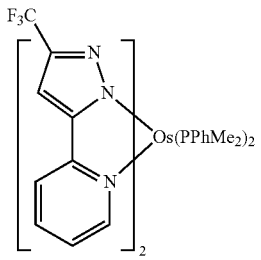 | Chem. Mater. 17, 3532 (2005) |
| Ruthenium (II) complexes | 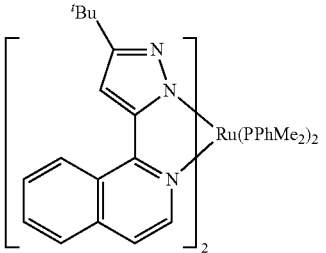 | Adv. Mater. 17, 1059 (2005) |
| Rhenium (I), (II), and (III) complexes | 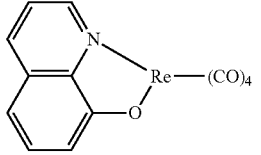 | US20050244673 |
Green dopants
| | | |
|---|---|---|
| Iridium (III) organometallic complexes | 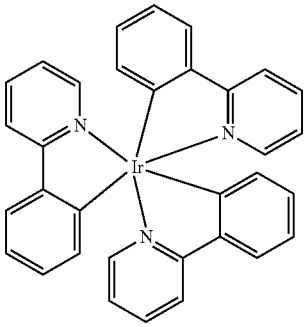<br>and it's derivatives | Inorg. Chem. 40, 1704 (2001) |
| | 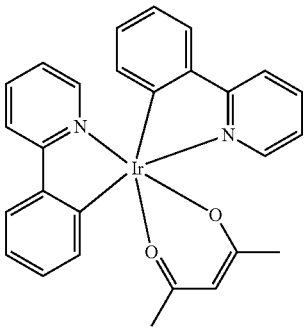 | US20020034656 |

TABLE 1-continued
| MATERIAL | EXAMPLES OF MATERIAL | PUBLICATIONS |
|---|---|---|
| | 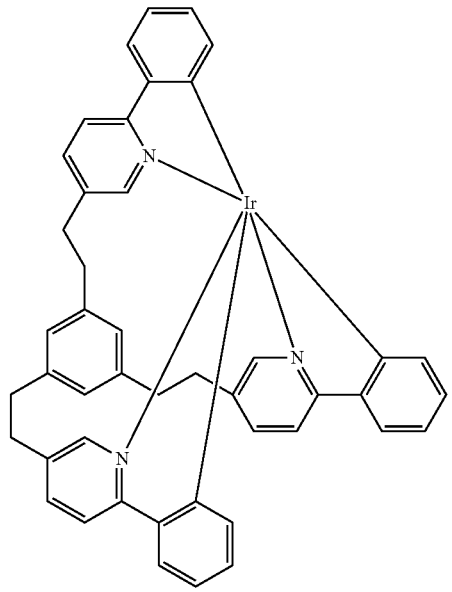 | US7332232 |
| | 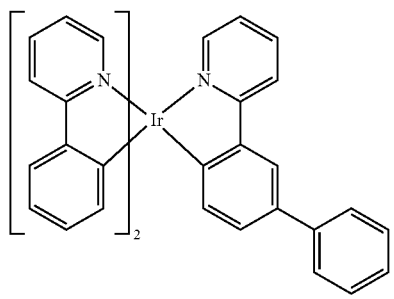 | US20090108737 |
| | 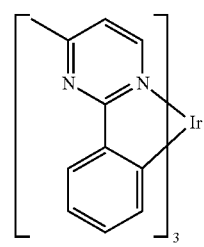 | US20090039776 |
| | 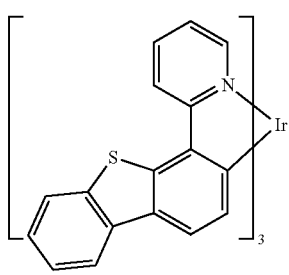 | US6921915 |

TABLE 1-continued
| MATERIAL | EXAMPLES OF MATERIAL | PUBLICATIONS |
|---|---|---|
| | 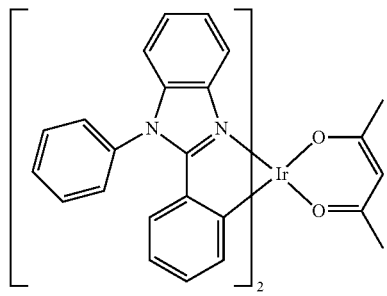 | US6687266 |
| | 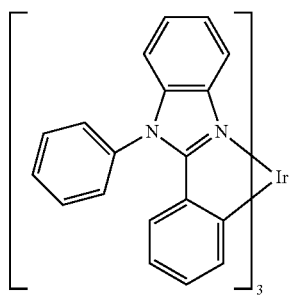 | Chem. Mater. 16, 2480 (2004) |
| | 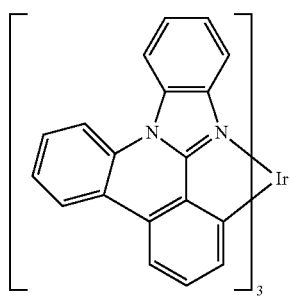 | US20070190359 |
| | 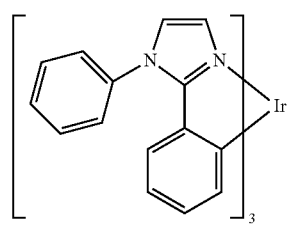 | US 20060008670 JP2007123392 |
| | 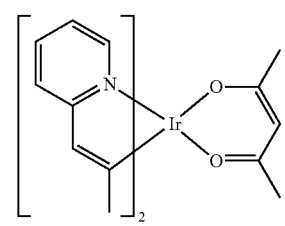 | Adv. Mater. 16, 2003 (2004) |

TABLE 1-continued
| MATERIAL | EXAMPLES OF MATERIAL | PUBLICATIONS |
|---|---|---|
| | 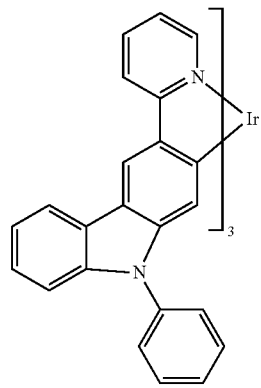 | Angew. Chem. Int. Ed. 2006, 45, 7800 |
| | 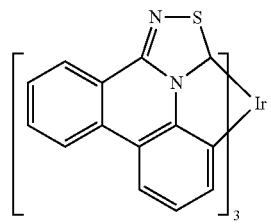 | WO2009050290 |
| | 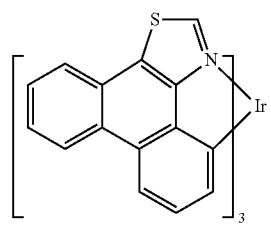 | US20090165846 |
| | 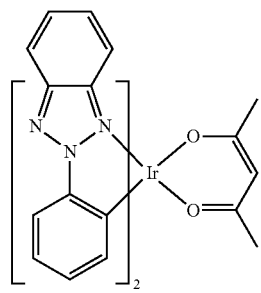 | US20080015355 |
| Monomer for polymeric metal organometallic compounds | 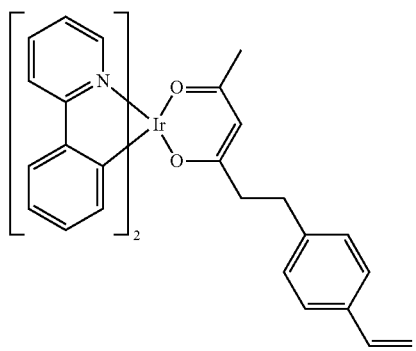 | US7250226, US7396598 |

TABLE 1-continued

| MATERIAL | EXAMPLES OF MATERIAL | PUBLICATIONS |
|---|---|---|
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 1-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium (III) complexes | | Inorg. Chem. 42, 1248 (2003) |
| Deuterated organometallic complexes | | US20030138657 |

| MATERIAL | EXAMPLES OF MATERIAL | PUBLICATIONS |
|---|---|---|
| Organometallic complexes with two or more metal centers | | US20030152802 |
| | | US7090928 |
| Blue dopants | | |
| Iridium(III) organometallic complexes | | WO2002002714 |
| | | WO2006009024 |
| | | US20060251923 |

TABLE 1-continued
| MATERIAL | EXAMPLES OF MATERIAL | PUBLICATIONS |
|---|---|---|
| | 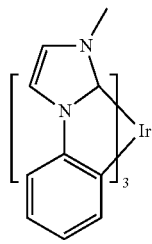 | US7393599, WO2006056418, US20050260441, WO2005019373 |
| | 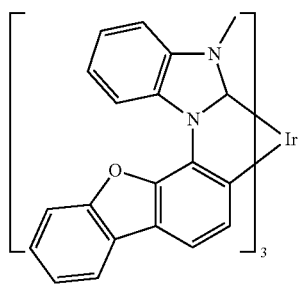 | US7534505 |
| | 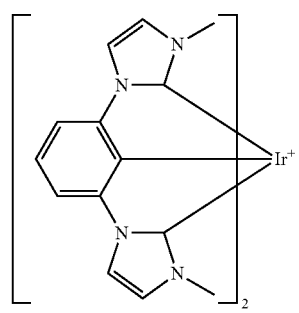 | US7445855 |
| | 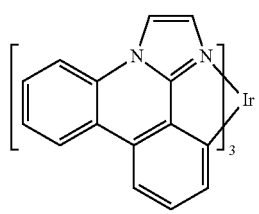 | US20070190359, US20080297033 |
| | 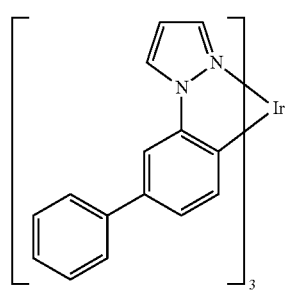 | US7338722 |
| | 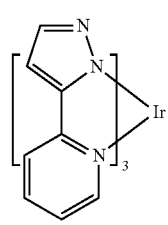 | US20020134984 |

| MATERIAL | EXAMPLES OF MATERIAL | PUBLICATIONS |
|---|---|---|
| | 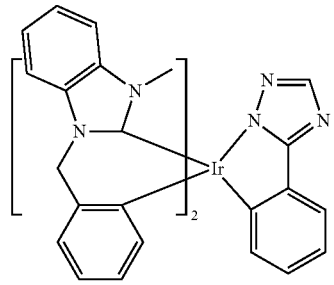 | Angew. Chem. Int. Ed. 47, 1 (2008) |
| | 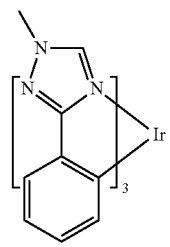 | Chem. Mater. 18, 5119 (2006) |
| | 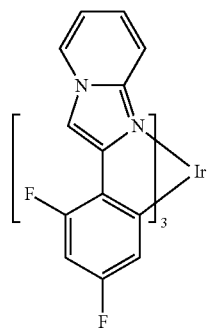 | Inorg. Chem. 46, 4308 (2007) |
| | 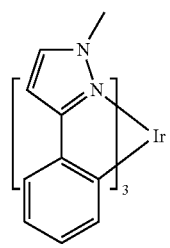 | WO2005123873 |
| | 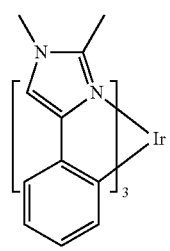 | WO2005123873 |

TABLE 1-continued
| MATERIAL | EXAMPLES OF MATERIAL | PUBLICATIONS |
|---|---|---|
| | 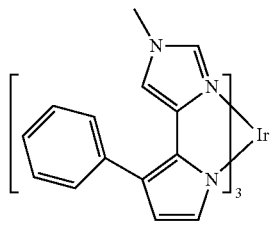 | WO2007004380 |
| | 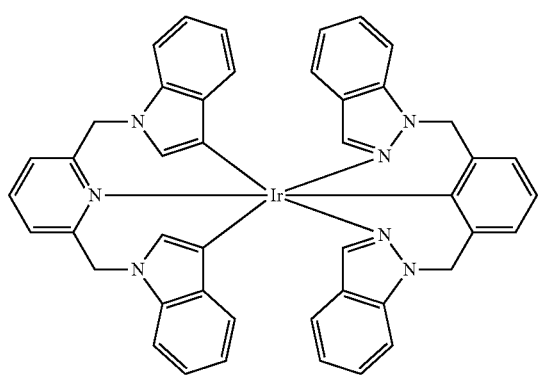 | WO2006082742 |
| Osmium (II) complexes | 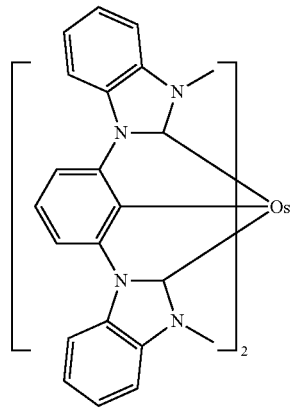 | US7279704 |
| | 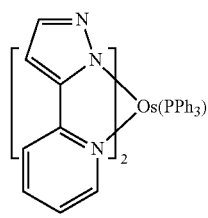 | Organometallics 23, 3745 (2004) |
| Gold complexes | 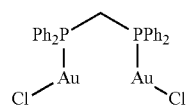 | Appl. Phys. Lett. 74, 1361 (1999) |

TABLE 1-continued

| MATERIAL | EXAMPLES OF MATERIAL | PUBLICATIONS |
|---|---|---|
| Platinum (II) complexes | | WO2006098120, WO2006103874 |

Exciton/hole blocking layer materials

| | | |
|---|---|---|
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 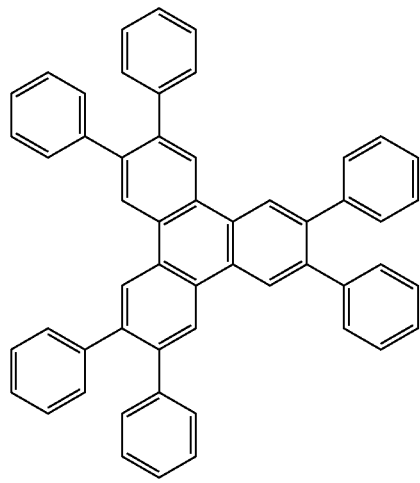 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 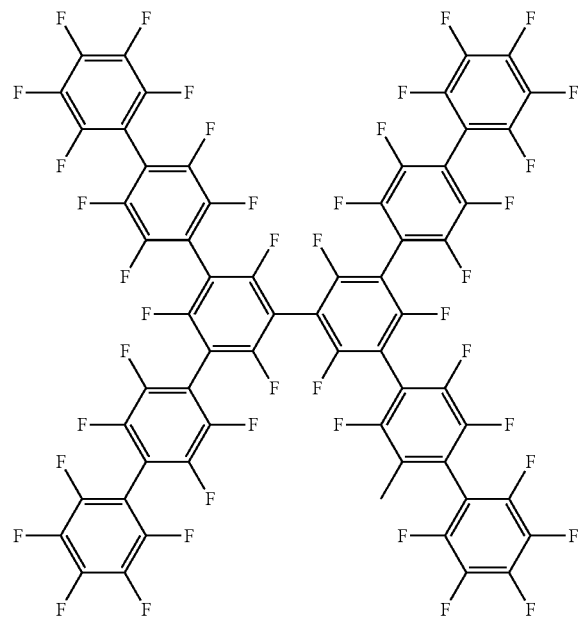 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 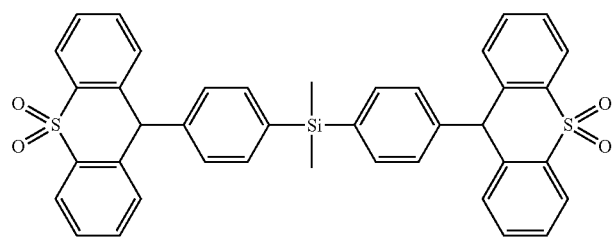 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 1-continued
| MATERIAL | EXAMPLES OF MATERIAL | PUBLICATIONS |
|---|---|---|
| Electron transporting materials | | |
| Anthracene-benzoimidazole compounds | 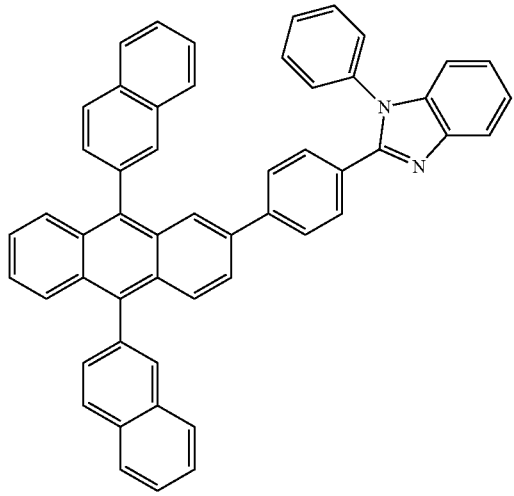 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 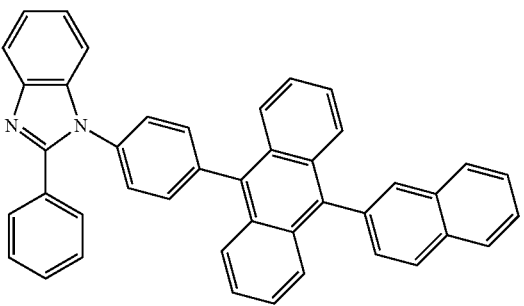 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 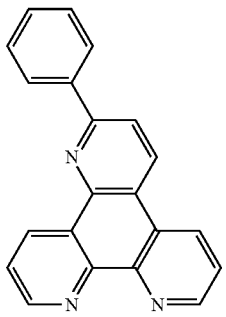 [SMILES: c1ccc(-c2ccc3c4cccnc4c4ncccc4c3n2)cc1] | US20090115316 |
| Anthracene-benzothiazole compounds | 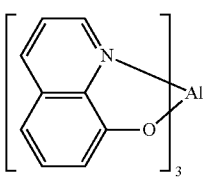 | Appl. Phys. Lett. 89, 063504 (2006) |
| Metal 8-hydroxyquinolates (e.g., Alq$_3$, Zrq$_4$) | | Appl. Phys. Lett. 51, 913 (1987) US7230107 |

TABLE 1-continued

| MATERIAL | EXAMPLES OF MATERIAL | PUBLICATIONS |
|---|---|---|
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 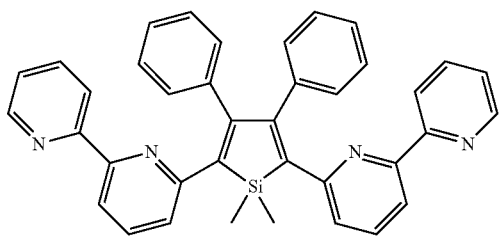 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 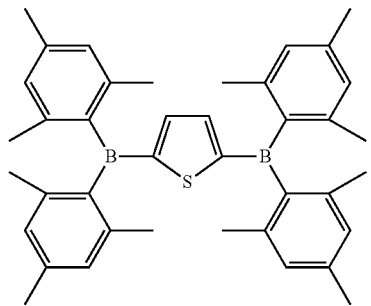 | J. Am. Chem. Soc. 120, 9714 (1998) |
| Fluorinated aromatic compounds | 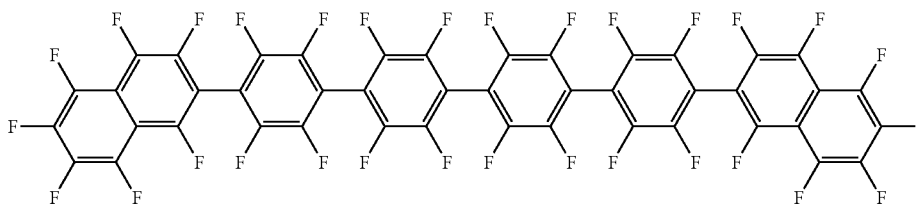 | J. Am. Chem. Soc. 122, 1832 (2000) |
| Fullerene (e.g., C60) | 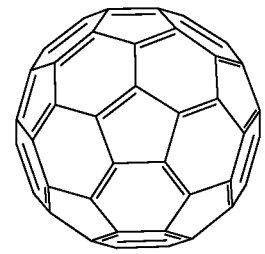 [SMILES: c1cc2c3ccc4c5ccc6c7ccc8c9ccc%10c1c1c2c2c3c4c3c5c6c4c7c8c5c9c%10c1c1c2c3c4c51] | US20090101870 |

TABLE 1-continued

| MATERIAL | EXAMPLES OF MATERIAL | PUBLICATIONS |
|---|---|---|
| Triazine complexes | | US20040036077 |
| Zn (N^N) complexes | | US6528187 |

EXPERIMENTAL

Synthetic Examples

Synthesis of Compound 3

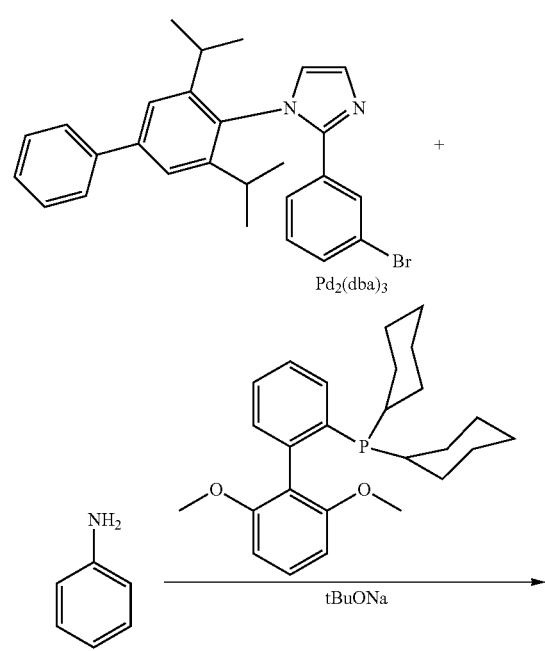

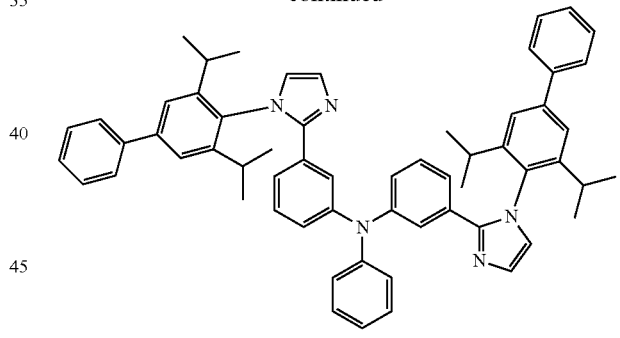

Synthesis of 3-(1-(3,5-diisopropyl-[1,1'-biphenyl]-4-yl)-1H-imidazol-2-yl)-N-(3-(1-(3,5-diisopropyl-[1,1'-biphenyl]-4-yl)-1H-imidazol-2-yl)phenyl)-N-phenylaniline. 2-(3-bromophenyl)-1-(3,5-diisopropyl-[1,1'-biphenyl]-4-yl)-1H-imidazole (2.496 g, 5.43 mmol), Pd$_2$(dba)$_3$ (0.045 g, 0.049 mmol), dicyclohexyl(2',6'-dimethoxy-[1,1'-biphenyl]-2-yl)phosphine (0.081 g, 0.198 mmol), and sodium t-butoxide (0.712 g, 7.41 mmol) were mixed in 100 mL of xylene. The solution was bubbled with nitrogen for 20 minutes, and aniline (0.23 g, 2.470 mmol) was added. The reaction was heated up to reflux for 6 h. TLC indicated the reaction was done. The reaction was filtered through celite and solvent was evaporated. The residue was coated on Celite® and columned with 1:1 hexanes/ethyl acetate. 1.5 g (71% yield) of product was obtained.

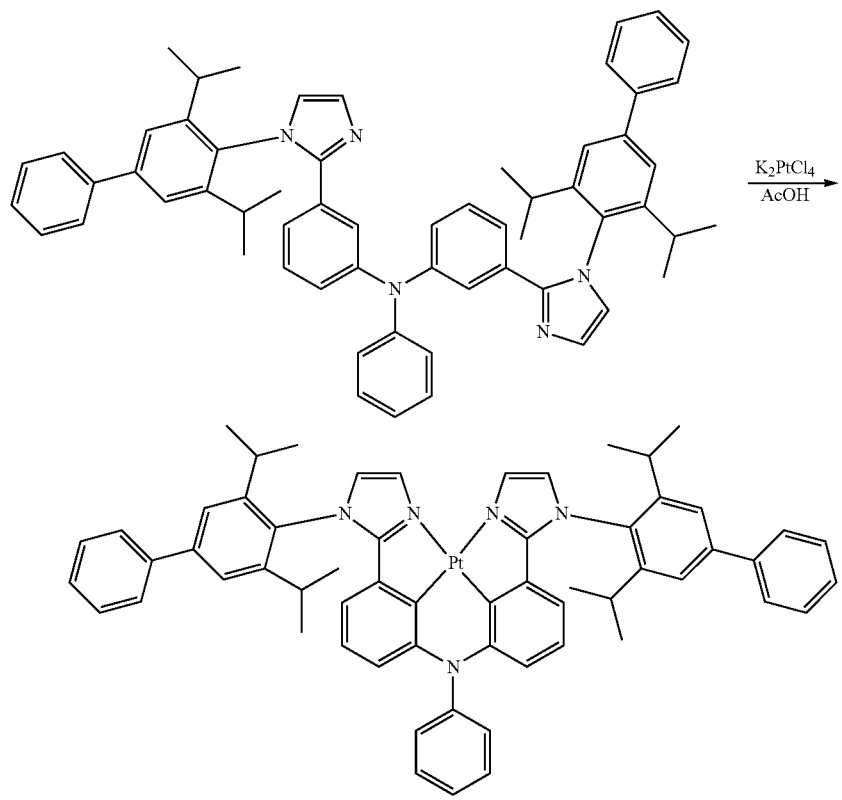

Synthesis of Compound 3. Potassium tetrachloroplatinate (0.425 g, 1.023 mmol) and 3-(1-(3,5-diisopropyl-[1,1'-biphenyl]-4-yl)-1H-imidazol-2-yl)-N-(3-(1-(3,5-diisopropyl-[1,1'-biphenyl]-4-yl)-1H-imidazol-2-yl)phenyl)-N-phenylaniline (0.87 g, 1.023 mmol) were mixed in 80 mL of acetic acid and heated to hard reflux for 2 days. Green precipitate formed. The reaction was cooled to room temperature and filtered through a Celite® pad. The compound was rinsed with methanol, then dissolved in DCM and coated on Celite®. The compound was columned with 2:3 DCM/hexanes. 0.5 g (47% yield) of product was obtained.

Synthesis of Compound 5

Synthesis of 4-bromo-2,6-diisopropylaniline

A solution of NBS (24.59 g, 137 mmol) in DMF (160 mL) was added slowly to a solution of 2,6-diisopropylaniline (25 g, 137 mmol) in DMF (300 mL) at 0-5° C. under a nitrogen atmosphere over a period of 20 minutes. The reaction mixture was stirred at 0-5° C. After the reaction was complete, water was added and the oil suspension was stirred at rt. The aqueous layer was decanted out and the remaining oil was dissolved in ethyl acetate. The organic layer was separated, washed water and brine. Evaporation gave light brown oil (35.1 g, 100% yield).

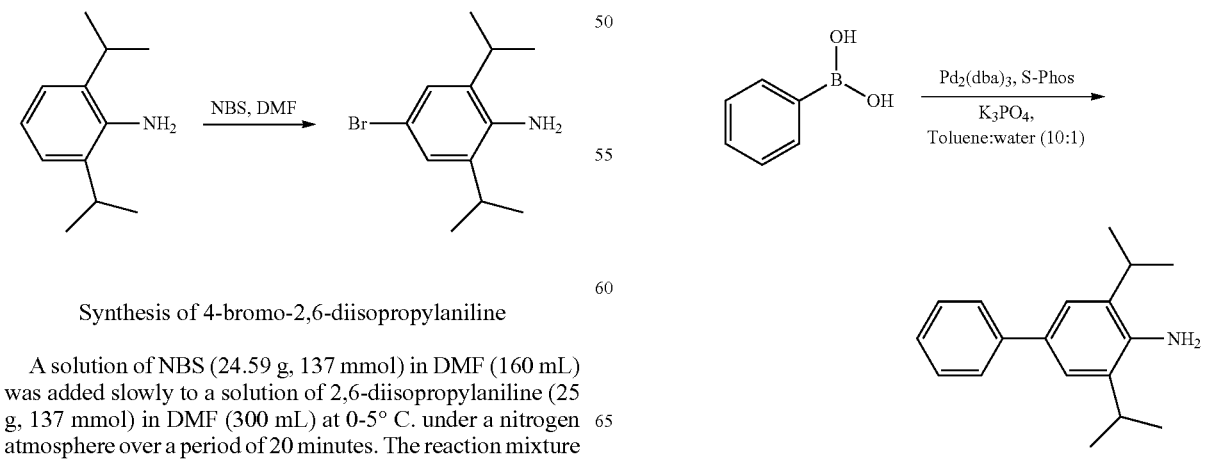

Synthesis of 3,5-diisopropyl-[1,1'-biphenyl]-4-amine

Dry nitrogen gas was bubbled into a mixture of 4-bromo-2,6-diisopropylaniline (35.1 g, 137 mmol), potassium phosphate tribasic monohydrate (126 g, 548 mmol) and 2-dicyclohexylphosphino-2',6'-dimethoxybiphenyl [S-Phos] (2.250 g, 5.48 mmol) in toluene:water (10:1, 1400 mL) at room temperature for a period of 40 minutes. Pd$_2$(dba)$_3$ (1.255 g, 1.370 mmol) was then added to the mixture above. The reaction was refluxed under a nitrogen atmosphere and monitored by GC-MS. The reaction was complete after overnight refluxing. The reaction mixture was cooled down and the organic layer was separated, washed with water (3×) and filtered through a bed of Celite®. Toluene was removed in vacuum to give a crude oil which was purified by silica gel column chromatography using hexane/AcOEt: 9/1 to 85/15 as eluants. Pure fractions were distilled to afford the title compound as an oil (17.43 g, 50% yield).

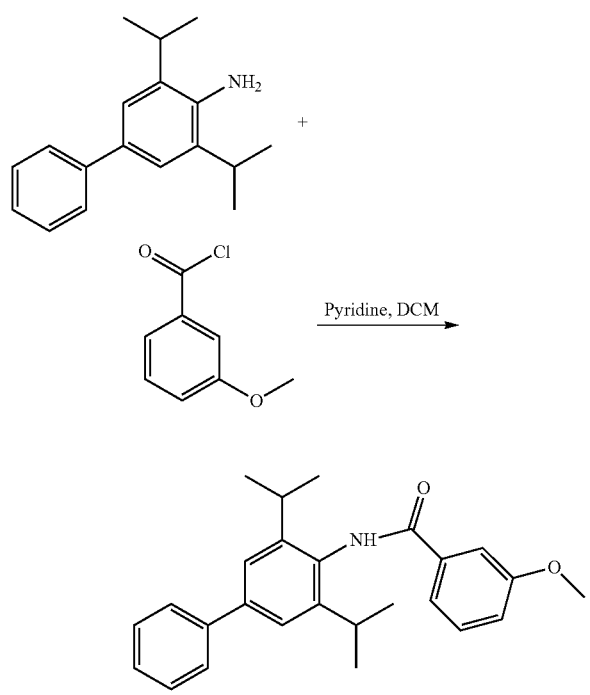

Synthesis of N-(3,5-diisopropyl-[1,1'-biphenyl]-4-yl)-3-methoxybenzamide

A solution of 3-methoxybenzoyl chloride (7.54 mL, 55.3 mmol) in DCM (dichloromethane) (50 mL) was added slowly to a 0° C., stirred solution of 3,5-diisopropyl-[1,1'-biphenyl]-4-amine (10 g, 39.5 mmol) and pyridine (5.43 mL, 67.1 mmol) in DCM (100 mL). The mixture was then warmed up and stirred overnight at room temperature. After the reaction was complete, water was added into the reaction mixture. The aqueous mixture was extracted with DCM, and the DCM layer was separated, washed with water (2×), aq. Na$_2$CO$_3$, water (2×) and brine, and dried over anhydrous Na$_2$SO$_4$. Filtration and evaporation gave an off-white solid which was recrystallized from hexane/DCM (2/8) (v/v) to afford a snow white solid (9.93 g, 65%).

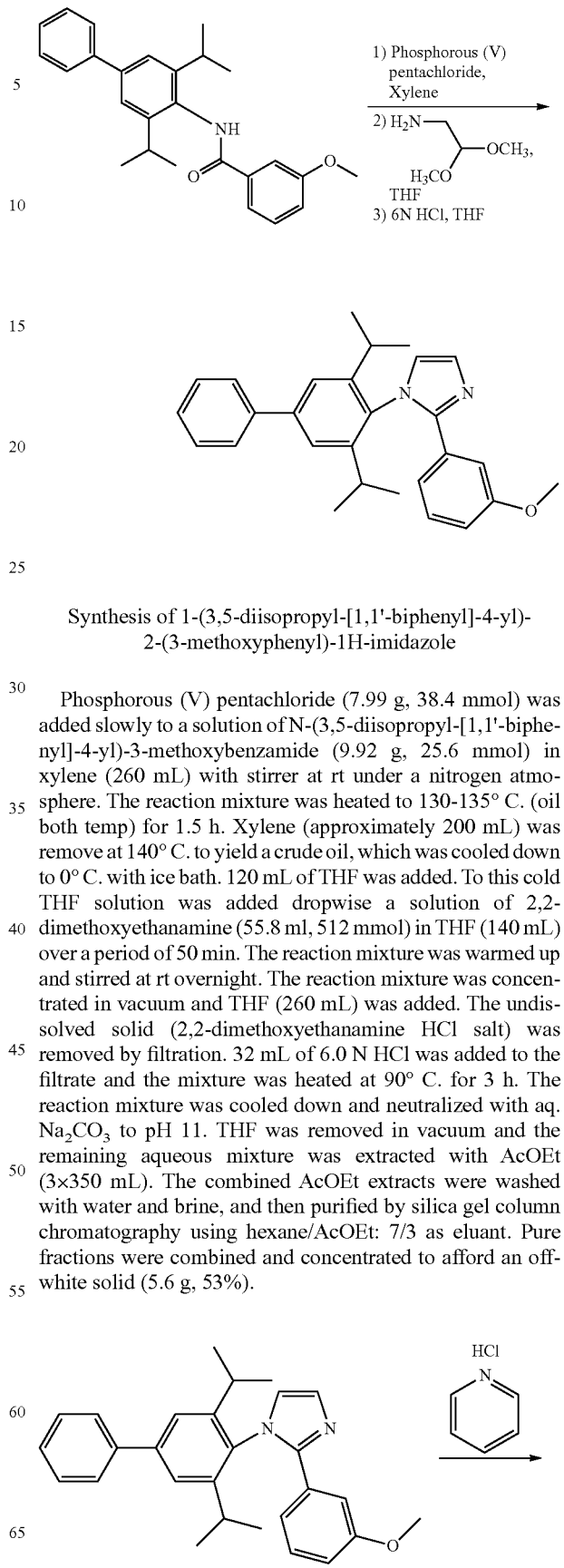

Synthesis of 1-(3,5-diisopropyl-[1,1'-biphenyl]-4-yl)-2-(3-methoxyphenyl)-1H-imidazole Phosphorous (V) pentachloride (7.99 g, 38.4 mmol) was added slowly to a solution of N-(3,5-diisopropyl-[1,1'-biphenyl]-4-yl)-3-methoxybenzamide (9.92 g, 25.6 mmol) in xylene (260 mL) with stirrer at rt under a nitrogen atmosphere. The reaction mixture was heated to 130-135° C. (oil both temp) for 1.5 h. Xylene (approximately 200 mL) was remove at 140° C. to yield a crude oil, which was cooled down to 0° C. with ice bath. 120 mL of THF was added. To this cold THF solution was added dropwise a solution of 2,2-dimethoxyethanamine (55.8 ml, 512 mmol) in THF (140 mL) over a period of 50 min. The reaction mixture was warmed up and stirred at rt overnight. The reaction mixture was concentrated in vacuum and THF (260 mL) was added. The undissolved solid (2,2-dimethoxyethanamine HCl salt) was removed by filtration. 32 mL of 6.0 N HCl was added to the filtrate and the mixture was heated at 90° C. for 3 h. The reaction mixture was cooled down and neutralized with aq. Na$_2$CO$_3$ to pH 11. THF was removed in vacuum and the remaining aqueous mixture was extracted with AcOEt (3×350 mL). The combined AcOEt extracts were washed with water and brine, and then purified by silica gel column chromatography using hexane/AcOEt: 7/3 as eluant. Pure fractions were combined and concentrated to afford an off-white solid (5.6 g, 53%).

-continued

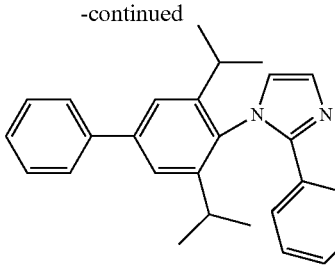

Synthesis of 3-(1-(3,5-diisopropyl-[1,1'-biphenyl]-4-yl)-1H-imidazol-2-yl)phenol A mixture of 1-(3,5-diisopropyl-[1,1'-biphenyl]-4-yl)-2-(3-methoxyphenyl)-1H-imidazole (5.57 g, 13.57 mmol) and pyridine hydrochloride (9.41 g, 81 mmol) were fused with stirring at 200° C. for 13 h. After the reaction was complete, the mixture was partitioned between water and AcOEt. AcOEt layer was separated, washed with water (3×) and brine, and then purified by silica gel column chromatography using DCM/MeOH (96/4) as eluant to afford an off-white solid (5.12 g, 95%).

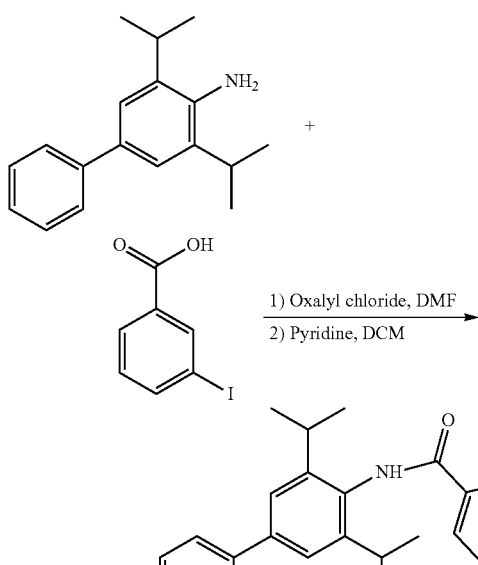

Synthesis of N-(3,5-diisopropyl-[1,1'-biphenyl]-4-yl)-3-iodobenzamide

Oxalyl chloride (2.66 mL, 30.4 mmol) was added dropwise to a suspension of 3-iodobenzoic acid (6.98 g, 27.6 mmol) in DCM (140 mL) under a nitrogen atmosphere at room temperature. The mixture was then stirred at rt for 4 h. After the reaction was complete, solvent was removed in vacuum to yield a residue (3-iodobenzoyl chloride), which was dried in high vacuum and used without further purification. This residue was dissolved in DCM (25 mL) and added slowly to a 0° C., stirred solution of 3,5-diisopropyl-[1,1'-biphenyl]-4-amine (5.0 g, 19.73 mmol) and pyridine (2.71 ml, 33.5 mmol) in DCM (50 mL). The mixture was then warmed up and stirred at rt overnight. After the reaction was complete water was added. Aqueous mixture was extracted with DCM. The DCM layer was separated, washed with water (2×) and brine, and then dried over anhydrous $Na_2SO_4$. Filtration and evaporation gave an off-white solid which was recrystallized from 10% hexane in DCM to afford the title compound (5.3 g, 55%).

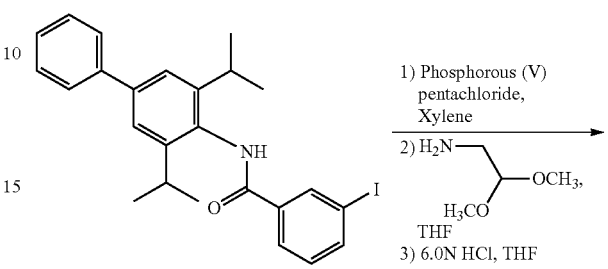

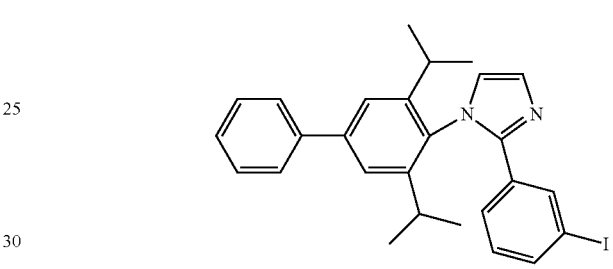

Synthesis of 1-(3,5-diisopropyl-[1,1'-biphenyl]-4-yl)-2-(3-iodophenyl)-1H-imidazole The title compound was prepared from N-(3,5-diisopropyl-[1,1'-biphenyl]-4-yl)-3-iodobenzamide and 2,2-dimethoxyethanamine in substantially the same manner, as described in Synthesis of 1-(3,5-diisopropyl-[1,1'-biphenyl]-4-yl)-2-(3-methoxyphenyl)-1H-imidazole.

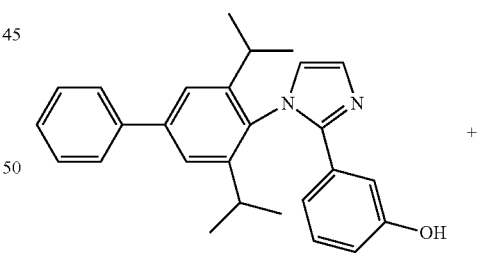

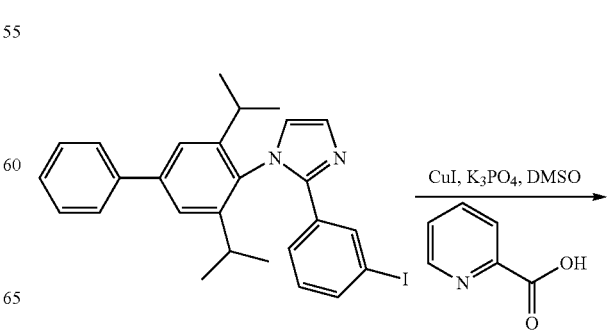

-continued

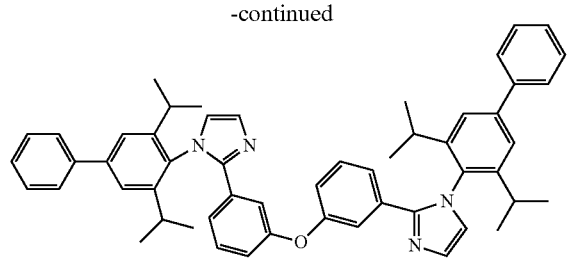

Synthesis of 2,2'-(oxybis(3,1-phenylene))bis(1-(3,5-diisopropyl-[1,1'-biphenyl]-4-yl)-1H-imidazole). A mixture of 3-(1-(3,5-diisopropyl-[1,1'-biphenyl]-4-yl)-1H-imidazol-2-yl)phenol (3.12 g, 7.87 mmol), 1-(3,5-diisopropyl-[1,1'-biphenyl]-4-yl)-2-(3-iodophenyl)-1H-imidazole (3.98 g, 7.87 mmol), copper(I) iodide (0.15 g, 0.787 mmol), picolinic acid (2.91 g, 23.61 mmol) and potassium phosphate (8.35 g, 39.3 mmol) in DMSO (45 mL) was heated at 100° C. under a nitrogen atmosphere. The reaction progress was monitored by HPLC (C18, 95% MeCN in water, 1.0 mL per min.). HPLC after 4 days indicated about 70% desired product. The reaction was worked up until no increase of desired product. 5% aqueous sodium carbonate was added to the reaction mixture until pH around 10. The resulting solid was isolated by filtration and washed with water (3×). This crude mixture was purified by aluminum column chromatography (eluants: DCM/MeOH: 99/1 to 9/5), followed by silica gel column chromatography (eluant: Hexane/acetone: 7/3) to afford a light yellow solid (3.6 g, 59% yield).

Synthesis of Compound 5

2,2'-(oxybis(3,1-phenylene))bis(1-(3,5-diisopropyl-[1,1'-biphenyl]-4-yl)-1H-imidazole) (2.5 g, 3.23 mmol) and potassium tetrachloroplatinate (1.339 g, 3.23 mmol) were added in acetic acid (50 mL). The reaction was bubbled with nitrogen for 20 min and then heated to 140° C. (oil bath temperature) for 3 days. The solid was collected by filtration and columned with 1:1 dichloromethane and hexanes to give the desired product. (1.0 g, 32% yield)

Synthesis of Compound 162

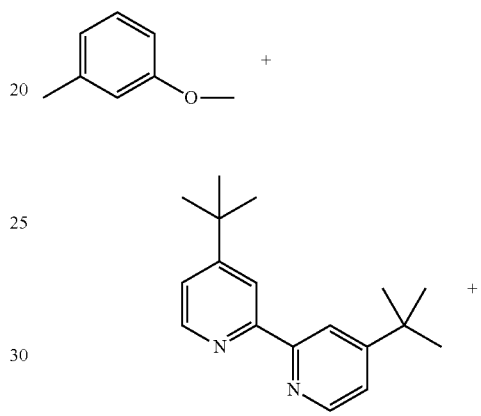

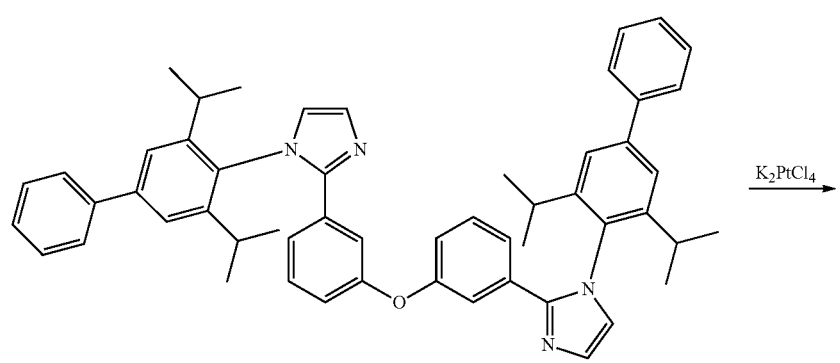

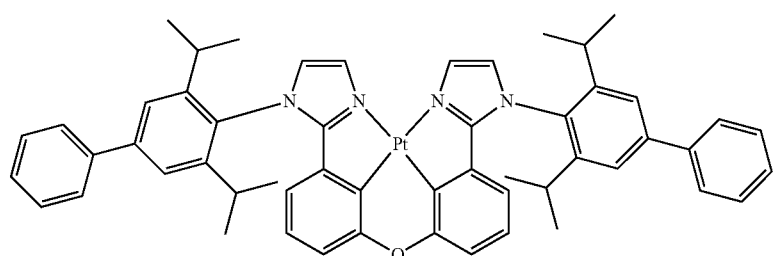

Compound 5

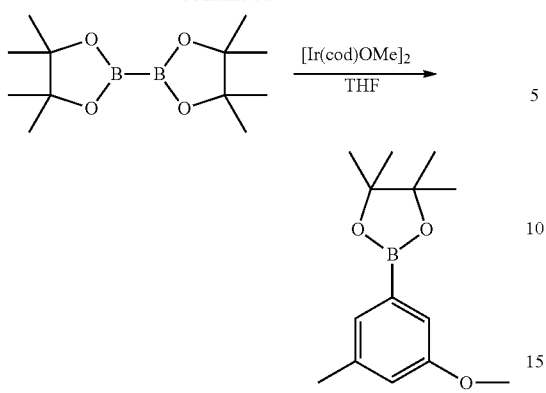

Synthesis 2-(3-methoxy-5-methylphenyl)-4,4,5,5,-tetramethyl-1,3,2-dioxaborolane To a sealable vessel was added 1-methoxy-3-methylbenzene (10.32 ml, 82 mmol), 4,4'-di-tert-butyl-2,2'-bipyridine (0.220 g, 0.819 mmol), 4,4,4',4',5,5,5',5'-octamethyl-2,2'-bi (1,3,2-dioxaborolane) (15.59 g, 61.4 mmol), [Ir(cod)OMe]₂ (0.271 g, 0.409 mmol), and 150 mL THF. The vessel was sealed and heated to 80° C. overnight. The solvent was evaporated and the residue was used as is in the next step. A yield of 15.23 g was estimated.

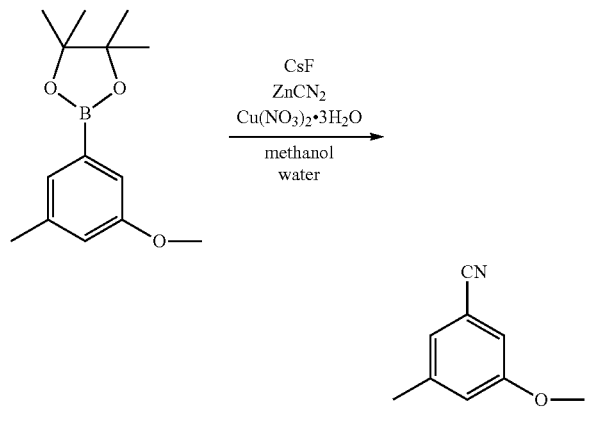

Synthesis of 3-methoxy-5-methylbenzonitrile

To a sealable vessel was added 2-(3-methoxy-5-methylphenyl)-4,4,5,5-tetramethyl-1,3,2-dioxaborolane (15.23 g, 61.4 mmol), copper(II)nitrate trihydrate (29.7 g, 123 mmol), zinc cyanide (21.62 g, 184 mmol), cesium fluoride (9.32 g, 61.4 mmol), 107 mL methanol, and 43 mL water. The vessel was sealed and heated to 100° C. overnight. The reaction mixture was cooled and an insoluble tan solid was filtered and washed with ethyl acetate. Water was added to the filtrate and the layers were separated. The aqueous layer was extracted with ethyl acetate. The organic layers were washed with water, brine, dried over magnesium sulfate, filtered and evaporated. The residue was purified by column chromatography eluting with 0 to 10% ethyl acetate/hexane (3.7 g, 41%)

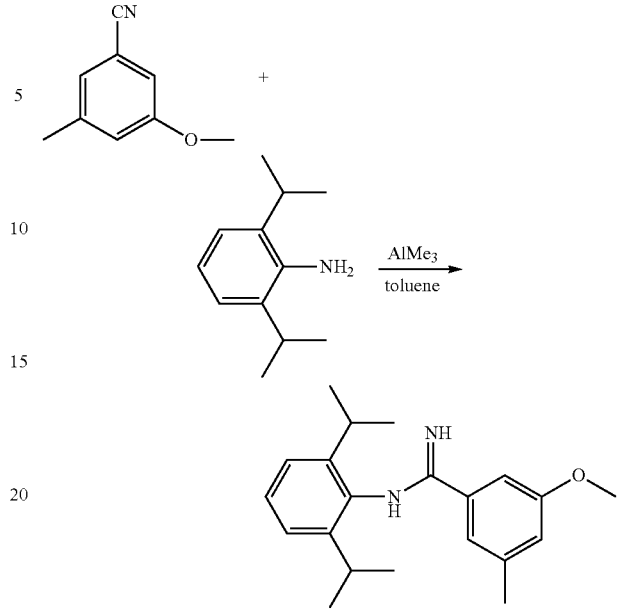

Synthesis of N-(2,6-diisopropylphenyl)-3-methoxy-5-methylbenzimidamide. To a 500 mL 3-neck round bottom flask was added 2,6-diisopropylaniline (4.82 g, 27.2 mmol) and 100 mL toluene. The solution was cooled in an ice bath under nitrogen and trimethylaluminum (2.0 M in toluene, 19 mL, 38.1 mmol) was added dropwise via dropping funnel. The reaction mixture was stirred at room temperature for 2 hours. Next, 3-methoxy-5-methylbenzonitrile (5.20 g, 35.3 mmol) in 50 mL toluene was added and the reaction mixture was heated to 70° C. overnight under nitrogen. The reaction mixture was cooled in an ice bath and was poured onto a stirring slurry of silica gel in 2:1 dichloromethane/methanol (v/v). The silica gel was filtered off and washed with dichloromethane and methanol. The filtrate was evaporated leaving a solid. Hexane was added to the solvent and the solid was filtered off and washed with hexane (5.83 g, 66%).

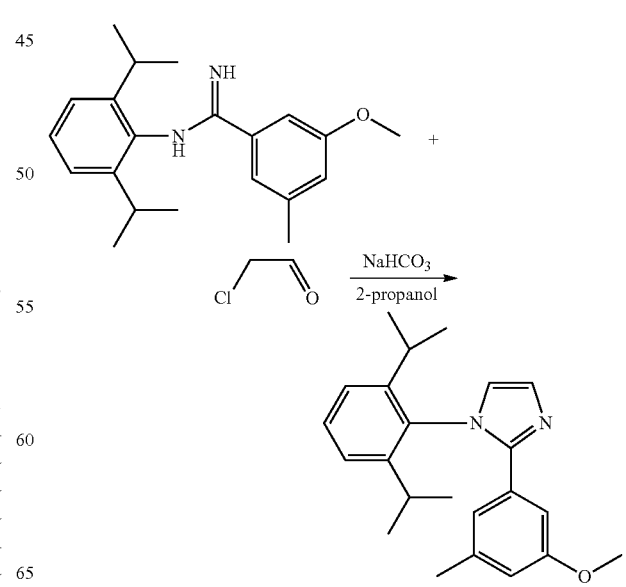

Synthesis of 1-(2,6-diisopropylphenyl)-2-(3-methoxy-5-methylphenyl)-1H-imidazole To a 250 mL round bottom flask was mixed N-(2,6-diisopropylphenyl)-3-methoxy-5-methylbenzimidamide (5.83 g, 17.97 mmol), sodium bicarbonate (3.02 g, 35.9 mmol), 2-chloroacetaldehyde (50%, 4.56 ml, 35.9 mmol), and 80 mL of 2-propanol. The reaction mixture was heated to reflux for 3 hours under nitrogen. The reaction mixture was diluted with water and ethyl acetate. The layers were separated and the aqueous layer was extracted with ethyl acetate. The organic layers were washed with 10% LiCl solution, brine, dried over magnesium sulfate, filtered, evaporated leaving a brown oil. The oil was purified by column chromatography eluting with 20% ethyl acetate/hexane (5.78 g, 92%).

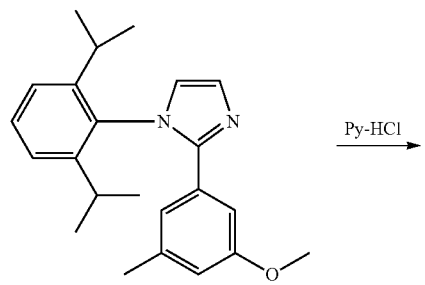

Synthesis of 3-(1-(2,6-diisopropylphenyl)-1H-imidaol-2-yl)-5-methylphenol

To a 250 mL round bottom flask was added 1-(2,6-diisopropylphenyl)-2-(3-methoxy-5-methylphenyl)-1H-imidazole (5.24 g, 15.04 mmol) and pyridine hydrochloride (13.90 g, 120 mmol). The reaction mixture was heated to 190° C. under nitrogen. After 4 hours the reaction mixture was cooled and water was added. A gray solid was filtered off and washed with water. The solid was dried under vacuum (4.36 g, 87%).

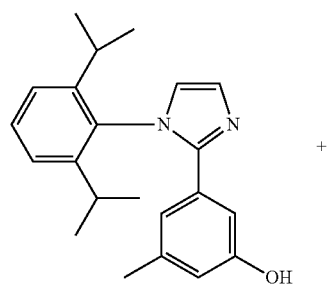

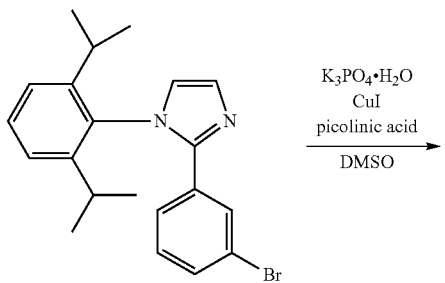

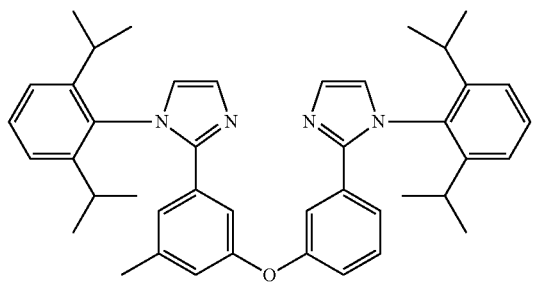

Synthesis of 1-(2,6-diisopropylphenyl)-2-(3-(3-(1-(2,6-diisopropylphenyl)-1H-imidazol-2-yl)-5-methylphenoxy)phenyl)-1H-imidazole To a 300 mL 3-neck round bottom flask was added 3-(1-(2,6-diisopropylphenyl)-1H-imidazol-2-yl)-5-methylphenol (2.5 g, 7.47 mmol), 2-(3-bromophenyl)-1-(2,6-diisopropylphenyl)-1H-imidazole (3.15 g, 8.22 mmol), picolinic acid (1.380 g, 11.21 mmol), copper(I) iodide (0.427 g, 2.242 mmol), potassium phosphate tribasic monohydrate (6.02 g, 26.2 mmol), 100 mL DMSO. Nitrogen was bubbled directly into the mixture and then was heated to 200° C. overnight under nitrogen. The reaction mixture was diluted with ethyl acetate and water and was filtered through Celite. The layers were separated and the aqueous layer was extracted with ethyl acetate. The organic layers were washed with 10% LiCl, brine, dried over magnesium sulfate, filtered, and evaporated leaving a residue. The residue was purified by column chromatography eluting with 40 and 50% ethyl acetate/hexane (1.95 g, 41%).

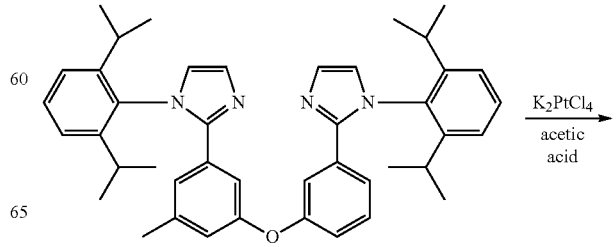

-continued

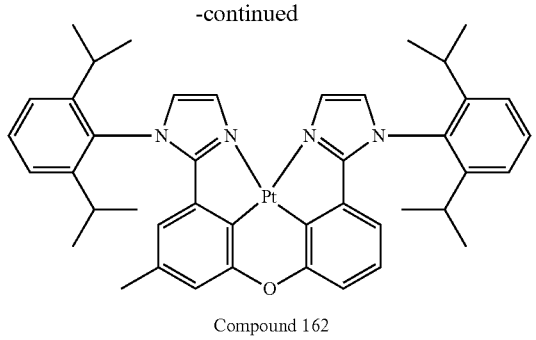

Compound 162

Synthesis of Compound 162

To a 3-neck 300 mL round bottom flask was added 1-(2,6-diisopropylphenyl)-2-(3-(3-(1-(2,6-diisopropylphenyl)-1H-imidazol-2-yl)-5-methylphenoxy)phenyl)-1H-imidazole (2.30 g, 3.61 mmol) and Reactant 1 (1.363 g, 3.28 mmol). Nitrogen was bubbled directly into the mixture. The reaction mixture was heated to 140° C. overnight under nitrogen for 2 days. The reaction mixture was cooled and diluted with hexane. A yellow solid was filtered off and washed with hexane first, then the filtration flask was switched and the solid washed with methanol. The solid was purified by column chromatography eluting with 50% dichloromethane/hexane. The methanol wash also had product in it so it was evaporated and the residue purified by column chromatography eluting with 50% dichloromethane/hexane. The material was combined, dried, and sublimed overnight at 270° C. (0.52 g, 19%).

Synthesis of Compound 163

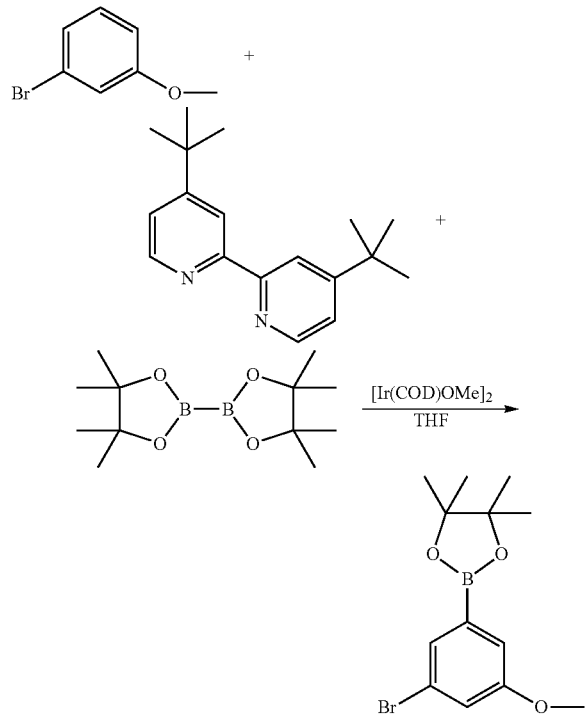

Synthesis of 2-(3-methoxy-5-bromophenyl)-4,4,5,5,-tetramethyl-1,3,2-dioxaborolane To a sealable 250 mL thick wall flask, added 1-bromo-3-methoxybenzene (20 g, 105 mmol), 4,4'-di-tert-butyl-2,2'-bipyridine (0.281 g, 1.048 mmol), 4,4,4',4',5,5,5',5'-octamethyl-2,2'-bi(1,3,2-dioxaborolane) (19.96 g, 79 mmol), [Ir(COD)OMe]$_2$ (0.347 g, 0.524 mmol) (COD is cyclooctadiene), and 200 mL THF and heated up to 80° C. for 19 hrs. After reaction cooled down with ice and slowly open the seal. The solvent was evaporated and the material was used in the next reaction directly. The product was confirmed by GC.

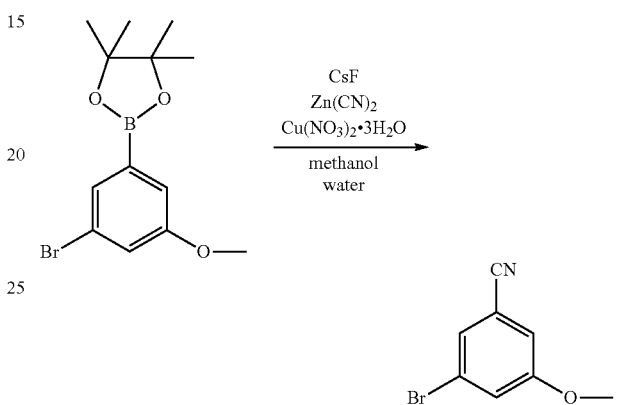

Synthesis of 3-methoxy-5-bromobenzonitrile

To a sealable flask was added the mixture from the previous reaction, cesium fluoride (13.35 g, 88 mmol), zinc cyanide (28.1 g, 240 mmol) and Cu(NO$_3$)$_2$ 3H$_2$O (38.6 g, 160 mmol) starting materials and 125 mL methanol and 50 mL water (2.5:1 ratio) and heated at 100° C. overnight. The product was confirmed by GC. After recrystallization from methanol 8.5 g of the product was obtained, and was used directly in the next step.

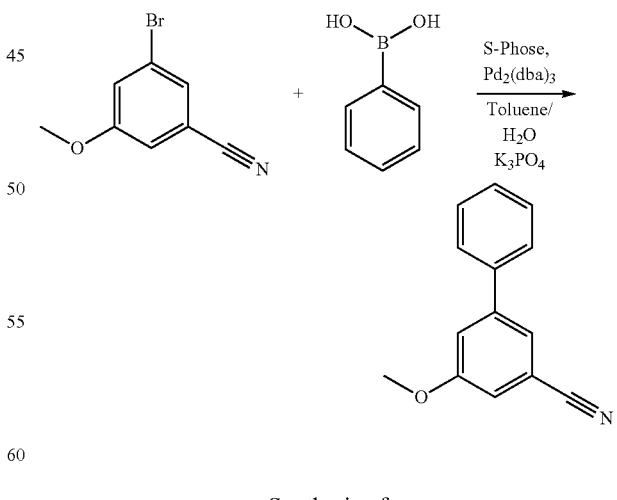

Synthesis of 5-methoxy-[1,1'-biphenyl]-3-carbonitrile 3-bromo-5-methoxybenzonitrile (8.3 g, 39.1 mmol), dicyclohexyl(2',6'-dimethoxy-[1,1'-biphenyl]-2-yl)phosphine (S-Phos) (1.286 g, 3.13 mmol), phenylboronic acid (5.84 g, 47.0 mmol), Pd$_2$(dba)$_3$ and 200 mL toluene were charged in a flask and refluxed overnight. The reaction was cooled down and 200 mL of ethyl acetate was added. The crude mixture was run though a silica gel plug, and the product was confirmed by GC. After distillation under vacuum, 7.5 g of a white product was obtained.

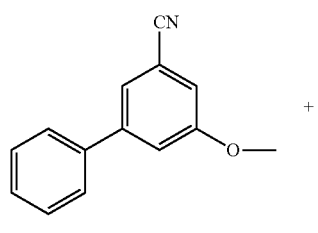

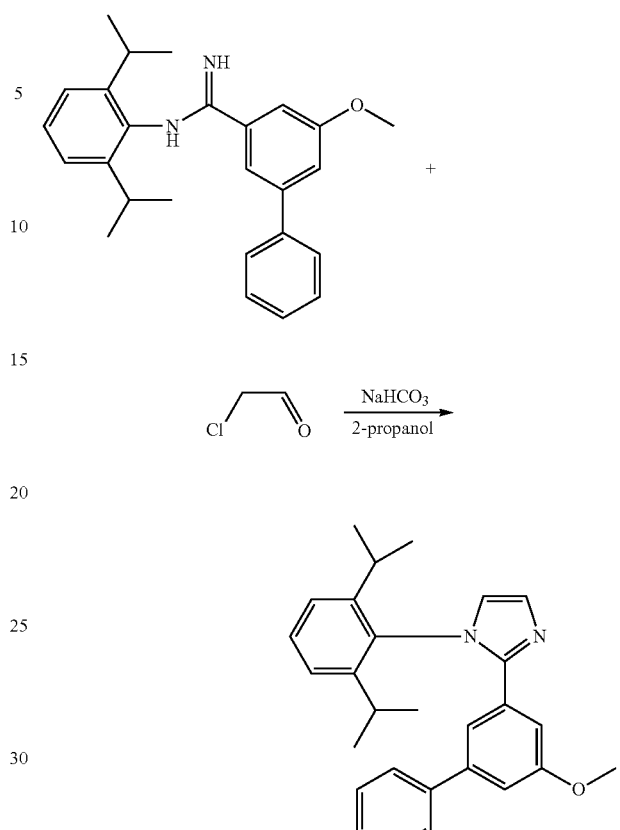

Synthesis of N-(2,6-diisopropylphenyl)-5-methoxy-[1,1'-biphenyl]-3-carboximidamide To a 500 mL 3 neck flask, 2,6-diisopropylaniline (4.99 g, 27.3 mmol) and 100 mL toluene were charged. The mixture was cooled down in ice bath. Trimethylaluminum (20.48 mL, 41.0 mmol) was added dropwise via additional funnel. The reaction mixture was stirring at RT for 2 hours. Then, to the mix, added 5-methoxy-[1,1'-biphenyl]-3-carbonitrile (6.0 g, 28.7 mmol) dissolved in 50 mL toluene. The reaction mixture was heated to 70° C. overnight under a nitrogen atmosphere. The reaction mixture was cooled in an ice bath and poured it into silica gel mixed with DCM and methanol (2:1 ratio of DCM:methanol). The slurry was stirred and filtered and washed with DCM and methanol. The solvent was evaporated. The solid remaining after evaporation of solvent was added to 150 mL hexane and the mixture was stirred. The mixture was filtered and washed with hexane. After removal of solvent, 6.8 g of product was obtained for next step.

Synthesis of 1-(2,6-diisopropylphenyl)-2-(5-methoxy-[1,1'-biphenyl]-3-yl)-1H-imidazole To a 250 mL round bottom flask was mixed 2-chloroacetaldehyde (5.36 g, 34.2 mmol), NaHCO$_3$ (2.87 g, 34.2 mmol), N-(2,6-diisopropylphenyl)-5-methoxy-[1,1'-biphenyl]-3-carboximidamide (6.6 g, 17.08 mmol) were charged in a flask and 100 mL of iso-propyl amine was added. The reaction mixture was heated up to reflux for 3 hours. The reaction mixture was diluted with water and ethyl acetate. The layers were separated and the aqueous layer was extracted with ethyl acetate. After silica gel chromatography with 10% ethyl acetate in hexane as solvent, 6.9 g of product was obtained.

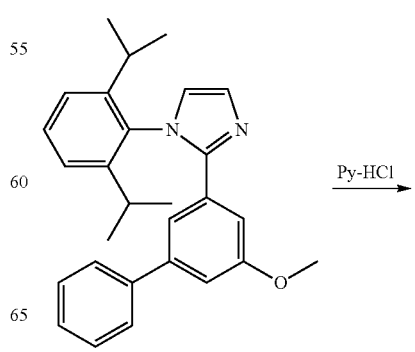

Synthesis of 5-(1-(2,6-diisopropylphenyl)-1H-imidazol-2-yl)-[1,1'-biphenyl]-3-ol To a 250 mL round bottom flask was added 1-(2,6-diisopropylphenyl)-2-(5-methoxy-[1,1'-biphenyl]-3-yl)-1H-imidazole (6.9 g, 16.81 mmol) and pyridine hydrochloride (15.85 g, 134 mmol). The reaction mixture was heated to 190° C. under a nitrogen atmosphere. After 4 hours the reaction mixture was cooled and water was added. A gray solid was filtered off and washed with water. The solid was dried under vacuum and 5.7 g of product was obtained.

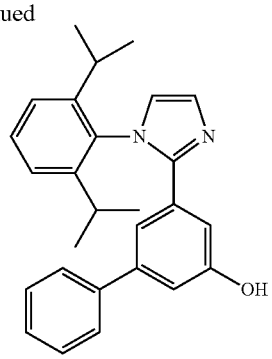

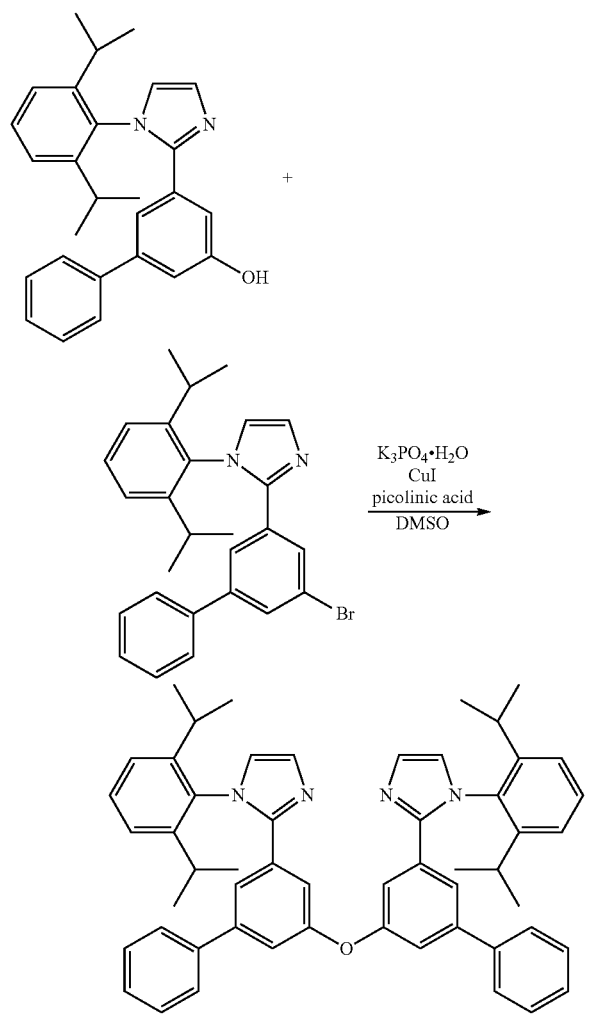

Synthesis of 2,2'-(oxybis([1,1'-biphenyl]-5,3-diyl))bis(1-2,6diisopropylphenyl)-1-H-imidazole)

To a 250 mL 3-neck round bottom flask was added 5-(1-(2,6-diisopropylphenyl)-1H-imidazol-2-yl)-[1,1'-biphenyl]-3-ol (2.5 g, 6.30 mmol), 2-(5-boromo-1,1'-biphenyl]-3-yl)-1-(2,6-diisopropylphenyl)-1-H-imidazole (3.19 g, 6.49 mmol), picolinic acid (1.164 g, 9.46 mmol), copper(I) iodide (0.427 g, 2.242 mmol), potassium phosphate tribasic monohydrate (5.02 g, 22.07 mmol), 100 mL DMSO. Nitrogen was bubbled directly into the mixture and then was heated to 190° C. overnight under nitrogen. The reaction mixture was diluted with ethyl acetate and water and was filtered through Celite®. The layers were separated and the aqueous layer was extracted with ethyl acetate. The organic layers were washed with 10% LiCl, brine, dried over magnesium sulfate, filtered, and evaporated leaving a residue. The residue was purified by column chromatography eluting with 25% ethyl acetate/hexane (3.45 g, 70.6%).

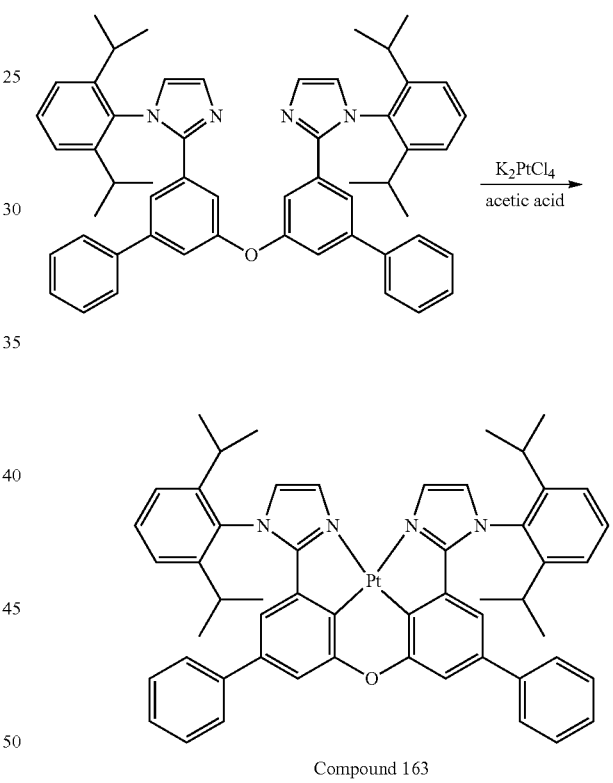

Compound 163

Synthesis of Compound 163

To a 3-neck 300 mL round bottom flask was added 2,2'-(oxybis([1,1'-biphenyl]-5,3-diyl))bis(1-2,6diisopropylphenyl)-1-H-imidazole) (3.4 g, 4.39 mmol) and potassium tetrachloroplatinate (1.734 g, 4.18 mmol). Nitrogen was bubbled directly into the mixture for 30 minutes. The reaction mixture was heated to 140° C. overnight under nitrogen for 2 days. The reaction mixture was cooled and diluted with hexane. A yellow solid was filtered off and washed with hexane first, then the filtration flask was switched and the solid washed with methanol. The solid was purified by column chromatography eluting with 50% dichloromethane/hexane to give 2.8 g (69.2% yield) pure product, which was confirmed by LC-MS.

Synthesis of Compound 30

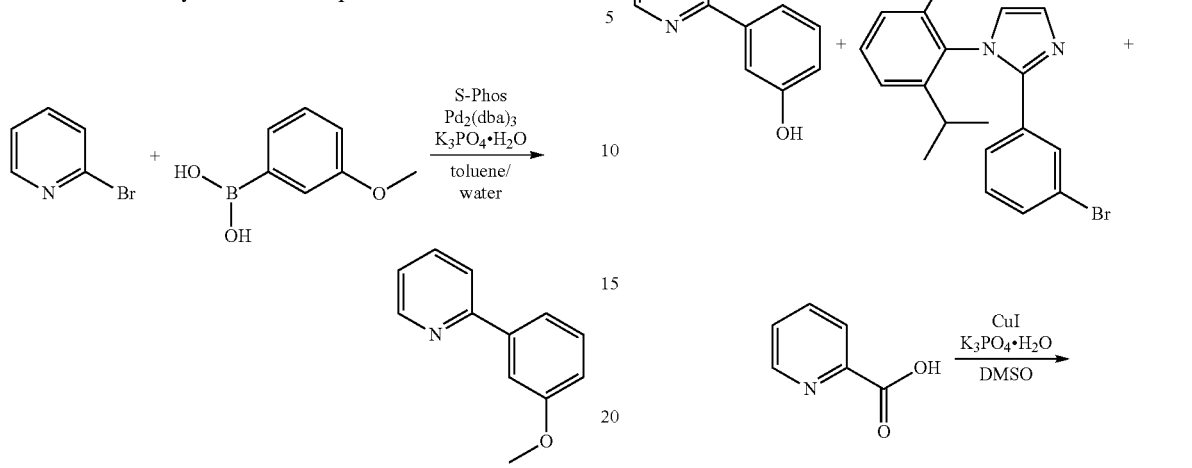

Synthesis of 2-(3-methoxyphenyl)pyridine

To a 1 L 3-neck round-bottom flask was added 2-bromopyridine (12.07 mL, 127 mmol), (3-methoxyphenyl)boronic acid (24.04 g, 158 mmol), potassium phosphate tribasic monohydrate (87 g, 380 mmol), dicyclohexyl(2',6'-dimethoxy-[1,1'-biphenyl]-2-yl)phosphine (S-phos) (2.079 g, 5.06 mmol), 450 mL toluene, and 45 mL water. Nitrogen was bubbled directly into the mixture. $Pd_2(dba)_3$ (1.159 g, 1.266 mmol) was added and the reaction mixture heated to reflux overnight under nitrogen. The reaction mixture was diluted with water and the layers were separated. The aqueous layer was extracted with ethyl acetate. The organic layers were dried over magnesium sulfate, filtered, and evaporated. The crude material was purified by column chromatography eluting with 20% ethyl acetate to afford a yellow liquid (21.5 g, 92%).

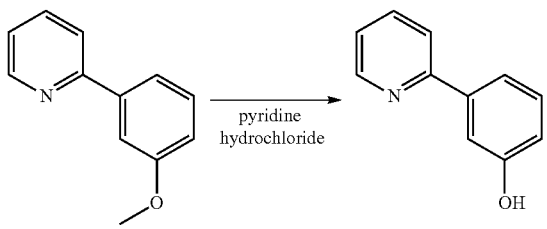

Synthesis of 3-(pyridine-2-yl)phenol

To a 500 mL round bottom flask was added 2-(3-methoxyphenyl)pyridine (21.3 g, 115 mmol) and pyridine hydrochloride (107.5 g, 930 mmol). The reaction mixture was heated to 190° C. for 8 hours under nitrogen. The reaction mixture was cooled slightly and water was added. The mixture was stirred overnight. The pH of the solution was adjusted to 7 with 10% sodium hydroxide solution, extracted three times with dichloromethane. The organic layers were washed with 10% LiCl solution, brine, dried over magnesium sulfate, filtered, and evaporated. The residue was distilled on a Kugelrohr to remove the remaining pyridine (18 g, 91%).

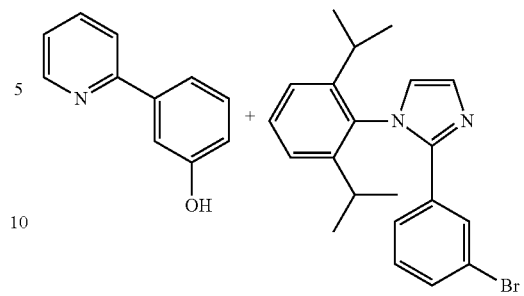

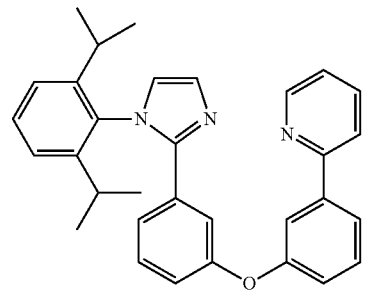

Synthesis of 2-(3-(3-(1-(2,6-diisopropyl)-1H-imidazol-2-yl)phenoxy)phenyl)pyridine. To a 250 mL 3-neck round-bottom flask was added 3-(pyridine-2-yl)phenol (0.983 g, 5.74 mmol), 2-(3-bromophenyl)-1-(2,6-diisopropylphenyl)-1H-imidazole (2.2 g, 5.74 mmol), picolinic acid (1.060 g, 8.61 mmol), copper(I) iodide (0.328 g, 1.722 mmol), potassium phosphate tribasic monohydrate (4.63 g, 20.09 mmol), and 70 mL DMSO. The mixture was purged with nitrogen and heated to 200° C. overnight under nitrogen. The cooled reaction mixture was diluted with ethyl acetate and water and the layers were separated. The aqueous layer was extracted with ethyl acetate. The organic layers were washed with 10% LiCl solution, brine, dried over magnesium sulfate, filtered, and evaporated leaving a brown oil. The oil was purified by column chromatography eluting with 30 and 40% ethyl acetate/hexane (2.07 g, 76%).

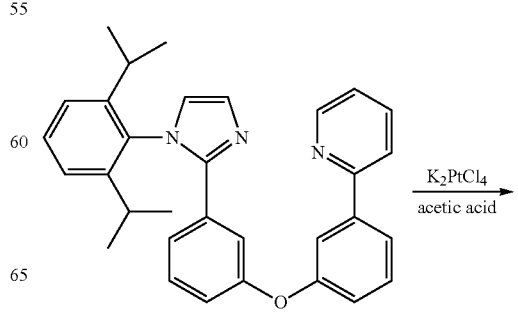

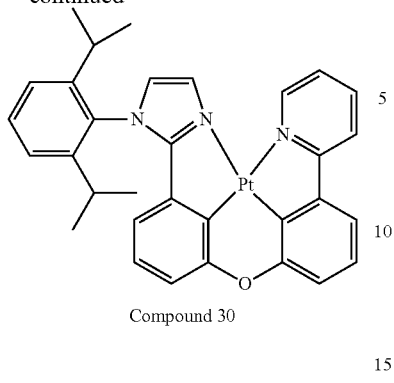

Compound 30

Synthesis of Compound 30

To a 500 mL round bottom flask was added 2-(3-(3-(1-(2,6-diisopropylphenyl)-1H-imidazol-2-yl)phenoxy)phenyl)pyridine (2.07 g, 4.37 mmol), potassium tetrachloroplatinate (1.649 g, 3.97 mmol), and 80 mL acetic acid. Nitrogen was bubbled into the mixture for 30 minutes and then heated to 140° C. overnight under nitrogen. After 2 days, the cooled reaction mixture was filtered to leave a yellow solid which was washed with hexane, 2.61 g. The solid was purified by column chromatography eluting with 50 and 60% dichloromethane/hexane. The material was sublimed at 290° C. overnight (1 g, 38%).

Synthesis of Compound 161

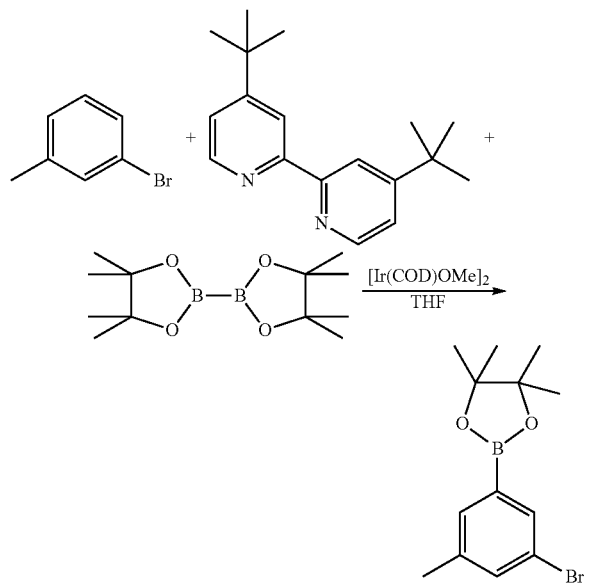

Synthesis of 2-(3-bromo-5-methylphenyl)-4,4,5,5,-tetramethyl-1,3,2-dioxaborolane To a sealable vessel was added 1-bromo-3-methylbenzene (20 g, 117 mmol), 4,4'-di-tert-butyl-2,2'-bipyridine (0.314 g, 1.169 mmol), 4,4,4',4',5,5,5',5'-octamethyl-2,2'-bi(1,3,2-dioxaborolane) (22.27 g, 88 mmol), [Ir(COD)OMe]₂ (0.388 g, 0.585 mmol), and 160 mL THF. The vessel was sealed and heated to 80° C. overnight. The solvent was evaporated and the residue was used as is in the next step. A yield of 26.1 g was estimated.

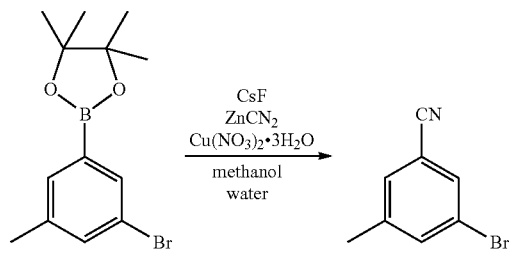

Synthesis of 3-bromo-5-methylbenzonitrile

To a sealable vessel was added 2-(3-bromo-5-methylphenyl)-4,4,5,5-tetramethyl-1,3,2-dioxaborolane (26.1 g, 88 mmol), copper(II)nitrate trihydrate (42.5 g, 176 mmol), zinc cyanide (31.0 g, 264 mmol), cesium fluoride (13.35 g, 88 mmol), 125 mL methanol, and 50 mL water. The vessel was sealed and heated to 100° C. for 5 hours. The reaction mixture was cooled and an insoluble tan solid was filtered and washed with ethyl acetate and water. The layers were separated and the aqueous layer was extracted with ethyl acetate. The organic layers were washed with brine, dried over magnesium sulfate, filtered and evaporated. The residue was purified by column chromatography eluting with 5 and 10% ethyl acetate/hexane (3.4 g, 20%)

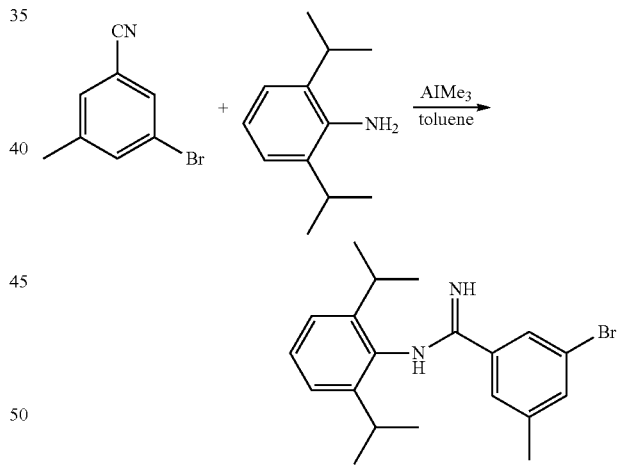

Synthesis of 3-bromo-N-(2,6-diisopropylphenyl)-5-methylbenzimidamide

To a 250 mL 3-neck round bottom flask was added 2,6-diisopropylaniline (2.365 g, 13.34 mmol) and 70 mL toluene. The solution was cooled in an ice bath under nitrogen and trimethylaluminum (2.0 M in toluene, 9.34 mL, 18.68 mmol) was added dropwise via dropping funnel. The reaction mixture was stirred at room temperature for 2 hours. Next, 3-bromo-5-methylbenzonitrile (3.4 g, 17.34 mmol) in 30 mL toluene was added and the reaction mixture was heated to 70° C. overnight under nitrogen. The reaction mixture was cooled in an ice bath and was poured onto a stirring slurry of silica gel in 2:1 dichloromethane/methanol (v/v). The silica gel was filtered off and washed with dichloromethane and methanol. The filtrate was evaporated leaving a solid. Hexane was added to the solvent and the solid was filtered off and washed with hexane (2.92 g, 59%).

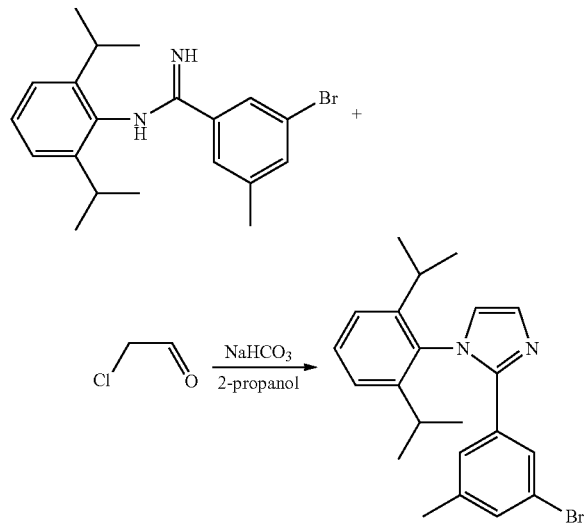

Synthesis of 2-(3-bromo-5-methylphenyl)-1-(2,6-diisopropylphenyl)-1H-imidazole

To a 250 mL round bottom flask was added 3-bromo-N-(2,6-diisopropylphenyl)-5-methylbenzimidamide (2.92 g, 7.82 mmol), 2-chloroacetaldehyde (50%, 2.456 g, 15.64 mmol), sodium bicarbonate (1.314 g, 15.64 mmol), 60 mL 2-propanol. The reaction mixture was heated to reflux overnight under nitrogen. The reaction mixture was cooled and diluted with ethyl acetate and water. The layers were separated and the aqueous layer was extracted with ethyl acetate. The organic layers were washed with 10% LiCl solution, brine, dried over magnesium sulfate, filtered, and evaporated. The material was purified by column chromatography eluting with 15 and 20% ethyl acetate/hexane to give desired product (2.45 g, 79%).

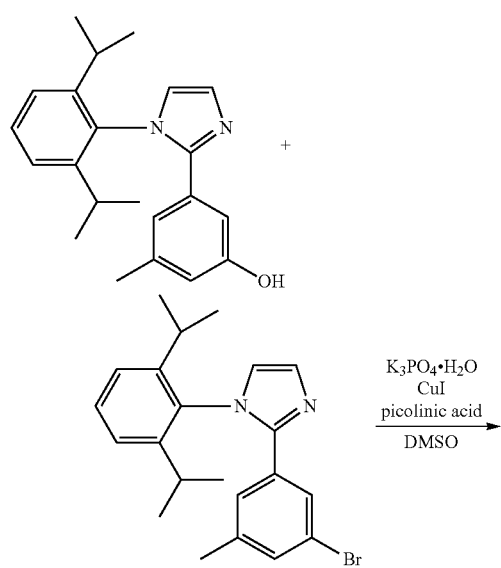

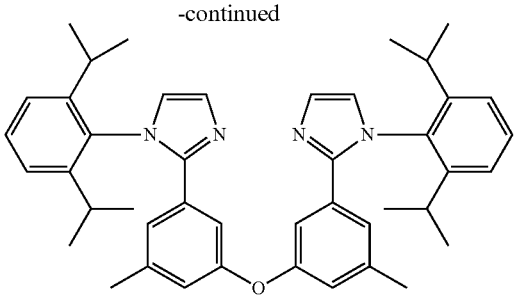

Synthesis of 2,2'-(oxybis(3-methyl-5,1-phenylene))bis(1-(2,6-diisopropylphenyl)-1H-imidazole To a 125 mL 3-neck round bottom flask was added 3-(1-(2,6-diisopropylphenyl)-1H-imidazol-2-yl)-5-methylphenol (0.979 g, 2.93 mmol), 2-(3-bromo-5-methylphenyl)-1-(2,6-diisopropylphenyl)-1H-imidazole (1.28 g, 3.22 mmol), picolinic acid (0.541 g, 4.39 mmol), copper(I) iodide (0.167 g, 0.879 mmol), potassium phosphate tribasic monohydrate (2.360 g, 10.25 mmol), and 50 mL DMSO. Nitrogen was bubbled directly into the mixture and was heated to 200° C. overnight under nitrogen. The reaction mixture was diluted with ethyl acetate and water. The mixture was filtered through Celite® and washed with ethyl acetate and water. The layers were separated and the aqueous layer was extracted with ethyl acetate. The organic layers were washed with brine, dried over magnesium sulfate, filtered, and evaporated leaving a residue. The residue was purified by column chromatography eluting with 30% ethyl acetate/hexane to ethyl acetate to give desired product (0.98 g, 51%).

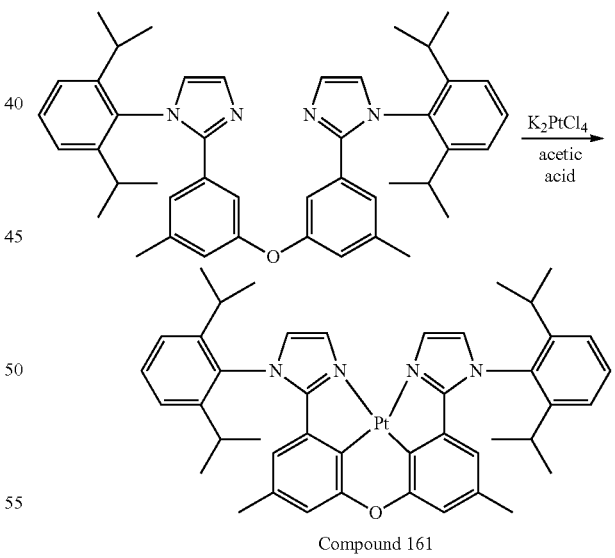

Compound 161

Synthesis of Compound 161

To a 250 mL round bottom flask was added 2,2'-(oxybis(3-methyl-5,1-phenylene))bis(1-(2,6-diisopropylphenyl)-1H-imidazole) (1.6 g, 2.458 mmol), potassium tetrachloroplatinate (0.928 g, 2.235 mmol), and 40 mL acetic acid. Nitrogen was bubbled into the mixture for 30 minutes. The reaction mixture was heated to 140° C. for 3 days. The reaction was cooled and diluted with hexane. The yellow solid was filtered off and washed with hexane. The material was purified by column chromatography eluting with 1:1 dichloromethane/hexane to give platinum complex (0.2 g, 10%).

Synthesis of Compound 164

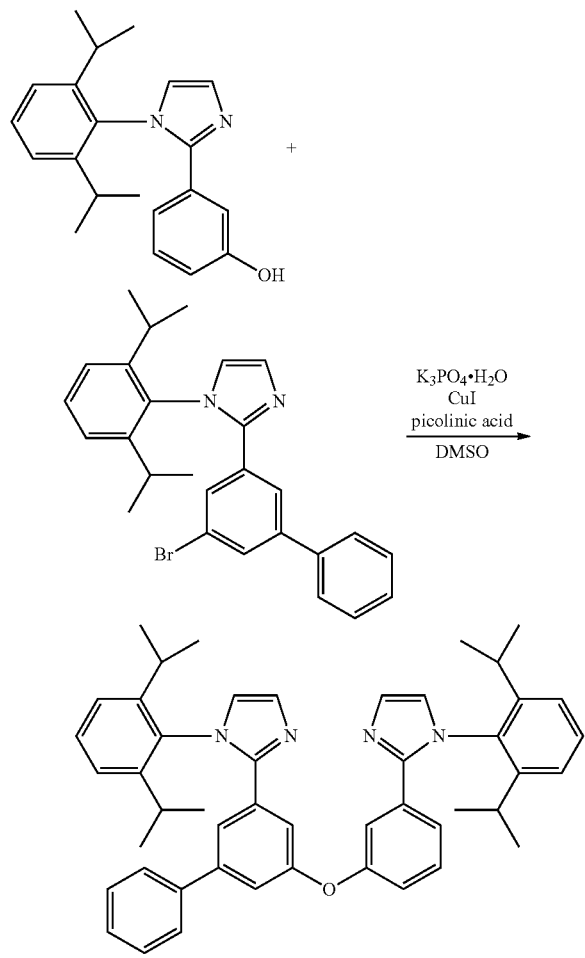

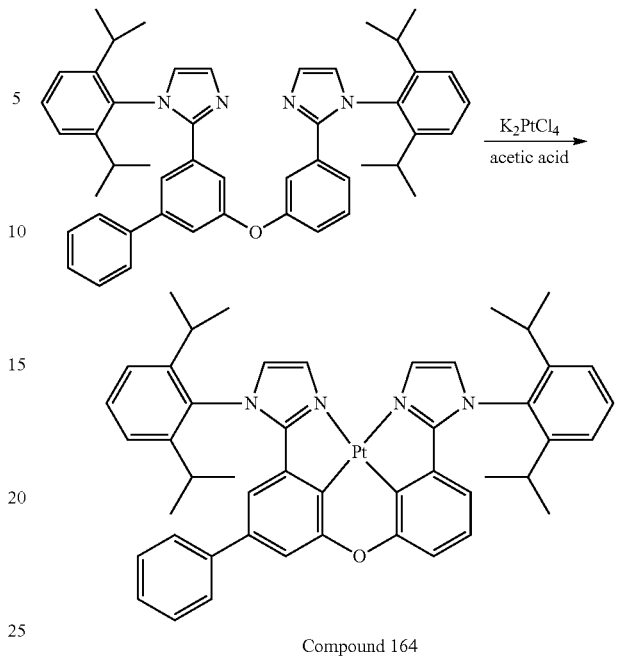

Compound 164

Synthesis of Compound 164

To a 250 mL round bottom flask was added 1-(2,6-diisopropylphenyl)-2-(3-((5-(1-(2,6-diisopropylphenyl)-1H-imidazol-2-yl)-[1,1'-biphenyl]-3-yl)oxy)phenyl)-1H-imidazole (2.5 g, 3.58 mmol), potassium tetrachloroplatinate (1.35 g, 3.25 mmol), and 100 mL acetic acid. Nitrogen was bubbled into the mixture for 30 minutes. The reaction mixture was heated to 140° C. for 3 days. The reaction was cooled; the product was soluble in acetic acid. The solvent was evaporated. The material was purified by column chromatography eluting with 30% dichloromethane/hexane to give desired product (0.3 g, 10%).

Synthesis of Compound 165

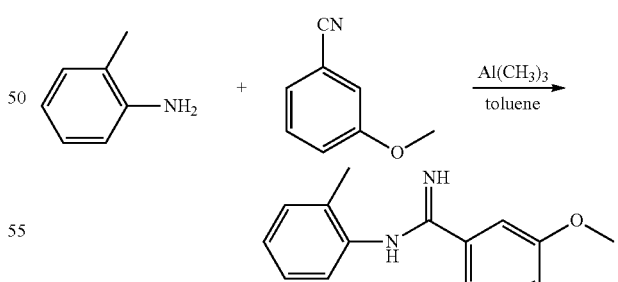

Synthesis of 2,2'-(oxybis(3-phenyl-5,1-phenylene))bis(1-(2,6-diisopropylphenyl)-1H-imidazole To a 125 mL 3-neck round bottom flask was added 3-(1-(2,6-diisopropylphenyl)-1H-imidazol-2-yl)phenol (2 g, 6.24 mmol), 2-(5-bromo-(1,1-biphenyl-3-yl)-methyl phenyl)-1H-imidazole (2.87 g, 6.24 mmol), picolinic acid (0.119 g, 0.624 mmol), copper(I) iodide (0.154 g, 0.624 mmol), potassium phosphate tribasic monohydrate (2.65 g, 12.48 mmol), and 50 mL DMSO. Nitrogen was bubbled directly into the mixture and was heated to 200° C. overnight under nitrogen. The reaction mixture was diluted with ethyl acetate and water. The mixture was filtered through Celite® and washed with ethyl acetate and water. The layers were separated and the aqueous layer was extracted with ethyl acetate. The organic layers were washed with brine, dried over magnesium sulfate, filtered, and evaporated leaving a residue. The residue was purified by column chromatography eluting with 30% ethyl acetate/hexane to yield 2.6 g (60% yield) of product.

Synthesis of 3-methoxy-N-(o-tolyl)benzamide

To a 500 mL 3-neck round bottom flask was added o-toluidine (4.50 g, 42.0 mmol) and 150 mL toluene. The solution was cooled in an ice bath under nitrogen. Trimethylaluminum (2.0 M in toluene, 29.4 ml, 58.8 mmol) was added dropwise via dropping funnel. The reaction mixture was stirred at room temperature for 2 hours under nitrogen. Next, 3-methoxybenzonitrile (7.27 g, 54.6 mmol) in 50 mL toluene was added and the reaction mixture was heated to 70° C. overnight under nitrogen. The reaction mixture was cooled in an ice bath and poured onto a stirring slurry of silica gel in 2:1 dichloromethane/methanol. The silica gel was filtered and washed with dichloromethane and methanol. The filtrate was evaporated leaving a solid. The solid was triturated with hexane, filtered, washed with hexane (6 g, 59%).

pyridine hydrochloride (19.52 g, 169 mmol). The reaction mixture was heated to 200° C. for 5 hours. The reaction was cooled slightly, and water was added and cooled in an ice bath. The mixture was stirred overnight under nitrogen. A gray solid was filtered off, washed with water, and dried under vacuum with heat to give 2.4 g of solid. The filtrate was adjusted to pH 7 with 10% sodium hydroxide solution, more product precipitated out of solution. The solid was filtered off, washed with water, and dried to obtain 1.85 g of product (4.25 g, 80%).

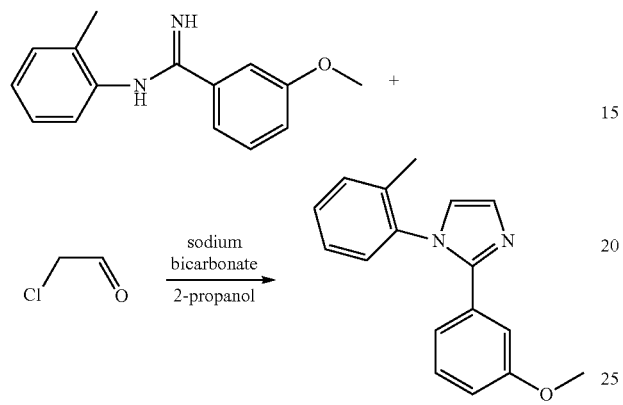

Synthesis of 2-(3-methoxyphenyl)-1-(o-tolyl)-1H-imidazole

To a 500 mL round bottom flask was added 3-methoxy-N-(o-tolyl)benzimidamide (6 g, 24.97 mmol), 2-chloroacetaldehyde (6.34 ml, 49.9 mmol), sodium bicarbonate (4.20 g, 49.9 mmol), and 100 mL 2-propanol. The reaction mixture was heated to reflux under nitrogen. The reaction mixture was concentrated, water was added, and the mixture was extracted three times with ethyl acetate. The organic extracts were dried over magnesium sulfate, filtered, and evaporated. The residue was purified by column chromatography eluting with 40% ethyl acetate/hexane (5.58 g, 85%).

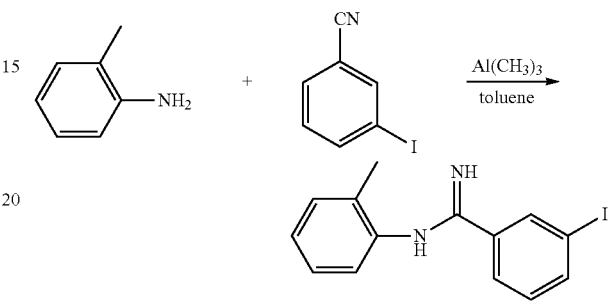

Synthesis of 3-iodo-N-(o-tolyl)benzamide

To a 500 mL 3-neck round bottom flask was added o-toluidine (3.60 g, 33.6 mmol) and 150 mL toluene. The solution was cooled in an ice bath under nitrogen. Trimethylaluminum (2.0 M in toluene, 23.51 ml, 47.0 mmol) was added dropwise via dropping funnel. The reaction mixture was stirred at room temperature for 2 hours. Next, 3-iodobenzonitrile (10 g, 43.7 mmol) in 50 mL toluene was added and the reaction mixture was heated to 70° C. overnight under nitrogen. The reaction mixture was cooled in an ice bath and poured onto a stirring slurry of silica gel in 2:1 dichloromethane/methanol. The silica gel was filtered off and washed with dichloromethane and methanol. The filtrate was evaporated leaving a solid. The solid was triturated with hexane, filtered, washed with hexane (7.77 g, 69%).

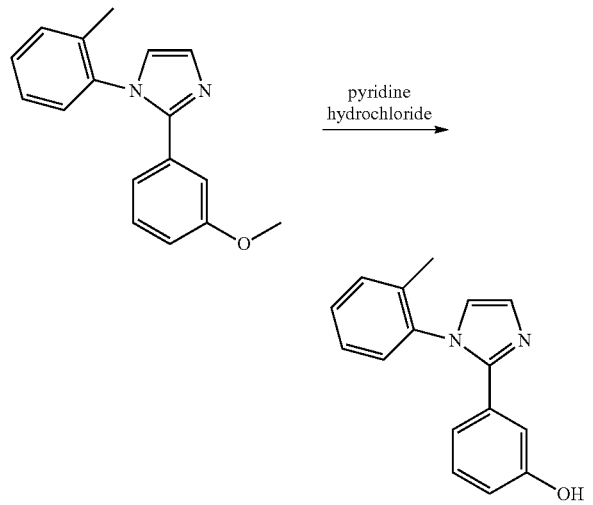

Synthesis of 3-(1-(o-tolyl)-1H-imidazol-2-yl)phenol

To a 500 mL round bottom flask was added 2-(3-methoxyphenyl)-1-(o-tolyl)-1H-imidazole (5.58 g, 21.11 mmol) and

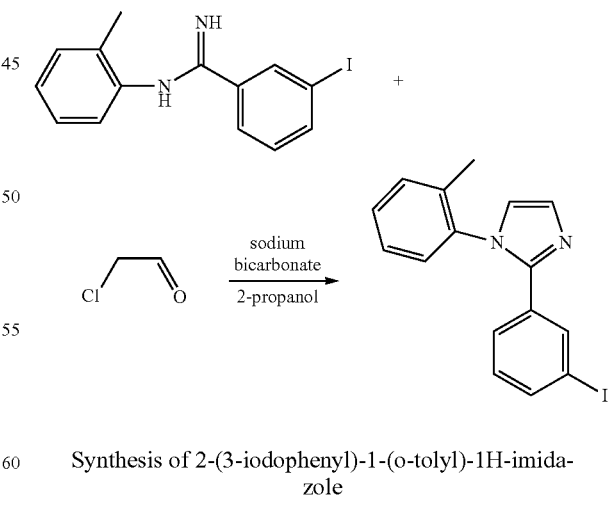

Synthesis of 2-(3-iodophenyl)-1-(o-tolyl)-1H-imidazole

To a 500 mL round bottom flask was added 3-iodo-N-(o-tolyl)benzimidamide (7.77 g, 23.11 mmol), 2-chloroacetaldehyde (5.87 ml, 46.2 mmol), sodium bicarbonate (3.88 g, 46.2 mmol), and 100 mL 2-propanol. The reaction mixture was heated to reflux under nitrogen for 5 hours. The reaction mixture was concentrated, water was added, and the mixture extracted three times with ethyl acetate. The organic extracts were dried over magnesium sulfate, filtered, and evaporated. The residue was purified by column chromatography eluting with 40 and 50% ethyl acetate/hexane (4.6 g, 55%).

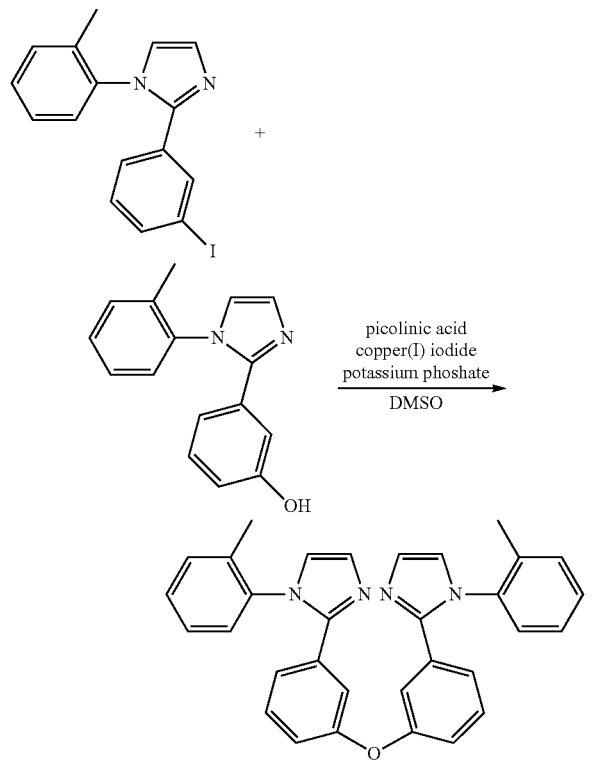

Synthesis of 2,2'-(oxybis(3,1-phenylene))bis(1-(o-tolyl)-1H-imidazole)

To a 250 mL round bottom flask was added 3-(1-(o-tolyl)-1H-imidazol-2-yl)phenol (2.009 g, 8.03 mmol), 2-(3-iodophenyl)-1-(o-tolyl)-1H-imidazole (3.18 g, 8.83 mmol), picolinic acid (1.482 g, 12.04 mmol), copper(I) iodide (0.459 g, 2.408 mmol), potassium phosphate tribasic monohydrate (6.47 g, 28.1 mmol), and 80 mL DMSO. Nitrogen was bubbled directly into the mixture and then was heated to 150° C. overnight under nitrogen. The reaction mixture was cooled to room temperature, added water, extracted twice with ethyl acetate, dried extracts over magnesium sulfate, filtered, and evaporated. The residue was purified by column chromatography eluting with 80% ethyl acetate/hexane (2.12 g, 55%).

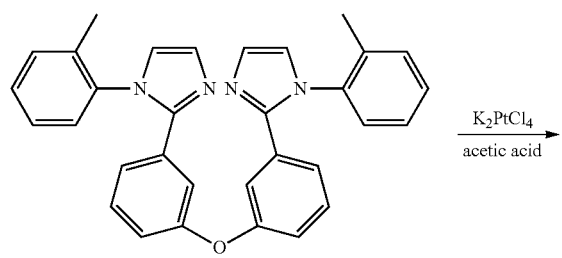

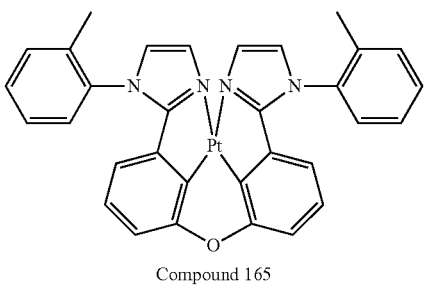

Compound 165

Synthesis of Compound 165

To a 250 mL round bottom flask was added 2,2'-(oxybis(3,1-phenylene))bis(1-(o-tolyl)-1H-imidazole) (2.08 g, 4.31 mmol), potassium tetrachloroplatinate (1.626 g, 3.92 mmol), and 80 mL acetic acid. Nitrogen was bubbled into the reaction mixture for 30 minutes then heated to 140° C. for 2 days under nitrogen. The reaction mixture was cooled; filtered off orange solid. The solid was purified by column chromatography twice using a column pretreated with 15% triethylamine/hexane. The first column was eluted with 70% dichloromethane/hexane and the second column was eluted with 50% dichloromethane/hexane (0.09 g, 3%).

Synthesis of Compound 29

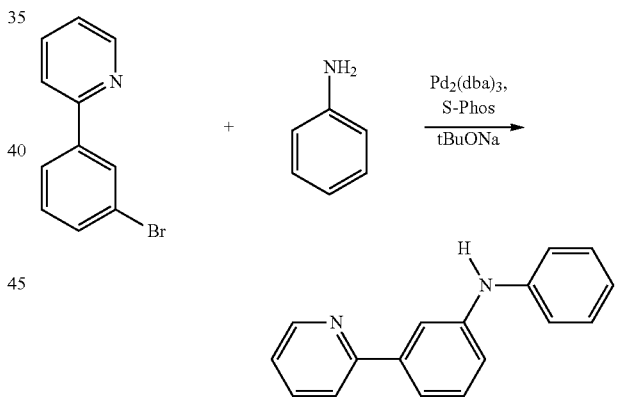

Synthesis of N-phenyl-3-(pyridin-2-yl)aniline 2-(3-bromophenyl)pyridine (4 g, 17.09 mmol), $Pd_2(dba)_3$ (0.156 g, 0.171 mmol), dicyclohexyl(2',6'-dimethoxy-[1,1'-biphenyl]-2-yl)phosphine (S-Phos) (0.281 g, 0.683 mmol), and sodium t-butoxide (2.463 g, 25.6 mmol) were mixed in 100 mL of xylene. The solution was bubbled with nitrogen for 20 min. Aniline (2.387 g, 25.6 mmol) was added. The reaction was heated up to reflux for 6 h. After cooled to rt, dichloromethane was added. The mixture was filtered through Celite®. The solvent was then evaporated. The residue was coated on Celite® and columned with 1:5 hexanes/ethyl acetate to give N-phenyl-3-(pyridin-2-yl)aniline (3.6 g, 14.62 mmol, 86% yield) as light yellow solid.

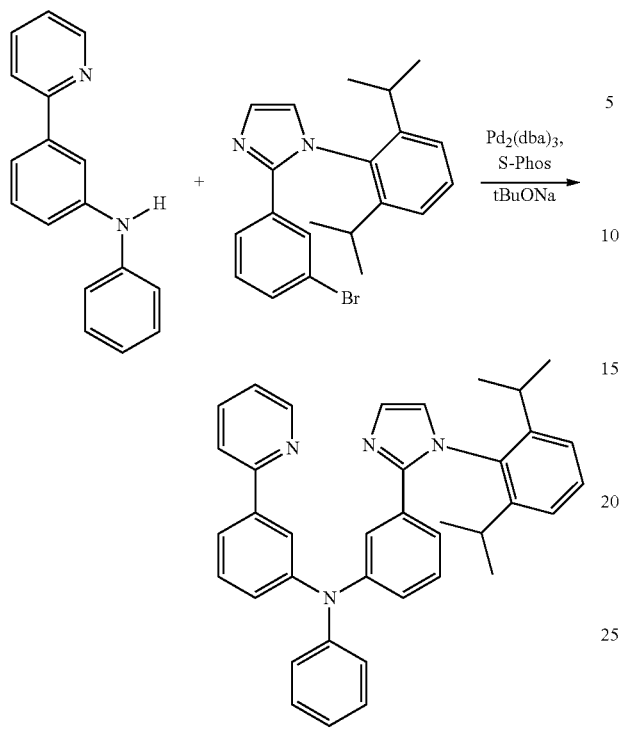

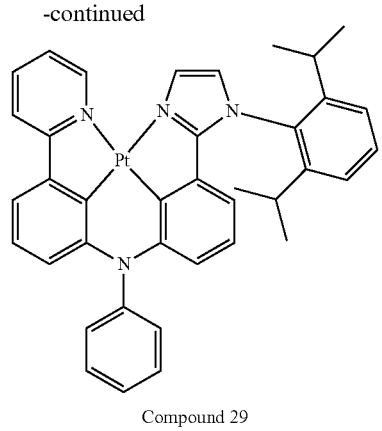

Compound 29

Synthesis of Compound 29

3-(1-(2,6-diisopropylphenyl)-1H-imidazol-2-yl)-N-phenyl-N-(3-(pyridin-2-yl)phenyl)aniline (2.85 g, 5.19 mmol) and potassium tetrachloroplatinate (2.156 g, 5.19 mmol) were mixed in 100 mL of acetic acid. The mixture was bubbled with nitrogen for 20 min. The reaction mixture was heated to 140° C. for 3 days. After cooling, water was added. The solid was collected by filtration and purified by column using 2:1 dichloromethane and hexanes as solvent to give platinum complex (1.2 g, 1.618 mmol, 31.1% yield).

Synthesis of Compound 166

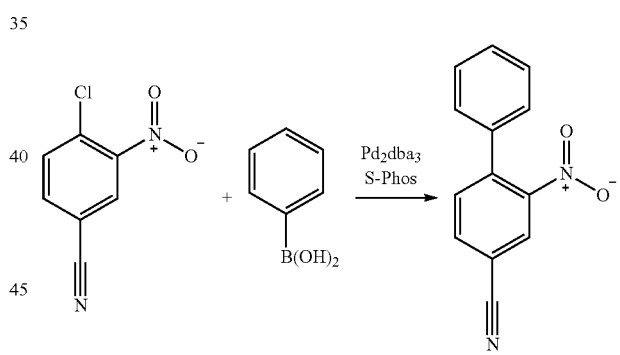

Synthesis of 2-nitro-[1,1'-biphenyl]-4-carbonitrile 4-chloro-3-nitrobenzonitrile (10 g, 54.8 mmol), phenylboronic acid (8.68 g, 71.2 mmol), $Pd_2dba_3$ (1.002 g, 1.096 mmol) and 2-dicyclohexylphosphino-2',6'-dimethoxybiphenyl (S-Phos) (1.797 g, 4.38 mmol) were charged into a 500 mL 3-neck flask. Toluene (250 mL) was then charged into the reaction mixture followed by potassium phosphate tribasic monohydrate (35.3 g, 153 mmol) dissolved in 60 mL of water. This mixture was degassed with nitrogen then heated at reflux overnight. The reaction mixture was cooled to room temperature then partitioned with water. The toluene layer was dried over magnesium sulfate, filtered, and dried under vacuum. This crude residue was passed through a silica gel column using 15-35% ethyl acetate/hexanes as the eluent. The product fractions were combined and solvents were removed under vacuum. This crude product was triturated with ethyl

Synthesis of 3-(1-(2,6-diisopropylphenyl)-1H-imidazol-2-yl)-N-phenyl-N-(3-(pyridin-2-yl)phenyl) aniline 2-(3-bromophenyl)-1-(2,6-diisopropylphenyl)-1H-imidazole (2.8 g, 7.30 mmol), Pd$_2$(dba)$_3$ (0.067 g, 0.073 mmol), dicyclohexyl(2',6'-dimethoxy-[1,1'-biphenyl]-2-yl)phosphine (S-Phos) (0.120 g, 0.292 mmol), and sodium t-butoxide (1.053 g, 10.96 mmol) were mixed in 100 mL of xylene. The solution was bubbled with nitrogen for 20 min. N-phenyl-3-(pyridin-2-yl)aniline (1.979 g, 8.03 mmol) was added. The reaction was heated up to reflux for 6 h. After cooled to rt, dichloromethane was added. The mixture was filtered through Celite®. The solvent was then evaporated. The residue was coated on Celite® and columned with hexanes/ethyl acetate (3:1) to give 3-(1-(2,6-diisopropylphenyl)-1H-imidazol-2-yl)-N-phenyl-N-(3-(pyridin-2-yl)phenyl)aniline (3.66 g, 6.67 mmol, 91% yield).

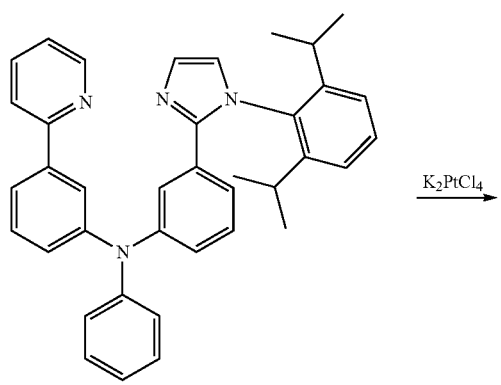

acetate/hexanes. The product, 2-nitro-[1,1'-biphenyl]-4-carbonitrile, (8.87 g, 39.6 mmol, 72.2% yield) was isolated via filtration as a yellow solid.

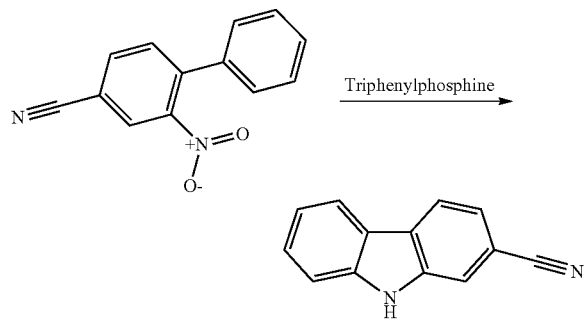

Synthesis of 9H-carbazole-2-carbonitrile 2-nitro-[1,1'-biphenyl]-4-carbonitrile (8.87 g, 39.6 mmol) and triphenylphosphine (25.9 g, 99 mmol) were charged into the reaction flask with 90 mL of 1,2-dichlorobenzene. This mixture was stirred and heated at reflux for 24 hours. The reaction mixture was diluted with 50 mL of toluene then was loaded directly onto a neutral alumina column. The column was eluted with 100% toluene followed by 5% ethyl acetate/toluene (v/v). The product fractions were combined and concentrated under vacuum. This product was then passed through a silica gel column eluting first with 80-99% DCM/hexanes then 5% ethyl acetate/DCM. The product, 9H-carbazole-2-carbonitrile (2.75 g, 14.31 mmol, 36.2% yield) was isolated as a light tan solid.

Synthesis of 9-(3-(1-(2,6-diisopropylphenyl)-1H-imidazol-2-yl)phenyl)-9H-carbazole-2-carbonitrile 2-(3-bromophenyl)-1-(2,6-diisopropylphenyl)-1H-imidazole (4.39 g, 11.45 mmol), 9H-carbazole-2-carbonitrile (2 g, 10.40 mmol), Pd$_2$dba$_3$ (0.333 g, 0.364 mmol) and 2-dicyclohexylphosphino-2',6' dimethoxybiphenyl (S-Phos) (0.597 g, 1.457 mmol) were charged into the reaction flask with 300 mL of m-xylenes. Potassium phosphate tribasic anhydrous (3.86 g, 18.21 mmol) was ground into a fine powder using a mortar and pestle then was added to the reaction mixture. The reaction mixture was degassed with nitrogen then was heated at reflux for 5½ days. This biphasic mixture was passed through a plug of Celite® to remove some insoluble materials. The organic layer was separated and dried over magnesium sulfate. The organics were filtered and concentrated under vacuum. The crude residue was passed through a silica gel column using 25% ethyl acetate/10% DCM/hexanes. The product fractions yielded 9-(3-(1-(2,6-diisopropylphenyl)-1H-imidazol-2-yl)phenyl)-9H-carbazole-2-carbonitrile (93.4% yield) as a tan solid.

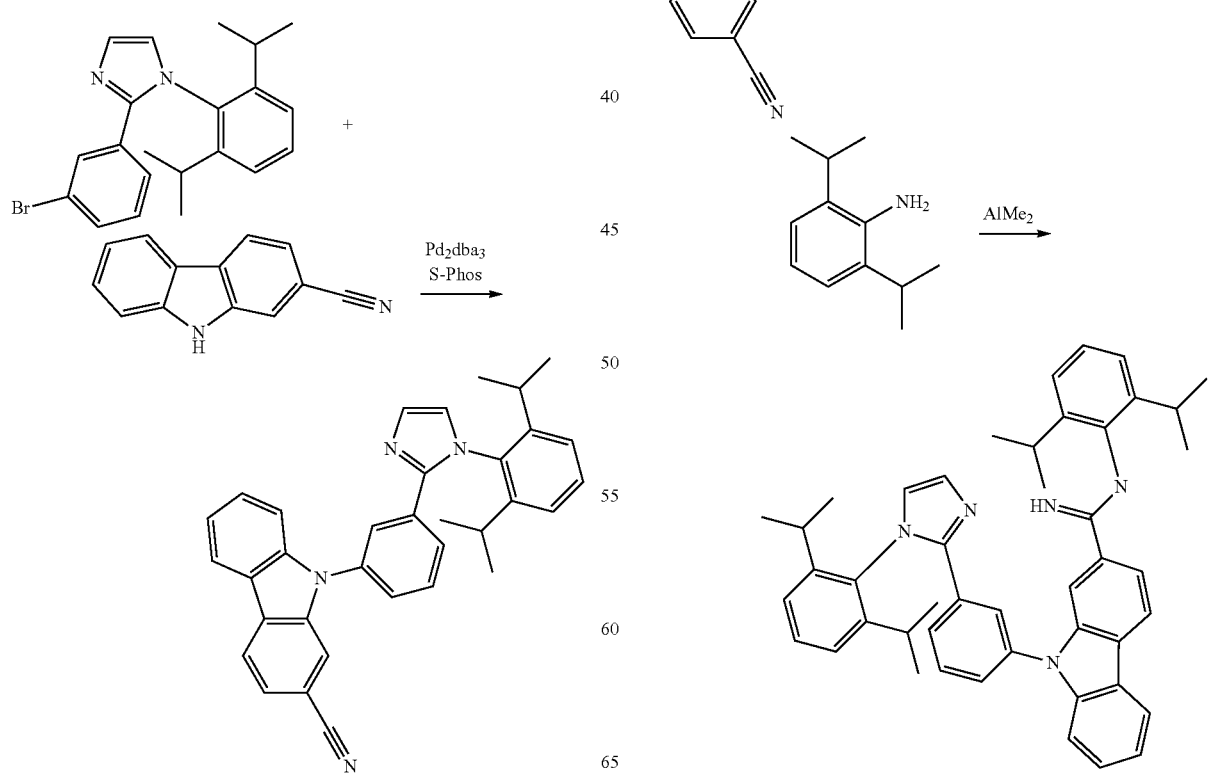

N-(2,6-diisopropylphenyl)-9-(3-(1-(2,6-diisopropylphenyl)-1H-imidazol-2-yl)phenyl)-9H-carbazole-2-carboximidamide 2,6-diisopropylaniline (3.5 g, 19.74 mmol) was charged into the reaction flask with 100 mL of toluene. This mixture was cooled to 0° C. followed by the dropwise addition of 2.0M trimethylaluminum in toluene (18 mL, 36.0 mmol) over a 15 minute period. The cooling bath was removed and the reaction mixture was stirred at room temperature for 2½ hours. 9-(3-(1-(2,6-diisopropylphenyl)-1H-imidazol-2-yl)phenyl)-9H-carbazole-2-carbonitrile (8.35 g, 16.88 mmol) was slurried into the reaction mixture with 20 mL of toluene. The reaction mixture was heated for 2½ days at a bath temperature of 90° C. The reaction mixture was cooled to room temperature then was added portionwise to a cooled mixture of 50 mL methanol/100 mL DCM/50 g silica gel. This mixture was stirred for ½ hour at room temperature then was filtered through a pad of Celite®. The filtrate was concentrated and dried under vacuum leaving the desired amidine product (11.3 g, 16.84 mmol, 100% yield) as a yellow foamy solid.

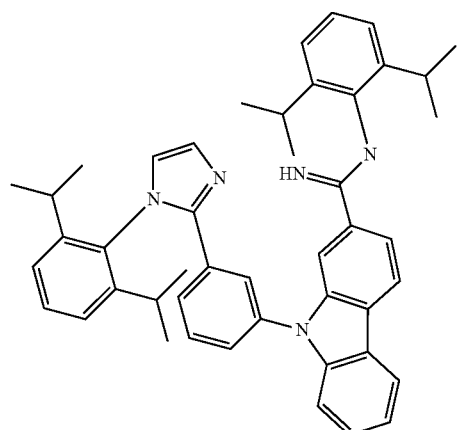

+

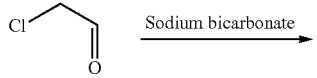

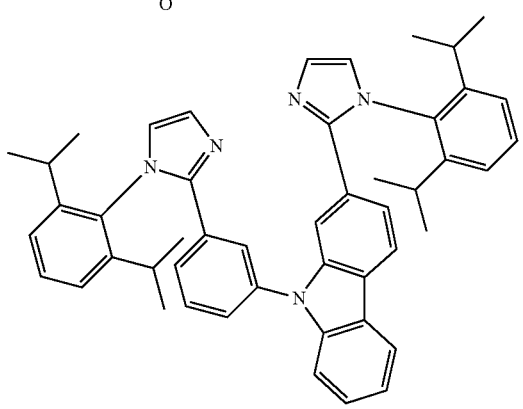

Synthesis of 2-(1-(2,6-diisopropylphenyl)-1H-imidazol-2-yl)-9-(3-(1-(2,6-diisopropylphenyl)-1H-imidazol-2-yl)phenyl)-9H-carbazole The amidine intermediate (11.3 g, 16.84 mmol), 2-chloroacetaldehyde (5.5 g, 35.0 mmol) and sodium bicarbonate (3.6 g, 42.9 mmol) were charged into the reaction flask with 150 mL of 2-propanol. This reaction mixture was stirred and heated at reflux for 48 hours. The reaction mixture was diluted with 300 mL of water then was extracted 3×300 mL ethyl acetate. These extracts were combined and dried over magnesium sulfate. The extracts were filtered and evaporated under vacuum. The crude residue was passed through a silica gel column using 7-30% acetone/DCM. The product fractions yielded 2-(1-(2,6-diisopropylphenyl)-1H-imidazol-2-yl)-9-(3-(1-(2,6-diisopropylphenyl)-1H-imidazol-2-yl)phenyl)-9H-carbazole (6.1 g, 8.77 mmol, 52.0% yield) as a light tan solid.

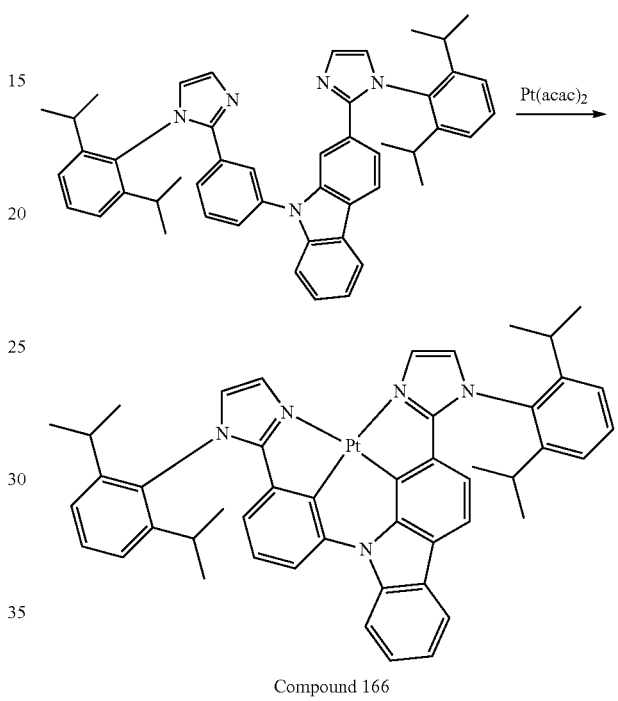

Compound 166

Synthesis of Compound 166

2-(1-(2,6-diisopropylphenyl)-1H-imidazol-2-yl)-9-(3-(1-(2,6-diisopropylphenyl)-1H-imidazol-2-yl)phenyl)-9H-carbazole (2.93 g, 4.21 mmol) and platinum(II) acetylacetonate (0.828 g, 2.11 mmol) and 10 drops of tridecane were charged into the reaction vessel. This mixture was evacuated and back-filled with nitrogen then was heated at 230° C. sand bath temperature for 38 hours. The reaction was cooled to room temperature and the crude residue was passed through a silica gel column that was pretreated with 20% triethylamine/hexanes. The column was eluted with 30% DCM/hexanes yielding (1.87 g, 100% yield) of the desired platinum complex.

Synthesis of Compound 50

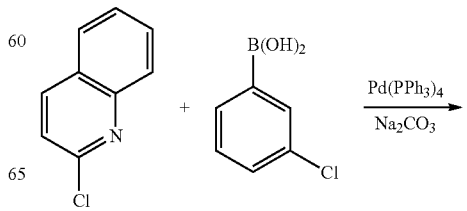

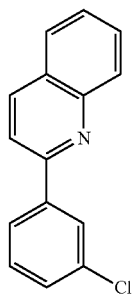

Synthesis of 2-(3-chlorophenyl)quinoline 2-chloroquinoline (9.25 g, 56.5 mmol), (3-chlorophenyl)boronic acid (9.28 g, 59.4 mmol), Pd(PPh$_3$)$_4$ (1.634 g, 1.413 mmol) were charged into the reaction flask with 300 mL of 1,2-dimethoxyethane. Sodium carbonate (14.98 g, 141 mmol) was dissolved in 50 mL of water and was charged into the reaction flask. The reaction flask was then evacuated and back-filled with nitrogen then was heated to reflux for 20 hours. The organic layer was separated and dried over magnesium sulfate. The organics were filtered and stripped under vacuum. The crude residue was passed through a silica gel column using 5-25% ethyl acetate/hexanes yielding 2-(3-chlorophenyl)quinoline (10.5 g, 77% yield) as a white solid.

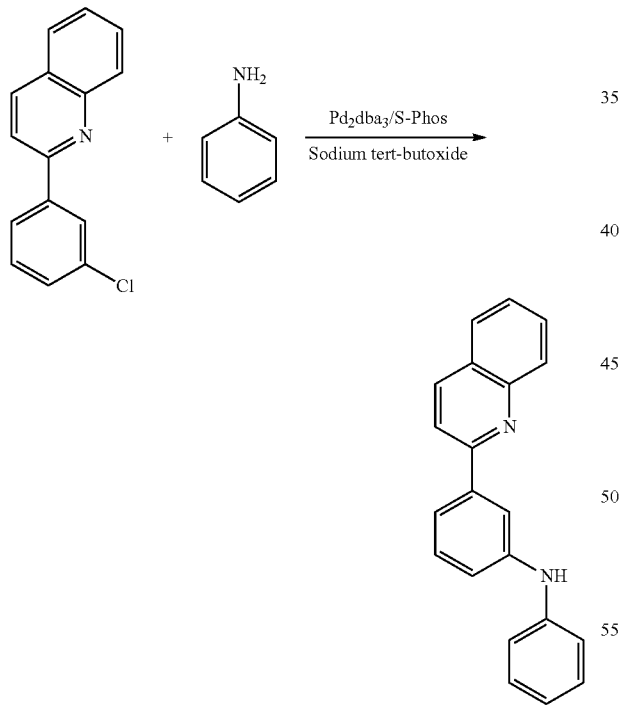

Synthesis of N-phenyl-3-(quinolin-2-yl)aniline

Aniline (2.75 g, 29.6 mmol), 2-(3-chlorophenyl)quinoline (5.25 g, 21.90 mmol), sodium tert-butoxide (3.36 g, 35.0 mmol), Pd$_2$dba$_3$ (0.501 g, 0.548 mmol) and 2-dicyclohexylphosphino-2',6'-dimethoxybephenyl (S-Phos) (0.898 g, 2.190 mmol) were charged into the reaction flask with 200 mL of toluene. This mixture was evacuated and back-filled with nitrogen then was heated at reflux for 20 h. The reaction mixture was cooled to room temperature then was diluted with 200 mL of water. The toluene layer was separated and the aqueous was extracted with 100 mL of toluene. The organic extracts were combined and removed under vacuum. The crude residue was passed through a silica gel column using 75% DCM/hexanes then was passed through a silica gel column using 1-5% ethyl acetate/DCM. The clean product fractions were combined and solvents were removed under vacuum yielding N-phenyl-3-(quinolin-2-yl)aniline (3 g, 10.12 mmol, 46.2% yield).

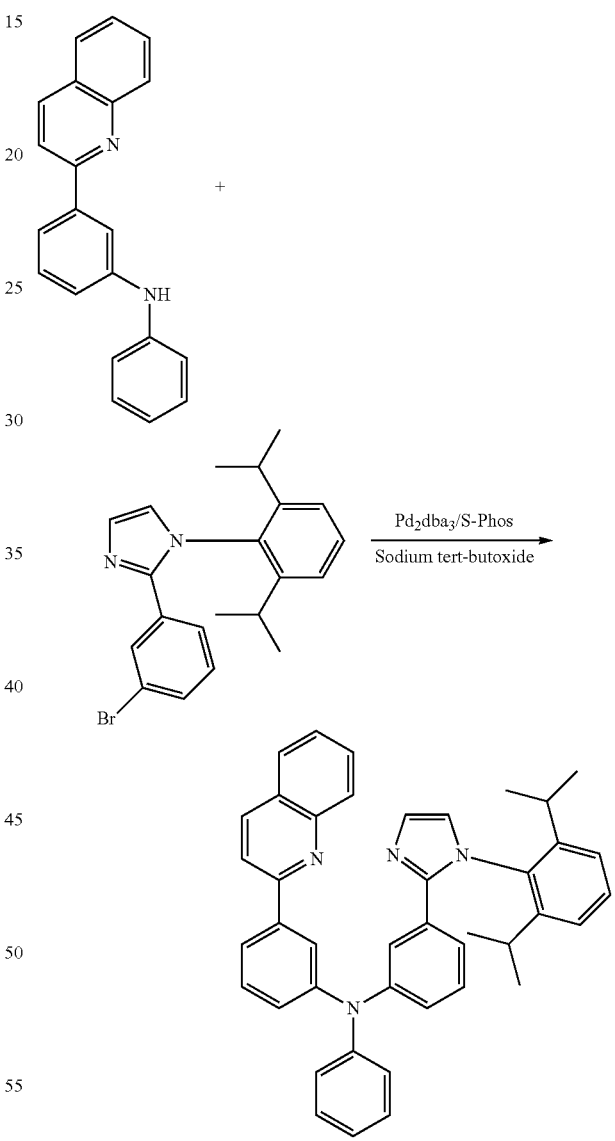

Synthesis of 3-(1-(2,6-diisopropylphenyl)-1H-imidazol-2-yl)-N-phenyl-N-(3-(quinolin-2-yl)phenyl)aniline N-phenyl-3-(quinolin-2-yl)aniline (3 g, 10.12 mmol), sodium tert-butoxide (1.555 g, 16.20 mmol), 2-(3-bromophenyl)-1-(2,6-diisopropylphenyl)-1H-imidazole (4.07 g, 10.63 mmol), Pd$_2$dba$_3$ (0.232 g, 0.253 mmol) and 2-dicyclohexylphosphino-2',6'-dimethoxybiphenyl (S-Phos) (0.415 g, 1.012 mmol) were charged into the reaction vessel with 250 mL of toluene. This mixture was evacuated and back-filled with nitrogen. The reaction mixture was then heated at reflux for 20 h. The reaction mixture was cooled to room temperature then was diluted with 200 mL of water. The toluene layer was separated and the aqueous was extracted with 100 mL of toluene. The organic extracts were combined and removed under vacuum. The crude residue was passed through a silica gel column using 5-25% ethyl acetate/DCM yielding 3-(1-(2, 6-diisopropylphenyl)-1H-imidazol-2-yl)-N-phenyl-N-(3-(quinolin-2-yl)phenyl)aniline (5.5 g, 91% yield) as a yellow foamy solid.

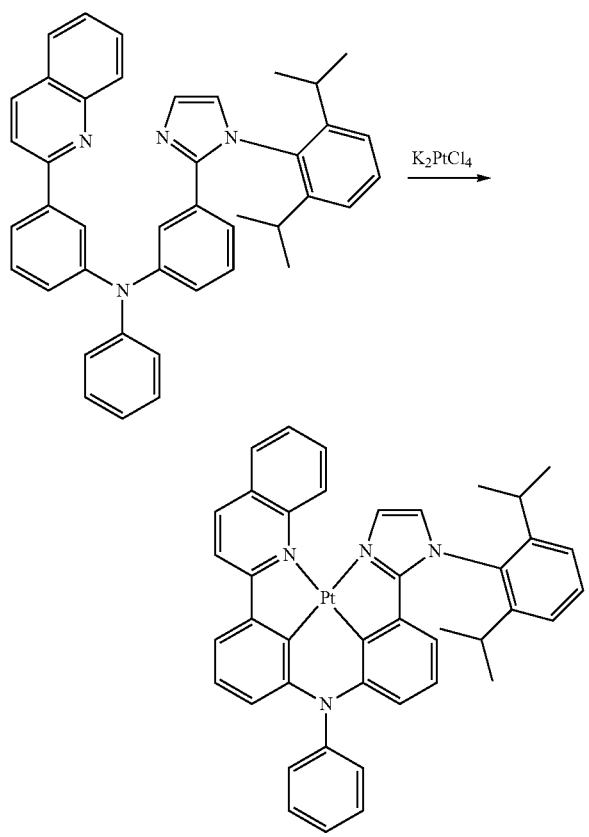

Compound 50

Synthesis of Compound 50

3-(1-(2,6-diisopropylphenyl)-1H-imidazol-2-yl)-N-phenyl-N-(3-(quinolin-2-yl)phenyl)aniline (4.5 g, 7.52 mmol) and potassium tetrachloroplatinate(II) (2.58 g, 7.67 mmol) were charged into the reaction vessel with 150 mL of acetic acid. This mixture was degassed with nitrogen for ½ hour then was heated to reflux for 30 h. The acetic acid was stripped under vacuum and the crude product was triturated with ethyl acetate. This crude product was dissolved in DCM and was washed with sodium bicarbonate. The organics were dried over magnesium sulfate then were filtered and absorbed onto Celite®. The Celite® material was washed onto a silica gel column that was pre-treated with 10% triethylamine/hexanes. The column was eluted with 40-60% DCM/hexanes. The cleanest product fractions were combined and stripped under vacuum yielding a dark red solid. This material was recrystallized 4 times from DCM/hexanes then was sublimed under vacuum yielding (1.3 g, 21.9%) of the desired platinum complex.

Synthesis of Compound 37

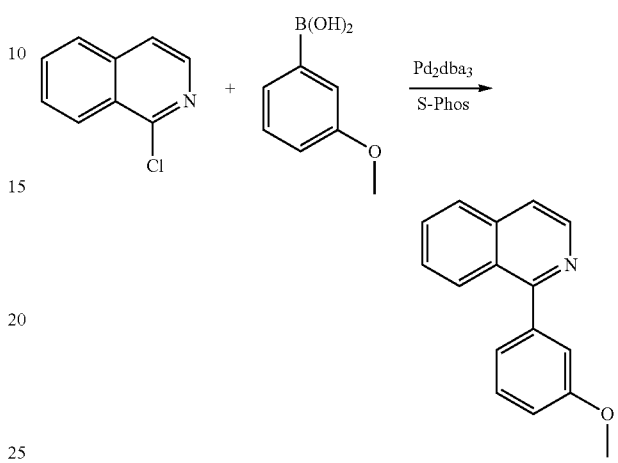

Synthesis of 1-(3-methoxyphenyl)isoquinoline 1-chloroisoquinoline (7 g, 42.8 mmol), (3-methoxyphenyl)boronic acid (8.78 g, 57.8 mmol), Tris(dibenzylideneacetone)palladium(0) (0.783 g, 0.856 mmol) and 2-dicyclohexylphosphino-2',6'-dimethoxybiphenyl (S-Phos) (1.403 g, 3.42 mmol) were charged into the reaction vessel with 250 mL of toluene. Lastly, potassium phosphate tribasic monohydrate (29.5 g, 128 mmol) was dissolved in 60 mL of water and was charged into the reaction mixture. The reaction was degassed with nitrogen gas then was heated to reflux for 18 h. The reaction mixture was cooled to room temperature and the toluene layer was separated and dried over magnesium sulfate. The organics were filtered and stripped under vacuum. The crude residue was purified by silica gel chromatography using 25-35% ethyl acetate/hexanes yielding 9.4 g (93%) of 1-(3-methoxyphenyl)isoquinoline as a viscous yellow oil.

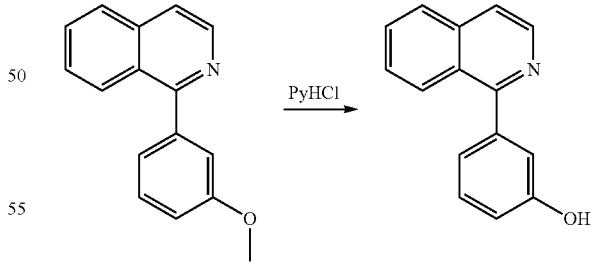

Synthesis of 3-(isoquinolin-1-yl)phenol 1-(3-methoxyphenyl)isoquinoline (9.4 g, 40.0 mmol) and pyridine hydrochloride (42 g, 363 mmol) were heated in an oil bath at 180-190° C. for 5 h. The reaction mixture was cooled to around 150° C. then 200 mL of water was slowly added to the reaction mixture as the reaction mixture continued to cool to room temperature. Ethyl acetate (200 mL) was added to the reaction mixture and this mixture was stirred at room temperature. A tan solid (5.25 g) was isolated via filtration and was dried under vacuum. The ethyl acetate portion was separated and was dried over magnesium sulfate. This mixture was filtered and stripped under vacuum. This residue was triturated with ethyl acetate and was filtered under vacuum. This solid was combined with the 5.25 g of tan solid yielding 3-(isoquinolin-1-yl)phenol (6.3 g, 28.5 mmol, 71.3% yield)

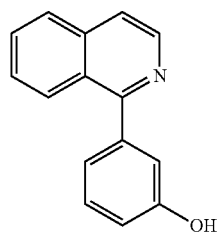

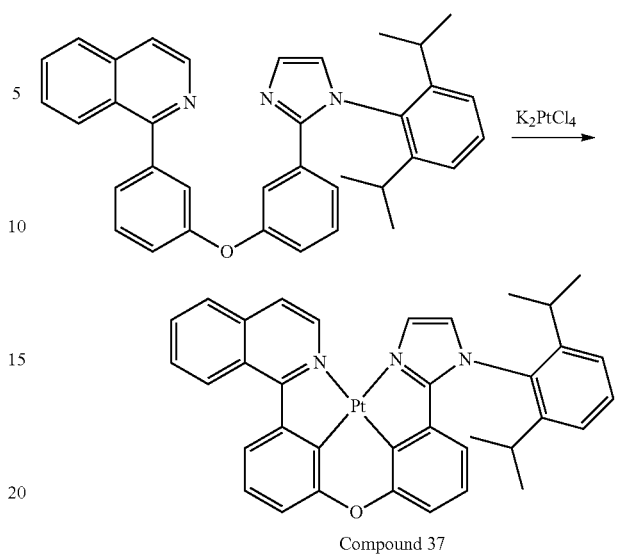

Compound 37

Synthesis of Compound 37

1-(3-(3-(1-(2,6-diisopropylphenyl)-1H-imidazol-2-yl)phenoxy)phenyl)isoquinoline (1.45 g, 2.77 mmol) and potassium tetrachloroplatinate(II) (0.94 g, 2.79 mmol) were charged into the reaction flask with 75 mL of glacial acetic acid. The reaction mixture was degassed with nitrogen then was heated at reflux for 3 days. The reaction mixture was cooled to room temperature. The majority of the acetic acid was removed under vacuum. The residue was dissolved in 200 mL of ethyl acetate and washed with aqueous sodium bicarbonate. The organics were dried over magnesium sulfate then were filtered and stripped under vacuum. The crude residue was passed through a silica gel column using 60% DCM/hexanes. The cleanest fractions were combined, solvents were removed and the material was sublimed under vacuum yielding (0.75 g, 37.5% yield) of the desired platinum complex.

Synthesis of 1-(3-(3-(1-(2,6-diisopropylphenyl)-1H-imidazol-2-yl)phenoxy)phenyl)isoquinoline 3-(isoquinolin-1-yl)phenol (1.5 g, 6.78 mmol), potassium carbonate (2.5 g, 18.12 mmol), 2-(3-bromophenyl)-1-(2,6-diisopropylphenyl)-1H-imidazole (2.60 g, 6.78 mmol), copper(I) iodide (0.039 g, 0.203 mmol) and ferric acetylacetonate (0.144 g, 0.407 mmol) were charged into the reaction flask with 45 mL of DMF. This heterogeneous mixture was degassed with nitrogen then was heated at 135-140° C. for 2½ days. The reaction mixtures were filtered through a pad of Celite® and the pad was rinsed with ethyl acetate. The filtrate was diluted with 300 mL of water. This mixture was then extracted 2×200 mL ethyl acetate. These extracts were dried over magnesium sulfate then were filtered and stripped under vacuum. The crude residue was passed through a silica gel column using 7-15% acetone/DCM. The cleanest fractions were combined and stripped under vacuum yielding 1-(3-(3-(2,6-diisopropylphenyl)-1H-imidazol-2-yl)phenoxy)phenyl)isoquinoline (1.45 g, 40.8% yield) as a light tan solid.

Synthesis of Compound 36

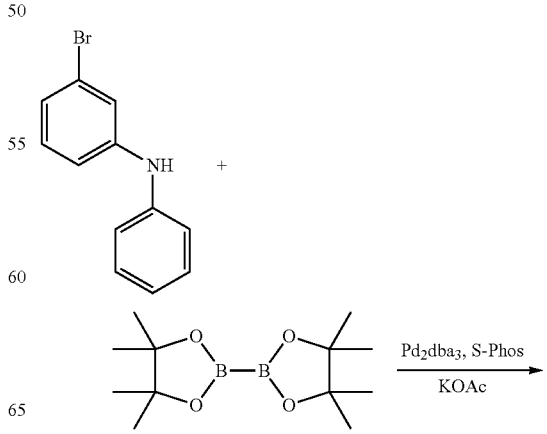

-continued

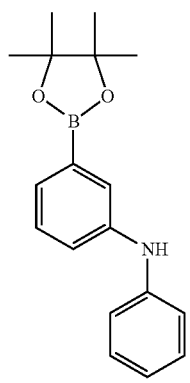

Synthesis of 2-((3-(4,4,5,5-tetramethyl-1,3,2-dioxaborolan-2-yl)phenyl)amino)benzene-1-ylium 3-Bromo-N-phenylaniline (6 g, 24.18 mmol), 4,4,4',4',5,5,5',5'-octamethyl-2,2'-bi(1,3,2-dioxaborolane) (8.29 g, 32.6 mmol), $Pd_2dba_3$ (0.443 g, 0.484 mmol) and 2-dicyclohexylphosphino-2',6'-dimethoxybiphenyl (S-Phos) (0.793 g, 1.935 mmol) and potassium acetate (2.78 g, 28.3 mmol) were charged into the reaction vessel with 200 mL of 1,4-dioxane. This mixture was degassed and put under a nitrogen atmosphere. The mixture was then refluxed overnight. The reaction mixture was cooled to room temperature then was diluted with 300 mL of water. This mixture was extracted with ethyl acetate. This extracts were dried over magnesium sulfate then were filtered and stripped under vacuum. The crude residue was passed through a silica gel column using 2-15% ethyl acetate/hexanes. The cleaniest product fractions were combined and stripped under vacuum yielding 2-((3-(4,4,5,5-tetramethyl-1,3,2-dioxaborolan-2-yl)phenyl)amino)benzene-1-ylium (4.3 g, 60.7% yield) as a yellow oil.

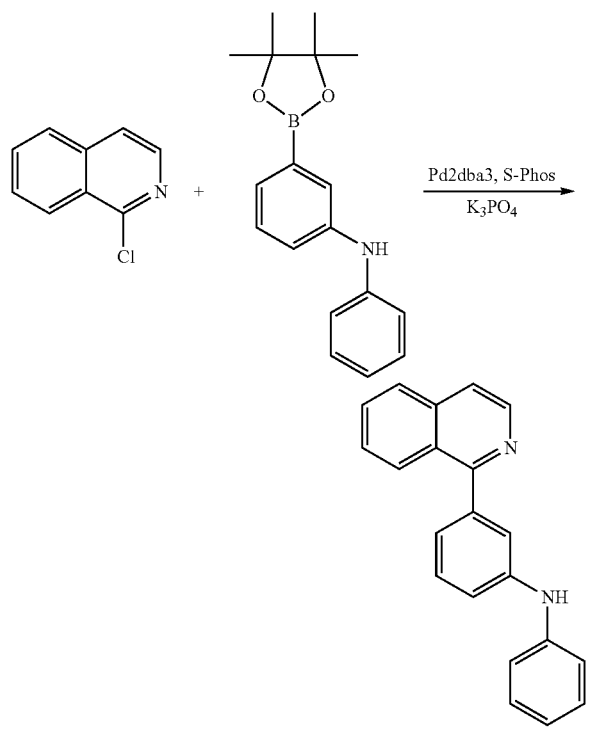

Synthesis of 2-((3-(isoquinolin-1-yl)phenyl)amino)benzene-1-ylium 1-chloroisoquinoline (2.000 g, 12.22 mmol), 2-((3-(4,4,5,5-tetramethyl-1,3,2-dioxaborolan-2-yl)phenyl)amino)benzene-1-ylium (4.3 g, 14.67 mmol), $Pd_2dba_3$ (0.224 g, 0.244 mmol) and 2-dicyclohexylphosphino-2',6'-dimethoxybiphenyl (S-Phos) (0.401 g, 0.978 mmol) were charged into the reaction flask with 200 mL of toluene. Potassium phosphate tribasic monohydrate (7.31 g, 31.8 mmol) was dissolved in 30 mL of water and was charged into the reaction flask. This mixture was degassed with nitrogen and heated at reflux for 18 h. The toluene layer was separated and dried under vacuum. The crude residue was passed through a silica gel using 5-65% ethyl acetate/hexanes. The cleaniest fractions were combined and stripped under vacuum to yield 2-((3-(isoquinolin-1-yl)phenyl)amino)benzene-1-ylium (1.65 g, 45.9% yield).

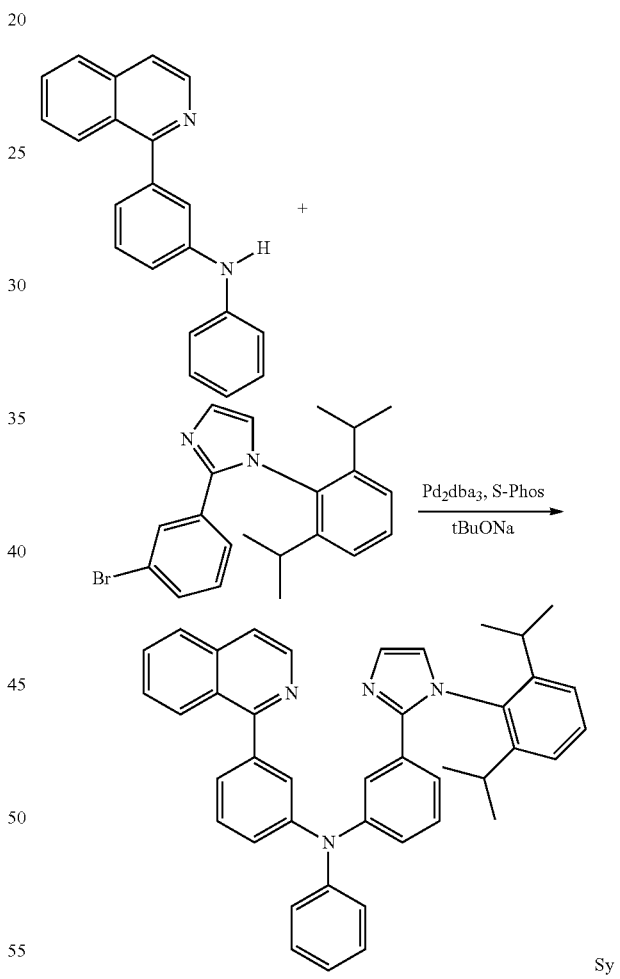

Synthesis of 3-(1-(2,6-diisopropylphenyl)-1H-imidazol-2-yl)-N-(3-(isoquinolin-1-yl)phenyl)-N-phenylaniline 3-(isoquinolin-1-yl)-N-phenylaniline (1.65 g, 5.57 mmol), 2-(3-bromophenyl)-1-(2,6-diisopropylphenyl)-1H-imidazole (2.256 g, 5.89 mmol), sodium tert-butoxide (0.802 g, 8.35 mmol), $Pd_2dba_3$ (0.102 g, 0.111 mmol) and 2-dicyclohexylphosphino-2',6'-dimethoxybiphenyl (S-Phos) (0.184 g, 0.449 mmol) were charged into the reaction vessel with 150 mL of toluene. This mixture was evacuated and back-filled with nitrogen. The reaction mixture was then heated to reflux for 18 h. The reaction mixture was cooled to room temperature then was diluted with 75 mL of water. This mixture was then filtered through a pad of Celite®. The toluene layer was separated and dried over magnesium sulfate. The organics were filtered and stripped under vacuum. The crude residue was passed through a silica gel column using 2-40% ethyl acetate/DCM yielding 3-(1-(2,6-diisopropylphenyl)-1H-imidazol-2-yl)-N-(3-(isoquinolin-1-yl)phenyl)-N-phenylaniline (2.60 g, 4.34 mmol, 78% yield).

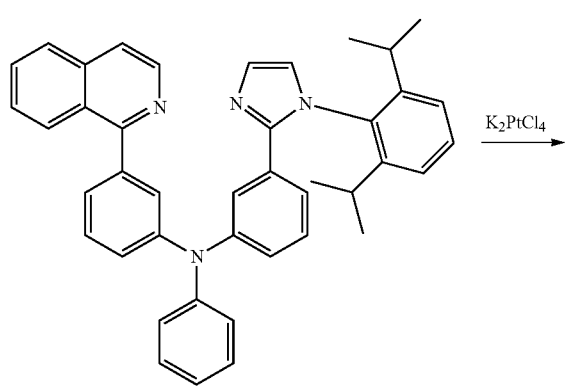

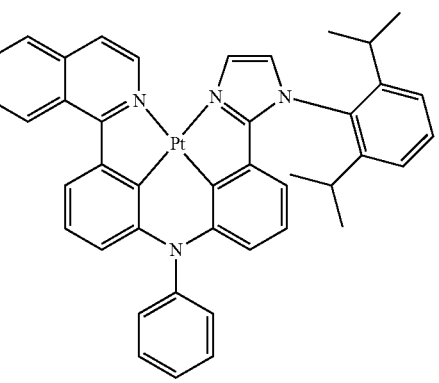

Compound 36

Synthesis of Compound 36

3-(1-(2,6-diisopropylphenyl)-1H-imidazol-2-yl)-N-(3-(isoquinolin-1-yl)phenyl)-N-phenylaniline (2.65 g, 4.43 mmol) and potassium tetrachloroplatinate(II) (1.526 g, 4.53 mmol) were charged into the reaction flask with 80 mL of acetic acid. This mixture was degassed with nitrogen for 30 min then was heated at reflux for 2½ days. The reaction mixture was stripped under vacuum. The crude product was dissolved in ethyl acetate then was washed with aqueous sodium bicarbonate. The organics were dried over magnesium sulfate then were filtered and stripped under vacuum. The crude residue was 1$^{st}$ passed through a silica gel column using 50% DCM/hexanes and was then passed through a silica gel column that was treated with 20% triethylamine/hexanes. This column was eluted with 35% DCM/hexanes. Solvents were removed and the desired product was sublimed under vacuum yielding (0.50 g, 0.631 mmol, 14% yield) of the desired platinum complex.

Synthesis of Compound D

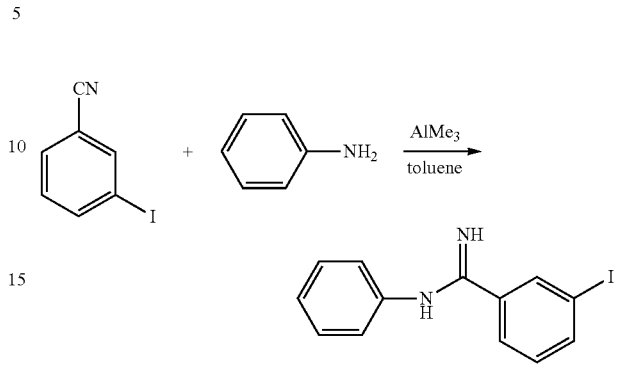

Synthesis of 3-iodo-N-phenylbenzimidamide

To a 500 mL 3-neck round bottom flask was added aniline (3.13 g, 33.6 mmol) and 150 mL of toluene. The solution was cooled in an ice bath under nitrogen. Next trimethylaluminum solution in toluene was added dropwise via dropping funnel (2.0 M, 23.5 mL, 47.0 mmol) and the reaction mixture was stirred at room temperature for 2 h. Next 3-iodobenzonitrile (10 g, 44 mmol) in 50 mL of toluene was added and the reaction mixture was heated to 70° C. overnight under nitrogen. The reaction mixture was cooled in an ice bath and then poured onto a stirring slurry of silica gel in 2:1 dichloromethane/methanol. The silica gel was filtered off and washed with dichloromethane and methanol. The filtrate was evaporated leaving a solid which was triturated with hexane, filtered, and washed with more hexane and dried (7.84 g, 73%).

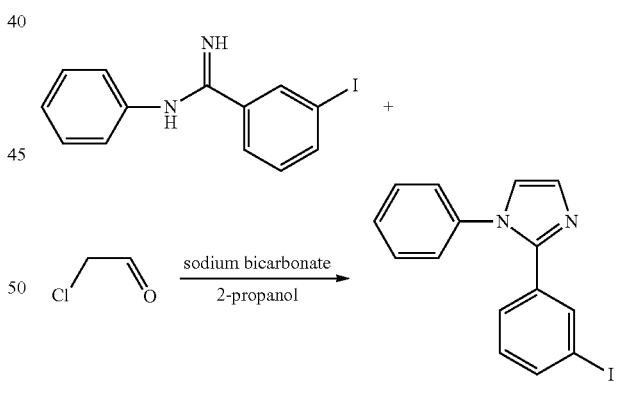

Synthesis of 2-(3-iodophenyl)-1-phenyl-1H-imidazole

To a 500 mL round bottom flask was added 3-iodo-N-phenylbenzimidamide (7.84 g, 24.34 mmol), 2-chloroacetaldehyde solution (50%, 6.7 mL, 48.7 mmol), sodium bicarbonate (4.09 g, 48.7 mmol), and 150 mL 2-propanol. The reaction mixture was heated at reflux for 3 h under nitrogen. The solvent was removed under vacuum and the residue dissolved in ethyl acetate. The ethyl acetate solution was washed with water, brine, dried over magnesium sulfate, filtered, and evaporated. The residue was purified by column chromatography eluting with 20-40% ethyl acetate/hexane (4.67 g, 55%).

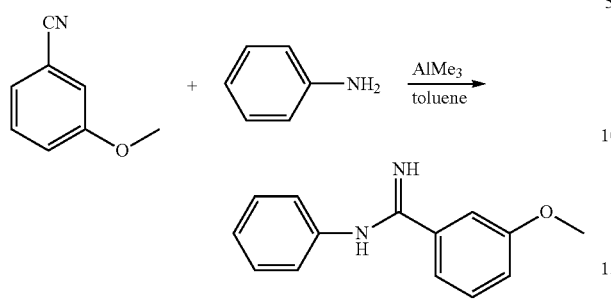

Synthesis of 3-methoxy-N-phenylbenzimidamide

To a 500 mL 3-neck round bottom flask was added aniline (5.38 g, 57.8 mmol) and 150 mL toluene. The solution was cooled in an ice bath under nitrogen. Next trimethylaluminum solution in toluene was added dropwise via dropping funnel (2.0 M, 40.4 mL, 81 mmol) and the reaction mixture was stirred at room temperature for 2 h. Next 3-methoxybenzonitrile (10 g, 75 mmol) in 50 mL toluene was added and the reaction mixture was heated to 70° C. overnight under nitrogen. The reaction mixture was cooled in an ice bath and then poured onto a stirring slurry of silica gel in 2:1 dichloromethane/methanol. The silica gel was filtered off and washed with dichloromethane and methanol. The filtrate was evaporated leaving a solid which was triturated with hexane, filtered, and washed with more hexane and dried to give desired product (7.81 g, 60%).

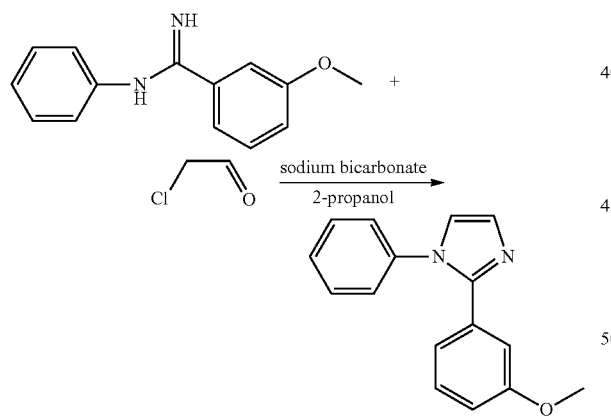

Synthesis of 2-(3-methoxyphenyl)-1-phenyl-1H-imidazole

To a 500 mL round bottom flask was added 3-methoxy-N-phenylbenzimidamide (7.81 g, 34.5 mmol), 2-chloroacetaldehyde solution (50%, 9.4 mL, 69 mmol), sodium bicarbonate (5.80 g, 69 mmol), and 150 mL 2-propanol. The reaction mixture was heated at reflux for 3 h under nitrogen. The solvent was removed under vacuum and the residue dissolved in ethyl acetate. The ethyl acetate solution was washed with water, brine, dried over magnesium sulfate, filtered, and evaporated. The residue was purified by column chromatography eluting with 50% and 100% ethyl acetate/hexane to give pure product (6.52 g, 75%).

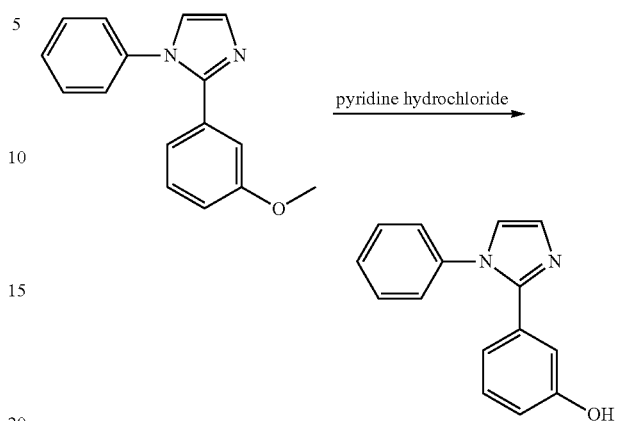

Synthesis of 3-(1-phenyl-1H-imidazol-2-yl)phenol

To a 500 mL round bottom flask was added 2-(3-methoxyphenyl)-1-phenyl-1H-imidazole (6.52 g, 26.0 mmol) and pyridine hydrochloride (24.08 g, 208 mmol). The reaction mixture was heated to 200° C. for 3 h under nitrogen. The reaction mixture was cooled to room temperature and the solid was added to water. The aqueous mixture was adjusted to pH 7 with sodium hydroxide solution. A gray solid was filtered off, washed with water, and dried (5.38 g, 83%).

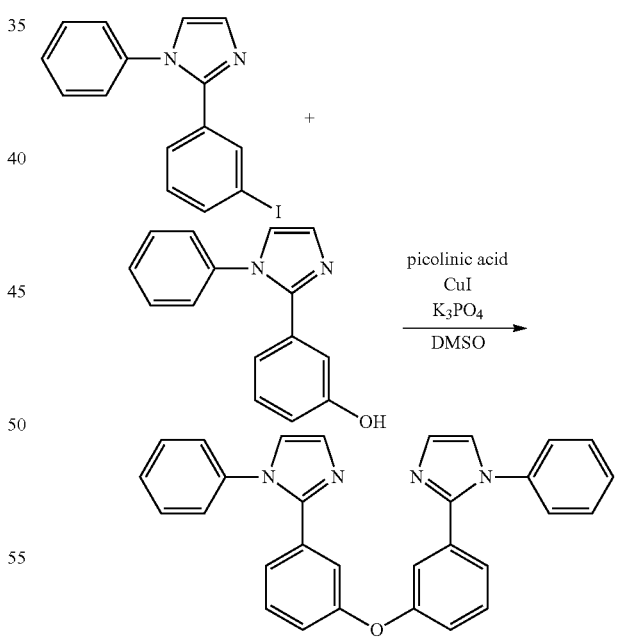

Synthesis of 2,2'-(oxybis(3,1-phenylene))bis(1-phenyl-1H-imidazole)

To a 500 mL 3-neck round bottom flask was added 3-(1-phenyl-1H-imidazol-2-yl)phenol (3.05 g, 12.26 mmol), 2-(3-iodophenyl)-1-phenyl-1H-imidazole (4.67 g, 13.49 mmol), picolinic acid (2.27 g, 18.40 mmol), copper(I) iodide (0.70 g, 3.68 mmol), potassium phosphate tribasic monohydrate (9.88 g, 42.9 mmol), and 200 mL DMSO. Nitrogen was bubbled directly into the mixture and was heated to 200° C. for 3 h and then at 120° C. overnight under nitrogen. The cooled reaction mixture was diluted with ethyl acetate and water. The mixture was filtered through Celite® and the Celite® was washed with ethyl acetate and water. The layers were separated and the aqueous layer was extracted with ethyl acetate. The organic layers were washed with brine, dried over magnesium sulfate, filtered, and evaporated. The residue was purified by column chromatography eluting with ethyl acetate to give pure product (2.4 g, 43%).

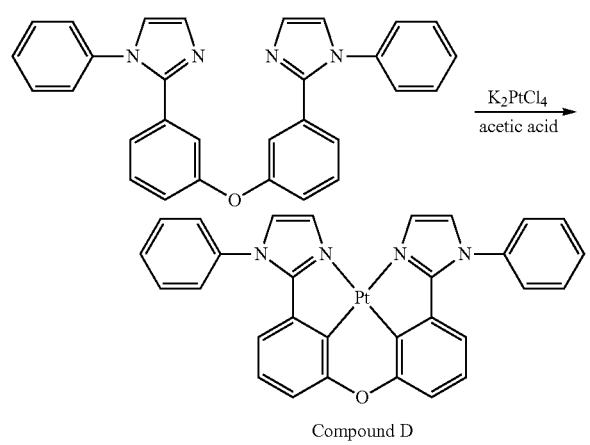

Compound D

Synthesis of Compound D

To a 500 mL round bottom flask was added 2,2'-(oxybis(3,1-phenylene))bis(1-phenyl-1H-imidazole) 2.4 g, 5.28 mmol), potassium tetrachloroplatinate (1.99 g, 4.8 mmol), and 100 mL acetic acid. Nitrogen was bubbled into the mixture for 20 minutes. The reaction mixture was heated to 140° C. under nitrogen for 3 days. The reaction mixture was cooled to room temperature and a solid was filtered off and washed with hexane. The crude solid was purified by column chromatography eluting with 70% dichloromethane/hexane. The column was pretreated with 20% triethylamine/hexane then rinsed with hexane prior to use. The material was sublimed at 300° C. overnight to produce Compound D (0.96 g, 31%).

Synthesis of Compound E

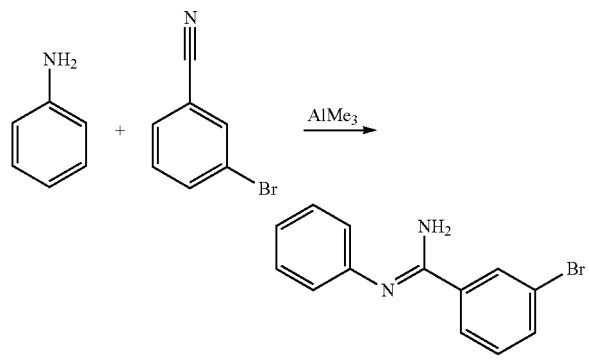

Synthesis of (E)-3-bromo-N'-phenylbenzimidamide

Aniline (5.12 g, 55.0 mmol) was charged into the reaction flask with 100 mL of toluene. This solution was chilled using a wet ice bath. A 2.0 M toluene solution of trimethylaluminum (41.2 mL, 82 mmol) was added dropwise to the chilled reaction mixture over a 15 min period. The cooling bath was removed and the reaction mixture was stirred at room temperature for 2 h. 3-bromobenzonitrile (10.01 g, 55 mmol) was dissolved in 80 mL of toluene and was added dropwise to the reaction mixture. The reaction mixture was then stirred at 75° C. for 18 h. The reaction mixture was cooled to room temperature then was slowing poured into a beaker containing 75 g of silica gel and 150 mL methanol/300 mL DCM. This mixture was stirred at room temperature for 30 min then was filtered through a pad of Celite®. The pad was rinsed with DCM/methanol. The filtrate was stripped under vacuum and the crude residue was triturated with hexanes yielding (E)-3-bromo-N'-phenylbenzimidamide (6.95 g, 25.3 mmol, 45.9%)

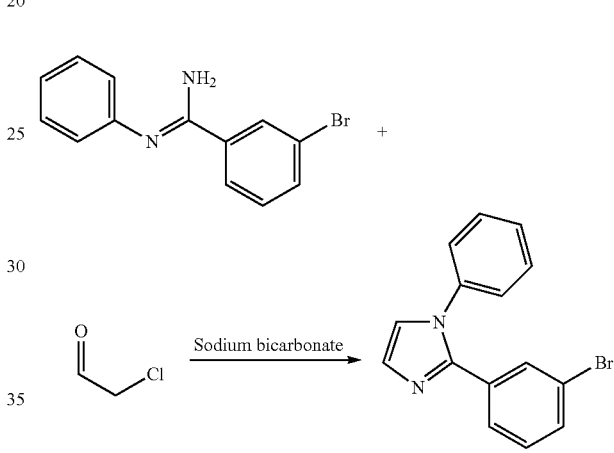

Synthesis of 2-(3-bromophenyl)-1-phenyl-1H-imidazole (E)-3-bromo-N'-phenylbenzimidamide (6.95 g, 25.3 mmol), 2-chloroacetaldehyde (6.94 g, 44.2 mmol) and sodium bicarbonate (5.30 g, 63.1 mmol) were charged into the reaction flask with 200 mL of 2-propanol. This reaction mixture was heated at reflux for 18 h. The reaction mixture was cooled to room temperature, was diluted with 200 mL of water then was extracted with ethyl acetate. The extracts were washed with aqueous lithium chloride then were dried over magnesium sulfate. These dried extracts were then filtered and stripped under vacuum. The crude residue was passed through a silica gel column using 30-35% ethyl acetate/hexanes yielding 2-(3-bromophenyl)-1-phenyl-1H-imidazole (2.8 g, 9.36 mmol, 37% yield).

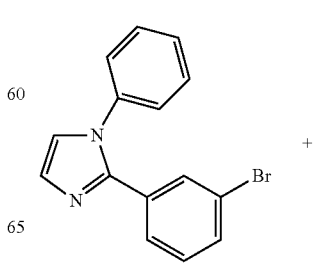

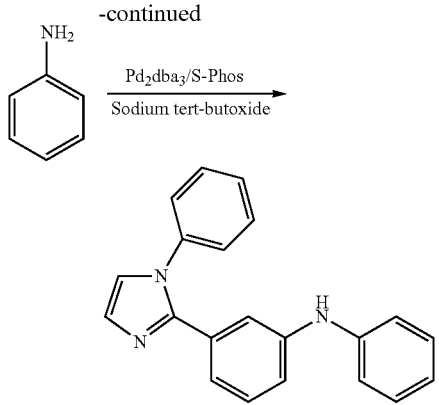

Synthesis of N-phenyl-3-(1-phenyl-1H-imidazol-2-yl)aniline 2-(3-bromophenyl)-1-phenyl-1H-imidazole (5.7 g, 19.05 mmol), aniline (0.85 g, 9.13 mmol), sodium tert-butoxide (2.55 g, 26.6 mmol), Pd$_2$dba$_3$ (0.167 g, 0.183 mmol) and 2-dicyclohexylphosphino-2',6'-dimethoxybiphenyl (S-Phos) (0.299 g, 0.730 mmol) were charged into the reaction flask with 150 mL of m-xylenes. This mixture was heated at reflux for 1 day. The reaction mixture was diluted with 100 mL of water then was filtered through a pad of Celite®. The m-xylene layer was separated and dried over magnesium sulfate. The organics were filtered and stripped under vacuum. The crude residue was passed through a silica gel column using 10-30% acetone/DCM yielding N-phenyl-3-(1-phenyl-1H-imidazol-2-yl)aniline (1.72 g, 5.5 mmol, 60.6% yield).

Synthesis of N-phenyl-3-(1-phenyl-1H-imidazol-2-yl)-N-(3-(1-phenyl-1H-imidazol-2-yl)phenyl)aniline Sodium tert-butoxide (1.082 g, 11.27 mmol), N-phenyl-3-(1-phenyl-1H-imidazol-2-yl)aniline (2.45 g, 7.87 mmol), 2-(3-bromophenyl)-1-phenyl-1H-imidazole (2.1 g, 7.04 mmol), tris(dibenzylideneacetone)palladium(0) (Pd$_2$dba$_3$) (0.161 g, 0.176 mmol) and 2-Dicyclohexylphosphino-2',6'-dimethoxybiphenyl (S-Phos) (0.289 g, 0.704 mmol) were charged into the reaction vessel with 100 mL of toluene. This mixture was degassed with nitrogen then was heated to reflux for 24 h. The reaction mixture was cooled to room temperature then was partitioned with 100 mL of water. The toluene layer was separated and the aqueous was extracted with another 100 mL of toluene. The toluene extracts were combined, dried over magnesium sulfate then were filtered and stripped under vacuum. The crude residue was passed through a silica gel column (15-30% acetone/DCM) and was purified if necessary using neutral alumina chromatography (7-10% ethyl acetate/DCM) yielding N-phenyl-3-(1-phenyl-1H-imidazol-2-yl)-N-(3-(1-phenyl-1H-imidazol-2-yl)phenyl)aniline (1.35 g, 2.55 mmol, 36.2%).

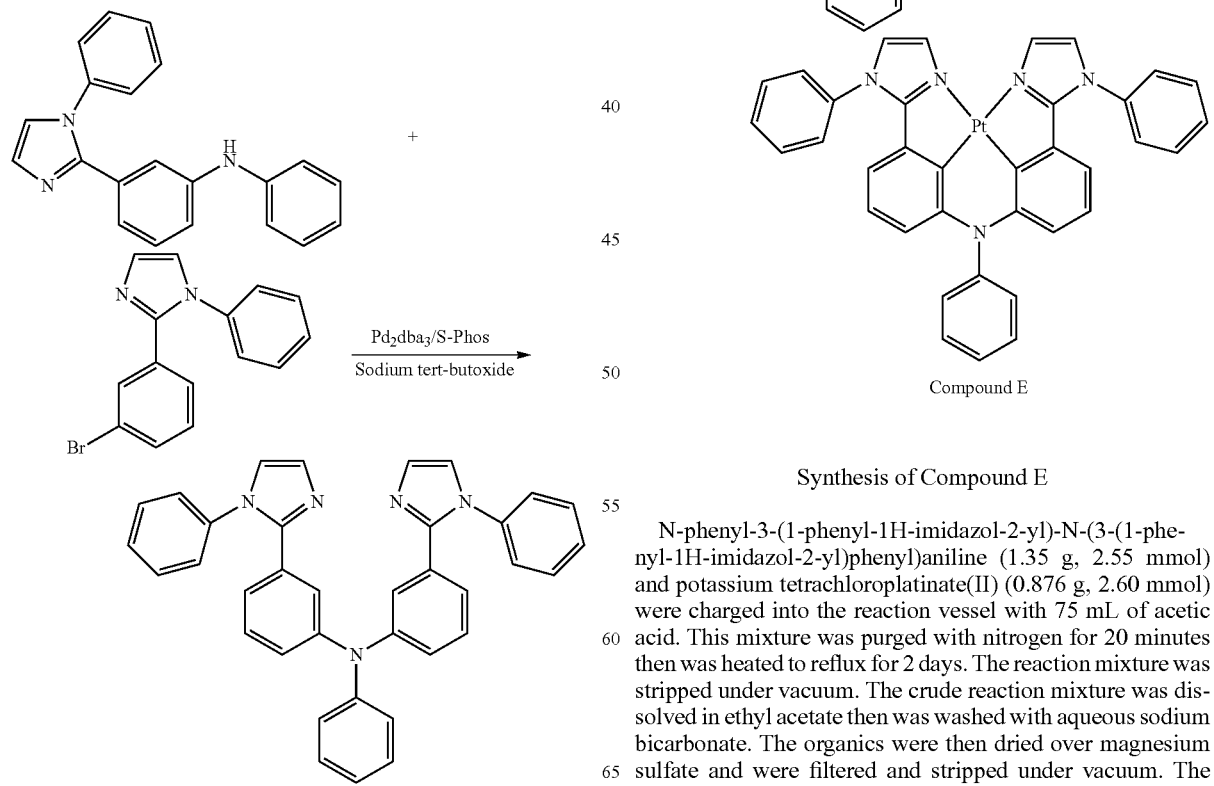

Compound E

Synthesis of Compound E

N-phenyl-3-(1-phenyl-1H-imidazol-2-yl)-N-(3-(1-phenyl-1H-imidazol-2-yl)phenyl)aniline (1.35 g, 2.55 mmol) and potassium tetrachloroplatinate(II) (0.876 g, 2.60 mmol) were charged into the reaction vessel with 75 mL of acetic acid. This mixture was purged with nitrogen for 20 minutes then was heated to reflux for 2 days. The reaction mixture was stripped under vacuum. The crude reaction mixture was dissolved in ethyl acetate then was washed with aqueous sodium bicarbonate. The organics were then dried over magnesium sulfate and were filtered and stripped under vacuum. The crude residue was passed through a silica gel column that was washed with 10% triethylamine/hexanes. The column was eluted with 40-60% DCM/hexanes. The cleanest product fractions were combined and solvents were removed under vacuum. This product was then sublimed under vacuum yielding (0.5 g, 0.692 mmol, 27.2% yield) of the desired platinum complex.

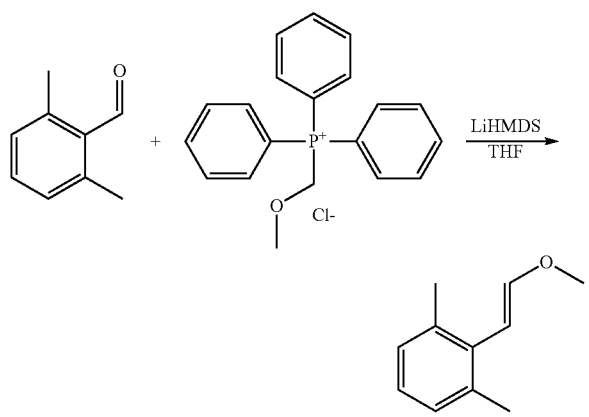

Synthesis of 2-(2-methoxyvinyl)-1,3-dimethylbenzene (Methoxymethyl)triphenyl-phosphonium chloride (34.3 g, 100 mmol) was dissolved in THF (100 mL) and the resulting solution was cooled to −78° C. LiHMDS (100 mL, 100 mmol) (1.0 M in THF) was then added dropwise over 30 minutes, while the temperature was maintained between −70° C. and −78° C. The cooling bath was removed and the reaction was allowed to warm to 0° C. before re-cooling to −78° C. 2,6-Dimethylbenzaldehyde (11.18 g, 83 mmol) was dissolved in 100 mL of THF and added dropwise to the reaction mixture over a period of 30 minutes, while the temperature was maintained between −70° C. and −78° C. The reaction mixture was then allowed to slowly warm to room temperature overnight, before it was quenched with NH$_4$Cl (sat.) and extracted with ether (3×100 mL). The organic layers were washed with water and 10% LiCl (aq.), dried and rotovapped to give a light orange liquid. The crude material was chromatographed on silica gel with 8/2 hexane/DCM to give 13.2 g of a colorless oil. Bulb-to-bulb distillation (130° C., 200 mbar) gave 11.2 g (83%) of 2-(2-methoxyvinyl)-1,3-dimethylbenzene as a mixture of cis- and trans-isomers as confirmed by GC/MS and NMR. The mixture was used without further purification.

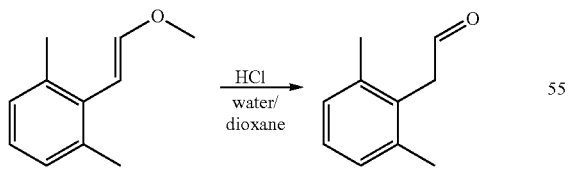

Synthesis of 2-(2,6-dimethylphenyl)acetaldehyde

Concentrated HCl (35 mL, 420 mmol) was slowly added to water (55 mL) and then 2-(2-methoxyvinyl)-1,3-dimethylbenzene (11.2 g, 69.0 mmol) in dioxane (35 mL) was added in one portion. The biphasic mixture was heated to reflux for 16 h, cooled to room temperature and extracted with ethyl acetate (3×100 mL). After drying over sodium sulfate, filtering and removing the solvent under reduced pressure, the crude material was purified by bulb-to-bulb distillation (100° C., 93 mbar) to give 8.8 g (86%) of 2-(2,6-dimethylphenyl) acetaldehyde as a white solid. The product was confirmed by GC/MS and NMR.

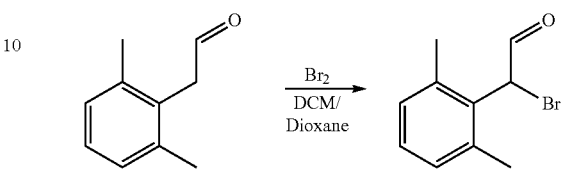

Synthesis of 2-bromo-2-(2,6-dimethylphenyl)acetaldehyde 2-(2,6-dimethylphenyl)-acetaldehyde (4.4 g, 29.7 mmol) was dissolved in DCM (30 mL) and dioxane (50 mL) and a solution of bromine (1.7 mL, 32.7 mmol) in DCM (30 mL) was added dropwise at room temperature. Completion of reaction was determined by GC/MS. Upon completion, sodium thiosulfate aqueous solution was added and stirred for 10 minutes. The layers were separated, and washed twice with DCM (100 mL) and combined organics with 10% aqueous LiCl solution (100 mL). The organic layers were dried over sodium sulfate, filtered and the solvent was removed under reduced pressure to give 7 g (93%) of 2-bromo-2-(2,6-dimethylphenyl)acetaldehyde as an orange oil. NMR confirmed the product, which was used without further purification.

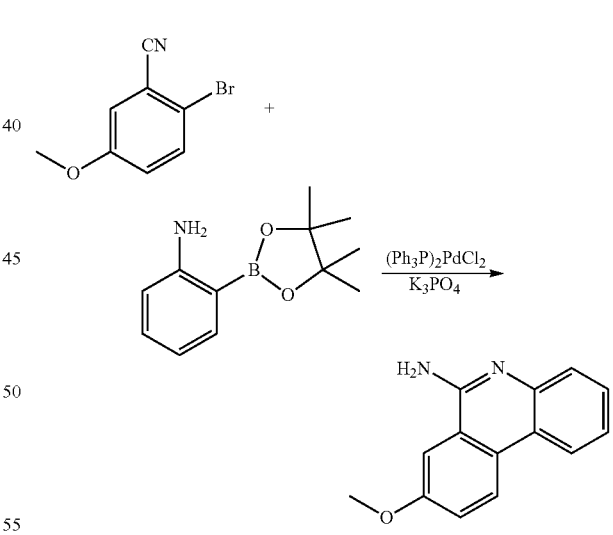

Synthesis of 8-methoxyphenanthridin-6-amine

2-Bromo-5-methoxybenzonitrile (1.32 g, 6.23 mmol), 2-(4,4,5,5-tetramethyl-1,3,2-dioxaborolan-2-yl)aniline (1.36 g, 6.23 mmol), bis(triphenylphosphine)palladiumdichloride (0.437 g, 0.623 mmol) and potassium phosphate monohydrate (4.30 g, 18.68 mmol) were added to toluene (30 mL) and water (3 mL). The reaction mixture was degassed with bubbled nitrogen gas for 30 minutes before being refluxed under nitrogen for 15 h. After cooling, the reaction mixture was filtered through Celite® and the organic layer was extracted with ethyl acetate. After removal of the solvents, the crude material was triturated with 40 mL of DCM followed by 50 mL of hexanes to give 8-methoxyphenanthridin-6-amine (0.95 g, 68%) as a light yellow solid. The product was confirmed by GC/MS and NMR.

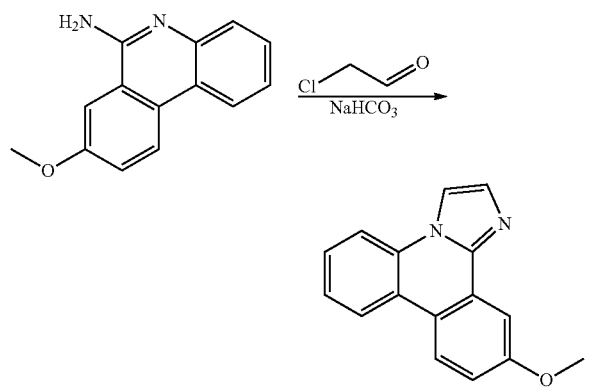

Synthesis of 11-methoxyimidazo[1,2-f]phenanthridine

8-Methoxyphenanthridin-6-amine (0.95 g, 4.24 mmol), 2-chloroacetaldehyde (0.807 mL, 12.71 mmol), and sodium bicarbonate (1.25 g, 14.83 mmol) were added to 43 mL 2-propanol and refluxed for 15 h. After cooling to room temperature, the reaction mixture was filtered thru Celite®. After removal of the solvents, the crude material was triturated with 50 mL hexanes to give 11-methoxyimidazo[1,2-f]phenanthridine (0.99 g, 94%) as an off-white solid. The product was confirmed by GC/MS and NMR.

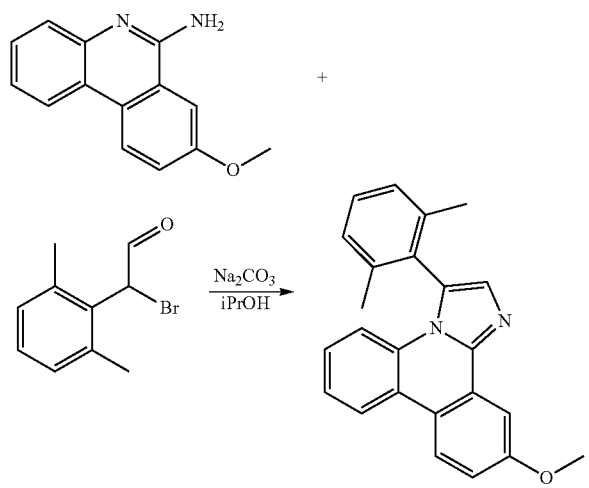

Synthesis of 3-(2,6-dimethylphenyl)-11-methoxyimidazo[1,2-f]phenanthridine

8-Methoxyphenanthridin-6-amine (2.2 g, 9.8 mmol) was suspended in 2-propanol (50 mL) and then 2-bromo-2-(2,6-dimethylphenyl)acetaldehyde (2.2 g, 9.8 mmol) in 2-propanol (25 mL) was added in one portion. The mixture was heated to reflux for 24 h and then cooled to 60° C. Sodium bicarbonate (1.6 g, 19.6 mmol) was added and the mixture again heated to reflux for 16 h before it was cooled to room temperature. Water (100 mL) and DCM (100 mL) were added the layers, the aqueous was washed with DCM (2×100 mL) and the combined organics were washed with water (2×100 mL). The organic layers were dried over sodium sulfate, filtered and rotovapped to give a crude solid that was chromatographed on silica with 8/2 hexane/EtOAc to give 2.3 g (66%) of 3-(2,6-dimethylphenyl)-11-methoxyimidazo[1,2-] phenanthridine as a tan solid. The product was confirmed by GC/MS and NMR.

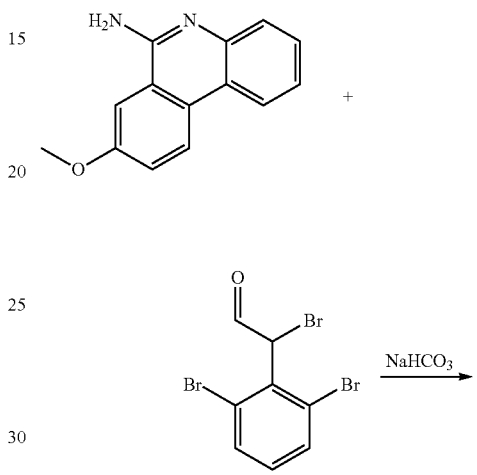

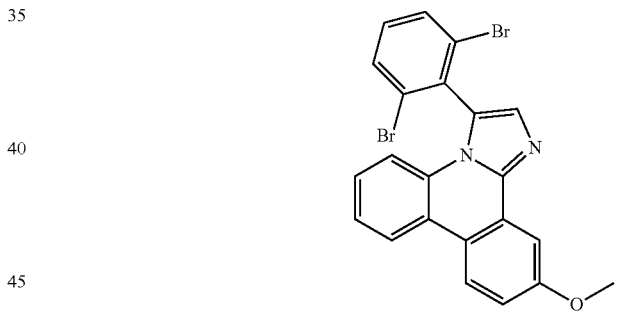

Synthesis of 3-(2,6-dibromophenyl)-11-methoxyimidazo[1,2-f]phenanthridine

8-Methoxyphenanthridin-6-amine (8.60 g, 36.4 mmol) was added to a solution of 2-bromo-2-(2,6-dibromophenyl) acetaldehyde (13.0 g, 36.4 mmol) dissolved in 225 mL isopropanol and refluxed for 24 h. The reaction mixture was cooled to 60° C. and sodium bicarbonate (6.12 g, 72.9 mmol) was added. The reaction mixture was then refluxed for another 24 h before being cooled to room temperature and filtered through a Celite® pad. The solvents were removed under reduced pressure. The crude material was purified by column chromatography on silica gel with 20/80 ethylacetate/hexanes. 3-(2,6-dibromophenyl)-11-methoxyimidazo [1,2-]phenanthridine (12.96 g, 70%) was isolated as an off-white solid. The product was confirmed by GC/MS and NMR.

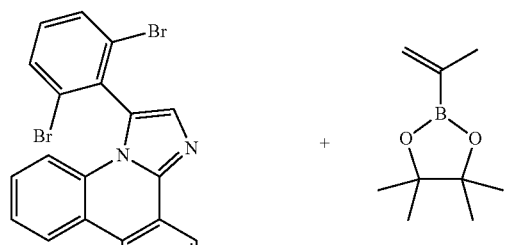
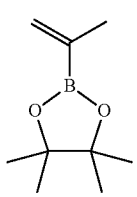
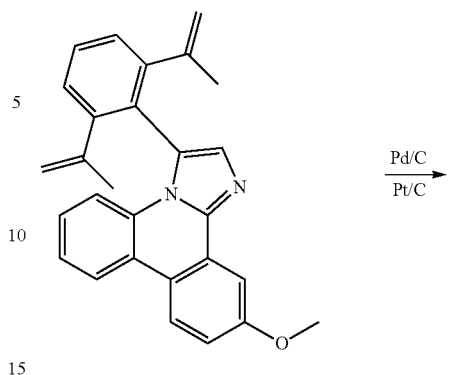

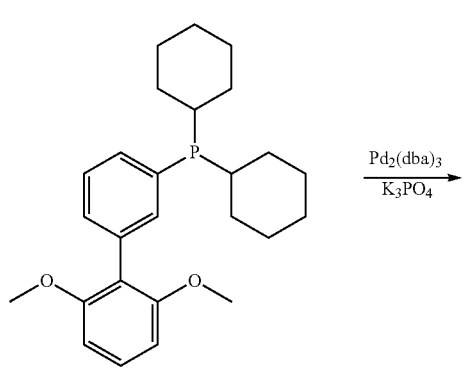

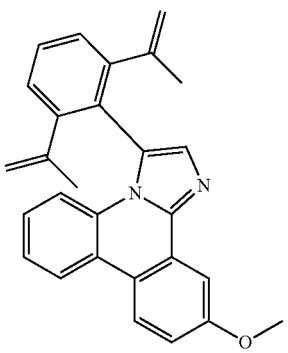

Synthesis of 3-(2,6-di(prop-1-en-2-yl)phenyl)-11-methoxyimidazo[1,2-J]phenanthridine 3-(2,6-dibromophenyl)-11-methoxyimidazo[1,2-]phenanthridine (6.96 g, 14.43 mmol), potassium phosphate monohydrate (13.30 g, 57.7 mmol), $Pd_2(dba)_3$ (0.66 g, 0.72 mmol), 2-dicyclohexylphosphino-2',6'-dimethoxybiphenyl (1.19 g, 2.89 mmol) and 4,4,5,5-tetramethyl-2-(prop-1-en-2-yl)-1,3,2-dioxaborolane (27.1 mL, 144 mmol) were added to toluene (130 mL) and water (15 mL). The reaction mixture was heated to reflux for 18 h before being cooled to room temperature and filtered through a Celite® pad. The solvents were removed under reduced pressure, and the crude material was purified by column chromatography on silica gel using 1-8% ethyl acetate in DCM to give 3-(2,6-di(prop-1-en-2-yl)phenyl)-11-methoxyimidazo[1,2-]phenanthridine (3.4 g, 57%) as an off-white solid. The product was confirmed by GC/MS and NMR.

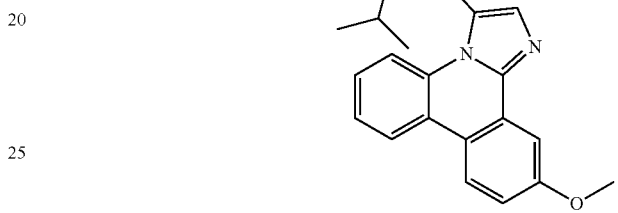

Synthesis of 3-(2,6-diisopropylphenyl)-11-methoxyimidazo[1,2-f]phenanthridine 3-(2,6-Di(prop-1-en-2-yl)phenyl)-11-methoxyimidazo[1,2-f]phenanthridine (2.46 g, 6.08 mmol) was dissolved in 100 mL ethanol and degassed with bubbled nitrogen gas. 10% palladium/carbon (1.294 g, 1.216 mmol) and 5% platinum/carbon (2.373 g, 0.608 mmol) were added to reaction mixture under a stream of nitrogen gas. Reaction mixture was hydrogenated at 50 psi for 12 h on a Parr hydrogenator. After complete reduction, the crude product was filtered through a Celite® pad and the filtrate was concentrated under reduced pressure. The crude product was chromatographed on silica gel using DCM/ethyl acetate as eluent to give 3-(2,6-diisopropylphenyl)-11-methoxyimidazo[1,2-]phenanthridine (2.1 g, 85%) as an off-white solid. The product was confirmed by GC/MS and NMR.

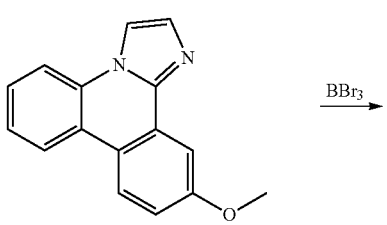
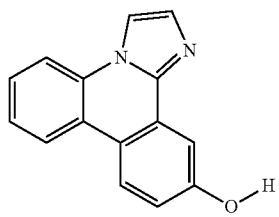

Synthesis of imidazo[1,2-f]phenanthridin-11-ol

11-Methoxyimidazo[1,2-f]phenanthridine (2.1 g, 8.46 mmol) was dissolved in DCM and cooled to −78° C. Boron tribromide (42.3 ml, 42.3 mmol) was added to the reaction mixture dropwise. After complete addition, the reaction mixture was allowed to come to room temperature, and poured into a saturated ammonium chloride solution. The solids were filtered out from the slurry, and washed with saturated sodium bicarbonate solution followed by ethyl acetate to give imidazo[1,2-]phenanthridin-11-ol (1.6 g, 82%) as an off-white solid. The product was confirmed by NMR.

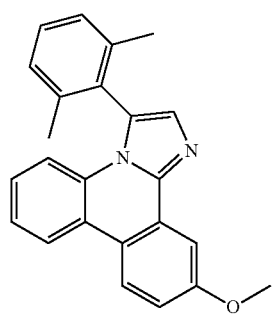

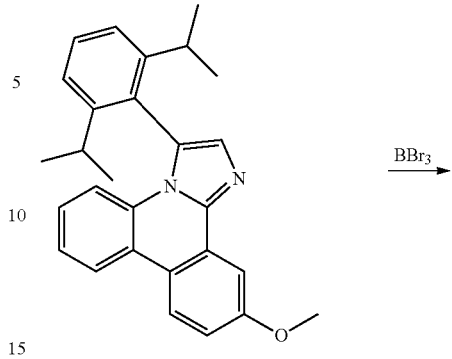

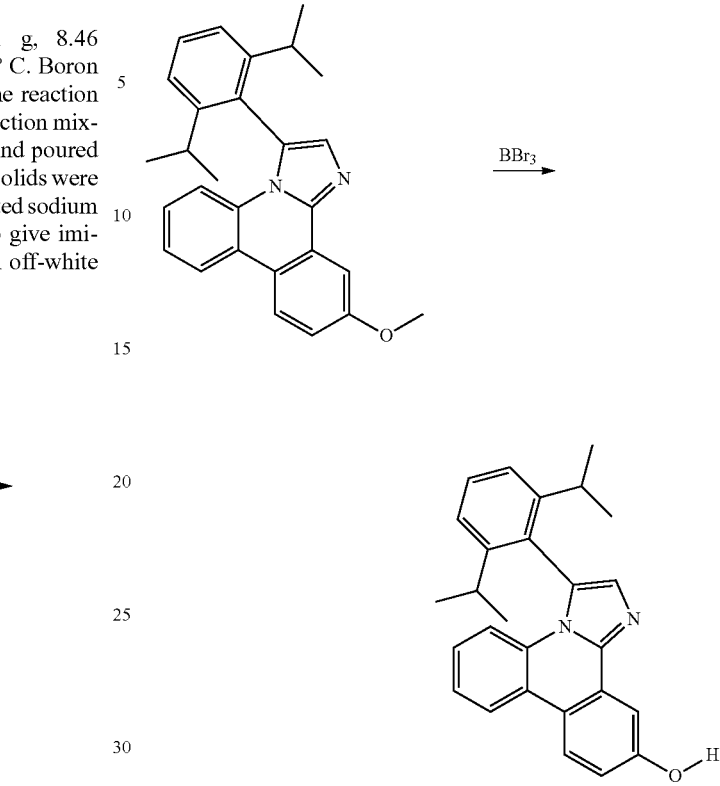

Synthesis of 3-(2,6-dimethylphenyl)imidazo[1,2-f]phenanthridin-11-ol 3-(2,6-Dimethylphenyl)-11-methoxyimidazo[1,2-]phenanthridine (2.3 g, 6.53 mmol) was dissolved in DCM and cooled to −78° C. Boron tribromide (32.6 ml, 32.6 mmol) was added to the reaction mixture dropwise. After complete addition, the reaction mixture was allowed to come to room temperature and stirred for another 24 h. The reaction mixture was poured over 500 mL ice-water mixture and the organic portion was extracted with ethylacetate (3×100 mL). The solvents were removed under reduced pressure to give 3-(2,6-dimethylphenyl)imidazo[1,2-]phenanthridin-11-ol (2.1 g, 95% yield) as a grey solid. The product was confirmed by NMR.

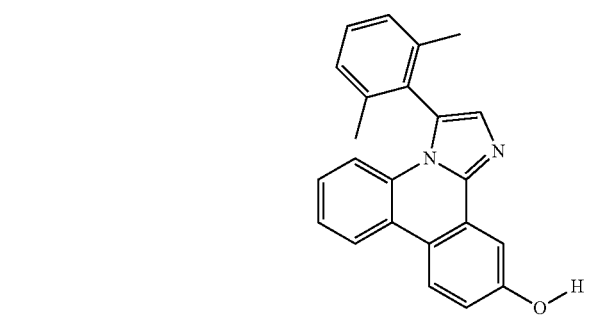

Preparation of 3-(2,6-diisopropylphenyl)imidazo[1,2-f]phenanthridin-11-ol

Diisopropylphenyl)-11-methoxyimidazo[1,2-]phenanthridine (2.1 g, 5.1 mmol) was dissolved in 200 mL dry DCM and cooled to −78° C. Boron tribromide (25.7 ml, 25.7 mmol) was added dropwise to the cold solution under heavy stirring. After complete addition, the reaction mixture was allowed to warm to room temperature. It was stirred for 18 h, and then poured over cold water. The precipitated solids were collected, washed with ethyl acetate and dried under vacuum to give 3-(2,6-diisopropylphenyl)imidazo[1,2-]phenanthridin-11-ol (2.0 g, 99%) as white solid. The product was confirmed by NMR.

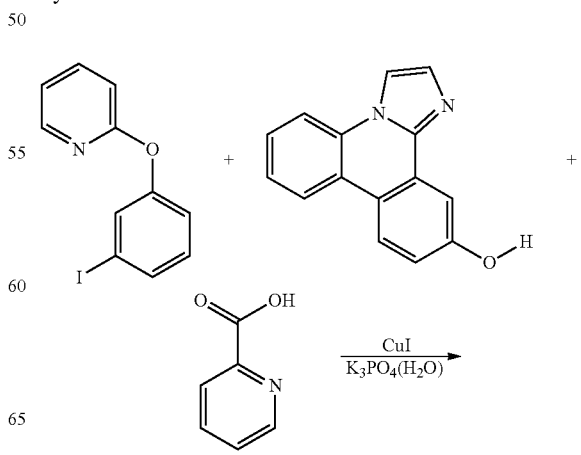

287
-continued

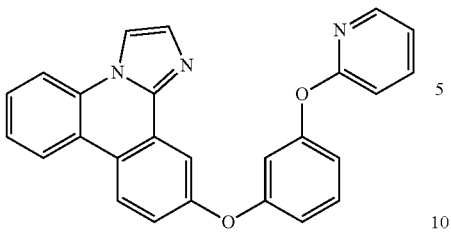

Synthesis of 11-(3-(pyridin-2-yloxy)phenoxy)imidazo[1,2-f]phenanthridine 2-(3-Iodophenoxy)pyridine (0.634 g, 2.13 mmol), imidazo[1,2-]phenanthridin-11-ol (0.5 g, 2.13 mmol), copper(I) iodide (0.122 g, 0.640 mmol), picolinic acid (0.394 g, 3.20 mmol) and potassium phosphate monohydrate (1.72 g, 7.47 mmol) were added to 70 mL DMSO and degassed for 30 minutes with bubbling nitrogen gas. The reaction mixture was heated to 100° C. for 24 h, cooled to room temperature and poured over 100 mL water. The organic materials were extracted with ethyl acetate (3×50 mL) and the combined extracts washed with 1N NaOH (1×50 mL) and saturated ammonium chloride solution (1×50 mL), dried over sodium sulfate and the solvents were removed under reduced pressure. The crude material was purified by column chromatography over silica gel using ethyl acetate/hexanes as eluent to give 11-(3-(pyridin-2-yloxy)phenoxy)imidazo[1,2-f]phenanthridine (0.58 g, 67%) was isolated as a white solid.

288
-continued

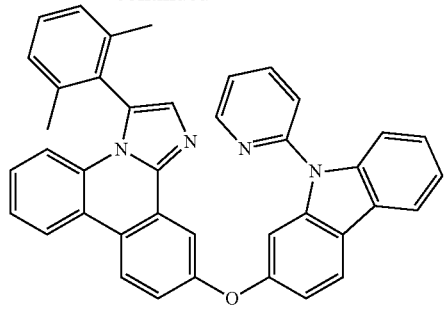

Synthesis of 3-(2,6-dimethylphenyl)-11-((9-(pyridin-2-yl)-9H-carbazol-2-yl)oxy)imidazo[1,2-f]phenanthridine 3-(2,6-Dimethylphenyl)imidazo[1,2-f]phenanthridin-11-ol (2.0 g, 5.91 mmol), 2-bromo-9-(pyridin-2-yl)-9H-carbazole (2.48 g, 7.68 mmol), picolinic acid (1.82 g, 14.8 mmol), copper(I) iodide (0.563 g, 2.96 mmol) and potassium phosphate monohydrate (6.80 g, 29.6 mmol) were added to 200 mL DMSO and degassed by bubbling nitrogen gas for 20 minutes. The reaction mixture was heated to 150° C. for 24 h, cooled to room temperature and poured over cold water. The organic materials were extracted with ethyl acetate (3×50 mL), dried over sodium sulfate and the solvents were removed under reduced pressure. The crude material was purified by column chromatography over silica gel using ethyl acetate/hexanes followed by lixiviation with hexanes to give 3-(2,6-dimethylphenyl)-11-((9-(pyridin-2-yl)-9H-carbazol-2-yl)oxy)imidazo[1,2-]phenanthridine (2.1 g, 61% yield) as a white solid.

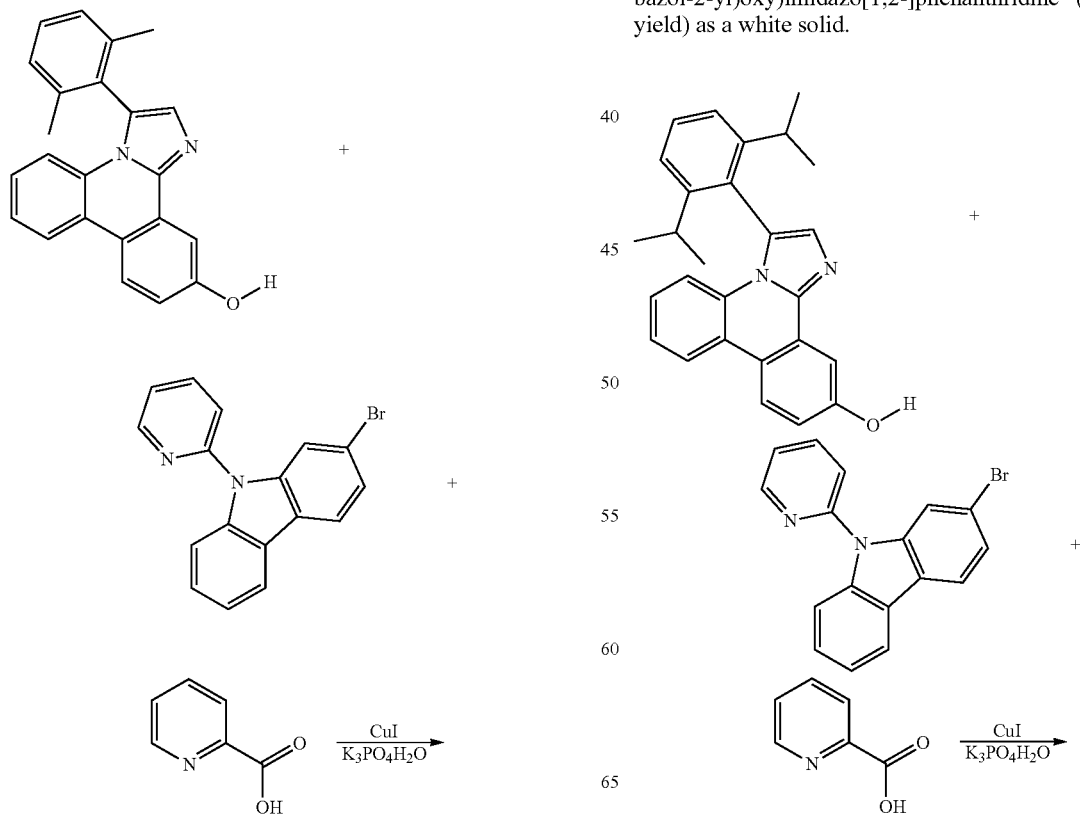

289

-continued

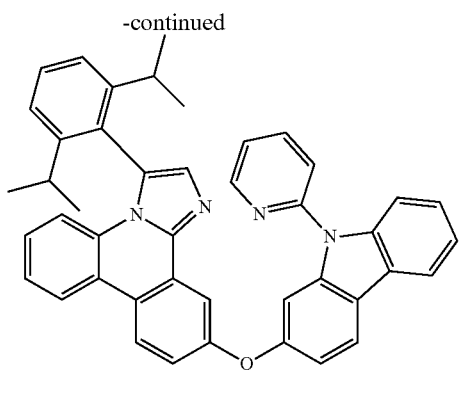

Synthesis of 3-(2,6-diisopropylphenyl)-11-((9-(pyridin-2-yl)-9H-carbazol-2-yl)oxy)imidazo[1,2-f]phenanthridine 3-(2,6-Diisopropylphenyl)imidazo[1,2-]phenanthridin-11-ol (2.0 g, 5.1 mmol), 2-bromo-9-(pyridin-2-yl)-9H-carbazole (2.1 g, 6.6 mmol), picolinic acid (1.6 g, 12.7 mmol), copper(I) iodide (0.48 g, 2.5 mmol) and potassium phosphate (5.84 g, 25.3 mmol) were added to 150 mL DMSO. The reaction mixture was heated to 150° C. for 16 h, cooled to room temperature and poured over cold water. The organic materials were extracted with ethyl acetate (4×100 mL), dried over sodium sulfate, and the solvents were removed under reduced pressure. The crude material was purified by column chromatography over silica gel using DCM/ethyl acetate to give 3-(2,6-diisopropylphenyl)-11-((9-(pyridin-2-yl)-9H-carbazol-2-yl)oxy)imidazo[1,2-]phenanthridine (2.2 g, 67%) as a white solid.

290

-continued

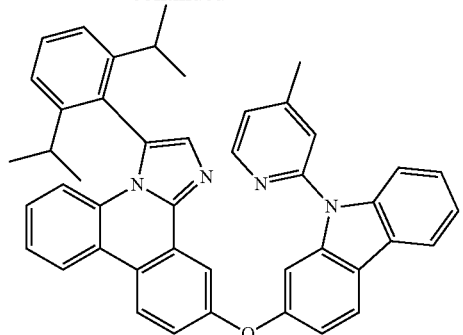

Synthesis of 3-(2,6-diisopropylphenyl)-11-((9-(4-methylpyridin-2-yl)-9H-carbazol-2-yl)oxy)imidazo[1,2-f]phenanthridine 3-(2,6-Diisopropylphenyl)imidazo[1,2-]phenanthridin-11-ol (1.5 g, 3.8 mmol), 2-bromo-9-(4-methylpyridin-2-yl)-9H-carbazole (1.7 g, 4.9 mmol), picolinic acid (1.2 g, 9.5 mmol), copper(I) iodide (0.36 g, 1.9 mmol) and potassium phosphate monohydrate (4.4 g, 19.0 mmol) were added to 150 mL DMSO. The reaction mixture was heated to 150° C. for 16 h, cooled to room temperature and poured over cold water. The organic materials were extracted with ethyl acetate (4×100 mL), dried over sodium sulfate, and the solvents were removed under reduced pressure. The crude material was purified by column chromatography over silica gel using DCM/ethyl acetate to give 3-(2,6-diisopropylphenyl)-11-((9-(4-methylpyridin-2-yl)-9H-carbazol-2-yl)oxy)imidazo[1,2-]phenanthridine (1.5 g, 61%) as white solid.

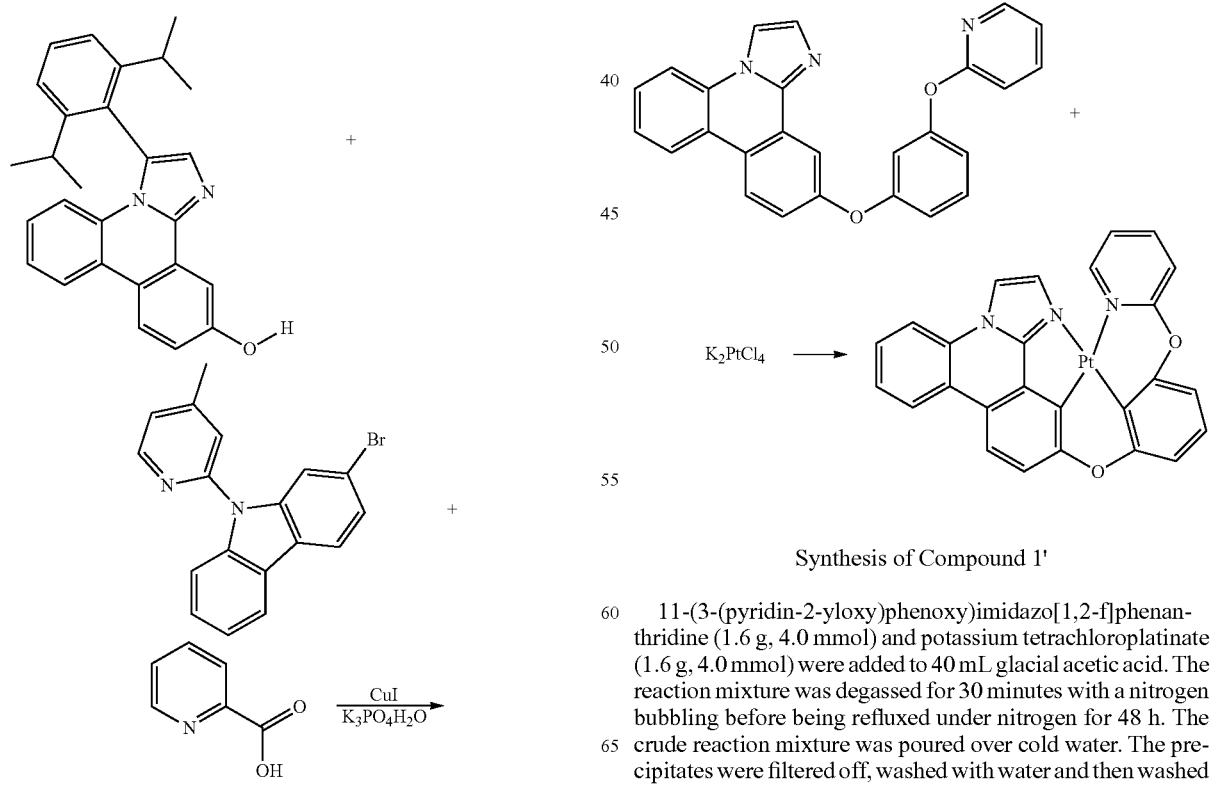

Synthesis of Compound 1'

11-(3-(pyridin-2-yloxy)phenoxy)imidazo[1,2-f]phenanthridine (1.6 g, 4.0 mmol) and potassium tetrachloroplatinate (1.6 g, 4.0 mmol) were added to 40 mL glacial acetic acid. The reaction mixture was degassed for 30 minutes with a nitrogen bubbling before being refluxed under nitrogen for 48 h. The crude reaction mixture was poured over cold water. The precipitates were filtered off, washed with water and then washed with ethanol. The resulting solid was dissolved in DCM, washed with saturated Na₂CO₃ solution, brine and water, and dried over Na₂SO₄. The crude material was purified by column chromatography over silica gel using DCM to give Compound 1' (0.39 g, 17% yield) as bright yellow solid.

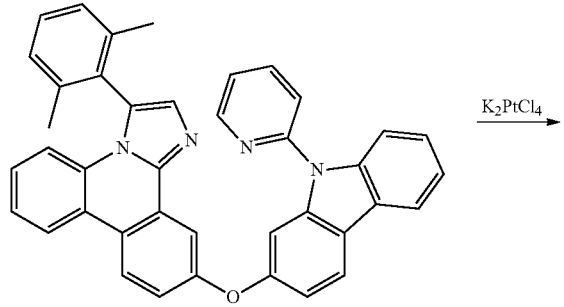

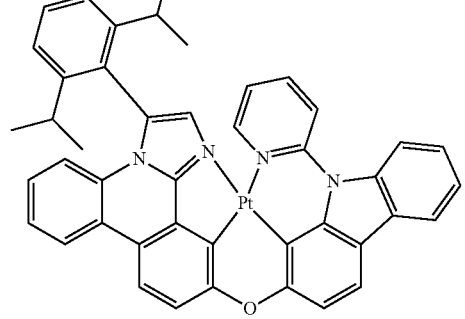

Synthesis of Compound 3'

3-(2,6-diisopropylphenyl)-11-((9-(pyridin-2-yl)-9H-carbazol-2-yl)oxy)imidazo[1,2-f]phenanthridine (2.2 g, 3.4 mmol) and potassium tetrachloroplatinate (1.4 g, 3.4 mmol) were mixed together in 150 mL acetic acid and degassed with bubbling nitrogen gas. The reaction mixture was refluxed for 18 h before being cooled to room temperature. Water was added to the reaction mixture. The solids were filtered off, and washed with a copious amount of water. The crude solid was purified by column chromatography over silica gel using 1/1 DCM/hexanes as eluent to yield Compound 3' (0.58 g, 21% yield) as a yellow solid.

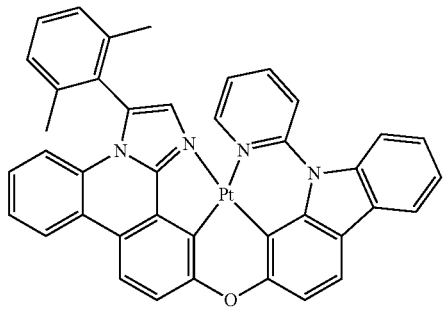

Synthesis of Compound 2'

3-(2,6-Dimethylphenyl)-11-((9-(pyridin-2-yl)-9H-carbazol-2-yl)oxy)imidazo[1,2-f]phenanthridine (1.0 g, 1.7 mmol) and potassium tetrachloroplatinate (0.72 g, 1.7 mmol) were added to 115 mL acetic acid and the reaction mixture was degassed with bubbling nitrogen gas. The reaction mixture was refluxed for 24 h before being cooled to room temperature. Water was added to the reaction mixture. The solids were filtered off, and washed with a copious amount of water. The crude solid was purified by column chromatography over silica gel using DCM/hexanes as eluent to yield Compound 2' (0.40 g, 30% yield) as a yellow solid.

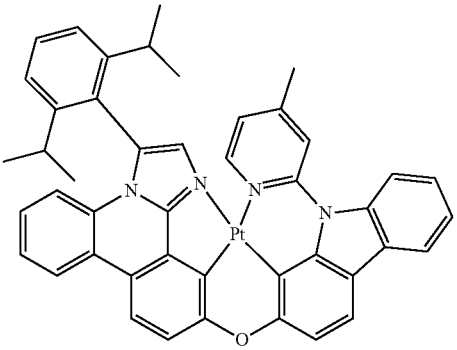

Synthesis of Compound 4'

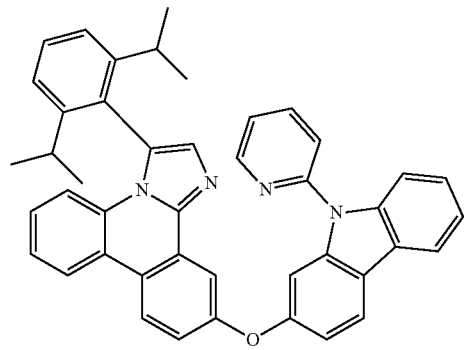

3-(2,6-Diisopropylphenyl)-11-((9-(4-methylpyridin-2-yl)-9H-carbazol-2-yl)oxy)imidazo[1,2-f]phenanthridine (1.50 g, 2.30 mmol) and potassium tetrachloroplatinate (0.96 g, 2.30 mmol) were added to 130 mL acetic acid and the reaction mixture was degassed with bubbling nitrogen gas.

The reaction mixture was refluxed for 18 h before being cooled to room temperature. Water was added to the reaction mixture and solids were filtered off, washing with copious water. The crude solid was purified by column chromatography over silica gel using 1/1 DCM/hexanes as eluent to yield Compound 4' (0.48 g, 24.7% yield) as a light yellow solid.

Device Examples

The device examples in Tables 2 and 3 were fabricated by high vacuum (<10$^{-7}$ Torr) thermal evaporation. The anode electrode is 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the devices in Tables 2 and 3 consisted of sequentially, from the ITO surface, 100 Å of Compound B as the hole injection layer (HIL), 300 Å of 4,4'-bis[N-(1-naphthyl)-N-phenylamino]biphenyl (α-NPD) as the hole transporting later (HTL), 300 Å of Compound A doped with Compound 3 as the emissive layer (EML), 50 Å of Compound A as BL, and 450 Å of Alq as the ETL.

As used herein, the following compounds have the following structures:

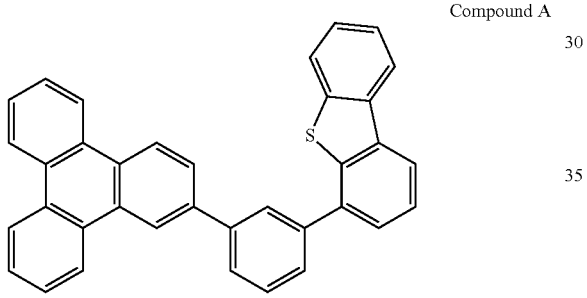

Compound A

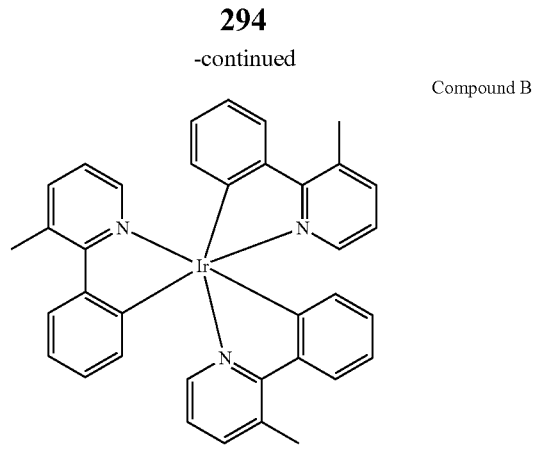

Compound B

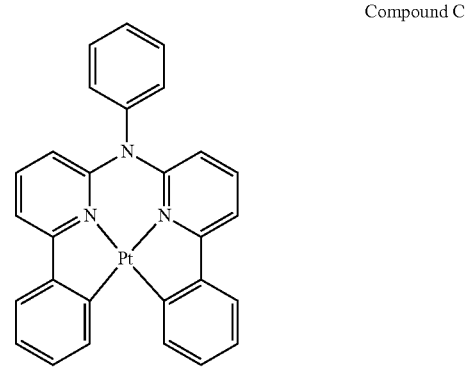

Compound C

Particular emissive dopants for the emissive layer of an OLED are provided. Devices containing these compounds have particularly good properties.

The device structures are summarized in Table 2, and the corresponding device data is summarized in Table 3.

TABLE 2

| | | | VTE PHOLEDs | | | |
|---|---|---|---|---|---|---|
| Example | HIL | HTL | EML (doping %) | | BL | ETL |
| Example 1 | Compound B | NPD | Compound A | Compound 3 6% | Compound A | Alq |
| Example 2 | Compound B | NPD | Compound A | Compound 3 10% | Compound A | Alq |
| Example 3 | Compound B | NPD | Compound A | Compound 3 15% | Compound A | Alq |
| Example 4 | Compound B | NPD | Compound A | Compound 5 10% | Compound A | Alq |
| Example 5 | Compound B | NPD | Compound A | Compound 5 15% | Compound A | Alq |
| Example 6 | Compound B | NPD | Compound F | Compound 5 10% | Compound F | Alq |
| Example 7 | Compound B | NPD | Compound F | Compound 5 15% | Compound F | Alq |
| Example 8 | Compound B | NPD | Compound A | Compound 29 10% | Compound A | Alq |
| Example 9 | Compound B | NPD | Compound A | Compound 29 15% | Compound A | Alq |
| Example 10 | Compound G | NPD | Compound A | Compound 30 7% | Compound A | Alq |
| Example 11 | Compound G | NPD | Compound A | Compound 30 10% | Compound A | Alq |
| Example 12 | Compound B | NPD | Compound F | Compound 162 15% | Compound F | Alq |
| Example 13 | Compound B | NPD | Compound F | Compound 162 20% | Compound F | Alq |
| Example 14 | Compound B | NPD | Compound A | Compound 163 10% | Compound A | Alq |
| Example 15 | Compound B | NPD | Compound A | Compound 163 15% | Compound A | Alq |
| Example 16 | Compound G | NPD | Compound A | Compound 164 7% | Compound A | Alq |
| Example 17 | Compound G | NPD | Compound A | Compound 164 10% | Compound A | Alq |
| Example 18 | Compound G | NPD | Compound F | Compound 164 7% | Compound F | Alq |
| Example 19 | Compound G | NPD | Compound F | Compound 164 10% | Compound F | Alq |
| Example 20 | Compound G | NPD | Compound A | Compound 166 10% | Compound A | Alq |
| Example 21 | Compound G | NPD | Compound A | Compound 166 15% | Compound A | Alq |
| Comparative Example 1 | Compound B | NPD | Compound A | Compound C 10% | Compound A | Alq |
| Comparative Example 2 | Compound B | NPD | Compound A | Compound C 15% | Compound A | Alq |

TABLE 2-continued

VTE PHOLEDs

| Example | HIL | HTL | EML (doping %) | | BL | ETL |
|---|---|---|---|---|---|---|
| Comparative Example 3 | Compound B | NPD | Compound F | Compound C 10% | Compound F | Alq |
| Comparative Example 4 | Compound B | NPD | Compound F | Compound C 15% | Compound F | Alq |
| Comparative Example 5 | Compound G | NPD | Compound A | Compound D 7% | Compound A | Alq |
| Comparative Example 6 | Compound G | NPD | Compound A | Compound D 10% | Compound A | Alq |
| Comparative Example 7 | Compound G | NPD | Compound F | Compound D 7% | Compound F | Alq |
| Comparative Example 8 | Compound G | NPD | Compound F | Compound D 10% | Compound F | Alq |
| Comparative Example 9 | Compound G | NPD | Compound A | Compound E 7% | Compound A | Alq |
| Comparative Example 10 | Compound G | NPD | Compound A | Compound E 10% | Compound A | Alq |

TABLE 3

VTE device data

| | | | | | At 1000 nits | | | At 40 mA/cm$^2$ | |
|---|---|---|---|---|---|---|---|---|---|
| | 1931 CIE | | | FWHM | Voltage | LE | EQE | PE | | |
| Example | x | y | $\lambda_{max}$ | (nm) | (V) | (Cd/A) | (%) | (lm/W) | $L_0$ (nits) | LT80% (h) |
| Example 1 | 0.432 | 0.558 | 546 | 24 | 7.6 | 55.7 | 15.3 | 23.1 | 12,983 | 70 |
| Example 2 | 0.436 | 0.556 | 548 | 24 | 6.8 | 69.9 | 19.3 | 32.5 | 15,809 | 80 |
| Example 3 | 0.436 | 0.557 | 548 | 24 | 6.1 | 84.1 | 23.1 | 43.4 | 20,535 | 98 |
| Example 4 | 0.256 | 0.568 | 500 | 50 | 8.3 | 11 | 3.6 | 4.2 | 4,068 | 44 |
| Example 5 | 0.257 | 0.588 | 500 | 50 | 7.7 | 13.7 | 4.4 | 5.5 | 4,934 | 36 |
| Example 6 | 0.253 | 0.592 | 500 | 50 | 8 | 20.4 | 6.5 | 8.0 | 6,753 | 80 |
| Example 7 | 0.255 | 0.604 | 500 | 50 | 7.4 | 24.1 | 7.6 | 10.2 | 7,892 | 79 |
| Example 8 | 0.623 | 0.374 | 606 | 74 | 8.9 | 15.9 | 10.3 | 5.6 | 4,335 | 340 |
| Example 9 | 0.630 | 0.367 | 610 | 76 | 8.3 | 14.4 | 10.1 | 5.4 | 4,242 | 500 |
| Example 10 | 0.387 | 0.582 | 534 | 64 | 7.6 | 22.3 | 6.2 | 9.2 | 7,417 | 116 |
| Example 11 | 0.392 | 0.583 | 534 | 66 | 7.2 | 25.6 | 7.1 | 11.1 | 8,386 | 108 |
| Example 12 | 0.245 | 0.627 | 504 | 20 | 6.7 | 33.3 | 10.5 | 15.7 | 10,690 | 23 |
| Example 13 | 0.245 | 0.628 | 506 | 20 | 6.4 | 27.3 | 8.6 | 13.4 | 9,960 | 17 |
| Example 14 | 0.304 | 0.636 | 520 | 46 | 7.0 | 32.9 | 8.9 | 14.7 | 10,044 | 71 |
| Example 15 | 0.306 | 0.643 | 520 | 18 | 6.4 | 38.5 | 10.4 | 19.0 | 11,832 | 55 |
| Example 16 | 0.291 | 0.618 | 514 | 54 | 7.2 | 24.3 | 7 | 10.6 | 7,646 | 37 |
| Example 17 | 0.293 | 0.625 | 514 | 54 | 6.7 | 28.3 | 8.1 | 13.2 | 8,740 | 35 |
| Example 18 | 0.293 | 0.621 | 512 | 54 | 8.1 | 27.3 | 7.9 | 10.6 | 7,970 | 56 |
| Example 19 | 0.289 | 0.633 | 512 | 52 | 6.9 | 39.5 | 11.3 | 17.9 | 10,938 | 40 |
| Example 20 | 0.488 | 0.506 | 556 | 58 | 8.6 | 35.6 | 11.4 | 13.0 | 8,244 | 92 |
| Example 21 | 0.480 | 0.515 | 556 | 20 | 5.6 | 50.8 | 15.7 | 28.4 | 12,659 | 60 |
| Comparative Example 1 | 0.355 | 0.567 | 516 | 64 | 9.3 | 7.2 | 2.4 | 2.4 | 2,665 | 80 |
| Comparative Example 2 | 0.373 | 0.566 | 516 | 66 | 9.2 | 7.7 | 2.7 | 2.6 | 2,822 | 70 |
| Comparative Example 3 | 0.338 | 0.582 | 514 | 58 | 9.9 | 7.9 | 2.6 | 2.5 | 2,852 | 64 |
| Comparative Example 4 | 0.357 | 0.581 | 514 | 60 | 9.7 | 8.2 | 2.8 | 2.7 | 2,989 | 58 |
| Comparative Example 5 | 0.336 | 0.598 | 514 | 66 | 7.7 | 27.9 | 8.4 | 11.4 | 8,587 | 77 |
| Comparative Example 6 | 0.353 | 0.591 | 514 | 70 | 7.6 | 30.6 | 9.5 | 12.6 | 8,975 | 97 |
| Comparative Example 7 | 0.340 | 0.596 | 512 | 66 | 8.5 | 28.2 | 8.7 | 10.4 | 8,747 | 108 |
| Comparative Example 8 | 0.341 | 0.595 | 512 | 66 | 7.7 | 28.3 | 8.8 | 11.5 | 9,092 | 98 |
| Comparative Example 9 | 0.490 | 0.506 | 562 | 64 | 6.6 | 64.9 | 20.4 | 30.7 | 16,040 | 85 |
| Comparative Example 10 | 0.497 | 0.498 | 562 | 66 | 6.8 | 57.5 | 18.6 | 26.7 | 14,690 | 145 |

The structures of Compounds A-G used in the devices described herein are as follows:

Compound A

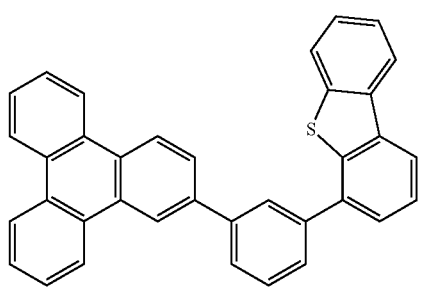

Compound B

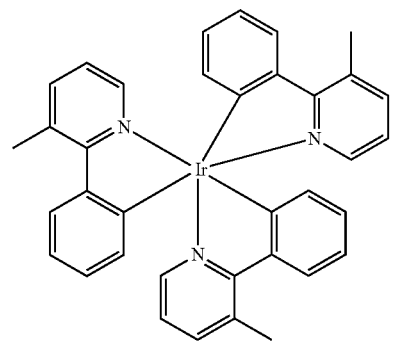

Compound C

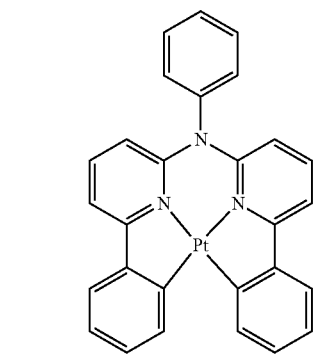

Compound D

Compound E

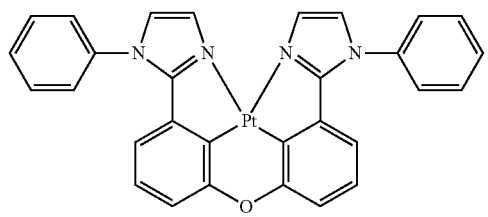

Compound F

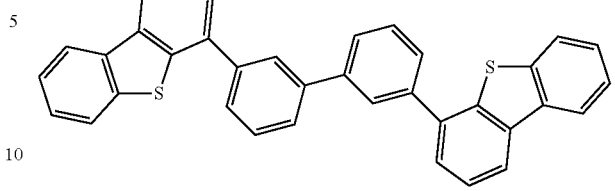

Compound G

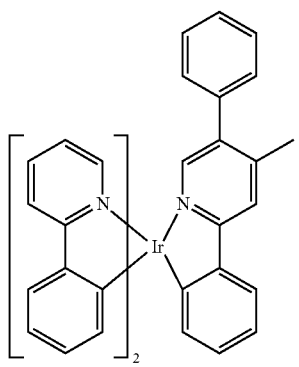

As can be seen in Table 3, the emission spectrum did not change when the doping concentration increased, which indicates no excimer formation. The observed FWHM, i.e., 24 nm, for these compounds is very narrow. Generally, the reported and/or observed FWHM for Ir-based compounds is greater than 60 nm, e.g., in the range of about 60 nm to about 70 nm. Additionally, the devices showed very high efficiency. For example, Device Example 3 showed an EQE of more than 23% at 1000 nits, which is believed to be the highest for any reported Pt complex. Generally, Ir-based compounds have efficiencies of roughly 16% at 1000 nits.

Table 2 lists device compositions containing Compounds 3, 5, 29, 30, 162, 163, 164, 166, and Comparative Compounds C, D, and E. Table 2 shows the device results obtained from the devices listed in Table 1.

The devices containing compounds of Formula I as the emitting dopants showed desirable characteristics, such as narrow full width at half maximum (FWHM), high device efficiency, saturated emission color, and longer device lifetimes. Selection of appropriate ligands in the compounds of Formula I allows for the emission color to be tuned to cover the full visible spectrum, such as from Compound 3 to Compound 29.

The advantage of introducing twisted aryl groups was clearly demonstrated. For example, device with Compound 3 as emitting dopant with 20% doping concentration achieved 23.1% EQE, 84.1 cd/A at 1000 cd/m² with an operating voltage of 6.1 V. In addition, the emission had a $\lambda_{max}$ of 548 nm and a FWHM of 24 nm. As can be seen from comparative example 9, when Compound E was used as the dopant, it should a $\lambda_{max}$ of 562 nm and a FWHM of 64 nm. The emission was red shifted and the FWHM was much broader than Compound 3. In an OLED device narrower FWHM is sometimes advantageous for generating purer color. Furthermore, the device efficiency was 20.4% and 64.9 cd/A at 1000 cd/m$^2$, much lower than 23.1% and 84.1. Device lifetime was also shorter for Comparative example 9 (85 h vs 98 h).

Improvement was also observed when comparing Compound 5 with Compound D. When Compound A was used as the host for Compound 5, the device efficiency was low due to partial quenching from the host because of the triplet energy level. When Compound F was used as the host, Compound 5 showed 7.6% EQE at 1000 cd/m$^2$ with CIE of (0.255, 0.604) and FWHM of 50 nm, while Compound D showed slightly improved efficiency (8.8% EQE), but much less saturated emission and broader spectrum (CIE (0.341, 0.595), FWHM 66 nm). Device lifetimes were comparable between devices containing Compound 5 (Example 7) and Compound D (Comparative Example 8) (79 h vs 98 h at 40 mA/cm$^2$.)

Device Examples 10 and 11 also showed better results than Comparative Device Examples 1-4. Devices with Compound 30 showed slightly red shifted color compared to that of Compound C (534 nm vs 516 nm), but the efficiencies were much higher. (9-11% vs 2.4-2.7%). Device lifetimes were also longer than the comparative examples. Thus, compounds of Formula I containing a twisted aryl substitution showed improved characteristics in devices compared to compounds without twisted aryl substitution.

Comparative device data is based on recently published results by Dileep A. K. Vezzu et al. in Inorg. Chem. 2010, 49, 5107. In the publication, Compound C was used as the emitter. The best efficiency obtained by their device was less than 13% at 1000 nits. In addition, when doping concentration increased, the excimer emission was observed. Therefore, the inventive compounds containing a twisted aryl group showed higher efficiency, i.e., greater than 23% at 1000 nits as compared to less than 13% at 1000 nits, and narrower emission spectra than the compounds without the twisted aryl groups.

The device examples in Tables 4 and 5 were fabricated by high vacuum (<10$^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the devices in Tables 4 and 5 consisted of sequentially, from the ITO surface, 100 Å of LG101 (purchased from LG Chemical) as the hole injection layer (HIL), 300 Å of NPD as the hole transporting layer (HTL), 300 Å of Host 1 doped with 10% of an inventive compound as the emissive layer (EML), 50 Å of BL1 as blocking layer (BL), and 400 Å of AlQ$_3$ as the electron transporting layer (ETL).

As used herein, the following compounds have the following structures:

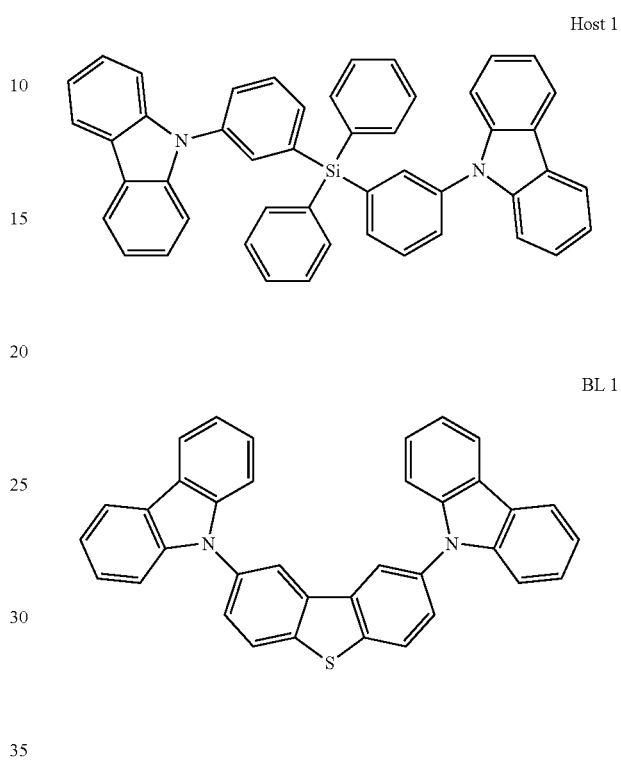

The device examples are detailed in Table 4, and the corresponding device data is summarized in Table 5. Ex. is an abbreviation of example.

TABLE 4

VTE PHOLEDs

| Device Ex. | HIL | HTL | EML | EML doping % | BL | ETL |
|---|---|---|---|---|---|---|
| 1 | LG101 | NPD | Host 1: Compound 2' | 10 | BL1 | AlQ$_3$ |
| 2 | LG101 | NPD | Host 1: Compound 4' | 10 | BL1 | AlQ$_3$ |

TABLE 5

VTE Device Data

| | | | | | At 1000 nits | | | | |
|---|---|---|---|---|---|---|---|---|---|
| Device Ex. | 1931 CIE X | Y | λ max (nm) | FWHM (nm) | Voltage (V) | LE (Cd/A) | EQE (%) | PE lm/W | 20 mA/cm$^2$ L$_0$ (nits) |
| 1 | 0.228 | 0.356 | 462 | 86 | 7.1 | 18.4 | 7.8 | 8.2 | 3305 |
| 2 | 0.181 | 0.295 | 460 | 52 | 7.0 | 14.1 | 6.9 | 6.4 | 2550 |

Device Examples 1 and 2 in Tables 4 and 5 demonstrate the effect of increased steric bulk on suppressing excimer formation. Both compounds have very similar 77K solution PL demonstrating that the monomeric $^3$MLCT transitions are similar in energy and lineshape. However, Device Example 1 which is a solid-state device that contains Compound 2', has a much broader electroluminescent emission and a correspondingly undesirable effect on the CIE. A lower energy Gaussian emission observed in the EL is attributed to excimer formation. By replacing the 2,6-methyl substitution with an isopropyl groups and adding a steric methyl group to the pyridine ring, as in Compound 4', excimeric emission can be suppressed. Device example 2, which contains Compound 4', demonstrated deep blue emission with a $\lambda_{max}$ at 460 nm, a narrow FWHM of 52 nm and improved CIE, which are characteristic of the monomeric emission from Compound 4'.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

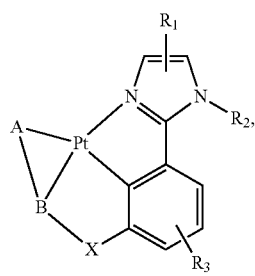

Formula II wherein A is a 5-membered carbocyclic or heterocyclic ring and B is a 5-membered or 6-membered carbocyclic or heterocyclic ring;
wherein A-B connects to Pt through one covalent bond and one covalent bond and one coordination bond;
wherein X is selected from the group consisting of BR, NR, PR, O, S, Se, C=O, S=O, SO$_2$, CRR', SiRR', and GeRR';
wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein R$_3$ may represent mono, di, or tri substitutions;
wherein R$_1$ may represent mono or di substitutions:
wherein R$_1$, R$_2$, and R$_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of R$_1$, R$_2$, and R$_3$ are optionally joined to form a fused ring;
wherein at least one of R$_1$ and R$_2$ is:

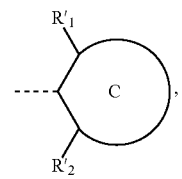

wherein R'$_1$ and R'$_2$ are independently selected from the group consisting of alkyl and aryl; and
wherein C is a 5-membered or 6-membered carbocyclic or heterocyclic ring that is optionally further substituted.

2. The compound of claim 1, wherein C is benzene.

3. The compound of claim 1, wherein the compound has a formula selected from the group consisting of:

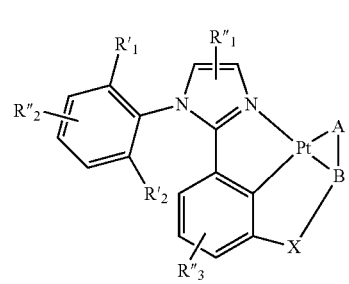

Formula V

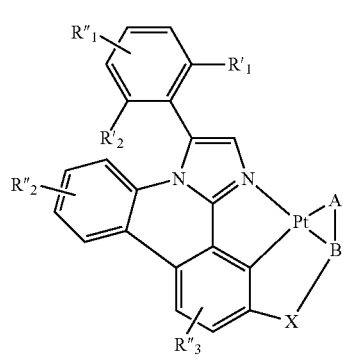

Formula VI

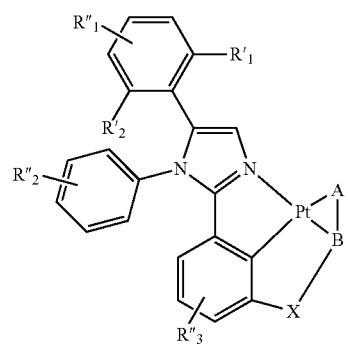

Formula VII

-continued

Formula VIII

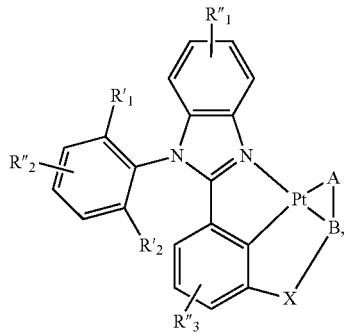

wherein R"$_1$, R"$_2$, and R"$_3$ may represent mono, di, tri, or tetra substitutions;

wherein R"$_1$, R"$_2$, and R"$_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of R"$_1$, R"$_2$, and R"$_3$ are optionally joined to form a fused ring.

4. The compound of claim 1, wherein A-B is selected from the group consisting of:

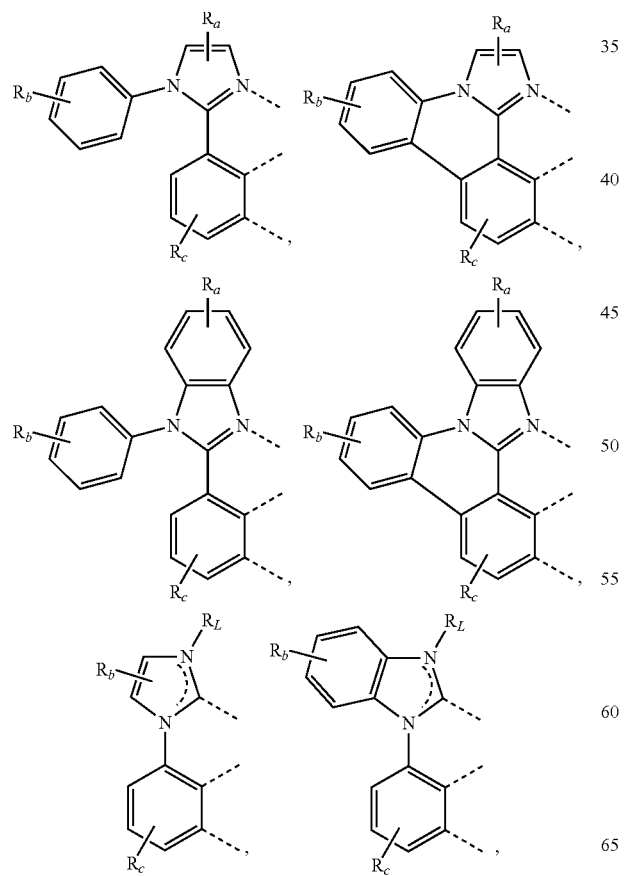

-continued

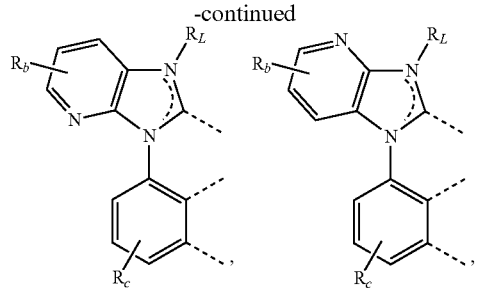

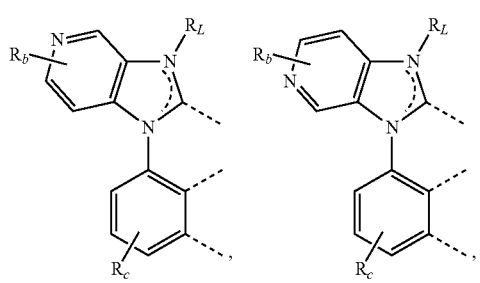

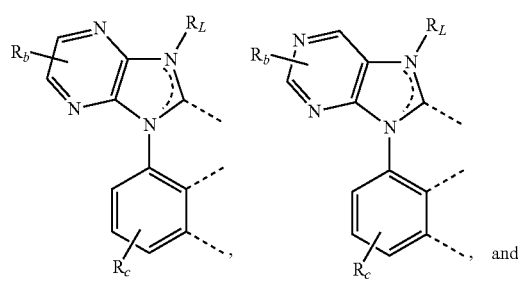

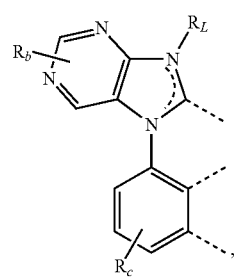

wherein $R_a$ and $R_b$ may represent mono, di, tri or tetra substitutions;

wherein $R_c$ may represent mono, di, or tri substitutions;

wherein $R_L$ may represent mono substitution;

wherein $R_a$, $R_b$, $R_c$ and $R_L$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$ and $R_L$ are optionally joined to form a fused ring.

5. The compound of claim 1, wherein the compound is selected from the group consisting of:
Compound 1G
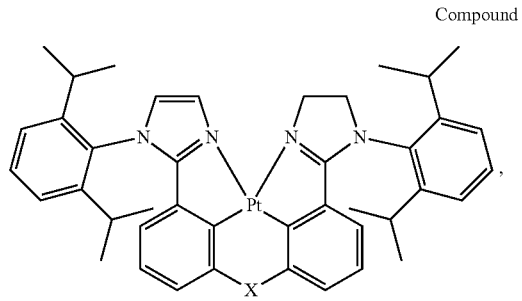
Compound 3G
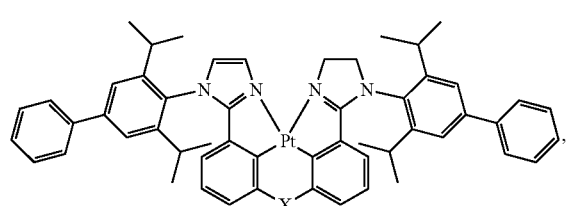
Compound 4G
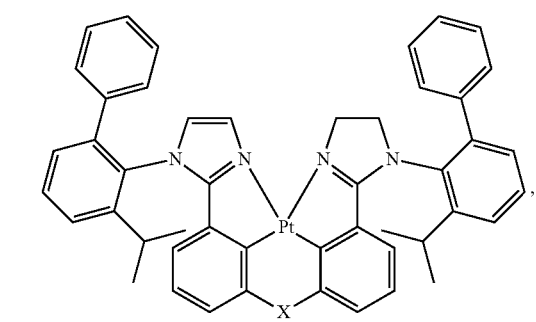
Compound 5G
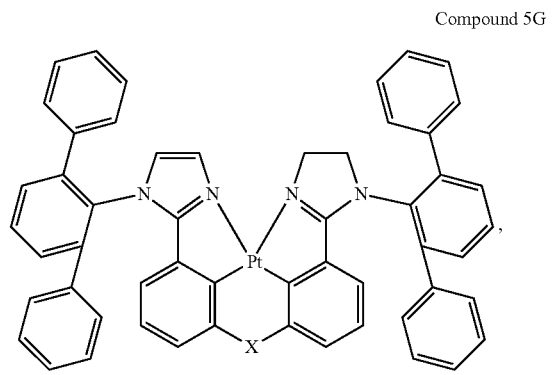
Compound 6G
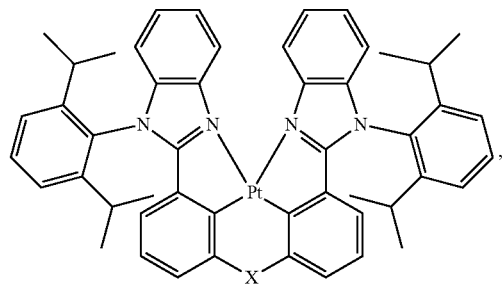
Compound 7G
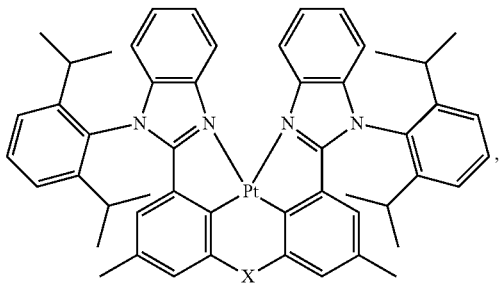
Compound 8G
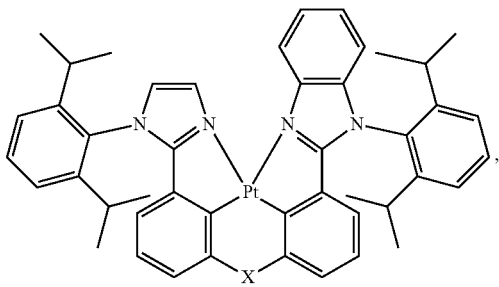
Compound 13G
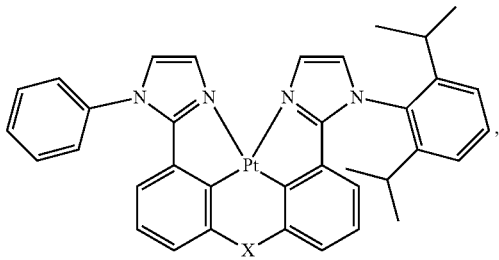
Compound 14G
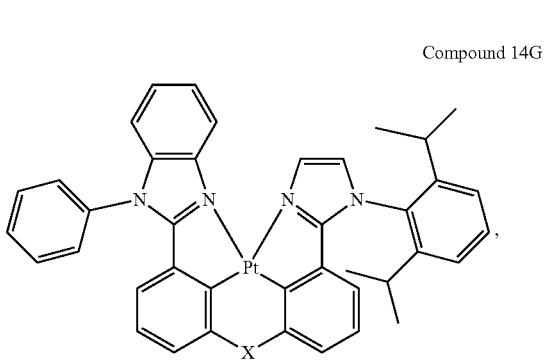
Compound 19G
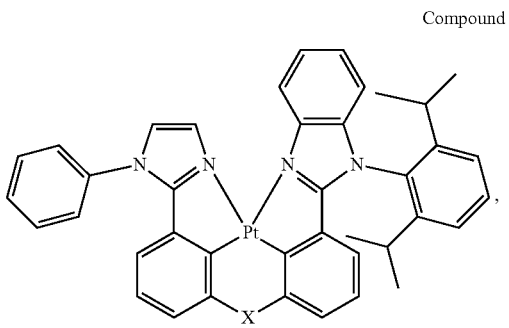

Compound 20G
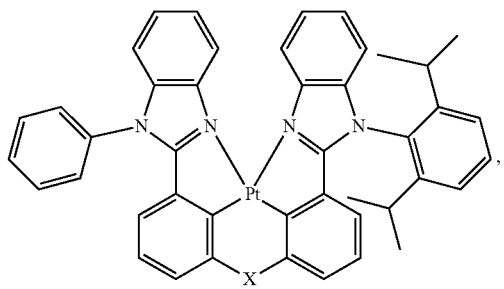
Compound 21G
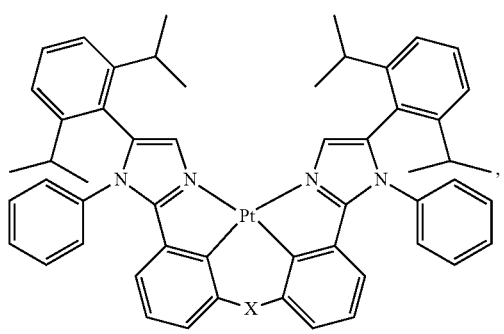
Compound 22G
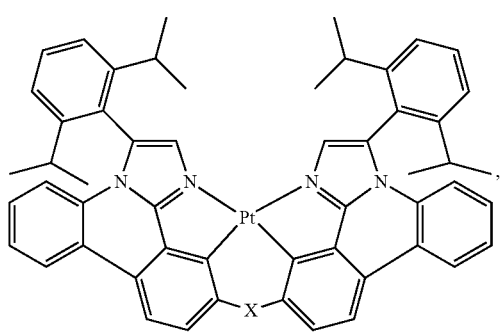
Compound 23G
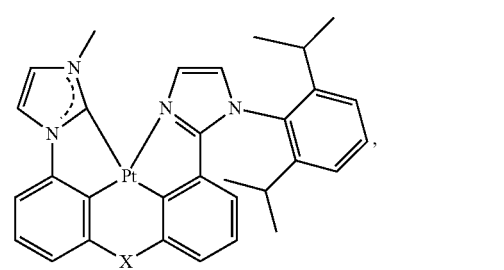
Compound 24G
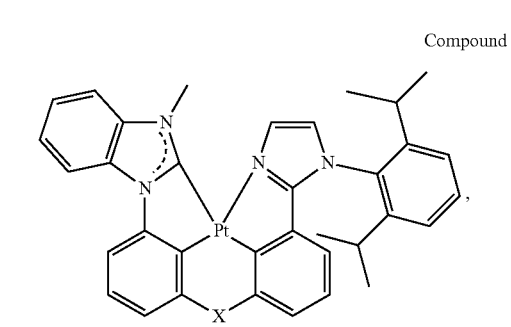
Compound 25G
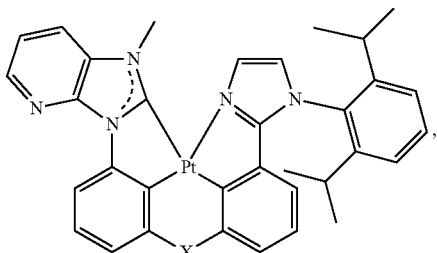
Compound 26G
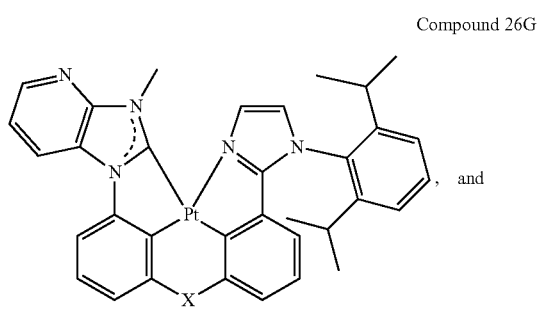
, and
Compound 28G
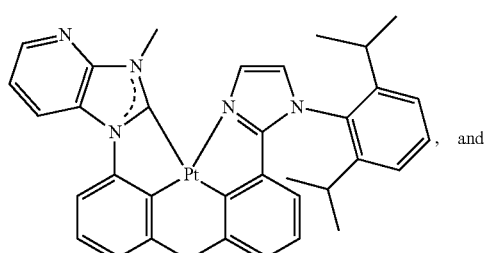
6. The compound of claim 1, wherein the compound is selected from the group consisting of:
Compound 1
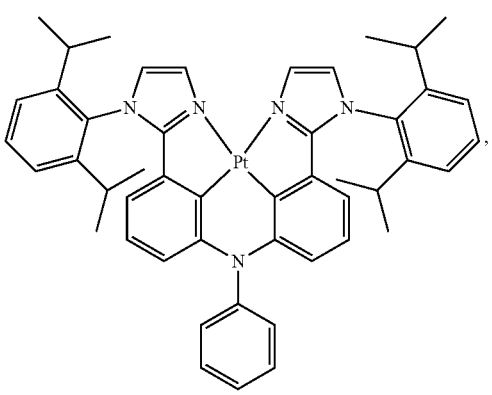
, Compound 2
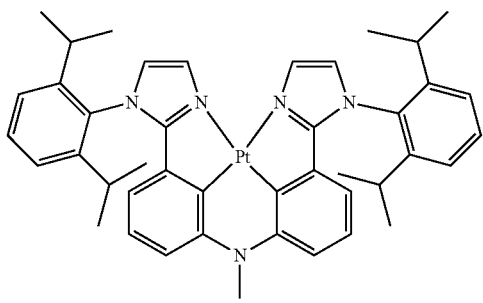
Compound 3
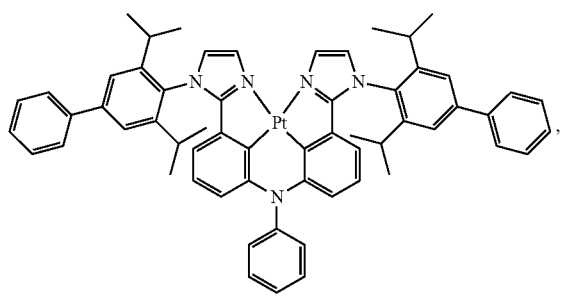
Compound 4
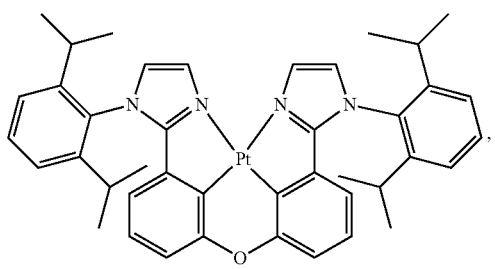
Compound 5
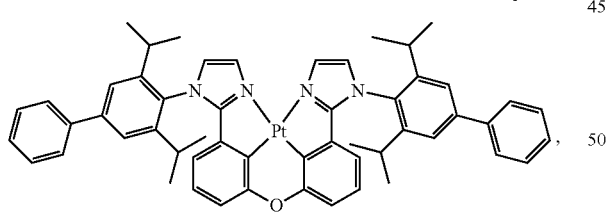
Compound 6
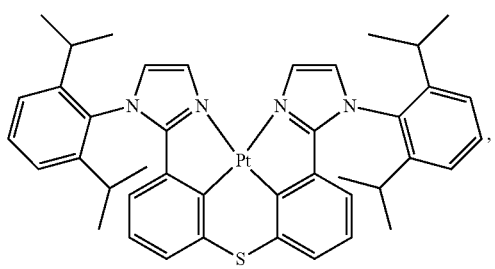
Compound 7
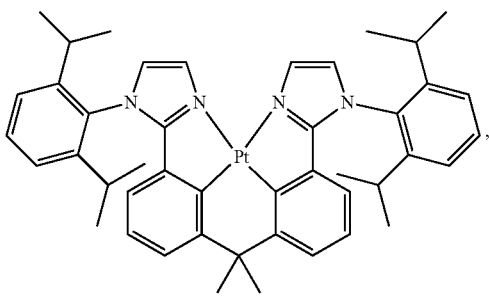
Compound 8
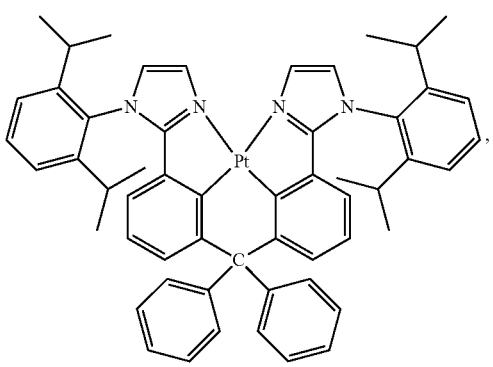
Compound 9
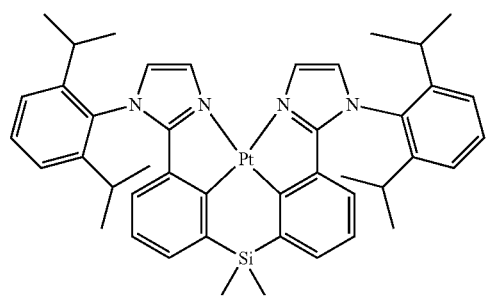
Compound 10
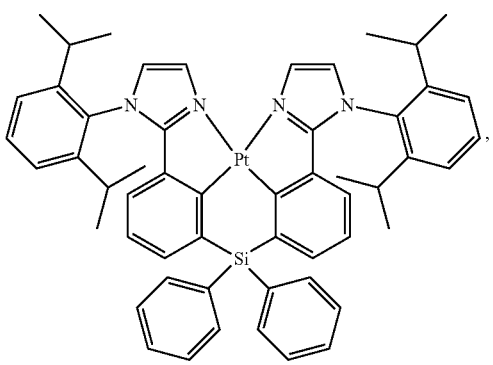

311
-continued
Compound 11
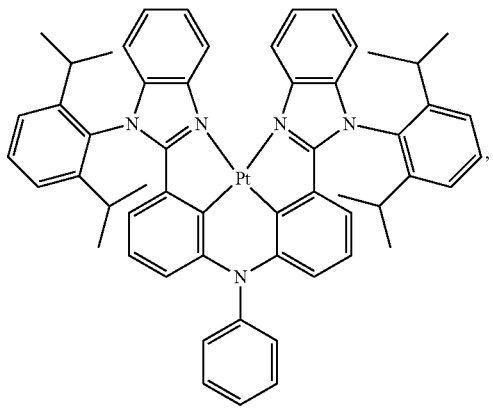
Compound 12
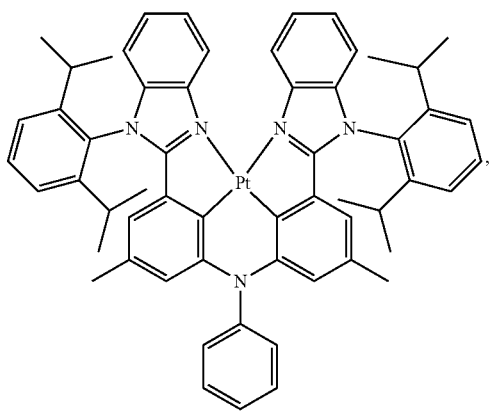
Compound 13
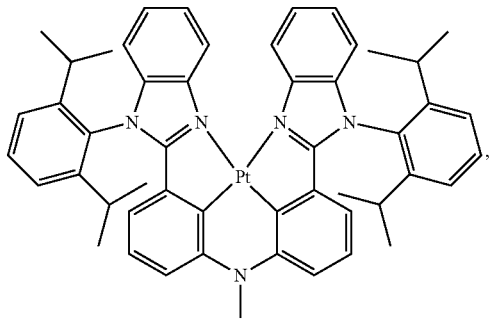
Compound 14
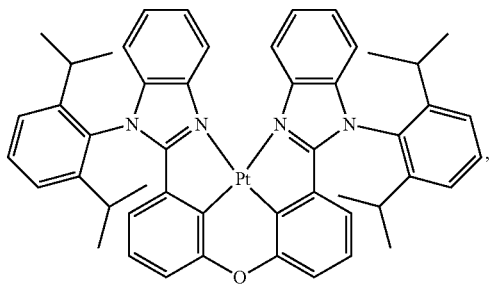
312
-continued
Compound 15
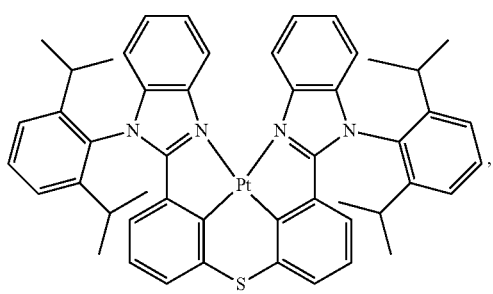
Compound 16
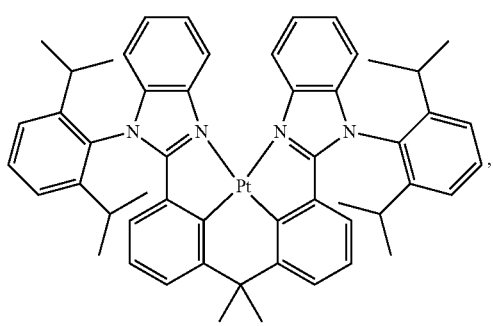
Compound 17
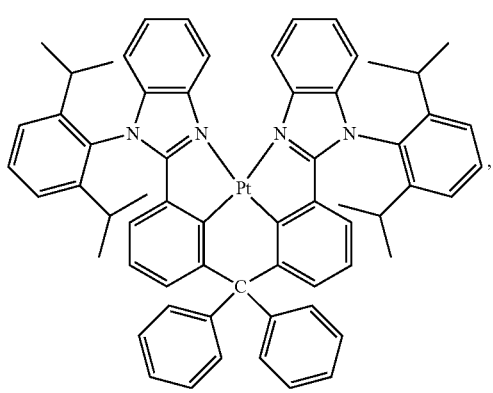
Compound 18
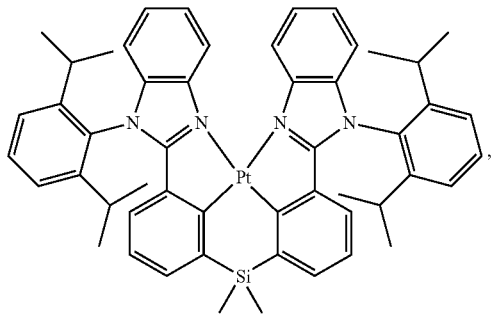

Compound 19
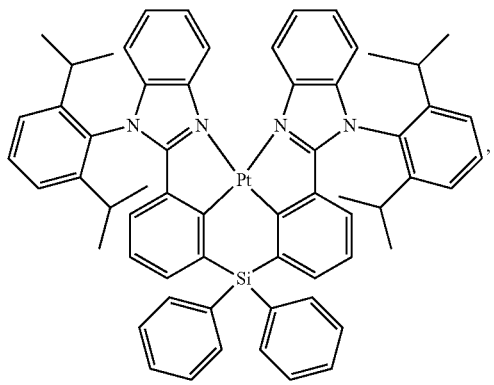
Compound 20
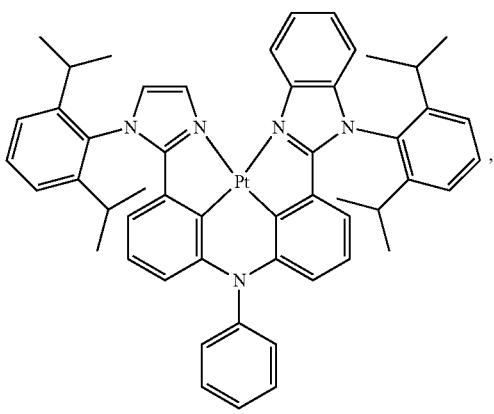
Compound 21
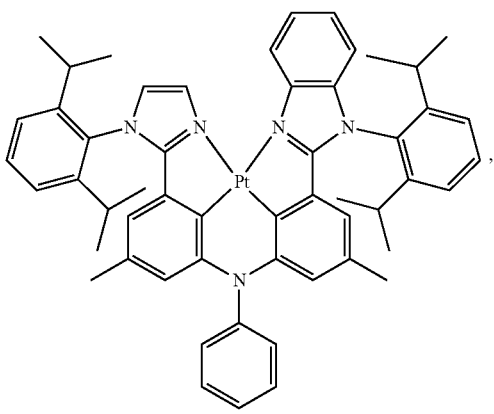
Compound 22
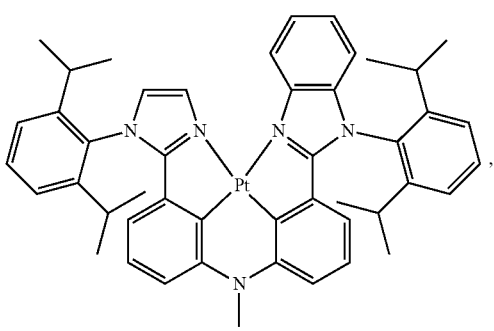
Compound 23
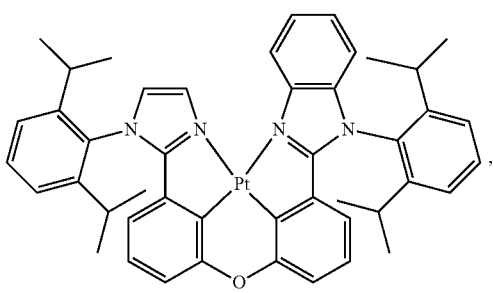
Compound 24
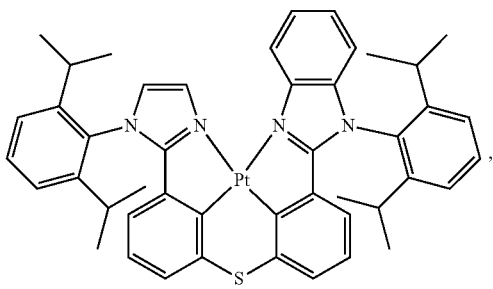
Compound 25
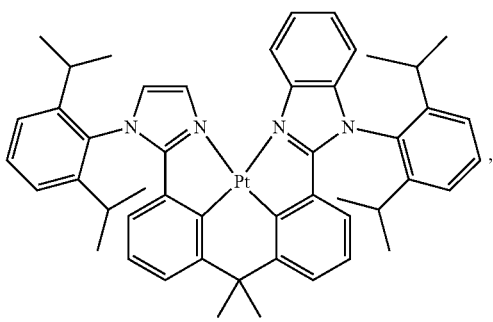
Compound 26
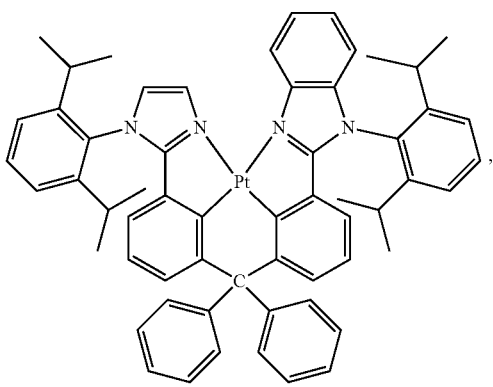

Compound 27
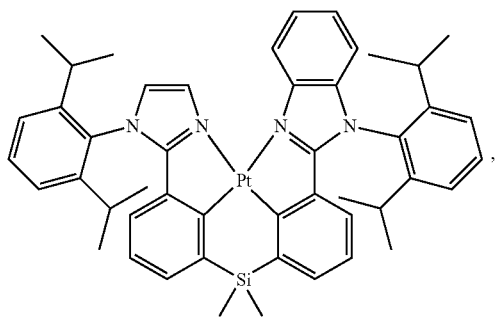
Compound 28
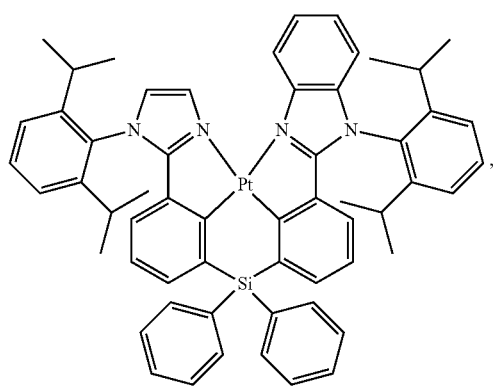
Compound 57
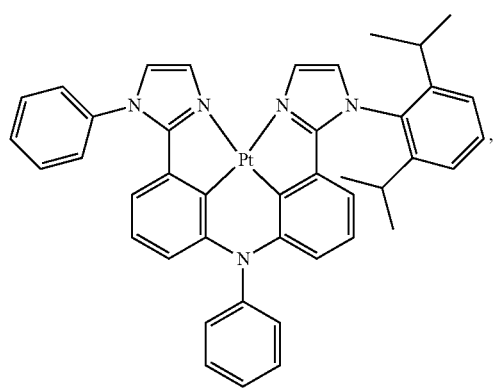
Compound 58
Compound 59
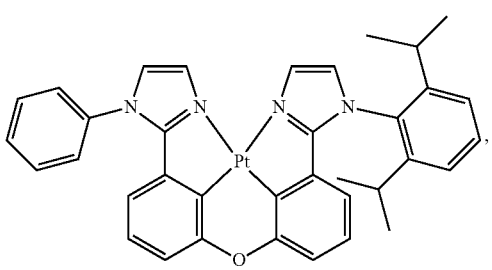
Compound 60
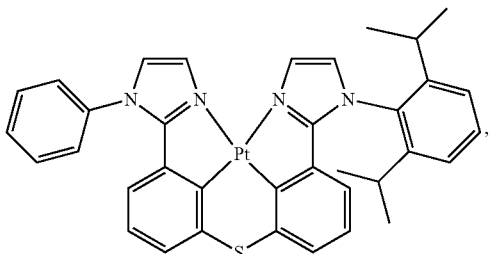
Compound 61
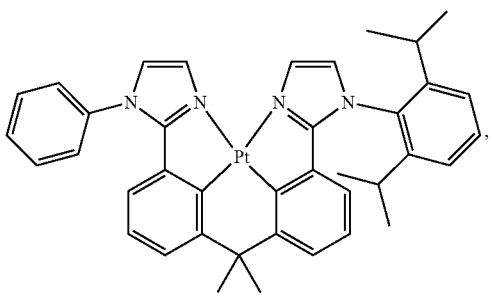
Compound 62
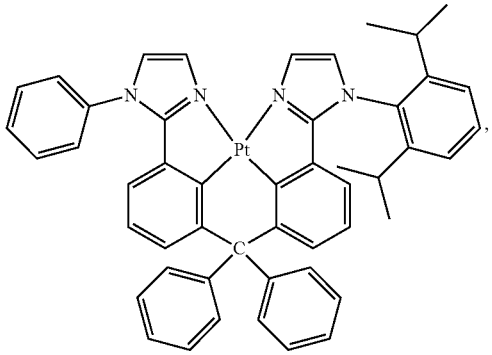
Compound 63
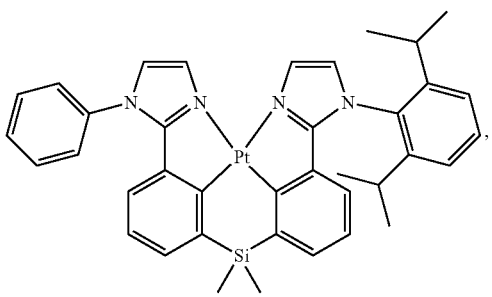

Compound 64
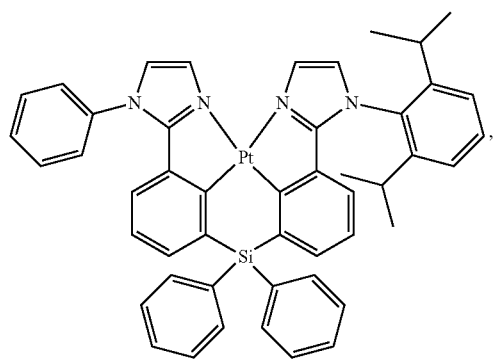
Compound 65
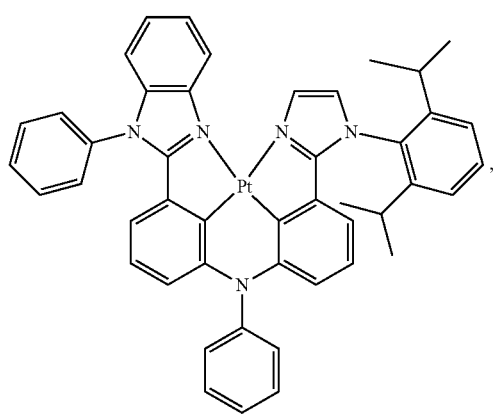
Compound 66
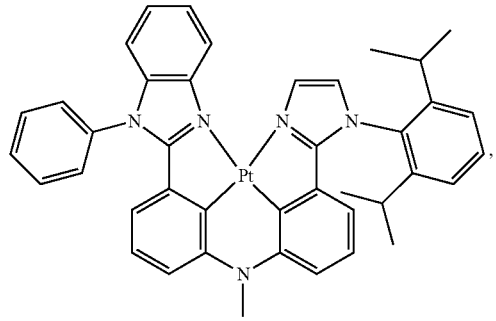
Compound 67
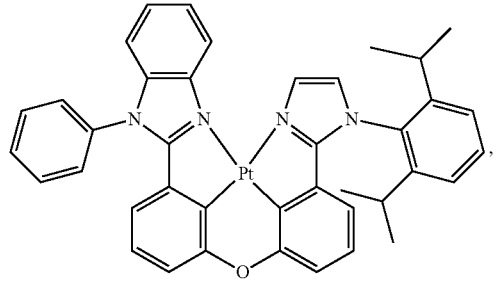
Compound 68
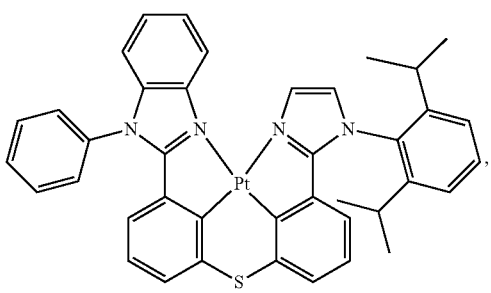
Compound 69
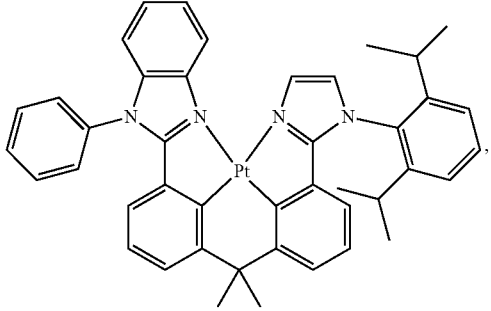
Compound 70
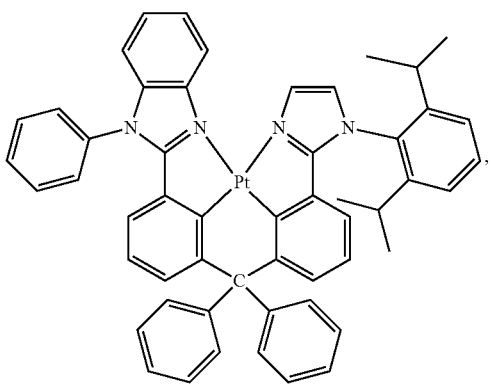
Compound 71
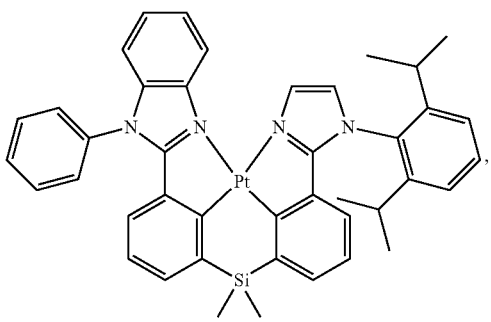

Compound 72
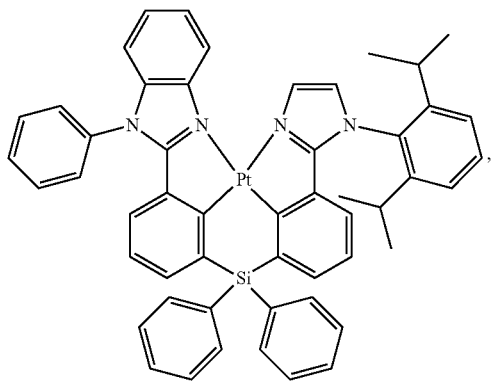
Compound 101
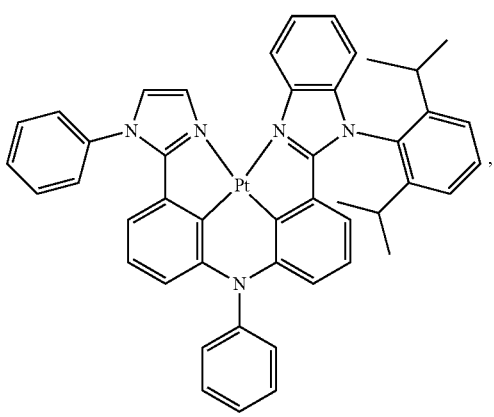
Compound 102
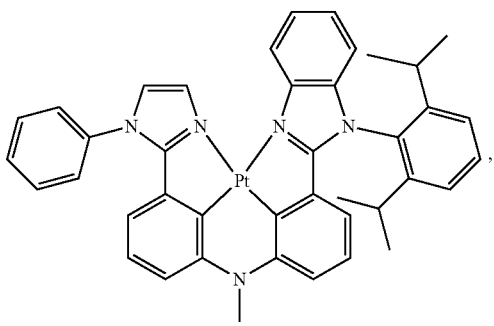
Compound 103
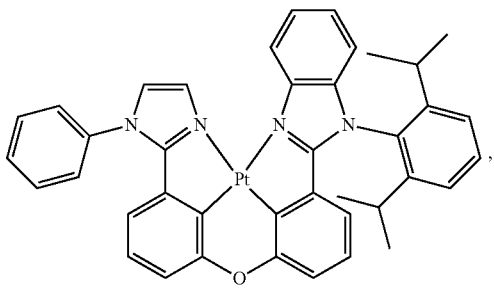
Compound 104
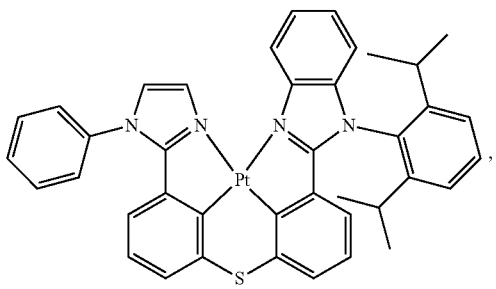
Compound 105
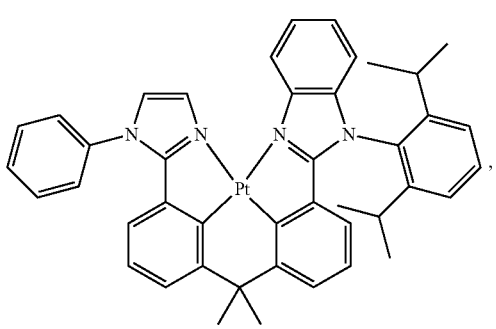
Compound 106
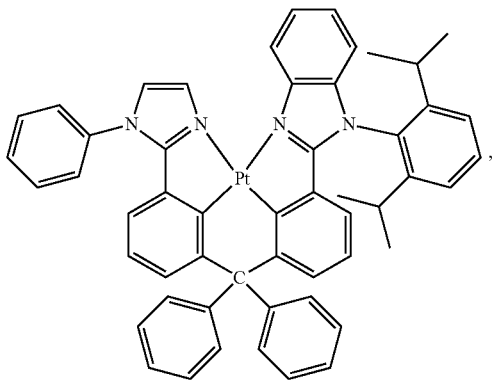
Compound 107
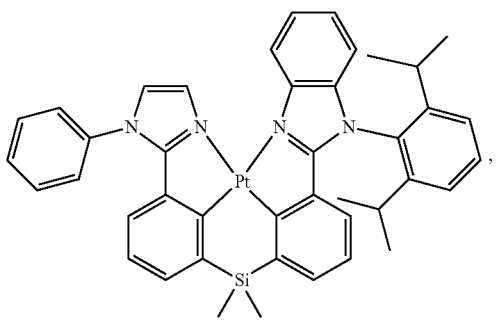

-continued
Compound 108
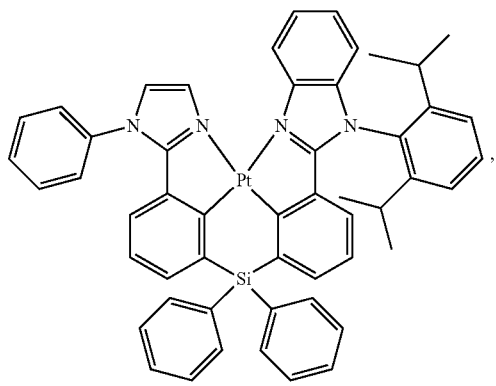
Compound 109
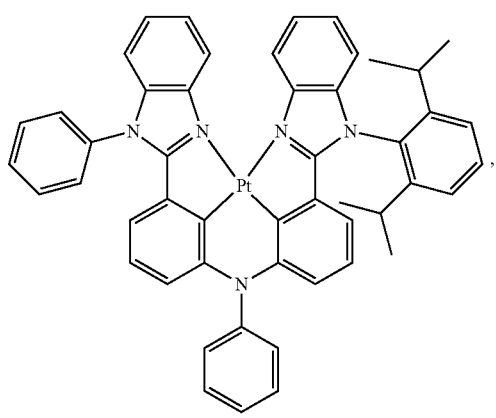
Compound 110
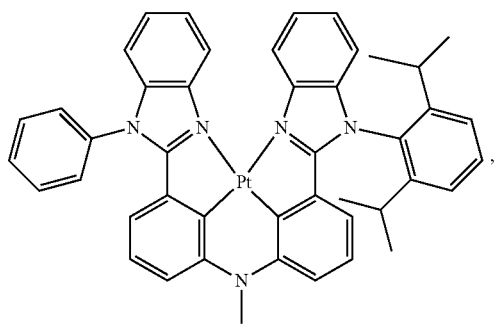
Compound 111
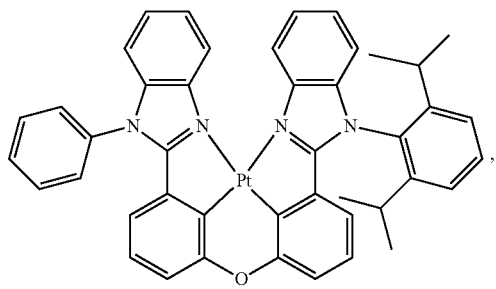
-continued
Compound 112
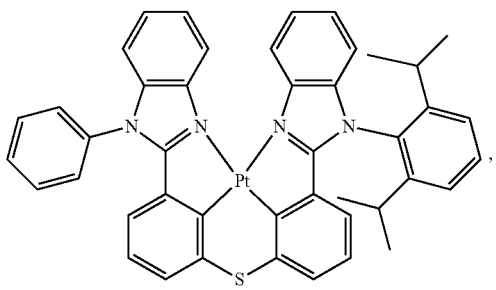
Compound 113
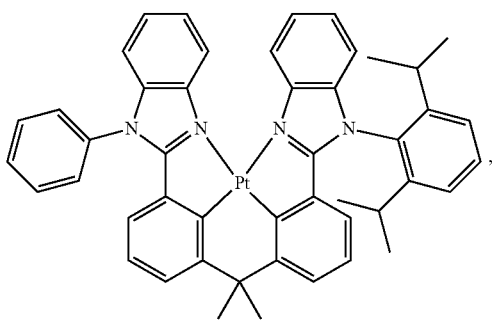
Compound 114
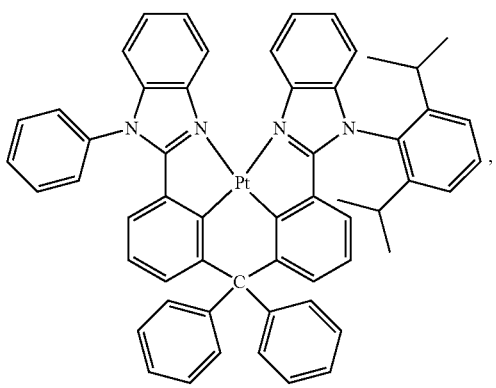
Compound 115
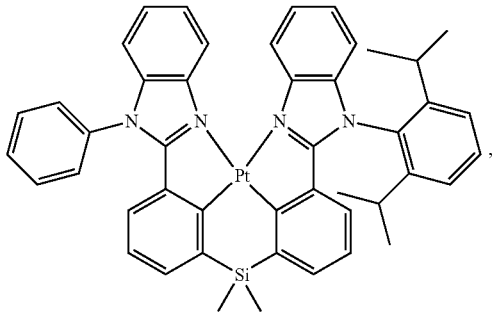

Compound 116
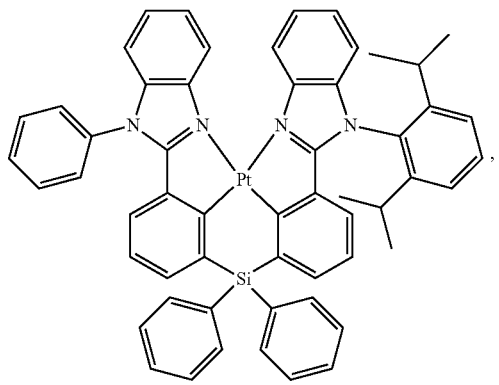
Compound 117
Compound 118
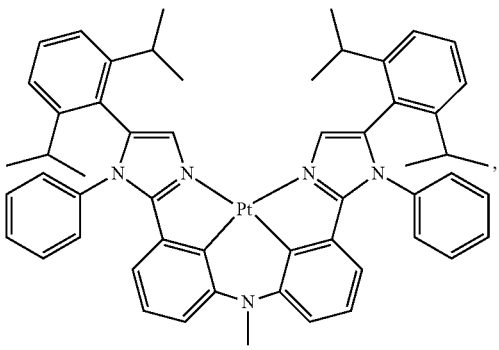
Compound 119
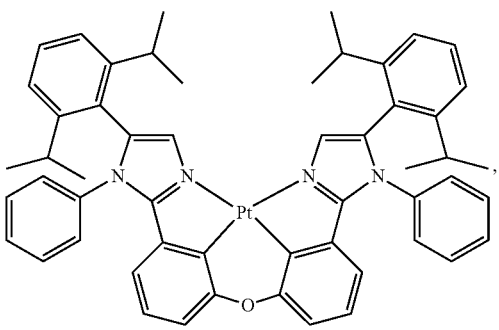
Compound 120
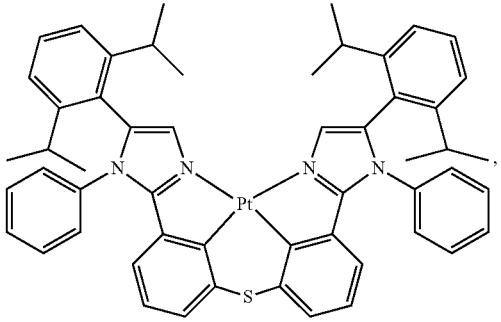
Compound 121
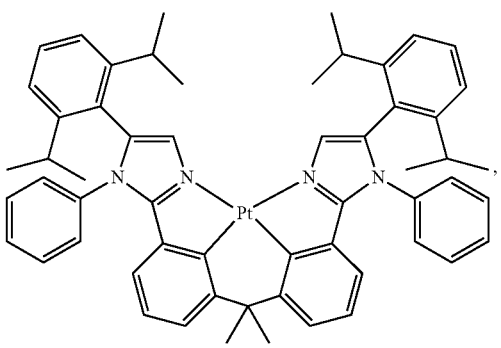
Compound 122
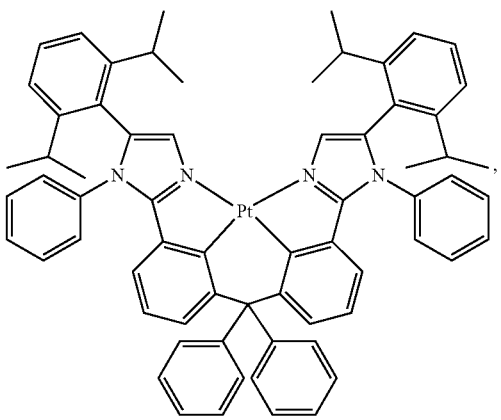
Compound 123
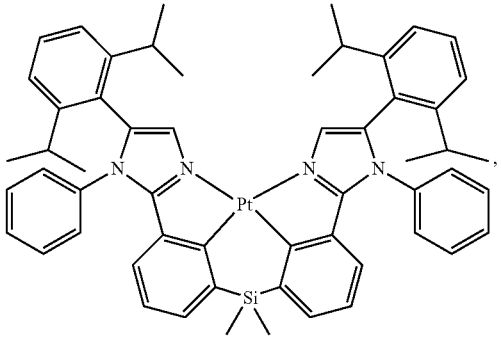

Compound 124
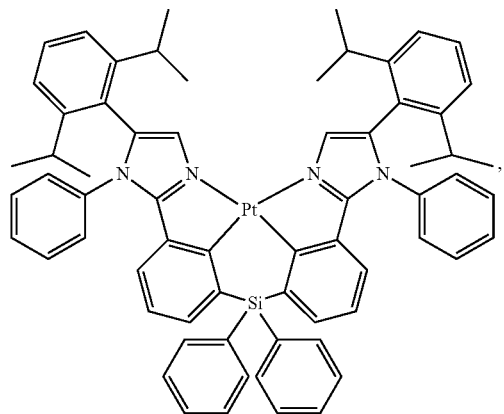
Compound 125
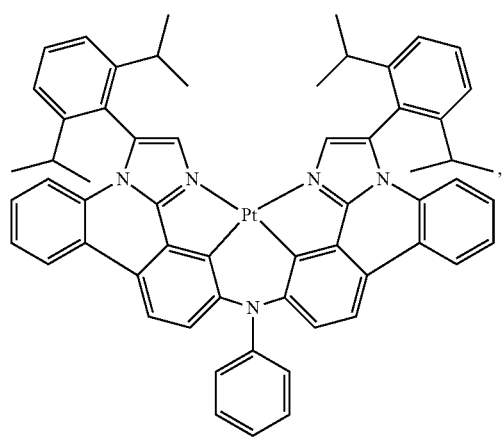
Compound 126
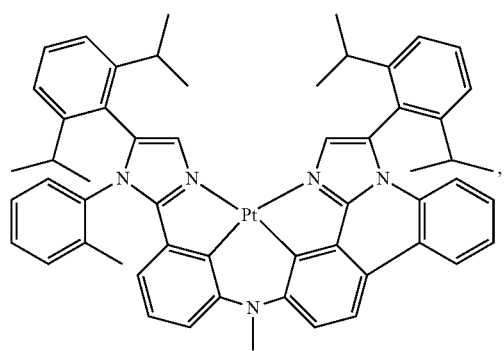
Compound 127
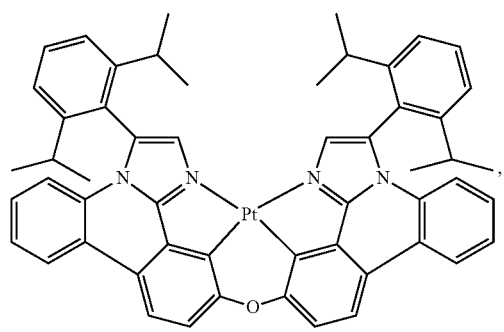
Compound 128
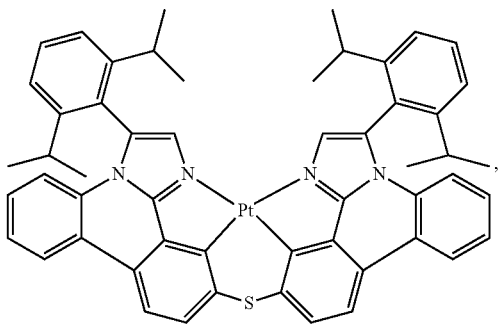
Compound 129
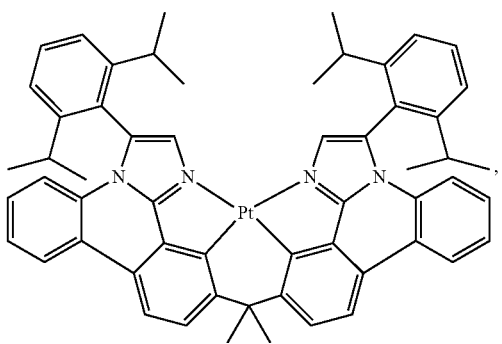
Compound 130
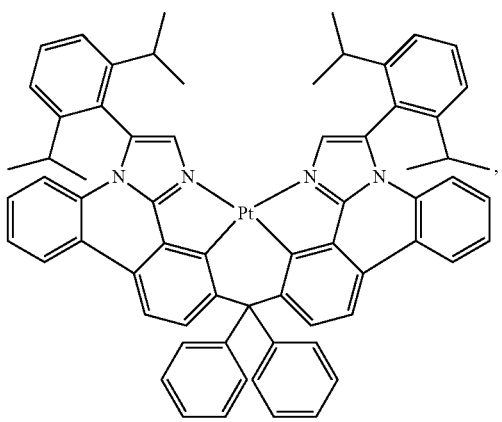
Compound 131
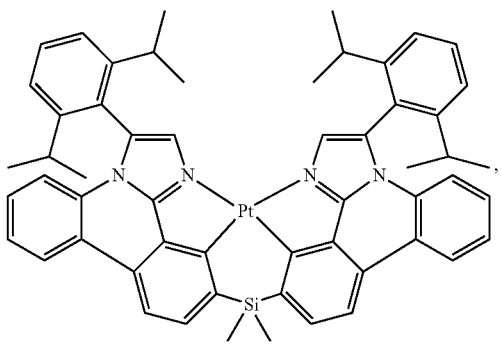

Compound 132
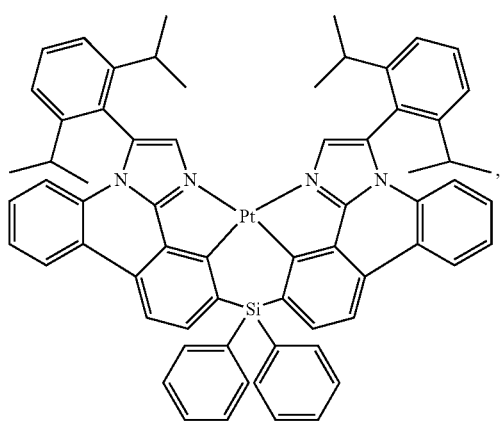
Compound 133
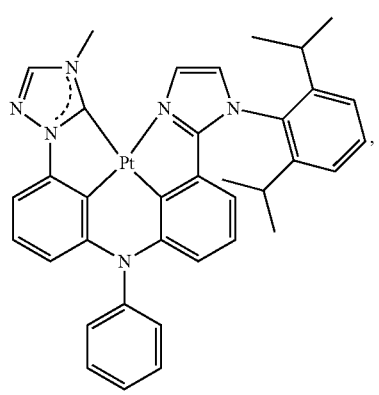
Compound 134
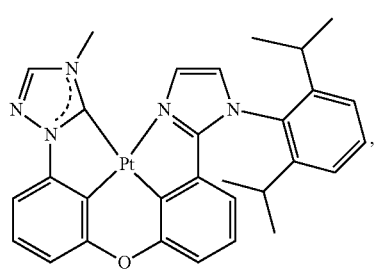
Compound 135
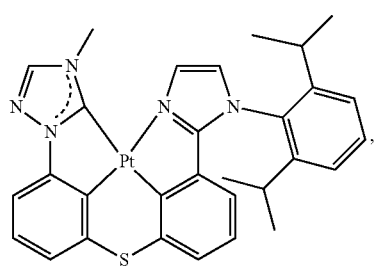
Compound 136
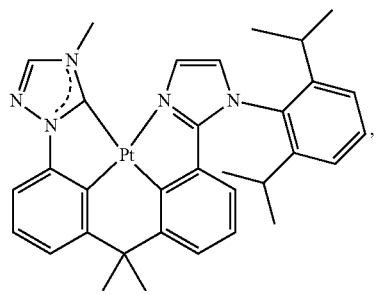
Compound 137
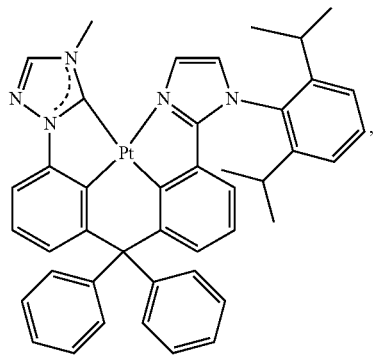
Compound 138
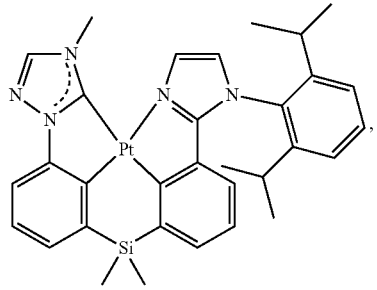
Compound 139
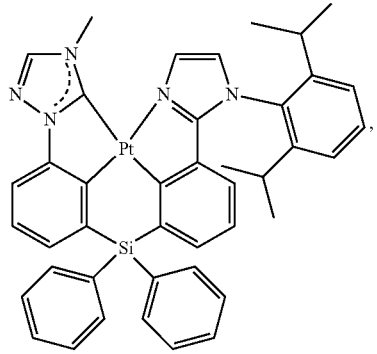
Compound 140
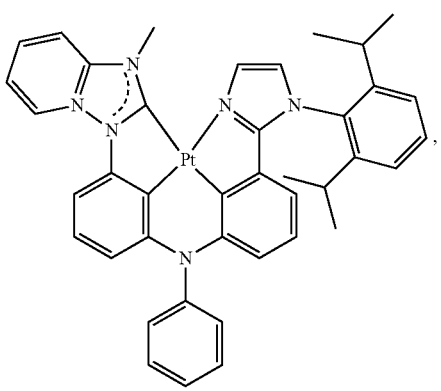

Compound 141
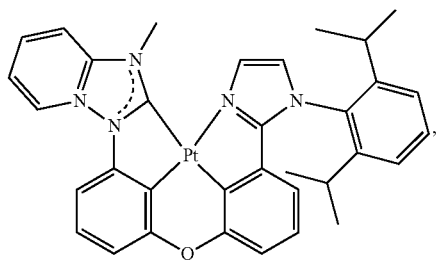
Compound 142
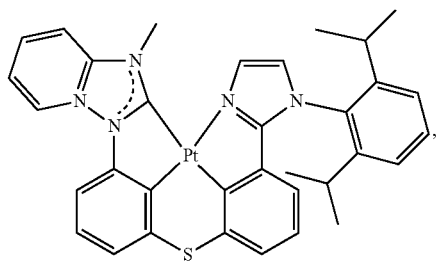
Compound 143
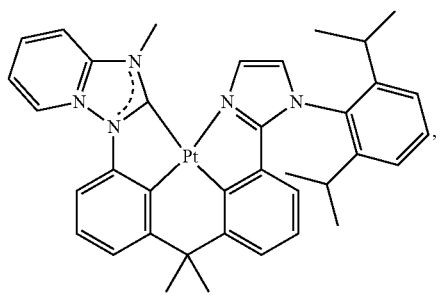
Compound 144
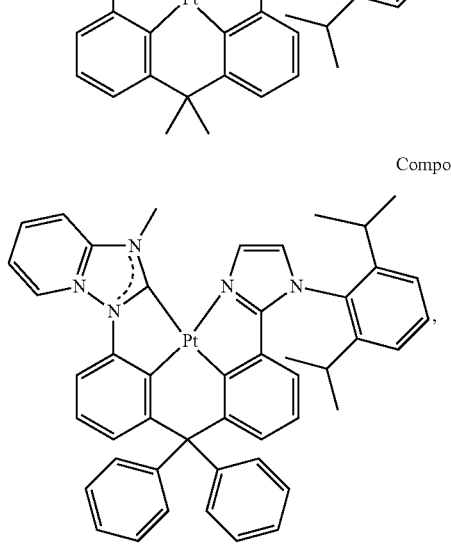
Compound 145
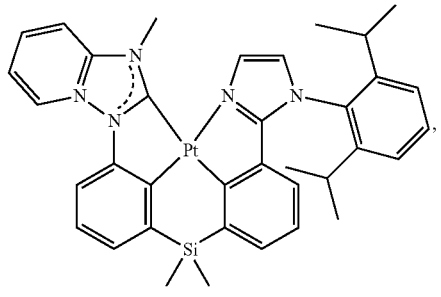
Compound 146
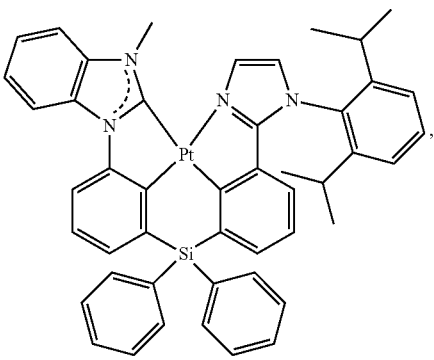
Compound 147
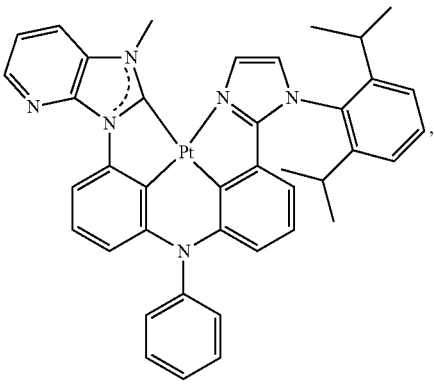
Compound 148
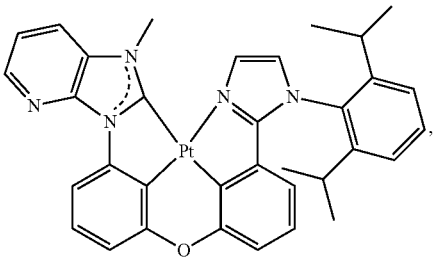
Compound 149
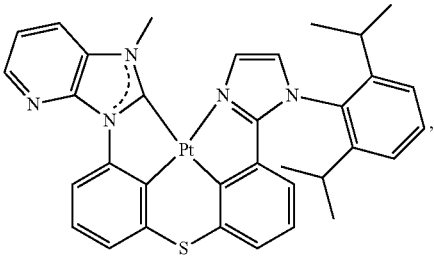

-continued
Compound 150
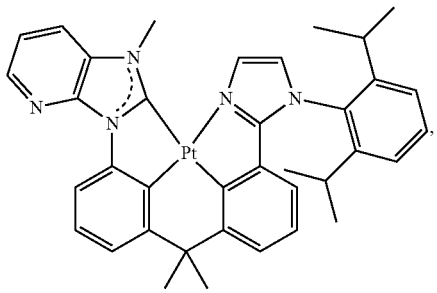
Compound 151
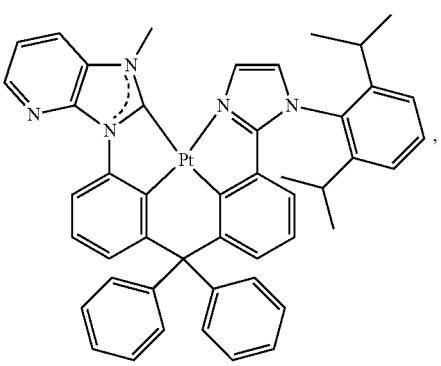
Compound 152
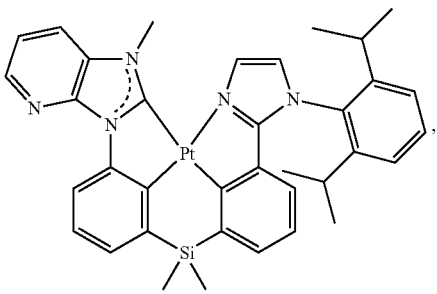
Compound 153
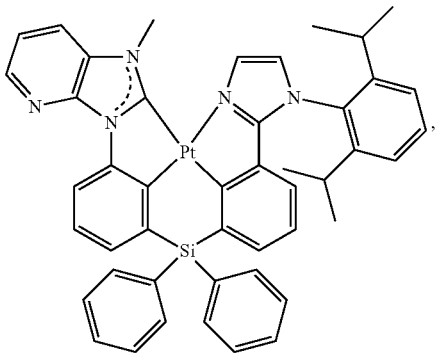
-continued
Compound 154
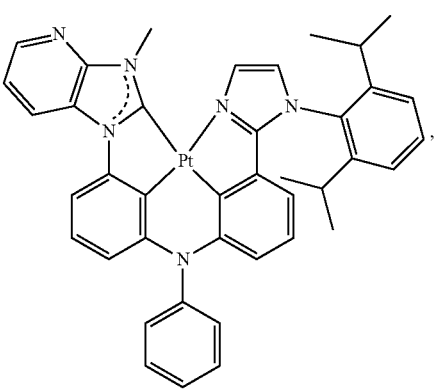
Compound 155
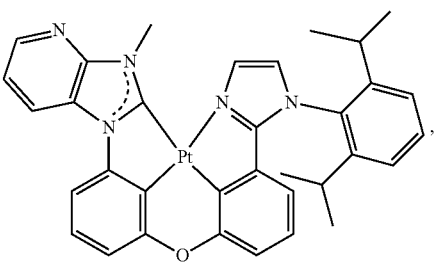
Compound 156
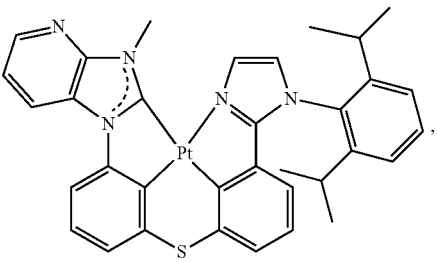
Compound 157
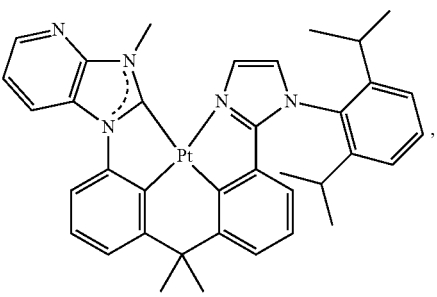

Compound 158
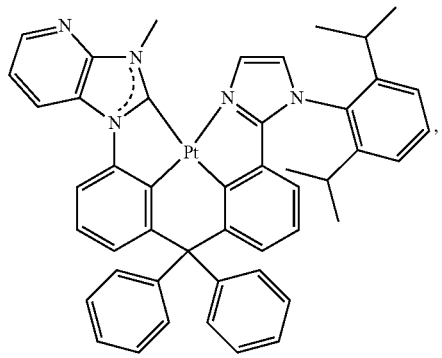
Compound 159
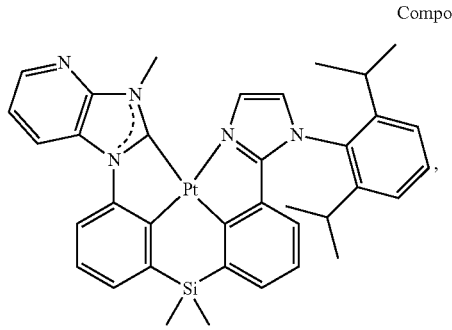
Compound 160
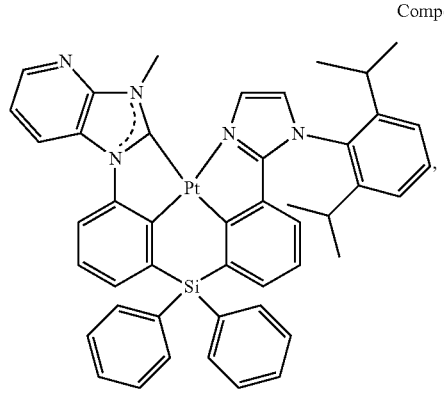
Compound 161
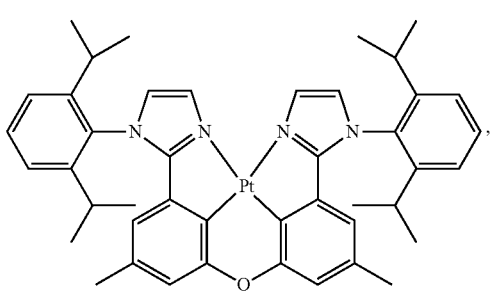
Compound 162
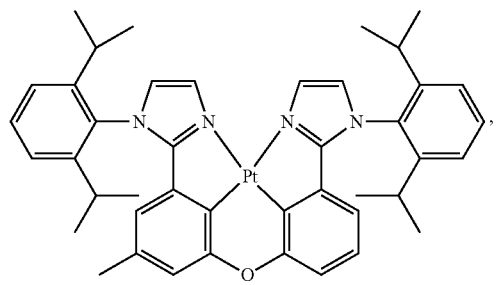
Compound 163
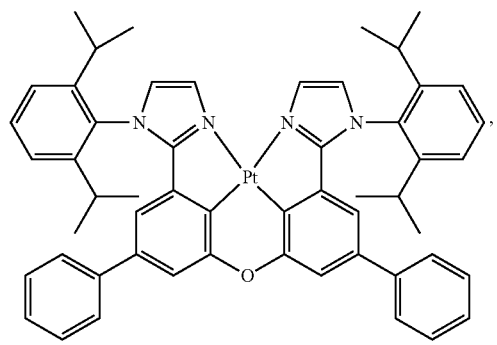
Compound 164
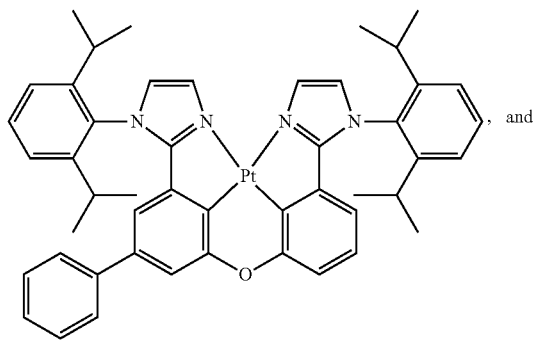
, and
Compound 166
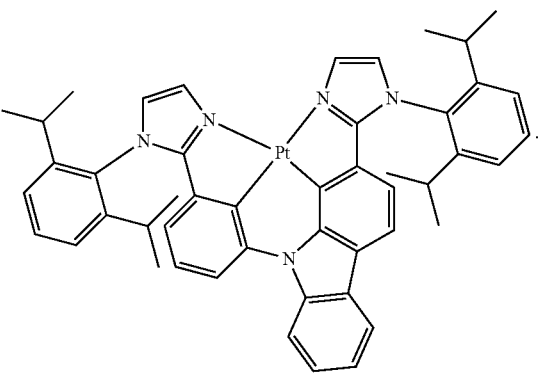

7. A first device comprising an organic light emitting device, comprising:

an anode;

a cathode; and an organic layer, disposed between the anode and the cathode, comprising a compound having the formula:

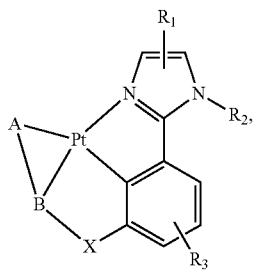

Formula II wherein A is a 5-membered carbocyclic or heterocyclic ring and B is a 5-membered or 6-membered carbocyclic or heterocyclic ring;

wherein A-B connects to Pt through one covalent bond and one coordination bond;

wherein X is selected from the group consisting of BR, NR, PR, O, S, Se, C=O, S=O, SO$_2$, CRR', SiRR', and GeRR';

wherein R and R' are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein R$_3$ may represent mono, di, or tri substitutions;

wherein R$_1$ may represent mono or di substitutions;

wherein R$_1$, R$_2$, and R$_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of R$_1$, R$_2$, and R$_3$ are optionally joined to form a fused ring;

wherein at least one of R$_1$ and R$_2$ is:

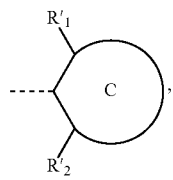

wherein R'$_1$ and R'$_2$ are independently selected from the group consisting of alkyl and aryl; and wherein C is a 5-membered or 6-membered carbocyclic or heterocyclic ring that is optionally further substituted.

8. A compound having the formula:

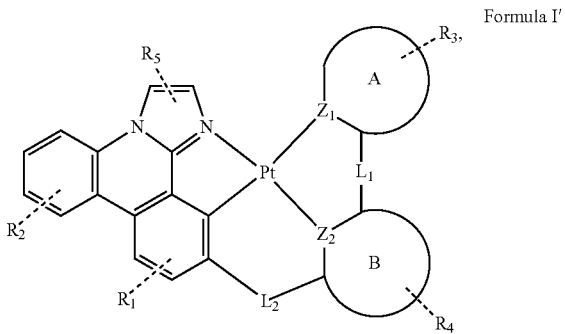

Formula I' wherein ring A is a 5-membered carbocyclic or heterocyclic ring and ring B is a 5-membered or 6-membered carbocyclic or heterocyclic ring;

wherein L$_1$ is a single bond and L$_2$ is selected from the group consisting of a single bond, BR, NR, PR, O, S, Se, C=O, S=O, SO$_2$, CRR', SiRR', and GeRR';

wherein Z$_1$ and Z$_2$ are independently a nitrogen atom or a carbon atom;

wherein R$_1$ and R$_5$ may represent mono or di substitutions;

wherein R$_2$, R$_3$, and R$_4$ may represent mono, di, tri, or tetra substitutions;

wherein R, R', R$_1$, R$_2$, R$_3$, R$_4$, and R$_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof; and wherein two adjacent substituents R, R', R$_1$, R$_2$, R$_3$, R$_4$, and R$_5$ are optionally joined to form a fused ring.

9. The compound of claim 8, wherein the compound has the formula:

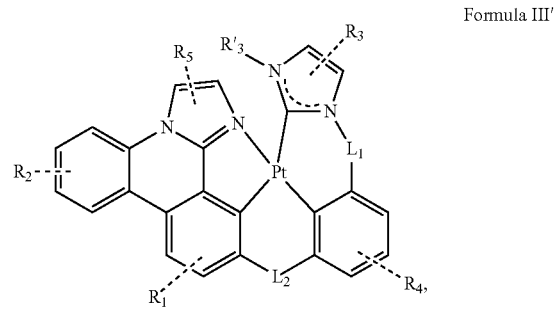

Formula III' wherein R'$_3$ is selected from the group consisting of hydrogen, deuterium, halide, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

10. The compound of claim 8, wherein the compound has the formula:

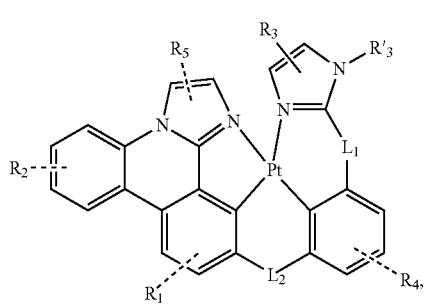

Formula IV' wherein R'₃ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

11. The compound of claim 8, wherein the compound is selected from the group consisting of:

Compound 103'

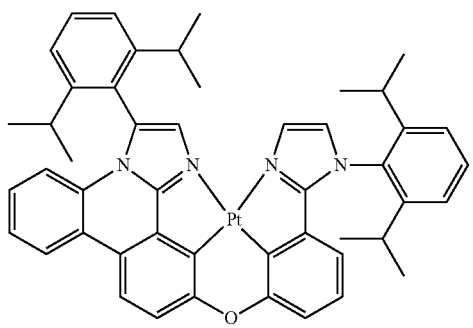

Compound 104'

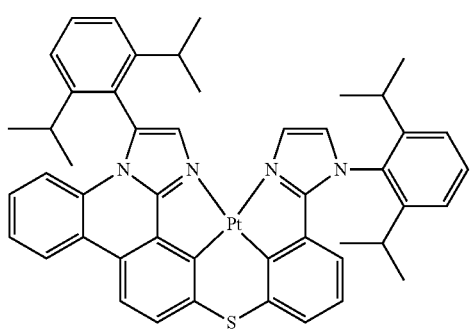

Compound 105"

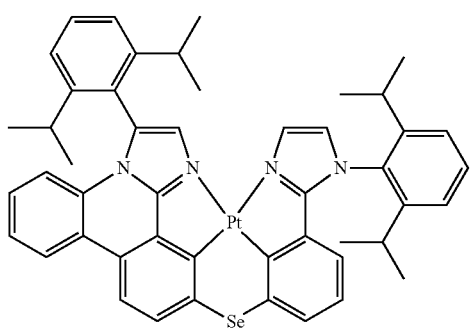

-continued

Compound 106'

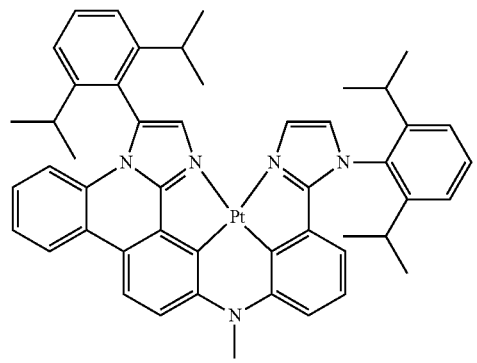

Compound 107¢

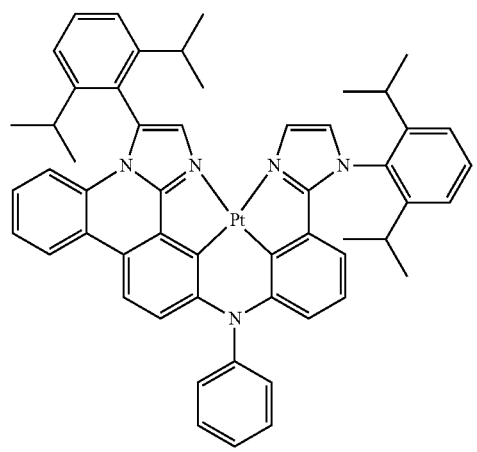

Compound 107'

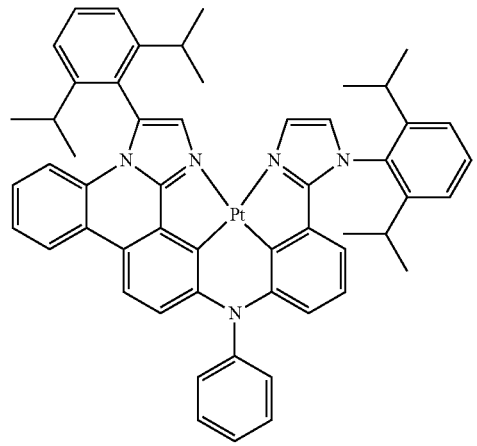

-continued
Compound 108'
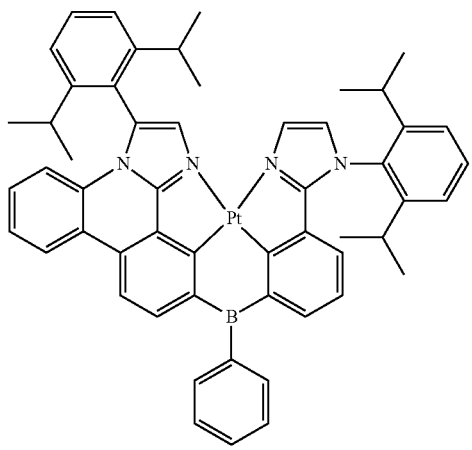
Compound 109'
Compound 110'
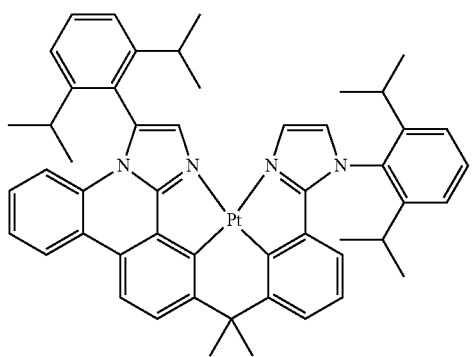
-continued
Compound 111'
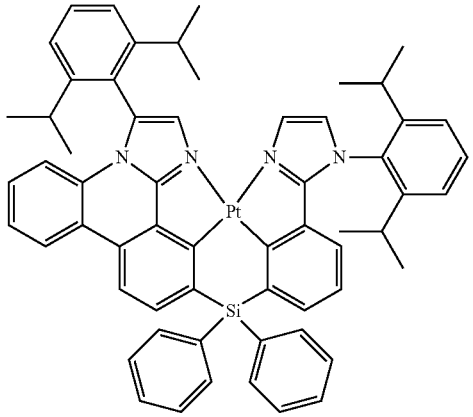
Compound 112'
Compound 113'
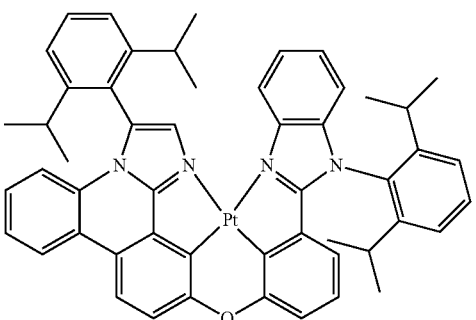
Compound 114'
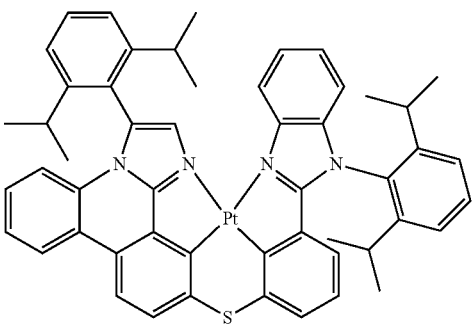
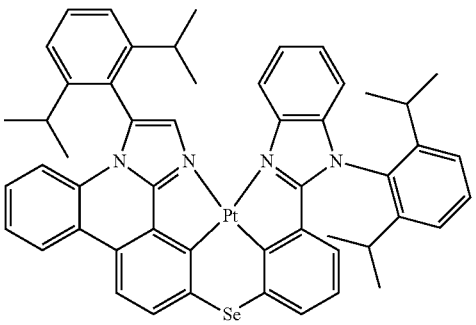

-continued
Compound 115'
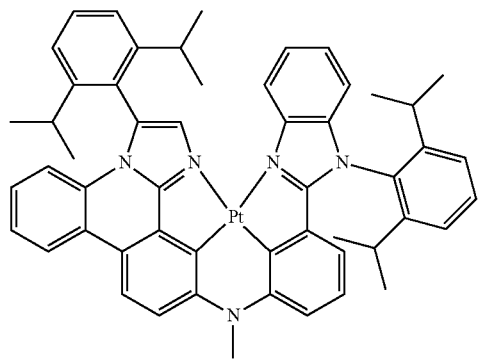
Compound 116'
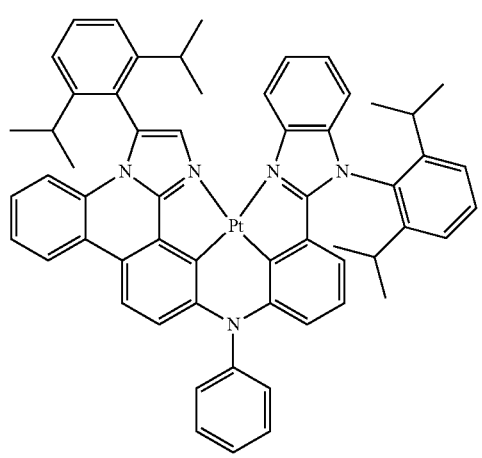
Compound 117'
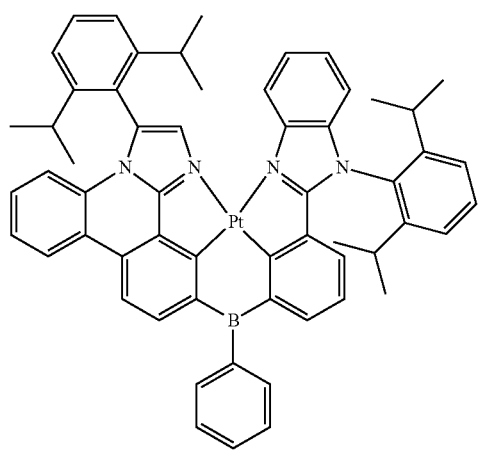
-continued
Compound 118'
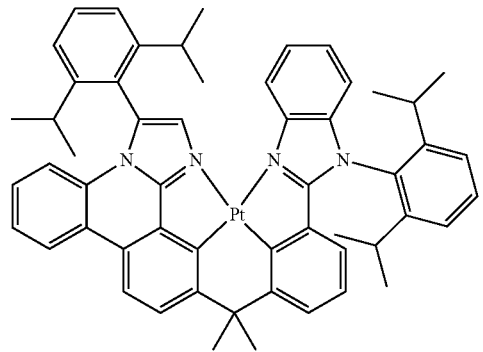
Compound 119'
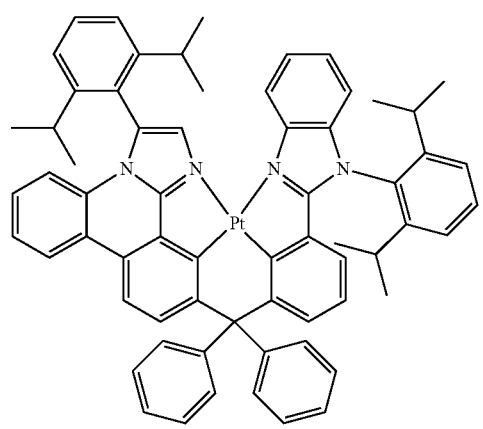
Compound 120'
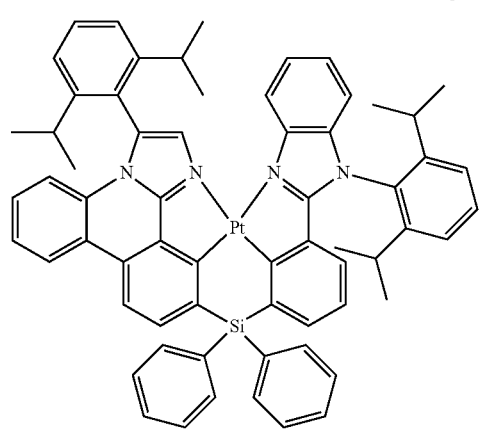
Compound 145'
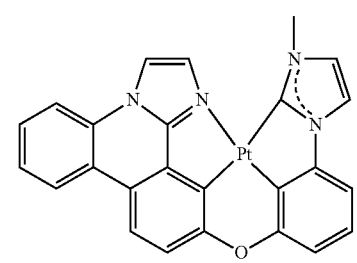

Compound 146'
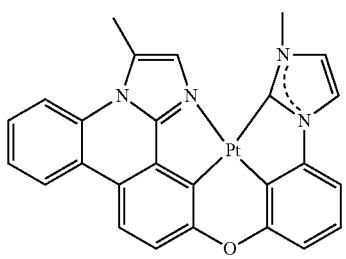
Compound 147'
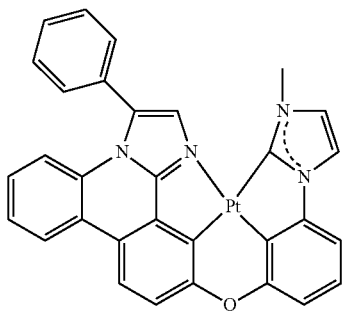
Compound 148'
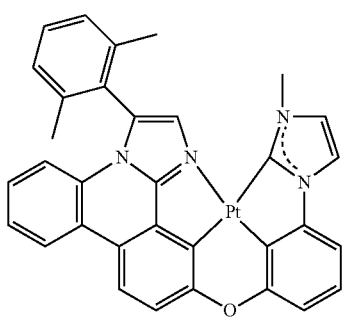
Compound 149'
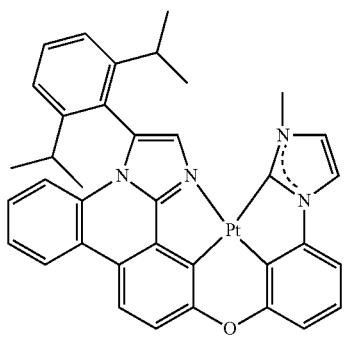
Compound 150'
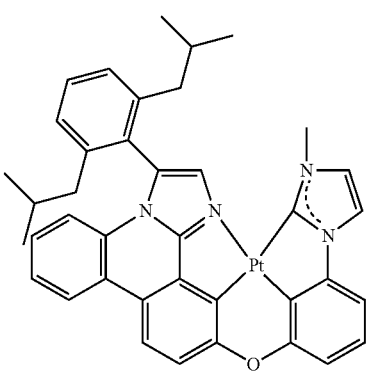
Compound 151'
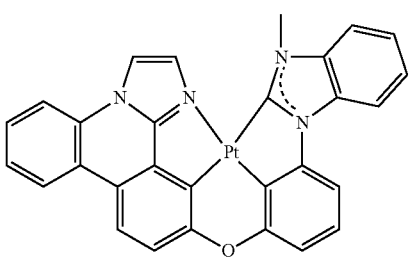
Compound 152'
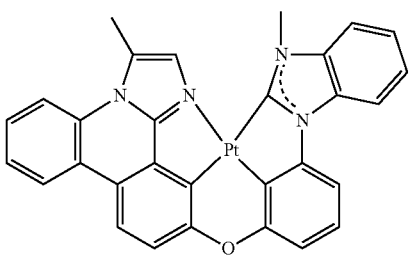
Compound 153'
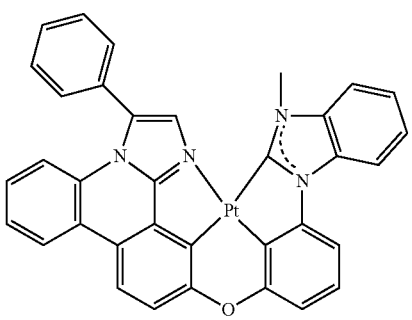
Compound 154'
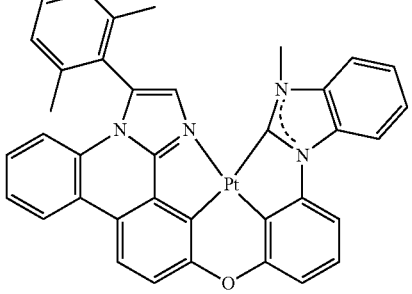
Compound 155'
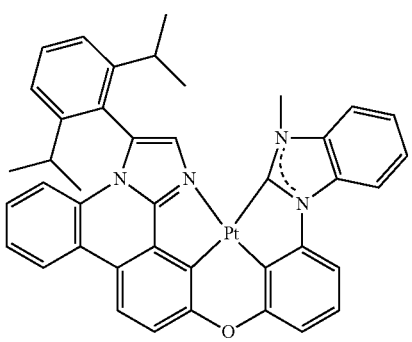

Compound 156'
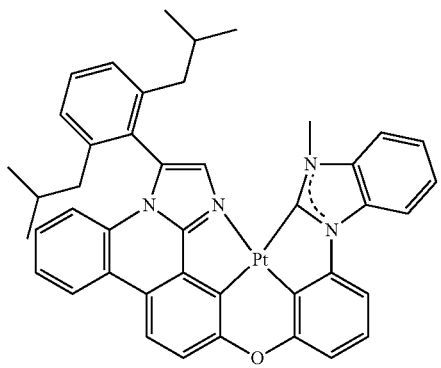
Compound 157'
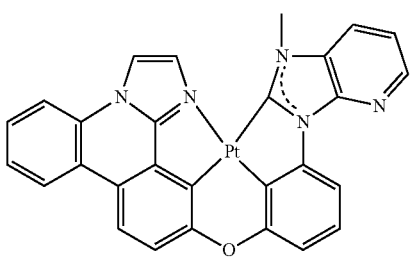
Compound 158'
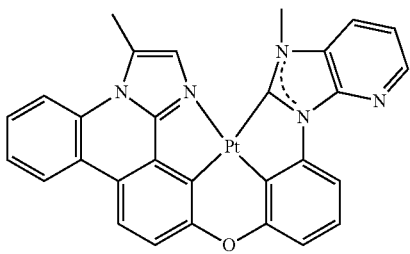
Compound 159'
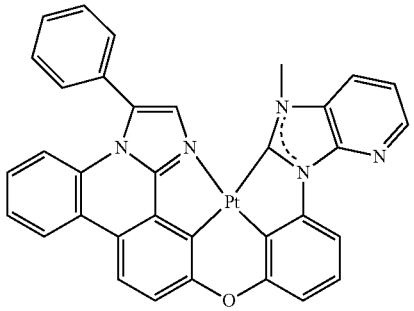
Compound 160'
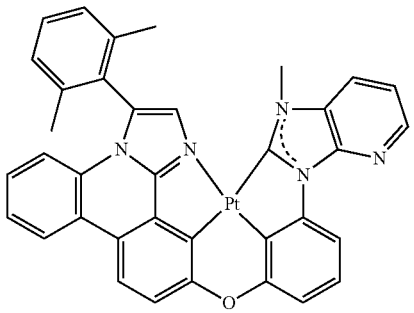
Compound 161'
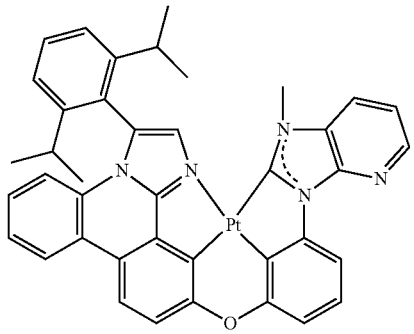
Compound 162'
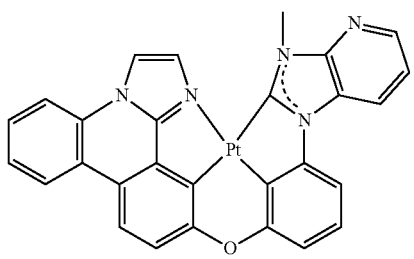
Compound 163'
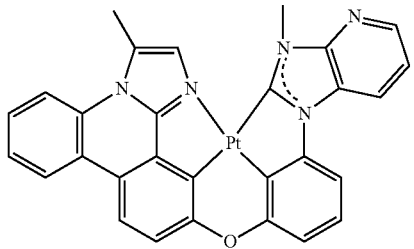
Compound 164'
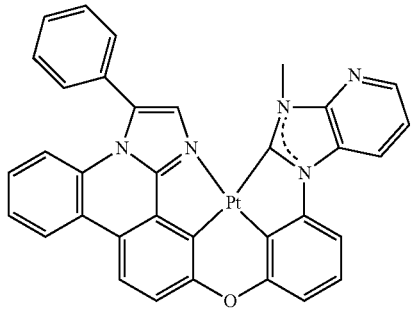
Compound 165'

-continued
Compound 166'
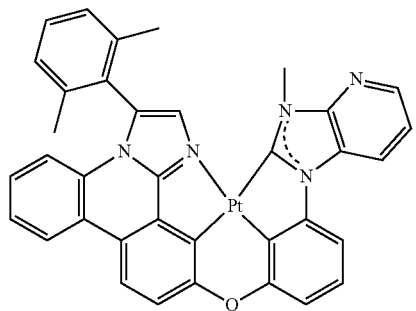
Compound 167'
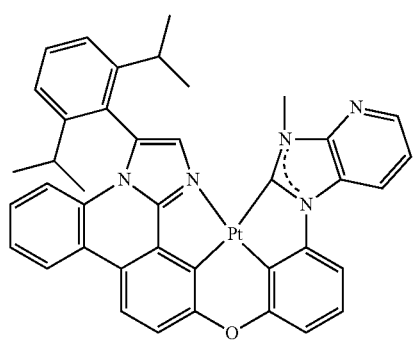
Compound 168'
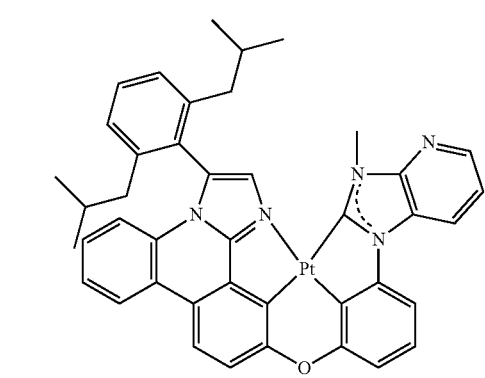
Compound 169'
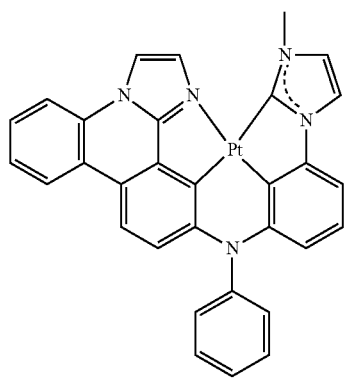
-continued
Compound 170'
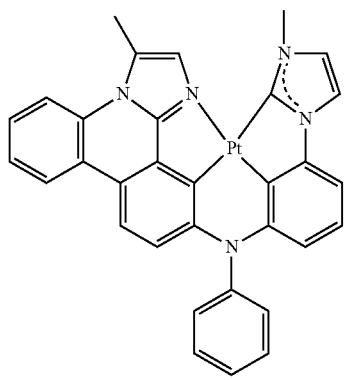
Compound 171'
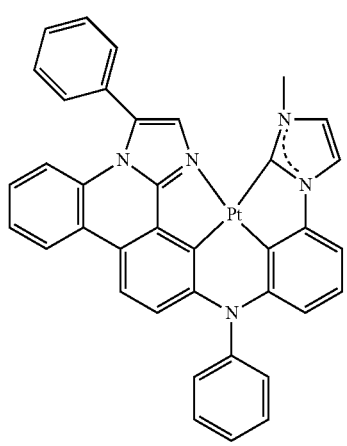
Compound 172'
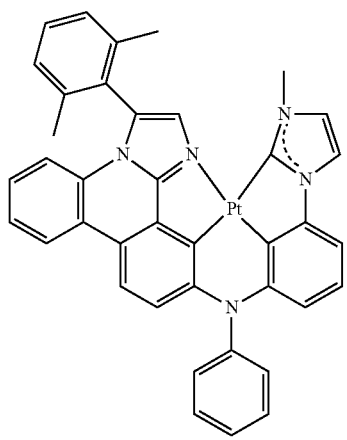

Compound 173'
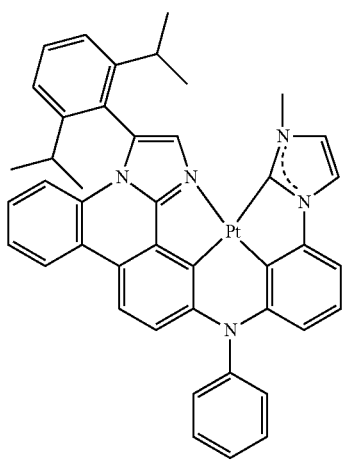
Compound 176'
Compound 177'
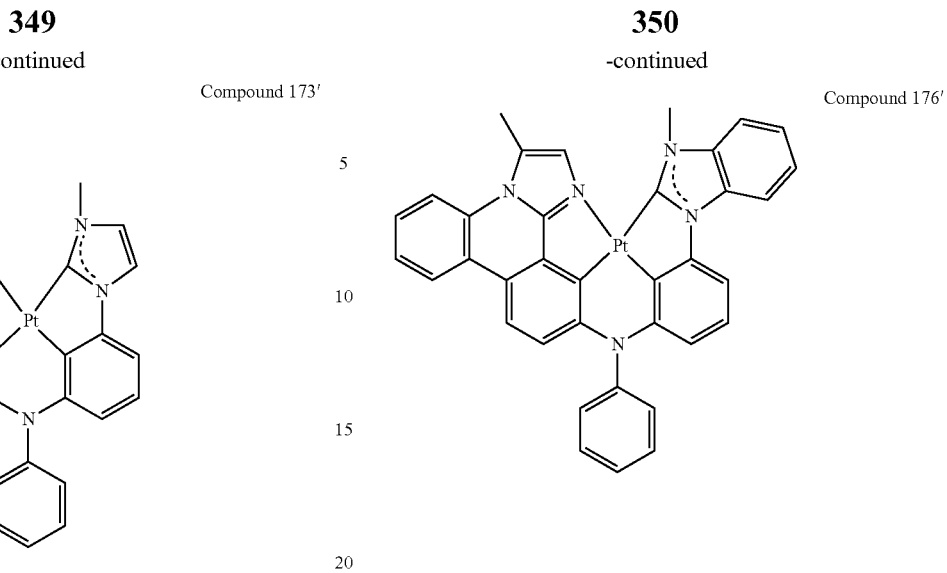
Compound 174'
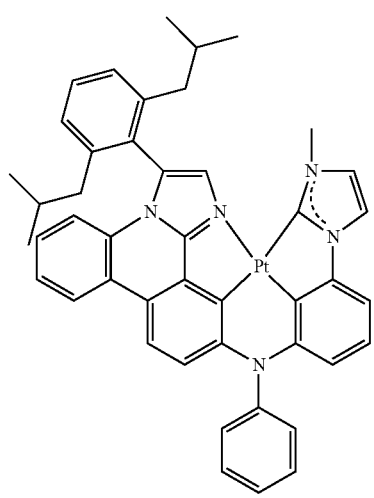
Compound 175'
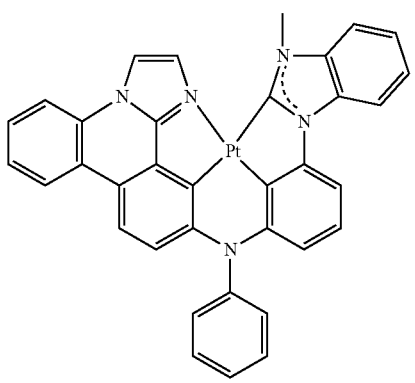
Compound 178'
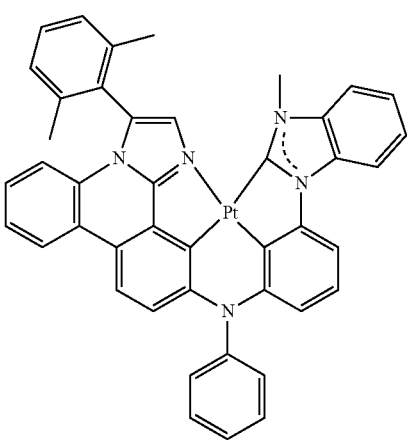

351
-continued
Compound 179'
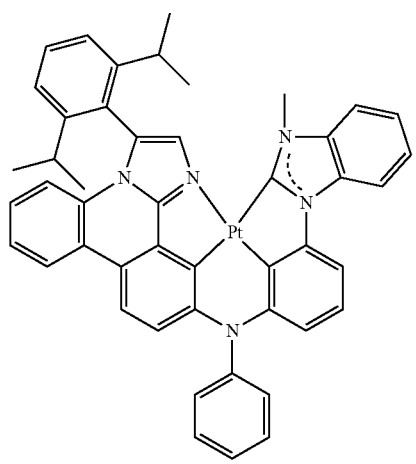
Compound 180'
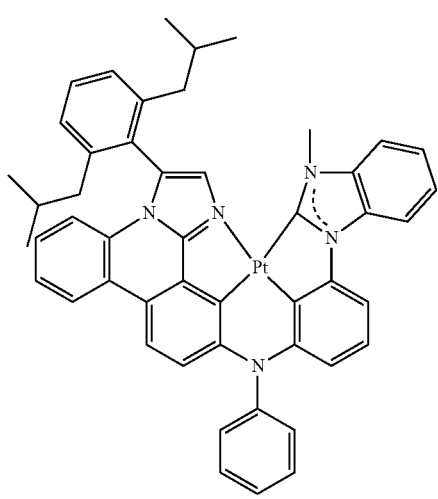
Compound 181'
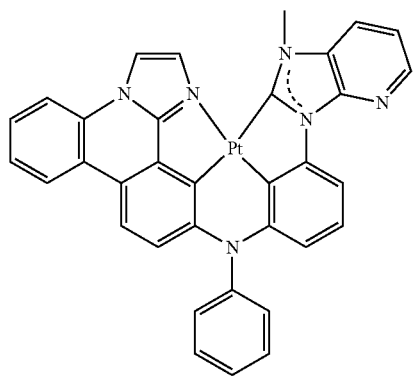
352
-continued
Compound 182'
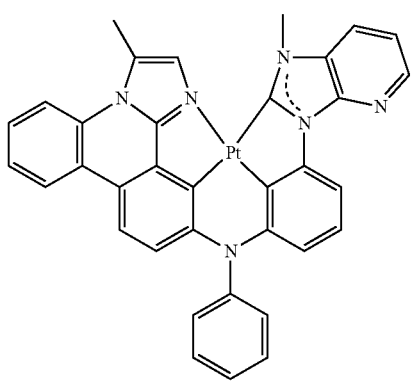
Compound 183'
Compound 184'

Compound 185'
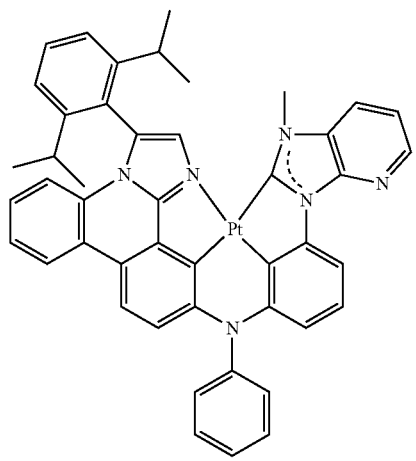
Compound 186'
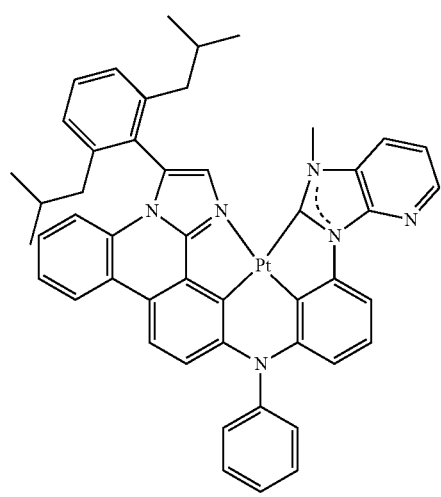
Compound 187'
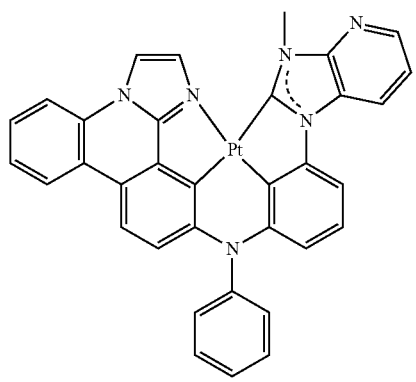
Compound 188'
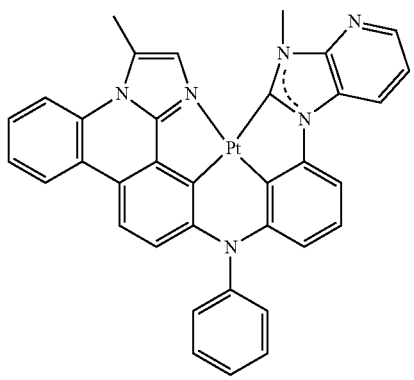
Compound 189'
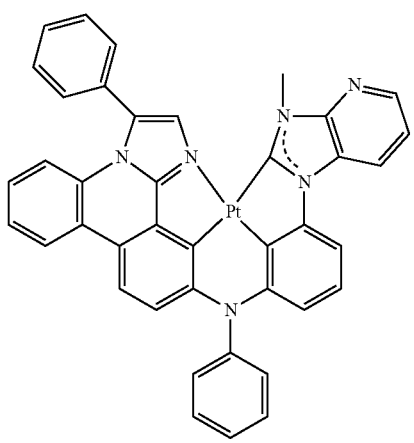
Compound 190'
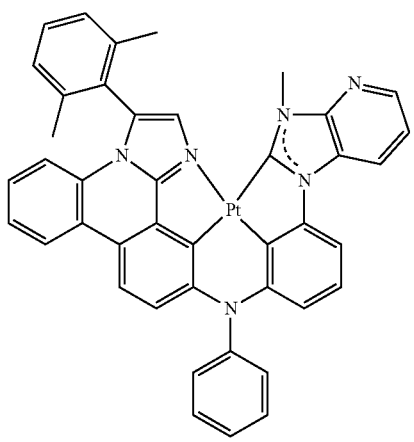

-continued
Compound 191'
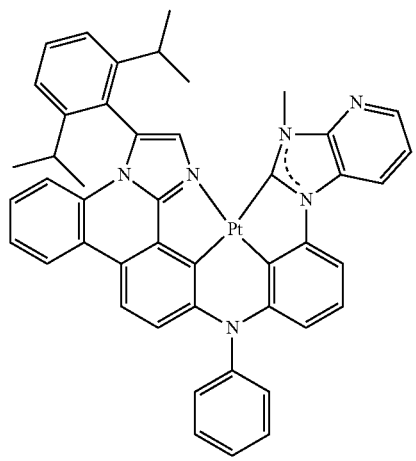
Compound 192'
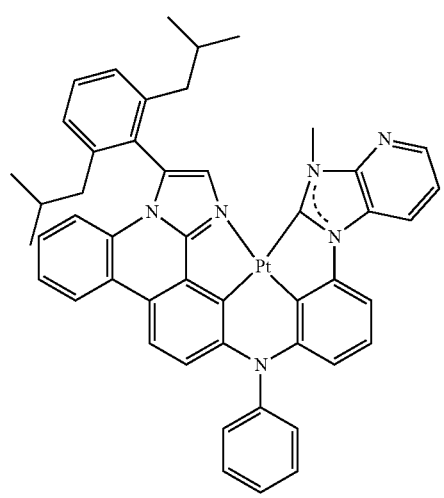
Compound 193'
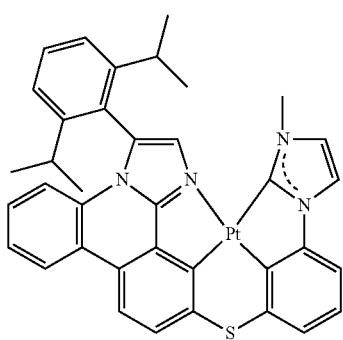
Compound 194'
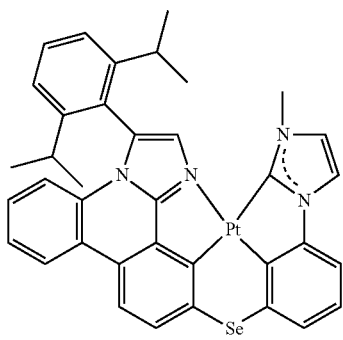
-continued
Compound 195'
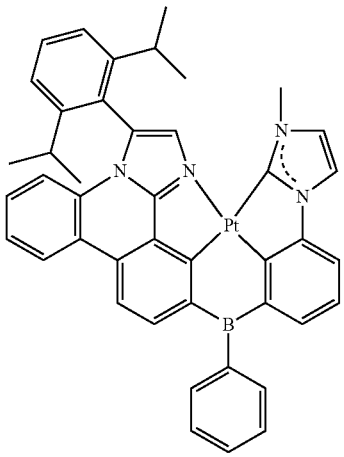
Compound 196'
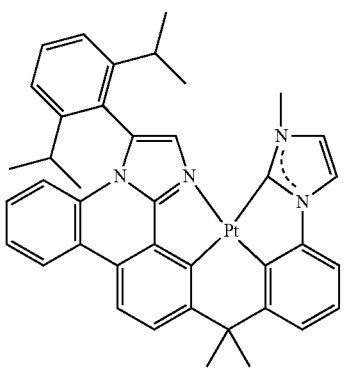
Compound 197'
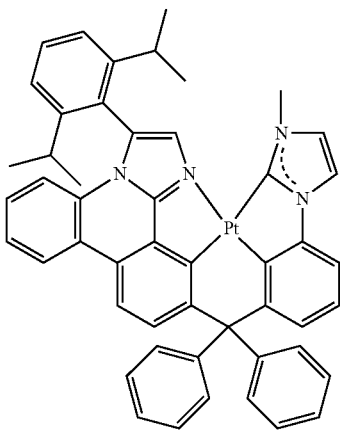

-continued
Compound 198'
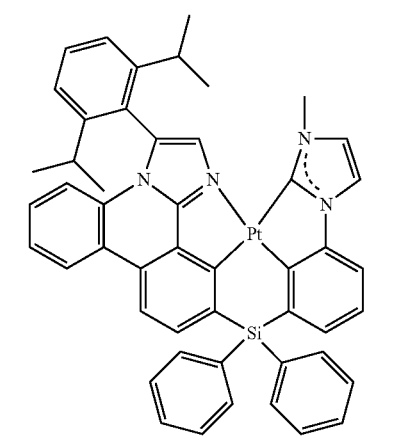
Compound 219'
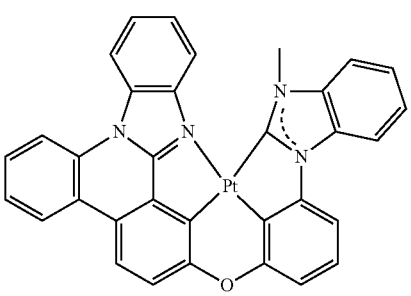
Compound 220'
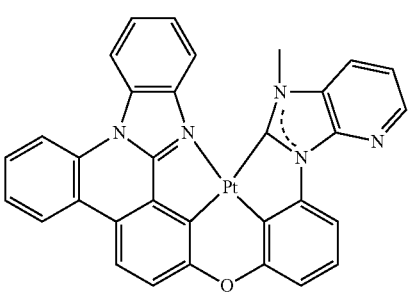
Compound 221'
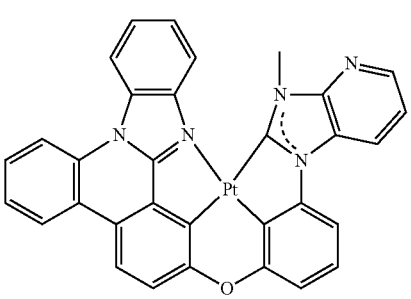
Compound 222'
-continued
Compound 223'
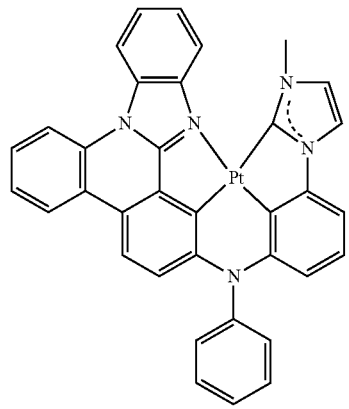
Compound 224'
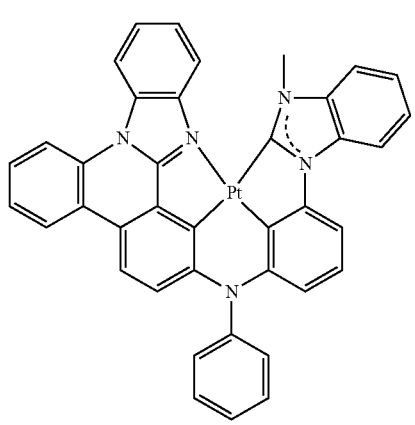
Compound 225'
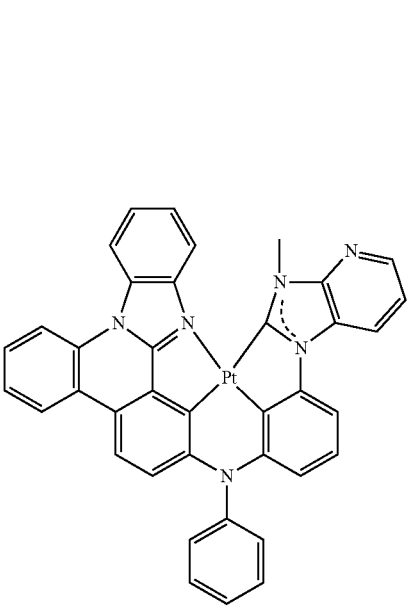

12. A first device comprising an organic light emitting device, comprising:
   an anode;
   a cathode; and
   an organic layer, disposed between the anode and the cathode, comprising a compound having the formula:

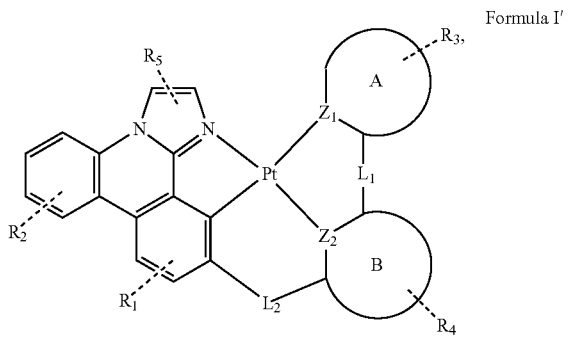

Formula I' wherein ring A is a 5-membered carbocyclic or heterocyclic ring and ring B is a 5-membered or 6-membered carbocyclic or heterocyclic ring;

wherein $L_1$ is a single bond and $L_2$ is selected from the group consisting of a single bond, BR, NR, PR, O, S, Se, C=O, S=O, $SO_2$, CRR', SiRR', and GeRR';

wherein $Z_1$ and $Z_2$ are independently a nitrogen atom or a carbon atom;

wherein $R_1$ and $R_5$ may represent mono or di substitutions;

wherein $R_2$, $R_3$, and $R_4$ may represent mono, di, tri, or tetra substitutions;

wherein R, R', $R_1$, $R_2$, $R_3$, $R_4$, and $R_5$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substitutents of R, R', $R_1$, $R_2$, $R_3$, $R_4$, and $R_5$ are optionally joined to form a fused ring.

* * * * *

UNITED STATES PATENT AND TRADEMARK OFFICE
CERTIFICATE OF CORRECTION

| | | |
|---|---|---|
| PATENT NO. | : 8,871,361 B2 | Page 1 of 1 |
| APPLICATION NO. | : 13/414479 | |
| DATED | : October 28, 2014 | |
| INVENTOR(S) | : Chuanjun Xia et al. | |

It is certified that error appears in the above-identified patent and that said Letters Patent is hereby corrected as shown below:

On title page 1, listed in the inventors section, the correct spelling of the inventor James Fiordelisio should be -- James Fiordeliso --.

In the Claims

In column 338, lines 25-45, the extraneous notation of

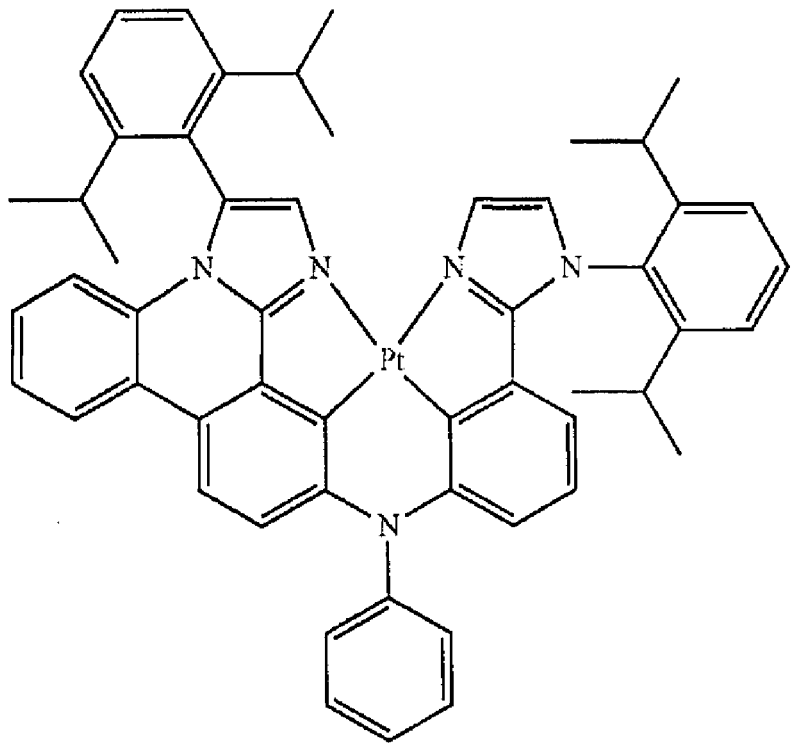

" should be deleted.

Signed and Sealed this
Tenth Day of February, 2015

Michelle K. Lee
*Deputy Director of the United States Patent and Trademark Office*